(12) United States Patent
Webber et al.

(10) Patent No.: US 11,692,005 B2
(45) Date of Patent: Jul. 4, 2023

(54) TLR7 AGONISTS

(71) Applicant: Primmune Therapeutics, Inc., Carlsbad, CA (US)

(72) Inventors: Stephen E. Webber, San Diego, CA (US); James Richard Appleman, San Diego, CA (US)

(73) Assignee: Primmune Therapeutics, Inc., Carlsbad, CA (US)

( * ) Notice: Subject to any disclaimer, the term of this patent is extended or adjusted under 35 U.S.C. 154(b) by 163 days.

(21) Appl. No.: 17/104,808

(22) Filed: Nov. 25, 2020

(65) Prior Publication Data

US 2021/0155652 A1    May 27, 2021

Related U.S. Application Data

(60) Provisional application No. 62/940,622, filed on Nov. 26, 2019.

(51) Int. Cl.
| | |
|---|---|
| *A01N 43/04* | (2006.01) |
| *A61K 31/70* | (2006.01) |
| *C07H 19/16* | (2006.01) |
| *A61K 31/708* | (2006.01) |
| *A61K 45/06* | (2006.01) |

(52) U.S. Cl.
CPC ........... *C07H 19/16* (2013.01); *A61K 31/708* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,011,828 A | 4/1991 | Goodman et al. | |
| 5,093,319 A | 3/1992 | Higham et al. | |
| 5,136,030 A | 8/1992 | Chen | |
| 5,476,659 A | 12/1995 | Goodman et al. | |
| 6,784,161 B2 | 8/2004 | Ismaili et al. | |
| 7,576,068 B2 | 8/2009 | Averett | |
| 7,858,637 B2 | 12/2010 | Averett | |
| 8,034,802 B2 | 10/2011 | Averett | |
| 8,097,718 B2 | 1/2012 | Webber | |
| 8,211,863 B2 | 7/2012 | Averett | |
| 8,853,375 B2 | 10/2014 | Kandimalla et al. | |
| 2005/0090660 A1 | 4/2005 | Watanabe et al. | |
| 2011/0269707 A1 | 11/2011 | Stuyver et al. | |
| 2012/0028999 A1 | 2/2012 | Averett | |
| 2016/0194350 A1 | 7/2016 | Chen et al. | |
| 2016/0331758 A1 | 11/2016 | Howbert et al. | |
| 2018/0000824 A1 | 1/2018 | Dai et al. | |
| 2018/0194782 A1 | 7/2018 | Finlay et al. | |
| 2018/0346572 A1 | 12/2018 | Li | |
| 2019/0359613 A1 | 11/2019 | Webber | |

FOREIGN PATENT DOCUMENTS

| | | |
|---|---|---|
| WO | 1994011003 A1 | 5/1994 |
| WO | 1998016184 A2 | 4/1998 |
| WO | 2010111290 A1 | 9/2010 |
| WO | 2013067597 A1 | 5/2013 |
| WO | 2017118407 A1 | 7/2017 |

OTHER PUBLICATIONS

Cadena-Amaro, et al., "Synthesis and incorporation into DNA fragments of the artificial n ucleobase, 2-amino-8-oxopurine," Bioorganic & Medicinal Chemistry Letters 15 (2005) 1069-1073.
Cecil Textbook of Medicine, edited by Bennett, J.C., and Plum F., 20th edition, vol. 1, 1004-1010, 1996.
Chen, et al., "Guanosine Derivatives as Immunostimulants. Discovery of Loxoribine," Nucleosides and Nucleotides, 13(1-3), 551-562 (1994) 13 pages.
Dermer et al., Bio/Technology, 1994, 12:320.
Freshney et al., Culture of Animal Cells, A Manual of Basic Technique, Alan R. Liss, Inc., 1983, New York, p. 4.
Golub et al., Science, 286, 531-537, 1999.
Ohto, et al., Structure and function of toll-like receptor 8, Institut Pasteur, Microbes and Infection 16 (2014) 273-282.
Reitz, et al., Small-Molecule Immunostimulants. Synthesis and Activity of 7,8-Disubstituted Guanosines and Structurally Related Compounds, J. Med Chem. 1994, 37, 3561-3578.
Yu, et al., "Dual character of Toll-liek receptor signaling: Pro-tumorigenic effects and anti-tumor functions," Biochimica et Biophysica Acta, 1835 (2013) 144-154.
Zhao, et al., "Toll-like receptors and prostrate cancer," Frontiers in Immunology, (2014) vol. 5, Article 352, (1 page).

*Primary Examiner* — Patrick T Lewis
(74) *Attorney, Agent, or Firm* — Mintz Levin Cohn Ferris Glovsky and Popeo, P.C.

(57) ABSTRACT

The present invention relates to TLR7 agonists according to Formula I and their use in the treatment of diseases such as cancer and infectious disease.

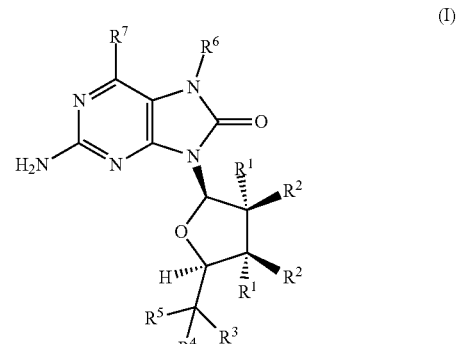

20 Claims, No Drawings

TLR7 AGONISTS

CROSS-REFERENCE TO RELATED APPLICATIONS

This application claims the priority of U.S. Provisional Application Ser. No. 62/940,622, filed Nov. 26, 2019, which is herein incorporated in its entirety.

FIELD OF THE INVENTION

The present invention provides TLR7 agonists and prodrugs and pharmaceutical compositions containing them and their use in therapeutic and prophylactic applications. The invention provides methods for treating and preventing infections, immune disorders, and cancer using TLR7 agonists.

BACKGROUND OF THE INVENTION

The ultimate goal of cancer immunotherapy is the eradication of tumor cells by the immune system. Both the innate and the adaptive arm of the immune system can contribute to eradication of tumor cells, with natural killer (NK) cells and T cells, respectively, as key players. Crucial in the adaptive immune response against tumor cells is the activation of CD8+ cytotoxic T lymphocytes (CTLs), able to exploit their cytotoxic potential against tumor cells after recognition of tumor-associated antigens (TAAs). Activation of naïve CD8+ cells occurs via antigen-presenting cells (APCs), with dendritic cells (DCs) considered as the most professional APCs. These cells capture and process TAAs, presenting the epitopes at their membrane in complex with major histocompatibility complex (MHC) molecules. Maturation of APCs by danger signals is essential for the presentation of epitopes in a stimulatory way to T cells.

Peripheral T-cell tolerance against TAAs prevents an effective immune response to tumors, despite the potential of TAA-specific T cells to eliminate tumor cells. The approaches to break this T-cell tolerance against TAAs can be divided into two groups: (a) active specific immunotherapy (also known as cancer vaccines) and (b) passive specific immunotherapy (by adoptive transfer of antitumor T cells or by monoclonal antibodies). Poor immunogenicity of tumor cells is also a potential problem in cancer immunotherapy. This low immunogenicity is a result of the fact that TAAs are mostly self-antigens, and also because of the downregulation of human leukocyte antigen and costimulatory molecules on the membranes of tumor cells. Moreover, tumor cells actively inhibit the immune system by the secretion of immunosuppressive factors that interfere with DC and T-cell function.

Toll-like receptors (TLRs) are a class of proteins that play a key role in the innate immune system. TLRs are a type of pattern recognition receptor (PRR) and recognize molecules that are broadly shared by pathogens but distinguishable from host molecules, collectively referred to as pathogen-associated molecular patterns (PAMPs). They are single, membrane-spanning, non-catalytic receptors usually expressed on sentinel cells such as macrophages and dendritic cells, that recognize structurally conserved molecules derived from microbes.

TLRs 3, 7, 8, and 9 form a group of intracellular TLRs and recognize bacterial or viral nucleic acids. The natural ligand for TLR7 and TLR8 is single-stranded RNA that is rich in guanosine and/or uridine. TLR7 and TLR8 are also activated by certain small synthetic compounds. The imidazoquinoline derivates imiquimod (R837) and resiquimod (R848) were described as TLR7 ligands in mice (Hemmi et al., 2002, Nat. Immunol. 3:196-200). Additionally, the guanosine analogue loxoribine was identified as a TLR7 ligand (Heil et al., 2003, Eur. J. Immunol. 33:2987-2997. Additional TLR7 and/or TLR8 ligands include CL097 (3M-001), 852A and CL075.

Despite the structural similarities between TLR7 and TLR8, their activation has distinct consequences on the innate immune cells and subsequent production of cytokines. TLR8 agonists are reportedly much more effective than TLR7 agonist at inducing pro-inflammatory cytokines and chemokines, such as tumor necrosis factor (TNF)-α, interleukin (IL)-12, and macrophage inflammatory protein (MIP)-1α, in peripheral blood mononuclear cells (PBMC). In contrast, TLR7 agonists reportedly activate plasmacytoid dendritic cells and induced the production of interferon (IFN)-α.

After the discovery of the effectiveness of the TLR7/8 agonist imiquimod to protect guinea pigs from herpes virus infection, imiquimod was also shown to be effective against several transplantable murine tumors. Clinical responsiveness to topical treatment with imiquimod (Aldara® 5% cream) was reportedly found to be effective for both primary skin tumors and cutaneous metastases. In these reports, no TAAs were added, and the immune-enhancing effects of imiquimod were sufficient to elicit an antitumor response. Imiquimod treatment was also reportedly associated with partial or total reversal of the aberrant expression of some genes in pre-malignant actinic keratoses, thereby demonstrating the ability of imiquimod to prevent the development of cancer.

Although treatment with TLR7 agonists in topical cancer show good anti-cancer effects, it has been challenging to administer these agonists by oral or systemic routes. In a clinical phase II study in hepatitis C virus infected patients, R848 was administered by the oral route and showed therapeutic effects on plasma hepatitis virus titers, but with dose-limiting toxicity. In another study, the TLR7 agonist 852A was tested in a phase II study in patients with metastatic melanoma with three weekly intravenous doses. The study showed prolonged disease stabilization in some patients, increased serum IFNα and IP-10, but dose-limiting toxicity in two patients. These studies indicate that systemic use of TLR7 agonists in patients may be a challenge due to a narrow therapeutic window.

SUMMARY OF THE INVENTION

The present invention generally relates to compounds useful as TLR7 agonists, compositions thereof, methods for their manufacture, and methods for their use.

In one embodiment the present invention is directed to TLR7 agonist compounds according to Formula I:

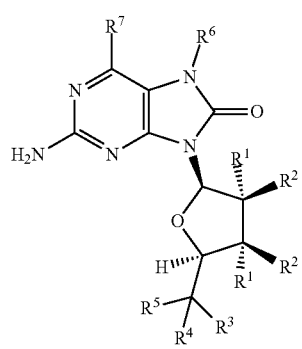

wherein
$R^1$ is independently —H, —OH, —O—C(O)—$R^8$ or —F,
$R^2$ is independently —H, —OH, —O—C(O)—$R^8$ or —F,
$R^3$ is —OH or —O—C(O)—$R^8$,
$R^4$ is —H, —OH, —O—C(O)—$R^8$ or —($C_1$-$C_8$)alkyl,
wherein $R^3$ and $R^4$ can be in the form of a carbonyl oxygen (=O),
$R^5$ is —H, —OH, —O—C(O)—$R^8$, —($C_1$-$C_8$)alkyl, —O—($C_1$-$C_8$)alkyl, —$NH_2$ or —$NHR^8$
wherein $R^4$ and $R^5$ can form a 3-6 membered cycloalkyl ring,
$R^6$ is —H, —($C_1$-$C_5$)alkyl, —C(H)=$CH_2$, —C(H)=CH($C_1$-$C_8$)alkyl), —C(H)=C($C_1$-$C_8$)alkyl)($C_1$-$C_8$)alkyl), —C(H)=C=$CH_2$, —C(H)=C=C($C_1$-$C_8$)alkyl)H, —$CH_2$C≡CH, —OH or —O($C_1$-$C_8$)alkyl,
$R^7$ is —H, —OH, —$OCH_3$, —SH or —Cl,
$R^8$ is independently —($C_1$-$C_8$)alkyl, aryl, —$(CH_2)_n$(aryl), heteroaryl or —$(CH_2)_n$(heteroaryl),
n is an integer 1, 2, 3, 4 or 5,
wherein at least one $R^4$ or $R^5$ is not —H,
wherein each alkyl, cycloalkyl, aryl and heteroaryl are independently optionally substituted by one or more of CN, $NO_2$, halogen, ($C_1$-$C_3$)alkyl, ($C_1$-$C_3$)haloalkyl, ($C_1$-$C_3$)cycloalkyl, aryl, heteroaryl, OH, alkenyl, alkynyl, O—($C_1$-$C_3$)alkyl, O—C(O)—$R^9$, O-(alkylene)aryl, O-(alkylene)heteroaryl, C(O)$R^9$, S($C_1$-$C_8$)alkyl, S(O)($C_1$-$C_8$)alkyl, $SO_2$($C_1$-$C_8$)alkyl, C(O)O$R^9$, C(O)N$R^9R^9$, C(O)N$R^9SO_2$($C_1$-$C_8$)alkyl, N$R^9R^9$, $N R^9$(CO)O$R^9$, NH(CO)$R^9$, NH($SO_2$)($C_1$-$C_8$)alkyl or NH($SO_2$)N$R^9R^9$, and $R^9$ is independently —H, —OH, —($C_1$-$C_8$)alkyl, cycloalkyl, heterocyclyl, or the two $R^9$'s of C(O)N$R^9R^9$ or N$R^9R^9$ combine together with the nitrogen atom to form a heterocycle;
or a stereoisomer, a tautomer or a pharmaceutically acceptable salt thereof.

In other embodiments, the TLR7 agonist compound(s) of the invention may be used alone, or in association with other, further therapeutic agents and therapeutic procedures, for treating or preventing cancer or an infection or infectious disease in a subject in need of such treatment or prevention.

In other embodiments, the present invention provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient. Pharmaceutical compositions comprising a pharmaceutically acceptable carrier, diluent, or excipient, in association with further therapeutic agents are also part of the present invention.

The above embodiments and other aspects of the invention are readily apparent in the detailed description that follows. To this end, various references are set forth herein which describe in more detail certain background information, procedures, compounds and/or compositions, and are each hereby incorporated by reference in their entireties.

DETAILED DESCRIPTION

The present invention provides compounds as TLR7 agonists. The present invention includes TLR7 agonists that activate TLR7 without substantial activation of TLR8.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the therapeutic agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

"Amino" refers to the —$NH_2$ substituent.
"Aminocarbonyl" refers to the —C(O)$NH_2$ substituent.
"Carboxyl" refers to the —$CO_2H$ substituent.
"Carbonyl" refers to a —C(O)— or —C(=O)— group. Both notations are used interchangeably within the specification.
"Cyano" refers to the —C≡N substituent.
"Acetyl" refers to the —C(O)$CH_3$ substituent.
"Hydroxy" or "hydroxyl" refers to the —OH substituent.
"Oxo" refers to a =O substituent.
"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like. Moieties with which the alkyl group can be substituted with are selected from but not necessarily limited to the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Lower alkyl" has the same meaning as alkyl defined above but having from one to three carbon atoms ($C_1$-$C_3$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group. The aryl group can be substituted with, but not necessarily limited to, one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated.

Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, 2 carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

The compounds of the invention may exhibit the phenomenon of tautomerism. While Formula I cannot expressly depict all possible tautomeric forms, it is to be understood that Formula I is intended to represent any tautomeric form of the depicted compound and not to be limited merely to a specific compound form depicted by the formula drawing. For example, when $R^7$ is OH it is understood for Formula I that regardless of whether or not the substituents are shown in their enol or keto form as shown below, they represent the same compound. It will be apparent to one skilled in the art, that compounds such as Compound 1:

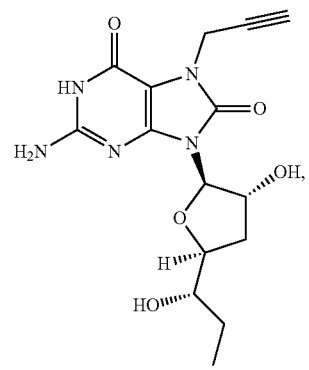

1 may exist in such tautomeric forms such as compounds 1A and 1B:

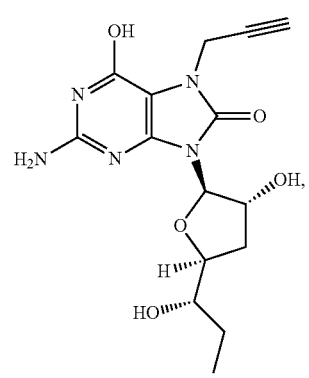

1A

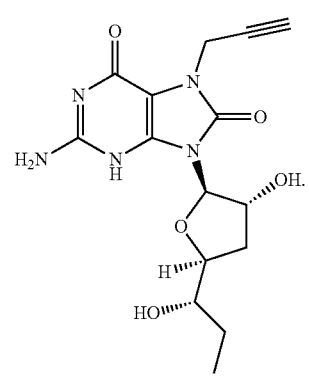

1B

It will also be apparent to one skilled in the art, that compounds with a trifluoromethylketone may also exist in its' corresponding hydrate form.

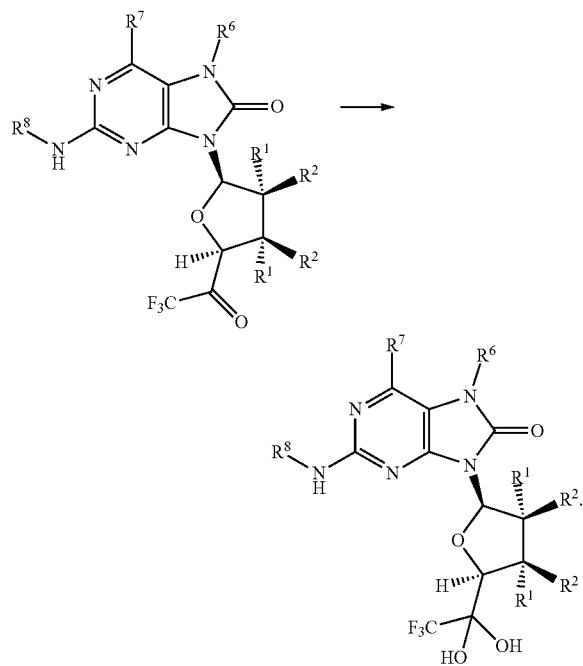

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

The term "in association with" indicates that the components administered in a method of the present invention can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

As used herein, the term "effective amount" refer to an amount of a TLR7 agonist compound of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of a compound or pharmaceutical composition thereof sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

A "subject" may be a mammal such as a human, dog, cat, horse, cow, mouse, rat, monkey (e.g., cynomolgous monkey, e.g., *Macaca fascicularis*) or rabbit. In preferred embodiments of the invention, the subject is a human subject.

TLR7 Agonists

In one embodiment of Formula I $R^1$ is —H or —OH.
In an embodiment $R^1$ is —H.
In an embodiment $R^2$ is —H or —OH.
In an embodiment $R^2$ is —H In an embodiment $R^2$ is —F.
In an embodiment $R^3$ is —OH or —O—C(O)—CH$_3$.
In an embodiment $R^3$ is —OH.
In an embodiment $R^4$ is —H or —(C$_1$-C$_8$)alkyl.
In an embodiment $R^4$ is —H or —CH$_2$CH$_3$.
In an embodiment $R^5$ is —H or —(C$_1$-C$_8$)alkyl.
In an embodiment $R^5$ is —H or —CH$_2$CH$_3$.
In an embodiment $R^6$ is —CH$_2$C≡CH. CH$_2$CH$_2$CH$_3$, or CH$_2$CH$_2$CH$_2$CH$_3$
In an embodiment $R^6$ is —CH$_2$C≡CH.
In an embodiment $R^7$ is —H or —OH.
In an embodiment $R^7$ is —OH.
In an embodiment $R^8$ is —(C$_1$-C$_8$)alkyl.
In an embodiment $R^8$ is —CH$_3$.

General Experimental Methods

Compounds of Formula I can be prepared via the general methods described below.

In one method (Scheme 1), a chlorine atom of the symmetrical 4,6-dichloropyrimidine-2,5-diamine [55583-59-0] can be displaced with a benzylic amine such as 4-methoxyl benzyl amine to form II. Exposing intermediate II to phosgene or a phosgene equivalent such as carbonyl diimidazole can form the corresponding cyclic urea III. The chlorine atom of III may be displaced with an appropriate alcohol, preferably benzylic to form the 2-amino-6, 9-dibenzylic-7,9-dihydro-8H-purin-8-one IV. The N-7-of purin-8-one IV can be alkylated under basic conditions with $R^6$-Lv to give N-7 alkyl compounds V. $R^6$ is a C$_1$-C$_8$ alkyl group and Lv is defined as a leaving group such as a halogen atom, OSO$_2$CH$_3$ (mesylate), OSO$_2$CF$_3$ (triflate), or OSO$_2$Ar where Ar is 4-methylphenyl (tosylate). After N-7 alkylation, O-6 and N-9 of V and may by deprotected under the appropriate conditions. For instance, under acidic conditions such as trifluoroacetic combined with trifluoromethane sulfonic acid, O-6 and N-9 of V are simultaneously removed to give 2-amino-7-alkyl-7,9-dihydro-1H-purine-6,8-dione VI. The primary 2-amino group may then be protected to form VII where P is a protecting group such as acyl or carbamyl. The synthesis of several furanose sugar intermediates VIII are known in the art and can be derived via multiple steps from their corresponding carboxaldehydes VIIIa or epoxides VIIIb. In general, purine intermediates VI and VII can then be exposed to a sugar derivative VIII under a variety of nucleoside forming reaction conditions, followed by hydroxyl and amine deprotection if required to give 9-β-furano-purine nucleoside analogs of Formula I. For a comprehensive review of the synthetic conditions to form nucleosides see Romeo, et al., *Chem. Rev.* 2010, 110, p. 3337-3370.

Scheme 1

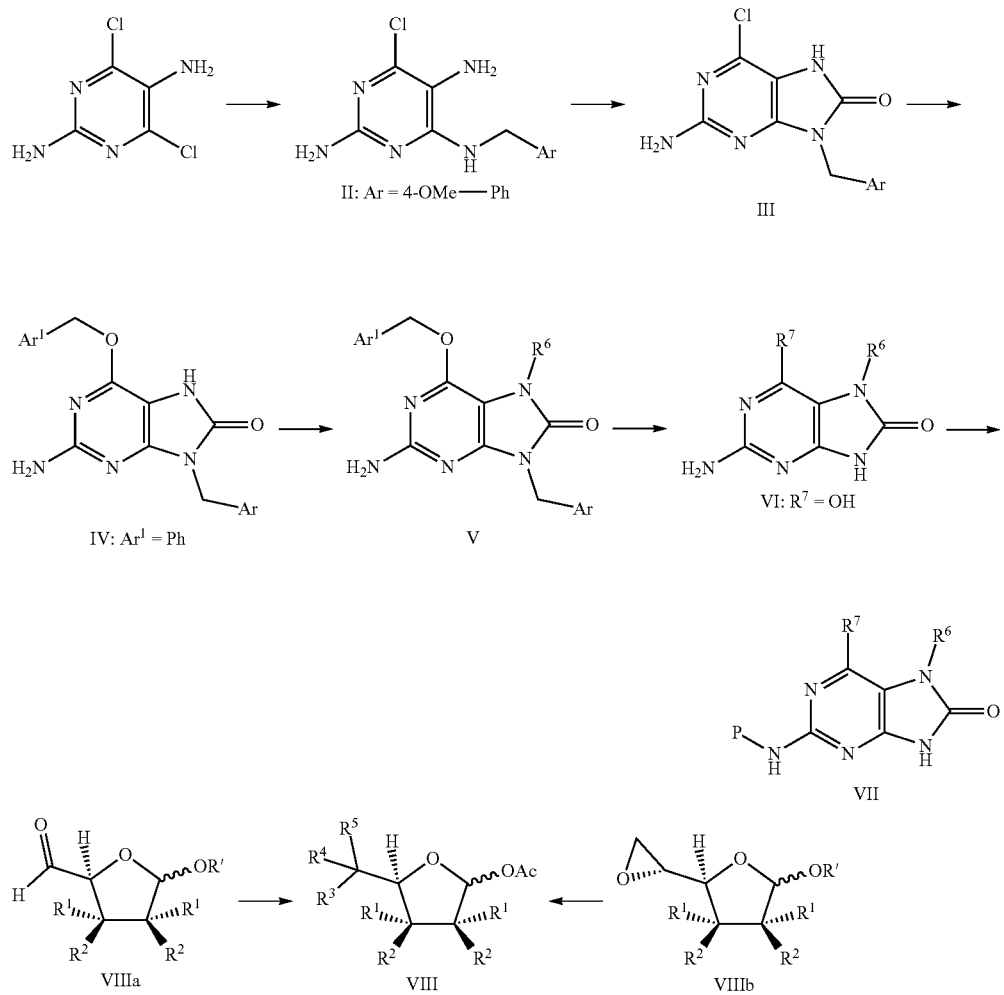

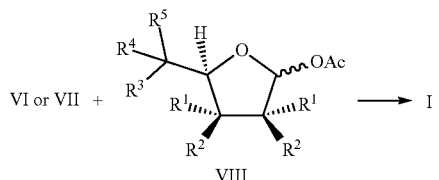

In another method (Scheme 2) the preparation begins with intermediate III (described above) where the 6-chlorine purine may be hydro-dehalogenated with hydrogen and catalytic Pd or Pt metal or with activated Zn under acidic conditions to form IX. N-7 alkylation of intermediate IX can be accomplished under basic conditions with $R^6$-Lv to give intermediate X. $R^6$ and Lv are defined above in the general method used in Scheme 1. After N-7 alkylation, N-9 of X and may by deprotected under the appropriate conditions. For instance, under acidic conditions such as trifluoroacetic combined with trifluoromethane sulfonic acid, the N-9 4-methoxybenzyl group of X is removed to give 2-amino-7-alkyl-7,9-dihydro-8H-purin-8-one XI. The primary 2-amino group of XI may then be protected to form XII where P is a protecting group such as acyl or carbamyl. In general, purine intermediates XI and XII can then be exposed to a sugar derivative VIII under a variety nucleoside forming reaction conditions, followed by hydroxyl and amine deprotection if required to give 9-β-furano-purine nucleoside analogs of Formula I.

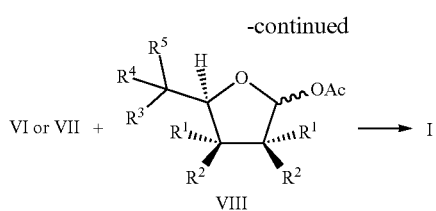

Alternatively, as shown in Scheme 3, 2-amino-9-benzylic-7,9-dihydro-8H-purin-8-ones IX can be prepared first by the hydro-dehalogenation of chloro-pyrimidine II with hydrogen and catalytic Pd or Pt metal or with activated Zn under acidic conditions to form $N^4$-benzylic-2,4,5-triamino-pyrimidines XIII. The imidazolone ring can then be formed by exposure of XIII to phosgene or a phosgene equivalent such as carbonyl diimidazole to give intermediate IX.

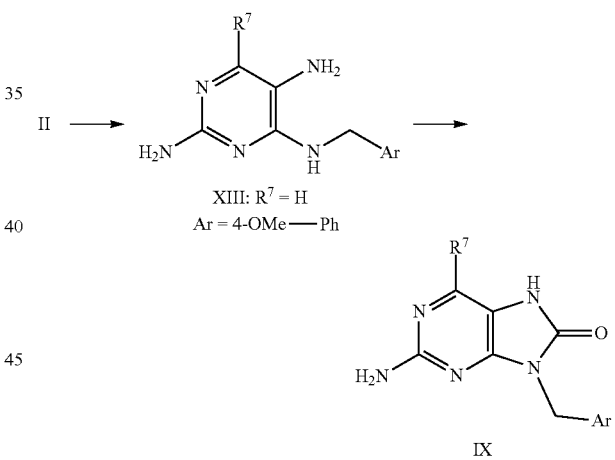

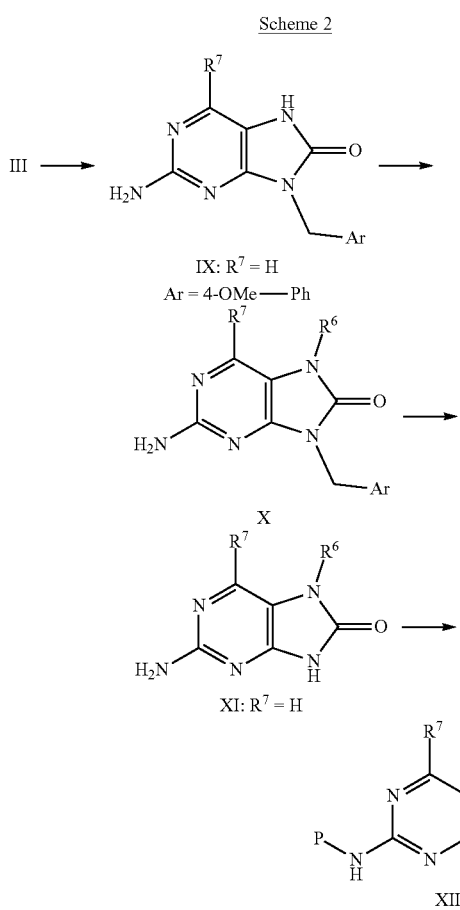

Using an alternative method (Scheme 4) the synthetic preparation of compounds of Formula I may originate from a guanosine nucleoside analog XIV where $R^1$ and $R^2$ can be H, OH, F, $R^3$ is OH, and $R^4$ and $R^5$ can be H or alkyl. The syntheses of modified sugar guanosine analogs can be accomplished using procedures described by Zou, et al, *Can. J. Chem.*, 1987, p. 1436 and Robins et al, *JOC*, 1996, p. 9207. The C-8 of the guanine base can be brominated under conditions described by Holmes, et al., *JACS*, 1964, p. 1242 and Sheu et al., *JACS*, 1995, p. 6439 to give an 8-bromo-guanosine derivative XV. Oxygen can be introduced at C-8 by the $S_NAr$ displacement of the bromine of XV with an alkoxide of benzyl alcohol described by Holmes, et al., *JACS*, 1965, p. 1772 and Sheu et al., *JACS*, 1995, p. 6439 to give an 8-benzyloxo-guanosine derivative XVI. Before debenzylation of the oxygen at C-8 it is necessary to protect the nitrogen at the N-1 position in order to achieve selective alkylation of N-7. Broom et al., *JOC*, 1969, p. 1025 describes the amination of the N-1 of guanosine that in essence acts as a protecting group. Thus, intermediate XVI can be exposed to hydroxylamine-O-sulfonic acid under basic conditions to give an N-1 amino-guanosine derivative XVII. The benzyl group can then be removed from the C-8 oxygen under a number of de-etherification reaction conditions, preferably via catalytic hydrogenation with palladium metal to give cyclic urea intermediate XVIII. N-7 alkylation of intermediate VI can be accomplished under basic conditions with $R^4$-Lv to give an N-7 alkyl intermediate XVIII. $R^6$ is a $C_1$-$C_8$ alkyl group and Lv is defined as a leaving group such as a halogen atom, $OSO_2CH_3$ (mesylate), $OSO_2CF_3$ (triflate), or $OSO_2Ar$ where Ar is 4-methylphenyl (tosylate). The final step in the synthesis is an N-1 deamination of XVIII achieved by forming a diazonium salt with sodium nitrite under aqueous acidic conditions as described in U.S. Pat. No. 5,093,318 to give the desired compounds of Formula I, where $R^7$ is OH.

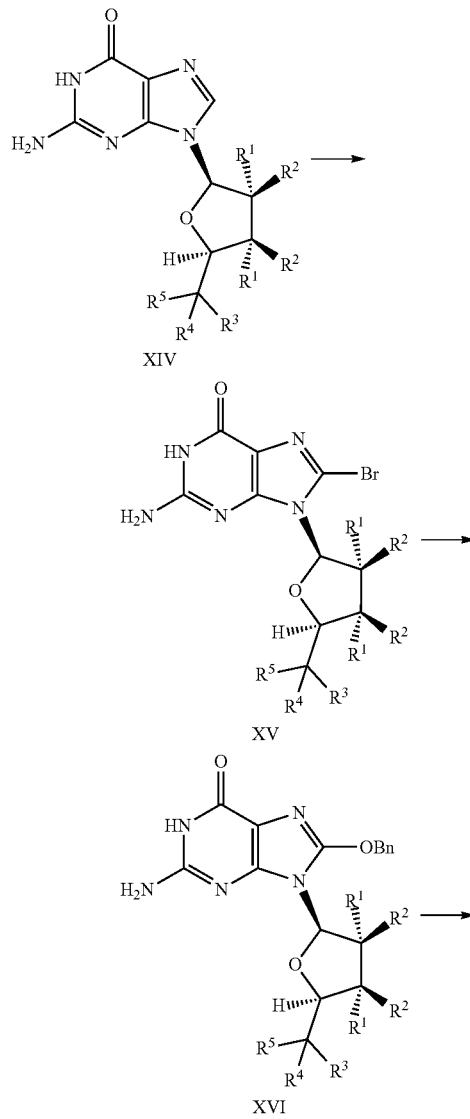

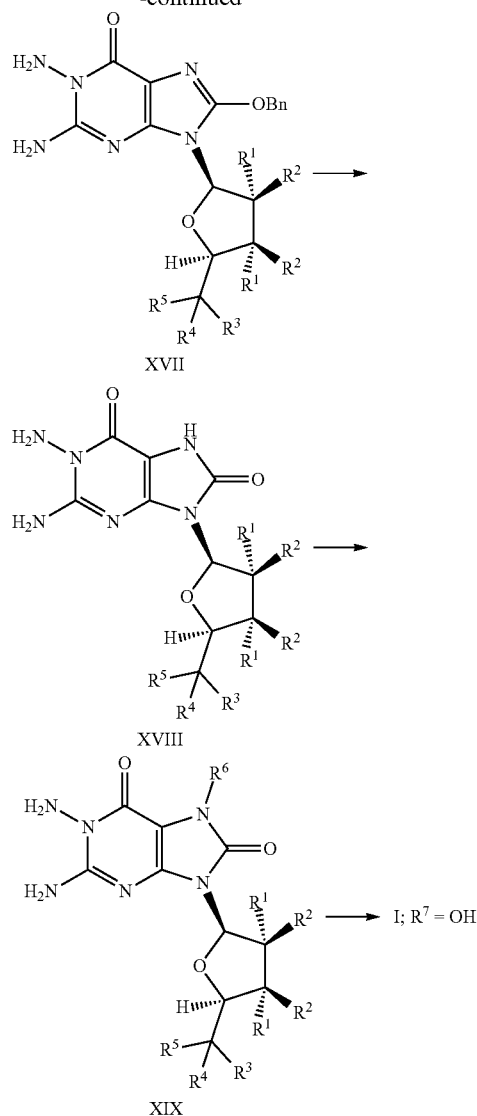

In another method (Scheme 5) using modified guanosines the amide oxygen of intermediate XVI (described above) can be converted to the 6-chlorine purine intermediate XX typically with phosphorus oxychloride. The benzyl ether at C-8 can then selectively be removed by catalytic hydrogenation or with a boron tri-halide such as $BCl_3$ to give intermediate XXI. N-7 alkylation of intermediate XXI can be accomplished under basic conditions with $R^6$-Lv to give an N-7 alkyl compounds of Formula I. $R^6$ and Lv are defined above.

Compounds of Formula I where $R^7$ is a chlorine may be further transformed into other compounds of Formula I where $R^7$ is H, OH or $OCH_3$. To obtain compounds of Formula I where $R^7$ is H, a hydro-dehalogenation reaction may be utilized. This transformation can usually be conducted under hydrogenation conditions with Pd of Pt or with activated zinc in acetic acid. Displacement of the C-6 chlorine to a hydroxyl group can be accomplished under aqueous basic or acidic conditions. This chlorine can also be displaced with methoxide anion to produce compounds of Formula I where $R^7$ is $OCH_3$.

Scheme 5

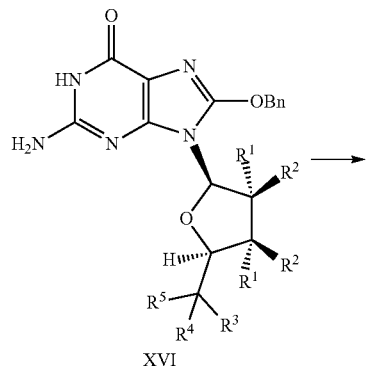

XVI

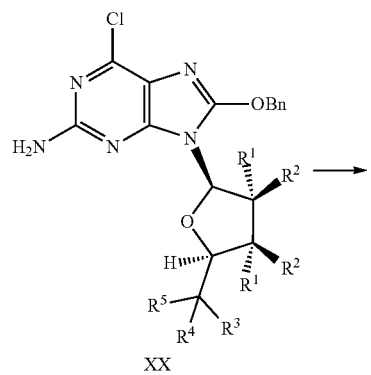

XX

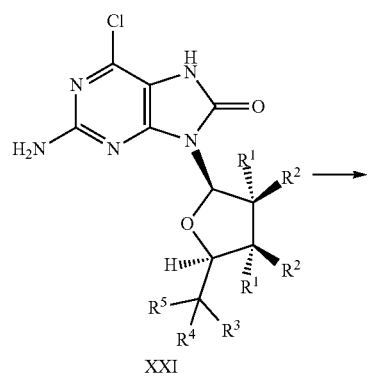

XXI

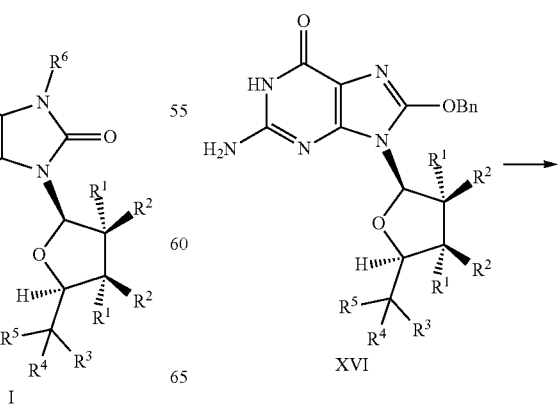

I

I

I; where R$^7$ = H, OH or OCH$_3$

In one other method (Scheme 6) intermediate XVI (described above) is utilized where the amide oxygen can be converted to the 6-thio purine intermediate XXII typically with phosphorus pentasulfide, Lawesson's reagent or equivalent. The thio group can be reduced with Raney nickel to afford intermediate XXIII. The benzyl ether at C-8 can then selectively be removed by catalytic hydrogenation or with a boron tri-halide such as BCl$_3$ to give compounds of Formula I. N-7 alkylation under basic conditions with R$^6$-Lv gives compounds of Formula I. R$^6$ and Lv are defined above.

Scheme 6

XVI

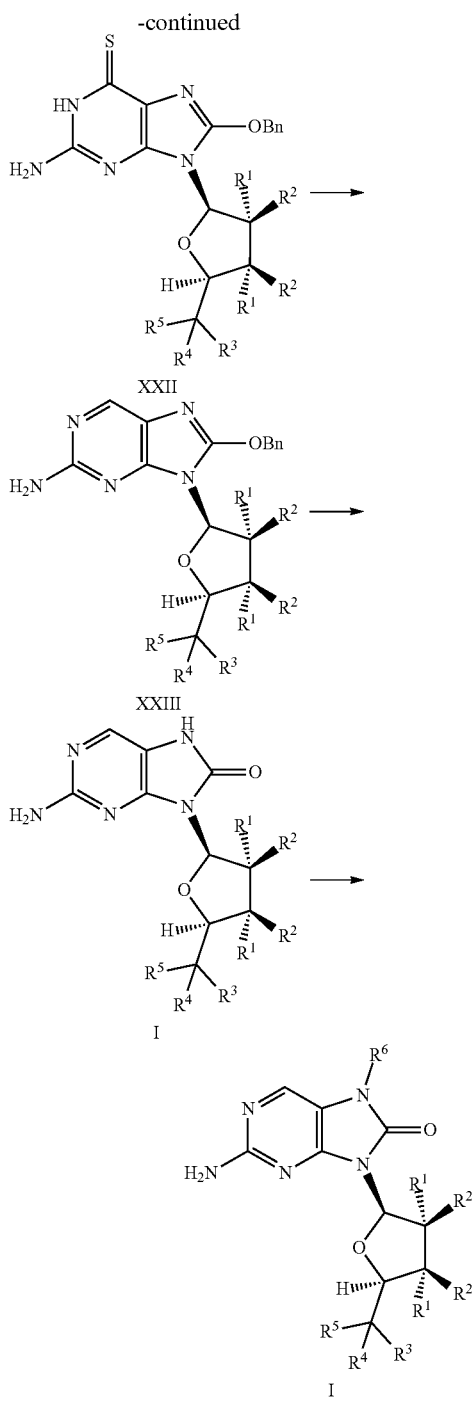

Therapeutic Uses of TLR7 Agonists

TLR7 activation of innate immunity is principally mediated through plasmacytoid dendritic cells (pDCs). These cells are the primary physiological producers of type I interferons—up to 1,000 times that of any other cell type. Activation of TLR7 is therefore an important "gatekeeper" to overall induction of the innate immune response. TLR7 has significant advantages as a therapeutic target when compared to other TLRs. For example, it can be activated by small molecules which enables oral administration. Unlike several other TLRs, systemic activation of TLR7 avoids stimulation of excessive TNF production.

Administration of a TLR7 agonist directly and indirectly engages a variety of anti-tumor mechanisms including: production of cytokines and chemokines that have direct anti-tumor activity; activation of natural killer (NK) cells, the primary effector cell of the innate immune system for control of cancer, which are then capable of lysing tumor cells by both antibody-dependent (antibody-dependent cellular cytotoxicity, or ADCC) and independent mechanisms; activation of T-cells and reversal of T-cell exhaustion through antigen presentation by direct cell-cell interactions with, and production of cytokines and chemokines from pDCs, all leading to increased T-cell mediated attack on tumor cells; increased proliferation and maturation of normal B-cells and their precursors, which can enhance endogenous production of antibodies with antitumor activities; and direct activity against aberrant B-cells through the activation of TLR7 on these cells which can induce apoptosis and hypersensitization to chemotherapy.

In one embodiment, the TLR7 agonist compound(s) of the invention may be used alone, or in association with other, further therapeutic agents and therapeutic procedures, for treating or preventing cancer or an infection or infectious disease in a subject in need of such treatment or prevention.

In an embodiment, the TLR7 agonist compound(s) of the invention may be used alone, or in association with tumor vaccines.

In an embodiment, the TLR7 agonist compound(s) of the invention may be used alone, or in association with chemotherapeutic agents.

In an embodiment, the TLR7 agonist compound(s) of the invention may be used alone, or in association with radiation therapy.

In an embodiment, the TLR7 agonist compound(s) of the invention may be used alone, or in association with targeted therapies. Examples of targeted therapies include: hormone therapies, signal transduction inhibitors (e.g., EGFR inhibitors, such as cetuximab (Erbitux) and erlotinib (Tarceva)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators, apoptosis inducers (e.g., bortezomib (Velcade) and carfilzomib (Kyprolis)), angiogenesis inhibitors (e.g., bevacizumab (Avastin) and ramucirumab (Cyramza), monoclonal antibodies attached to toxins (e.g., brentuximab vedotin (Adcetris) and ado-trastuzumab emtansine (Kadcyla)).

In an embodiment, the TLR7 agonist compound(s) of the invention may be used in combination with an anti-cancer therapeutic agent or immunomodulatory drug such as an immunomodulatory receptor inhibitor or an antibody or antigen-binding fragment thereof that specifically binds to the receptor.

In an embodiment, the TLR7 agonist compound(s) of the invention may be used in combination with an immune checkpoint inhibitor, an OX40 agonist, a 4-1BB agonist, an ICOS agonist, a GITR agonist or an IL2-receptor agonist.

In an embodiment, the TLR7 agonist compound(s) of the invention may be used in combination with an inhibitor or antagonist of PD-1, PD-L1, CTLA4, TIM3, LAG3, SIRPα, CD47, VISTA, BTLA or TIGIT.

In an embodiment, the TLR7 agonist compound(s) of the invention may be used in combination with a therapeutic antibody with anti-tumor activity mediated at least in part through ADCC.

In an embodiment, the TLR7 agonist compound(s) of the invention may be used in combination with a therapeutic antibody with anti-tumor activity mediated at least in part through ADCC, including rituximab, trastuzumab and alemtuzumab.

In an embodiment of the invention, a TLR7 agonist compound of the invention is in association with an anti-OX40 antibody, including MOXR0916 and GSK3174998, or other pathway agonist.

In an embodiment of the invention, a TLR7 agonist compound of the invention is in association with an anti-4-1BB antibody, including urelumab, utomilumab, or other pathway agonist.

In an embodiment of the invention, a TLR7 agonist compound of the invention is in association with an anti-ICOS antibody or other pathway agonist.

In an embodiment of the invention, a TLR7 agonist compound of the invention is in association with an anti-GITR antibody or other pathway agonist.

In an embodiment of the invention, a TLR7 agonist compound of the invention is in association with an IL-2-receptor or other pathway agonist.

In an embodiment of the invention, a TLR7 agonist compound of the invention is in association with an anti-PD1 or anti-PDL1 antibody, including nivlumab (Opdivo), pembrolizumab (Keytruda), atezoluzimab (Tecentriq), durvalumab (Imfinzi) or avelumab (Bavencio)).

In an embodiment of the invention, a TLR7 agonist compound of the invention is in association with a CTLA-4/CD80-CD86 antagonist, including ipilimumab (Yervoy).

In an embodiment of the invention, a TLR7 agonist compound of the invention is in association with a Tim-3 pathway antagonist, including MBG453 and TSR-022.

In an embodiment of the invention, a TLR7 agonist compound of the invention is in association with a LAG-3 pathway antagonist, including BMS-986016, GSK2831781 and IMP321.

In an embodiment of the invention, a TLR7 agonist compound of the invention is in association with an anti-SIRPα antibody.

In an embodiment of the invention, a TLR7 agonist compound of the invention is in association with an anti-CD47 antibody.

In an embodiment of the invention, a TLR7 agonist compound of the invention is in association with a Vista pathway antagonist.

In an embodiment of the invention, a TLR7 agonist compound of the invention is in association with a BTLA pathway antagonist.

In an embodiment of the invention, a TLR7 agonist compound of the invention is in association with a TIGIT pathway antagonist.

In another embodiment, the TLR7 agonist compound(s) of the invention increase the activity of an immune cell. The increase of the activity of an immune cell can be detected using any method known in the art. In one embodiment, the increase in activity of an immune cell can be detected by measuring the proliferation of the immune cell. For example, an increase in activity of a T cell can be detected by measuring the proliferation of the T cell or signal transduction events such as tyrosine phosphorylation of immune receptors or downstream kinases that transmit signals to transcriptional regulators. In other embodiments, the increase in activity of an immune cell can be detected by measuring CTL or NK cell cytotoxic function on specific target cells or IFNγ cytokine responses, which are associated with stimulation of anti-tumor immunity. In yet other embodiments, the increase in activity of an immune cell can be detected by measuring T cell activation ex vivo in a sample derived from the subject.

Additional agents which are beneficial to raising a cytolytic T cell response may be used in combination with the TLR7 agonist compound of the present invention. These include, without limitation, B7 costimulatory molecule, interleukin-2 (e.g., NKTR-214), interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions.

In an embodiment of the invention, a TLR7 agonist compound of the invention is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, NC), granisetron (sold as Kytril® by Hoffmann-La Roche Inc.; Nutley, N.J.), ondansetron (sold as Zofran® by Glaxosmithkline; Research Triangle Park, NC), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, a TLR7 agonist compound is in association with an agent which treats or prevents such a deficiency, including filgrastim, PEG-filgrastim, erythropoietin, epoetin alfa and darbepoetin alfa.

In another embodiment, the present invention relates to compositions comprising one or more TLR7 agonist compounds of the present invention and a pharmaceutically acceptable carrier or diluent. Such compositions can further comprise one or more other therapeutically active ingredients such as an agonistic antibody or antigen-binding fragment thereof, or a soluble fusion, of a TNF receptor protein, an immunoglobulin-like protein, a cytokine receptor, an integrin, a signaling lymphocytic activation molecules (SLAM proteins), OX40, 4-1BB (CD137), ICOS (CD278), GITR, IL2R beta (CD122) and/or IL2R gamma.

The present invention includes compositions comprising a TLR7 agonist compound of the present invention in association with one or more antibodies that target the PD-1/PD-L1 interaction or CTLA-4/CD80-CD86 interaction. Non-limiting examples of such antibodies include pembrolizumab, nivolumab, avelumab, REGN2810, MEDI-0680, PDR-001, SHR-1210, BGB-A317, PF-06801591, TSR-042, atezoluzimab, durvalumab, BMS-936559, ipilimumab and tremelimumab.

Compositions for inducing a T cell immune response which preferentially stimulate a cytolytic T cell response versus an antibody response are preferred, although those that stimulate both types of response can be used as well.

In another embodiment compositions comprising one or more TLR7 agonist compounds can further comprise one or more other therapeutically active ingredients that are an immune checkpoint inhibitor, an OX40 agonist, a 4-1BB agonist, an ICOS agonist, a GITR agonist or an IL2-receptor agonist.

In another embodiment compositions comprising one or more TLR7 agonist compounds can further comprise one or more other therapeutically active ingredients that are an inhibitor or antagonist of PD-1, PD-L1, CTLA4, TIM3, LAG3, SIRPα, CD47, VISTA, BTLA or TIGIT.

In another embodiment compositions comprising one or more TLR7 agonist compounds can further comprise one or more other therapeutically active ingredients that are a therapeutic antibody with anti-tumor activity mediated at least in part through ADCC.

In another embodiment compositions comprising one or more TLR7 agonist compounds can further comprise one or more other therapeutically active ingredients that are a therapeutic antibody with anti-tumor activity mediated at least in part through ADCC, including rituximab, trastuzumab and alemtuzumab.

Further provided in the invention are methods for treating or preventing cancer or an infection or infectious disease in a subject in need of such treatment or prevention, in subjects, including human subjects, with the TLR7 agonist compound(s) disclosed herein. In one embodiment of the invention, such subject suffers from cancer or a precancerous condition. In another embodiment of the invention, such subject suffers from an infection or an infectious disease.

In another embodiment the present invention also relates to methods of treating or preventing cancer in a human subject, comprising administering to the subject an effective amount of one or more TLR7 agonist compounds of the present invention, optionally in association with a further therapeutic agent or therapeutic procedure; and to methods of treating an infection or infectious disease in a human subject, comprising administering to the subject an effective amount of one or more TLR7 agonist compounds of the present invention, optionally in association with a further therapeutic agent or therapeutic procedure.

In yet another embodiment the present invention relates to a method of increasing the activity of an immune cell, comprising administering to a subject in need thereof an effective amount of one or more TLR7 agonist compounds of the present invention for treating or preventing cancer; treating an infection or infectious disease; acting as a vaccine adjuvant; or increasing immune cell activation.

In an embodiment, the invention provides methods for treating subjects using a TLR7 agonist compound of the invention, wherein the subject suffers from cancer or a precancerous condition. In an embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

In an embodiment, the invention provides methods for treating or preventing viral infections in a subject using a TLR7 agonist of Formula I. In one embodiment, the viral infection is infection with a virus selected from the group consisting of human immunodeficiency virus (HIV), hepatitis virus (A, B, C, or D), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus (e.g., SARS-CoV, MERS, and SARS-CoV-2), respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus.

The present invention includes methods for treating and preventing viral infections in a subject comprising administering an effective amount of the TLR7 agonist compound of Formula I and one or more additional treatment modalities (e.g. small-molecule therapeutic agents, protein or peptide therapeutics, antibodies, sera from persons that have recovered from viral infections, and therapeutic or preventative vaccines).

In an embodiment, the invention provides methods for treating subjects using a TLR7 agonist compound of the invention, wherein the subject suffers from a bacterial infection. In one embodiment, the bacterial infection is infection with a bacterium selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using a TLR7 agonist compound of the invention, wherein the subject suffers from a fungal infection. In one embodiment, the fungal infection is infection with a fungus selected from the group consisting of *Candida* (*albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

In an embodiment, the invention provides methods for treating subjects using a TLR7 agonist compound of the invention, wherein the subject suffers from a parasitic infection. In one embodiment, the parasitic infection is infection with a parasite selected from the group consisting of *Entamoeba histolytica, Balantidium coi, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

The present invention includes methods for treating or preventing cancer in a subject comprising administering an effective amount of the TLR7 agonist compound of the present invention and one or more antibodies that target the PD-1/PD-L1 or CTLA-4/CD80-CD86 interaction to the subject. In an embodiment of the invention, a TLR7 agonist compound of the invention is in association with an anti-PD1 or anti-PDL1 antibody.

The present invention includes methods for treating or preventing cancer in a subject comprising administering an effective amount of the TLR7 agonist compound of the present invention in combination with an immune checkpoint inhibitor, an OX40 agonist, a 4-1BB agonist, an ICOS agonist, a GITR agonist or an IL2-receptor agonist.

The present invention includes methods for treating or preventing cancer in a subject comprising administering an effective amount of the TLR7 agonist compound of the present invention in combination with an inhibitor or antagonist of PD-1, PD-L1, CTLA4, TIM3, LAG3, SIRPα, CD47, VISTA, BTLA or TIGIT.

The present invention includes methods for treating or preventing cancer in a subject comprising administering an effective amount of the TLR7 agonist compound of the present invention in combination with a therapeutic antibody with anti-tumor activity mediated at least in part through ADCC.

The present invention includes methods for treating or preventing cancer in a subject comprising administering an effective amount of the TLR7 agonist compound of the present invention in combination with a therapeutic antibody with anti-tumor activity mediated at least in part through ADCC, including rituximab, trastuzumab and alemtuzumab.

The present invention includes methods for treating or preventing cancer in a subject comprising administering an effective amount of the TLR7 agonist compound of the present invention in association with an anti-OX40 antibody, including MOXR0916 and GSK3174998, or other pathway agonist.

The present invention includes methods for treating or preventing cancer in a subject comprising administering an effective amount of the TLR7 agonist compound of the present invention in association with an anti-4-1BB antibody, including urelumab, utomilumab, or other pathway agonist.

The present invention includes methods for treating or preventing cancer in a subject comprising administering an effective amount of the TLR7 agonist compound of the present invention in association with an anti-ICOS antibody or other pathway agonist.

The present invention includes methods for treating or preventing cancer in a subject comprising administering an effective amount of the TLR7 agonist compound of the present invention in association with an anti-GITR antibody or other pathway agonist.

The present invention includes methods for treating or preventing cancer in a subject comprising administering an effective amount of the TLR7 agonist compound of the present invention in association with an IL-2-receptor or other pathway agonist.

The present invention includes methods for treating or preventing cancer in a subject comprising administering an effective amount of the TLR7 agonist compound of the present invention in association with an anti-PD1 or anti-PDL1 antibody, including nivlumab (Opdivo), pembrolizumab (Keytruda), atezoluzimab (Tecentriq), durvalumab (Imfinzi) or avelumab (Bavencio)).

The present invention includes methods for treating or preventing cancer in a subject comprising administering an effective amount of the TLR7 agonist compound of the present invention in association with a CTLA-4/CD80-CD86 antagonist, including ipilimumab (Yervoy).

The present invention includes methods for treating or preventing cancer in a subject comprising administering an effective amount of the TLR7 agonist compound of the present invention in association with a Tim-3 pathway antagonist, including MBG453 and TSR-022.

The present invention includes methods for treating or preventing cancer in a subject comprising administering an effective amount of the TLR7 agonist compound of the present invention in association with a LAG-3 pathway antagonist, including BMS-986016, GSK2831781 and IMP321.

The present invention includes methods for treating or preventing cancer in a subject comprising administering an effective amount of the TLR7 agonist compound of the present invention in association with an anti-SIRPα antibody.

The present invention includes methods for treating or preventing cancer in a subject comprising administering an effective amount of the TLR7 agonist compound of the present invention in association with an anti-CD47 antibody.

The present invention includes methods for treating or preventing cancer in a subject comprising administering an effective amount of the TLR7 agonist compound of the present invention in association with a Vista pathway antagonist.

The present invention includes methods for treating or preventing cancer in a subject comprising administering an effective amount of the TLR7 agonist compound of the present invention in association with a BTLA pathway antagonist.

The present invention includes methods for treating or preventing cancer in a subject comprising administering an effective amount of the TLR7 agonist compound of the present invention in association with a TIGIT pathway antagonist.

Pharmaceutical Compositions and Administration

The present invention also provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient. Pharmaceutical compositions comprising a pharmaceutically acceptable carrier, diluent, or excipient, in association with further therapeutic agents are also part of the present invention.

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in *Remington, The Science and Practice of Pharmacy 21$^{st}$ Edition* (Mack Publishing Co., Easton, Pa.) and Nielloud and Marti-Mestres, Pharmaceutical Emulsions and Suspensions: 2$^{nd}$ Edition (Marcel Dekker, Inc, New York). To prepare pharmaceutical or sterile compositions of the TLR7 agonist compound(s) of the invention, the compound(s) is(are) admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis* of *Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the compounds or compositions of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with a TLR7 agonist compound of the invention in accordance with the Physicians' Desk Reference 2003 (Thomson Healthcare; 57th edition (Nov. 1, 2002)).

The mode of administration can vary. For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Intra-tumoral (directly into the tumor mass) or peri-tumoral (around the tumor mass) administration of the compound(s) of the present invention are also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

The present invention provides a vessel (e.g., a plastic or glass vial, e.g., with a cap or a chromatography column, hollow bore needle or a syringe cylinder) comprising one or more compounds of the invention or a pharmaceutical composition thereof. The present invention also provides an injection device comprising one or more compounds of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., one or more compounds of the invention or a pharmaceutical composition thereof), a needle for piecing skin and/or blood vessels for injection of the fluid; and a plunger for pushing the fluid out of the cylinder and through the needle bore. In an embodiment of the invention, an injection device that comprises one or more compounds of the invention or a pharmaceutical composition thereof is an intravenous (IV) injection device. Such a device includes one or more compounds of the invention or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. The one or more compounds of the invention or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the one or more compounds of the invention or a pharmaceutical composition thereof to a patient's body. External infusion pumps are medical devices that deliver a pharmaceutical composition into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The compounds and pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the TLR7 agonist compound of the invention in a local rather than systemic manner, for example, via injection of the compound into a tumor. Furthermore, one may administer the TLR7 agonist compound of the invention in a targeted drug delivery system, for example, in a liposome coated with a tissue-specific antibody, targeting, for example, a tumor characterized by immunopathology. The liposomes will be targeted to and taken up selectively by the corresponding tissue. Such methods and liposomes are part of the present invention.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e., the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compound(s) of the invention are preferably pharmaceutically acceptable. Suitable pharmaceutically acceptable salts include those described by P. Heinrich Stahl and Camille G. Wermuth in *Handbook of Pharmaceutical Salts: Properties, Selection, and Use,* $2^{nd}$ ed. (Wiley-VCH: 2011) and also *Remington's Pharmaceutical Sciences,* $18^{th}$ ed. (Mack Publishing, Easton Pa.: 1990) and also *Remington: The Science and Practice of Pharmacy,* $19^{th}$ ed. (Mack Publishing, Easton Pa.: 1995).

Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, trifluoroacetate, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

Salts of a compound of the present invention may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like.

A pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

If a compound containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of a compound or a pharmaceutically acceptable salt, pharmaceutically acceptable solvate or pharmaceutically acceptable hydrate thereof, as described herein, for a particular patient may vary depending on factors such as the condition being treated, the overall health of the patient, the route and dose of administration and the severity of side effects.

"A pharmaceutically acceptable prodrug" is a compound that may be converted under physiological conditions or by solvolysis to the specified compound or to a pharmaceutically acceptable salt of such compound prior to exhibiting its pharmacological effect(s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry.* 1, 172-178, 949-982 (1995.) See also Bertolini et al., *J. Med. Chem.,* 40, 2011-2016 (1997); Shan, et al., *J. Pharm. Sci.,* 86 (7), 765-767; Bagshawe, *Drug Dev. Res,* 34, 220-230 (1995); Bodor, *Advances in Drug Res,* 13, 224-331 (1984); Bundgaard, *Design of Prodrugs* (Elsevier Press 1985); Larsen, *Design and Application of Prodrugs,* Drug Design and Development (Krogsgaard-Larsen et al, eds, Harwood Academic Publishers, 1991): Dear et al., *J. Chromatogr. B,* 748, 281-293 (2000); Spraul et al., *J. Pharmaceutical & Biomedical Analysis,* 10, 601-605 (1992); and Prox et al., *Xenobiol.,* 3, 103-112 (1992).

Methods for co-administration with an additional therapeutic agent are well known in the art (Hardman, et al. (eds.) (2001) Goodman and Gilman's *The Pharmacological Basis of Therapeutics,* 10th ed., McGraw-Hill, New York, N.Y.; Poole and Peterson (eds.) (2001) *Pharmacotherapeutics for Advanced Practice: A Practical Approach,* Lippincott, Williams & Wilkins, Phila., Pa.; Chabner and Longo (eds.) (2001) *Cancer Chemotherapy and Biotherapy,* Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g., same formulation) such that they are administered at the same time by the same route of administration.

Generally, each administration of a compound of the invention comprises between about 10 mg to about 2000 mg in an individual, e.g., from about 10 mg to about 50 mg, from about 50 mg to about 100 mg, from about 100 mg to about 250 mg, from about 250 mg to about 500 mg, from about 500 mg to about 1000 mg, from about 1000 mg to about 2000 mg.

General Methods

All synthetic chemistry was performed in standard laboratory glassware unless indicated otherwise in the examples. Commercial reagents were used as received. Microwave reactions were performed in a Biotage Initiator using the instrument software to control heating time and pressure. Analytical LC/MS was performed on an Agilent 1290 infinity, Mass: 6150 SQD(ESI/APCI) or an Agilent 1200 SERIES, Mass: 6130SQD(ESI/APCI); variable wavelength detector and Agilent 6130 single quadrupole mass spectrometer, alternating positive and negative ion scans using Chemistation software. Retention times were determined from the extracted 220 nm UV chromatogram. HPLC was performed on a Waters 2695 system with a variable wavelength detector using Empower software. Retention times were determined from the extracted 210 nm and 300 nm UV chromatograms. $^1$H NMR was performed on a Bruker Avance 400 at 400 MHz or a Bruker Avance DRX-500 at 500 MHz using Topspin software. For complicated splitting patterns, the apparent splitting was tabulated. Analytical thin layer chromatography was performed on silica (Macherey-Nagel ALUGRAM Xtra SIL G, 0.2 mm, $UV_{254}$ indicator) and was visualized under UV light. Silica gel chromatography was performed manually, or with Grace automated chromatography for gradient elution. Melting points were collected using a Büchi B-540 melting point apparatus.

EXAMPLES

Example 1: Compounds 1, 2 and 3

2-amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1

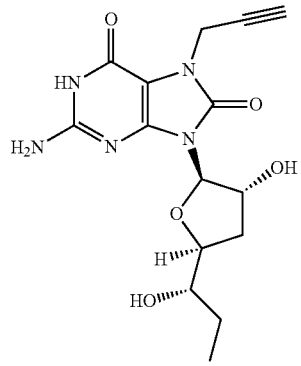 [SMILES: C#CCn1c(=O)n([C@@H]2O[C@H]([C@@H](O)CC)C[C@H]2O)c2nc(N)[nH]c(=O)c21]

33
2-amino-9-((2R,3R,5S)-3-hydroxy-5-((R)-1-hydroxypropyl)tetrahydrofuran-2-yl)-7-(prop-2-yn-1-yl)-7,9-dihydro-1H-purine-6,8-dione, Compound 2
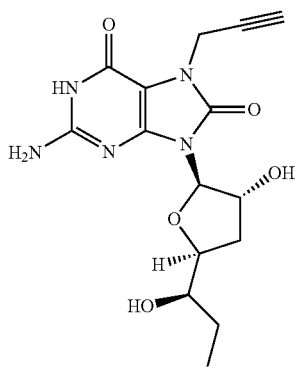 [SMILES: C#CCn1c(=O)n([C@@H]2O[C@H]([C@H](O)CC)C[C@H]2O)c2nc(N)[nH]c(=O)c21]
2-amino-9-((2R,3R,5S)-3-hydroxy-5-((R)-1-hydroxypropyl)tetrahydrofuran-2-yl)-7-(propa-1,2-dien-1-yl)-7,9-dihydro-1H-purine-6,8-dione, Compound 3
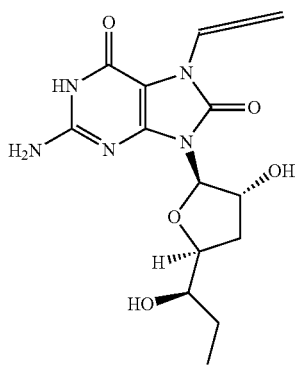 [SMILES: C=C=Cn1c(=O)n([C@@H]2O[C@H]([C@H](O)CC)C[C@H]2O)c2nc(N)[nH]c(=O)c21]
Compound 1, 2 and 3 were prepared according to the following multi-step procedures.
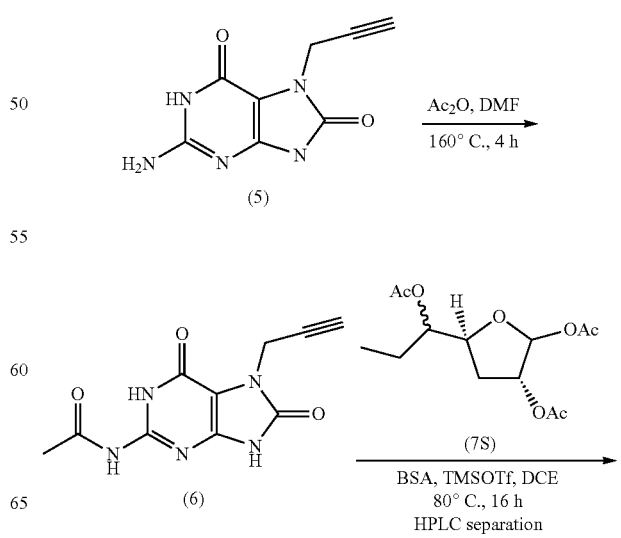
34
-continued
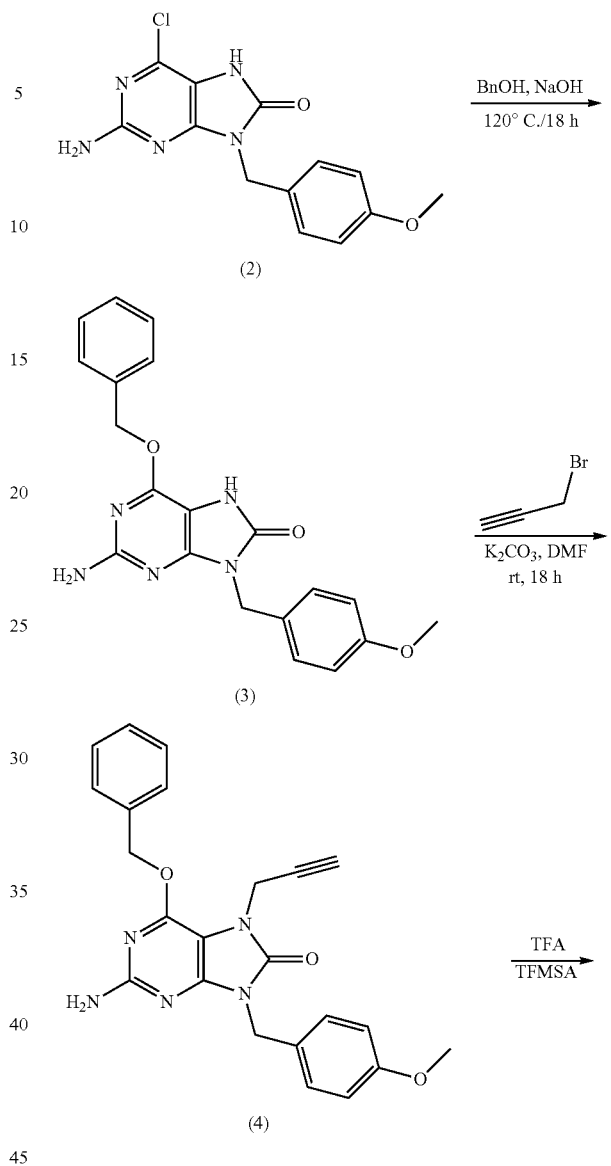

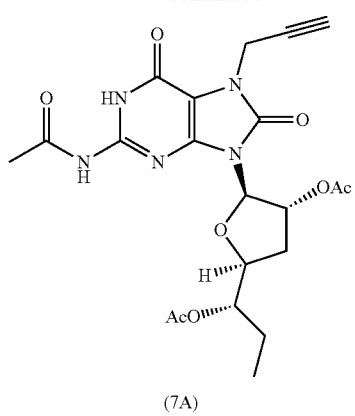
(7A)
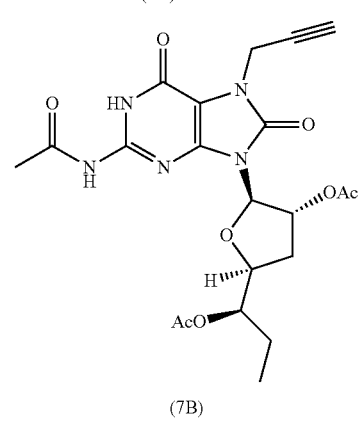
(7B)
(7A) →  K₂CO₃, MeOH
0° C.-rt, 16 h
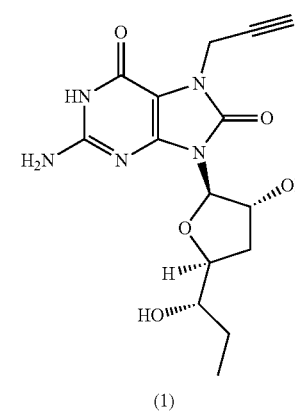
(1)
(7B) →  K₂CO₃, MeOH
0° C.-rt, 16 h
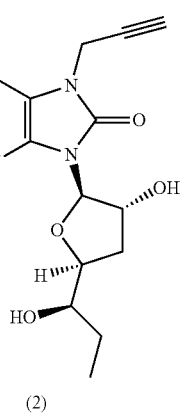
(2)
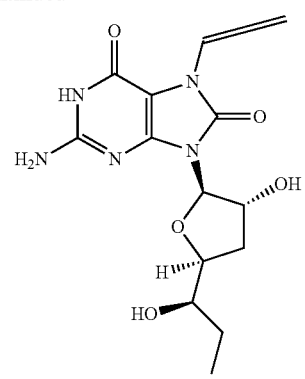
(3)
Preparation of (3R,5S)-5-(1-acetoxypropyl)tetrahydrofuran-2,3-diyl diacetate Intermediate (7S)
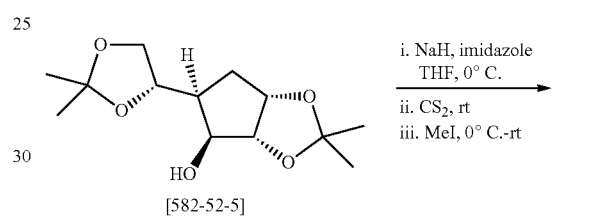
[582-52-5]
i. NaH, imidazole THF, 0° C.
ii. CS₂, rt
iii. MeI, 0° C.-rt
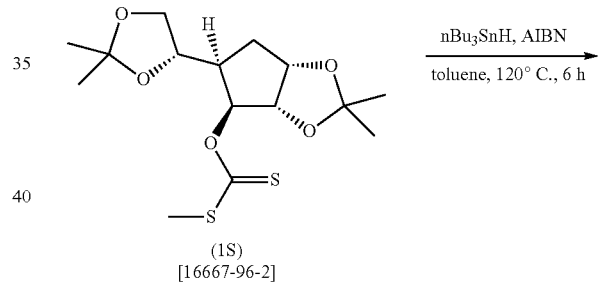
(1S)
[16667-96-2]
nBu₃SnH, AIBN
toluene, 120° C., 6 h
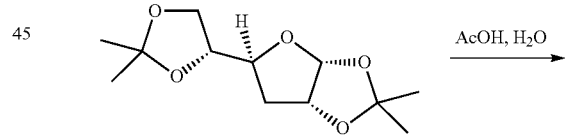
(2S)
[4613-62-1]
AcOH, H₂O
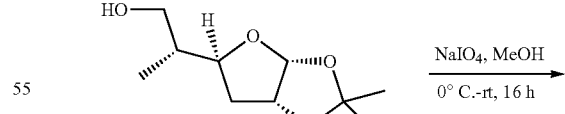
(3S)
[4005-46-3]
NaIO₄, MeOH
0° C.-rt, 16 h
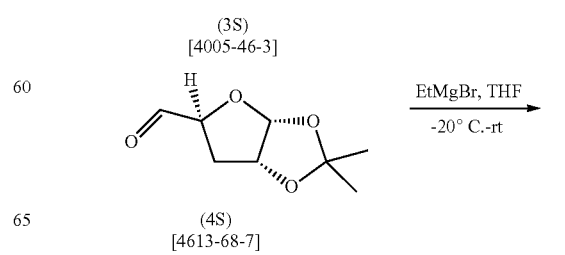
(4S)
[4613-68-7]
EtMgBr, THF
−20° C.-rt

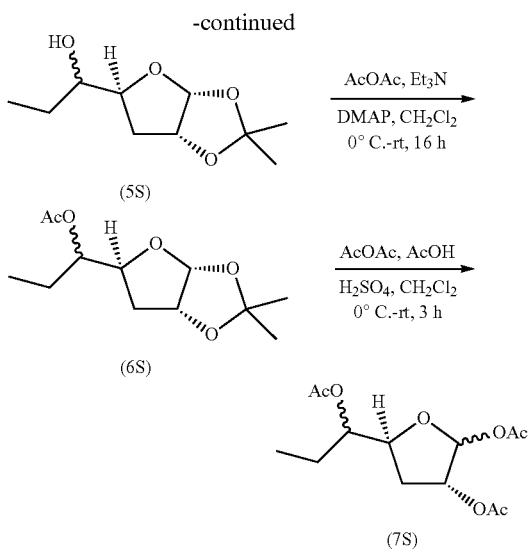

Step-1: O-((3aR,5R,6S,6aR)-5-((R)-2,2-Dimethyl-1,3-dioxolan-4-yl)-2,2-dimethyltetrahydrofuro[2,3-d][1,3]dioxol-6-yl) S-methyl carbonodithioate (1S)

To a suspension of NaH (60% in mineral oil, 36 g, 0.961 mol) in THF (500 mL) at 0° C. was added a solution of commercially available (3aR,5S,6S,6aR)-5-((R)-2,2-dimethyl-1,3-dioxolan-4-yl)-2,2-dimethyltetrahydrofuro[2,3-d][1,3]dioxol-6-ol [582-52-5](100 g, 0.384 mol) and imidazole (1.3 g, 1.92 mmol) in THF (500 mL) dropwise. The reaction mixture was stirred at 10° C. for 15 min. To this mixture was added carbon disulfide (121 mL, 1.92 mol) and the reaction mixture was stirred at RT for 1 h, followed by iodomethane (118 mL, 1.92 mol) at 0° C. Stirring was continued at RT for 2 h whereupon the reaction mixture was quenched with sat. NH$_4$Cl solution (1 L) and extracted with EtOAc (2×1.5 L). The combined organic layers were dried over Na$_2$SO$_4$ and concentrated under reduced pressure. The residue was purified by column chromatography over silica gel (100-200 mesh, eluting with 5% EtOAc in Pet-ether) to afford 120 g (89%) of O-((3aR,5R,6S,6aR)-5-((R)-2,2-dimethyl-1,3-dioxolan-4-yl)-2,2-dimethyltetrahydrofuro[2,3-d][1,3]dioxol-6-yl) S-methyl carbonodithioate (1S) [1667-96-2] as a colorless oil. $^1$H NMR (500 MHz, CDCl$_3$): δ 5.92-5.91 (m, 2H), 4.68-4.67 (m, 1H), 4.34-4.29 (m, 2H), 4.12-4.04 (m, 2H), 2.59 (s, 3H), 1.61 (s, 3H), 1.54 (s, 3H), 1.33-1.32 (m, 6H).

Step-2: (3aR,5S,6aR)-5-((R)-2,2-dimethyl-1,3-dioxolan-4-yl)-2,2-dimethyltetrahydrofuro[2,3-d][1,3]dioxole (2S)

A solution of O-((3aR,5R,6S,6aR)-5-((R)-2,2-dimethyl-1,3-dioxolan-4-yl)-2,2-dimethyltetrahydrofuro[2,3-d][1,3]dioxol-6-yl) S-methyl carbonodithioate (1S) (120 g, 342 mmol) in toluene (800 mL) was degassed with argon for 45 min. A solution of AIBN (39 g, 239 mmol) and nBu$_3$SnH (150 mL, 411 mmol) in toluene (400 mL) was degassed with argon for 30 min in a separate flask. This solution was added dropwise to the solution of (1S) in toluene. The reaction mixture was stirred at 120° C. for 6 h and then cooled to RT. Toluene was removed under reduced pressure and the residue was partitioned between acetonitrile and hexane (1:1, 1000 mL). The acetonitrile layer was washed with hexane (3×500 mL), and concentrated to give a residue that was purified by column chromatography on silica gel (100-200 mesh, eluting with 10% EtOAc in Pet-ether) to afford 70 g (83.7%) of (3aR,5S,6aR)-5-((R)-2,2-dimethyl-1,3-dioxolan-4-yl)-2,2-dimethyltetrahydrofuro[2,3-d][1,3]dioxole (2S) [4613-62-1] as a colorless oil. $^1$H NMR (400 MHz, CDCl$_3$): δ 5.82 (d, J=3.6 Hz, 1H), 4.76-4.74 (m, 1H), 4.17-4.10 (m, 3H), 3.84-3.81 (m, 1H), 2.21-2.16 (m, 1H), 1.80-1.73 (m, 1H), 1.54 (s, 3H), 1.51 (s, 3H), 1.36 (s, 3H), 1.32 (s, 3H).

Step-3: (R)-1-((3aR,5S,6aR)-2,2-Dimethyltetrahydrofuro[2,3-d][1,3]dioxol-5-yl)ethane-1,2-diol (3S)

A solution of (3aR,5S,6aR)-5-((R)-2,2-dimethyl-1,3-dioxolan-4-yl)-2,2-dimethyltetrahydrofuro[2,3-d][1,3]dioxole (2S) (70 g, 286 mmol) in 60% AcOH in water (350 mL, 5 Vol) was stirred at RT for 16 h. AcOH was removed under vacuum and the residue was partitioned between Acetonitrile and hexane (1:1, 500 mL). The acetonitrile layer was washed with hexane (3×300 mL), and the acetonitrile layer was concentrated. The residue was purified by column chromatography on silica gel (100-200 mesh, eluting with 50% EtOAc in Pet-ether) to afford 35 g (60%) of (R)-1-((3aR,5S,6aR)-2,2-dimethyltetrahydrofuro[2,3-d][1,3]dioxol-5-yl)ethane-1,2-diol (3S) [4005-46-3] as a colorless oil. $^1$H NMR (500 MHz, DMSO-d$_6$): δ 5.81 (d, J=3.5 Hz, 1H), 4.75 (t, J=4 Hz, 1H), 4.25-4.21 (m, 1H), 3.94-3.91 (m, 1H), 3.74-3.71 (m, 1H), 3.62-3.58 (m, 1H), 2.08-2.00 (m, 1H), 1.88-1.82 (m, 1H), 1.54 (s, 3H), 1.32 (s, 3H).

Step-4: (3aR,5S,6aR)-2,2-Dimethyltetrahydrofuro[2,3-d][1,3]dioxole-5-carbaldehyde (4S)

To a solution of (S)-1-((3aR,5S,6aR)-2,2-dimethyltetrahydrofuro[2,3-d][1,3]dioxol-5-yl)ethane-1,2-diol (3S) (3.3 g, 16.17 mmol) in methanol (35 mL) cooled by ice was added sodium metaperiodate (4.15 g, 19.411 mmol). After the reaction mixture was stirred at room temperature for 16 h, the resulting suspension was filtered. The filtrate was concentrated in vacuum and resultant residue was purified by column chromatography on silica gel (eluting with 1:2 EtOAc in Pet-ether) to afford 2.5 g of (3aR,5S,6aR)-2,2-dimethyltetrahydrofuro[2,3-d][1,3]dioxole-5-carbaldehyde (4S) [4613-68-7] as an colourless oil which was used immediately in the next step.

Step-5: 1-((3aR,5S,6aR)-2,2-Dimethyltetrahydrofuro[2,3-d][1,3]dioxol-5-yl)propan-1-ol (5S)

To a solution of (3aR,5S,6aR)-2,2-dimethyltetrahydrofuro[2,3-d][1,3]dioxole-5-carbaldehyde (4S) (2.6 g (crude), 15.11 mmol) in THF (30 mL) was added ethyl magnesium bromide (1M in THF, 15.1 mL, 15.11 mmol) at −20° C. under argon. After being stirred at room temperature for 16 h the reaction mixture was quenched with saturated NH$_4$Cl solution and extracted with EtOAc (3×100 mL). The combined organic layers were concentrated in vacuum and the resultant crude compound was purified by column chromatography on silica gel (eluting with 1:4 EtOAc in Pet-ether) to afford 2.1 g of 1-((3aR,5S,6aR)-2,2-dimethyltetrahydrofuro[2,3-d][1,3]dioxol-5-yl)propan-1-ol (5S) (mixture of diastereomers) as a colourless oil: $^1$H NMR (400 MHz, CDCl$_3$): δ 5.80 (t, J=3.2 Hz, 1H), 4.75 (t, J=4.2 Hz, 1H), 4.23-4.13 (m, 1H), 3.86-3.83 (m, 1H), 3.41-3.38 (m, 1H), 2.07-2.00 (m, 2H), 1.84-1.75 (m, 1H), 1.59-1.47 (m, 4H), 1.32 (s, 3H), 1.01 (t, J=7.4 Hz, 3H).

Step-6: 1-((3aR,5S,6aR)-2,2-Dimethyltetrahydrofuro[2,3-d][1,3]dioxol-5-yl)propyl acetate (6S)

To a solution of 1-((3aR,5S,6aR)-2,2-dimethyltetrahydrofuro[2,3-d][1,3]dioxol-5-yl)propan-1-ol (5S) (2.1 g, 10.39 mmol) in $CH_2Cl_2$ (20 mL) was added $Et_3N$ (2.9 mL, 20.79 mmol), DMAP (253 mg, 2.07 mmol). The stirred solution was cooled to 0° C. for 10 min at which time $Ac_2O$ (1.48 mL, 15.59 mmol) was added. The reaction mixture was warmed to room temperature and stirred for 16 h. The reaction was quenched with aqueous sat. $NaHCO_3$ and extracted with $CH_2Cl_2$ (3×100 mL). The combined organic layers were dried over $Na_2SO_4$, and concentrated under vacuum to afford 2.4 g of 1-((3aR,5S,6aR)-2,2-dimethyltetrahydrofuro[2,3-d][1,3]dioxol-5-yl)propyl acetate (6S) (mixture of diastereomers) as a colorless oil. The product was used in the next step as is.

Step-7: (3R,5S)-5-(1-Acetoxypropyl)tetrahydrofuran-2,3-diyl diacetate (7S)

To 1-((3aR,5S,6aR)-2,2-dimethyltetrahydrofuro[2,3-d][1,3]dioxol-5-yl)propyl acetate (6S) (2.4 g, 9.836 mmol) in dichloromethane (30 mL) was added AcOH (5.62 mL, 98.36 mmol), $Ac_2O$ (4.68 mL, 49.18 mmol) and conc. $H_2SO_4$ (0.5 mL) at 0° C. The reaction mixture was warmed to room temperature and stirred for 3 h. The reaction mixture was quenched with aqueous sat. $NaHCO_3$ and extracted with dichloromethane (3×100 mL). The combined organic layers were dried over $Na_2SO_4$ and concentrated in vacuum. The resultant residue was purified by flash chromatography ($SiO_2$, 0 to 15% EtOAc-Pet-ether) to afford 1.5 g of (3R,5S)-5-(1-acetoxypropyl)tetrahydrofuran-2,3-diyl diacetate (7S) (mixture of diastereomers) as a colorless oil: $^1$H NMR (400 MHz, $CDCl_3$): δ 6.12 (m, 1H), 5.19 (m, 1H), 4.91-4.83 (m, 1H), 4.44-4.34 (m, 1H), 2.19-2.09 (m, 9H), 1.74-1.51 (m, 2H), 1.48 (s, 2H), 0.94 (t, J=7.4 Hz, 3H).

Step-8: 6-Chloro-$N^4$-(4-methoxybenzyl)pyrimidine-2,4,5-triamine (1)

4-Methoxybenzyl amine (114.8 g, 83.728 mol) was added to a stirred solution mixture of 4,6-dichloropyrimidine-2,5-diamine [55583-59-0] (100 g, 55.81 mol) and TEA (169 mL, 167.45 mol) in ethanol (1.0 L) at 0° C. and the resulting reaction mixture was stirred at reflux temperature for 18 h. The solvent was evaporated under reduced pressure, the thick mass was poured into ice cold water and stirred for 30 min. The precipitated solid was collected by filtration, washed with water and dried under vacuum to afford 6-chloro-$N^4$-(4-methoxybenzyl)pyrimidine-2,4,5-triamine (1) (100 g, 64%) as a brown solid. ES+, m/z 280.1 [M+H]$^+$; $C_{12}H_{14}ClN_5O$; $^1$H NMR (500 MHz, DMSO-$d_6$): δ 8.25 (d, J=8.5 Hz, 2H), 6.92 (t, J=6.0 Hz, 1H), 7.87 (d, J=8.5 Hz, 2H), 5.63 (s, 2H), 4.47 (d, J=5.5 Hz, 2H), 3.91 (s, 2H), 3.72 (s, 3H).

Step-9: 2-Amino-6-chloro-9-(4-methoxybenzyl)-7,9-dihydro-8H-purin-8-one (2)

A mixture of 6-chloro-$N^4$-(4-methoxybenzyl)pyrimidine-2,4,5-triamine (1) (50 g, 17.92 mol) and 1,1'-carbonyldiimidazole (100 g, 61.64 mol) in acetonitrile (500 mL) was stirred at reflux temperature for 18 h. The reaction mixture was cooled to room temperature and concentrated under reduced pressure. To the resulting residue was added ice cold water and stirred for 30 min at room temperature. The precipitated solid was filtered, washed with water and dried to afford 2-amino-6-chloro-9-(4-methoxybenzyl)-7,9-dihydro-8H-purin-8-one (2) (50 g, 91%) as a brown solid; $C_{13}H_{12}ClN_5O_2$; $^1$H NMR (500 MHz, DMSO-$d_6$): δ 11.31 (s, 1H), 7.23 (d, J=9.0 Hz, 2H), 6.88 (d, J=5.0 Hz, 2H), 6.62 (s, 2H), 4.80 (s, 2H), 3.71 (s, 3H).

Step-10: 2-Amino-6-(benzyloxy)-9-(4-methoxybenzyl)-7,9-dihydro-8H-purin-8-one (3)

Sodium hydroxide (9.967 g, 262.29 mmol) was added to suspension of 2-amino-6-chloro-9-(4-methoxybenzyl)-7,9-dihydro-8H-purin-8-one (2) (40 g, 131.14 mmol) in benzyl alcohol (45.0 mL). The resulting reaction mixture was stirred at 120° C. for 18 h. The reaction mixture was quenched with ice water (200 mL), added diethyl ether (150 mL) and stirred for 15 min. The resulting precipitated solid was filtered, washed with water and dried to afford 2-amino-6-(benzyloxy)-9-(4-methoxybenzyl)-7,9-dihydro-8H-purin-8-one (3) (30 g, 60%) as an brown solid. ES+, m/z 378.1 [M+H]$^+$; $C_{20}H_{19}N_5O_3$; $^1$H NMR (400 MHz, DMSO-$d_6$): δ 10.81 (s, 1H), 7.48 (d, J=7.2 Hz, 2H), 7.40-7.36 (t, J=7.6 Hz, 2H), 7.34-7.31 (t, J=5.2 Hz, 1H), 7.21 (d, J=8.4 Hz, 2H), 6.87 (d, J=8.4 Hz, 2H), 6.27 (s, 2H), 5.41 (s, 2H), 4.78 (s, 2H), 3.71 (s, 3H).

Step-11: 2-Amino-6-(benzyloxy)-9-(4-methoxybenzyl)-7-(prop-2-yn-1-yl)-7,9-dihydro-8H-purin-8-one (4)

Propargyl bromide (7.1 ml, 63.66 mmol) was added to a suspension of 2-amino-6-(benzyloxy)-9-(4-methoxybenzyl)-7,9-dihydro-8H-purin-8-one (3) (20 g, 53.05 mmol), $K_2CO_3$ (10.98 g, 79.57 mmol) in DMF (100 mL) at 0° C. and stirred at room temperature for 18 h. The reaction mixture was quenched with ice water (200 mL), added diethyl ether (150 mL) and stirred for 15 min. The resulting precipitated solid was filtered, washed with water and dried to afford 2-amino-6-(benzyloxy)-9-(4-methoxybenzyl)-7-(prop-2-yn-1-yl)-7,9-dihydro-8H-purin-8-one (4) (20 g, 91%) as a brown solid. ES+, m/z 416.1 [M+H]$^+$; $C_{23}H_{21}N_5O_3$; $^1$H NMR (400 MHz, DMSO-$d_6$): δ 7.52 (d, J=7.2 Hz, 2H), 7.38 (t, J=7.6 Hz, 2H), 7.32 (t, J=5.2 Hz, 1H), 7.22 (d, J=8.4 Hz, 2H), 6.81 (d, J=8.4 Hz, 2H), 6.27 (s, 2H), 5.44 (s, 2H), 4.82 (s, 2H), 4.56 (s, 2H), 3.71 (s, 3H), 3.32-3.26 (m, 1H).

Step-12: 2-Amino-7-(prop-2-yn-1-yl)-7,9-dihydro-1H-purine-6,8-dione (5)

Trifluoromethanesulfonic acid (27 g, 180.72 mmol) was added to a suspension of 2-amino-6-(benzyloxy)-9-(4-methoxybenzyl)-7-(prop-2-yn-1-yl)-7,9-dihydro-8H-purin-8-one (4) (25 g, 60.24 mmol) in trifluoroacetic acid (21 mL, 180.72 mmol) at 0° C. under argon atmosphere and the resulting reaction mixture was stirred at room temperature for 18 h under argon atmosphere. The reaction mixture was quenched with ice cold water, basified with sat $NaHCO_3$ solution under vigorous stirring and filtered. The residual solid was taken into ethyl acetate, stirred for 30 min and filtered and dried to afford 2-amino-7-(prop-2-yn-1-yl)-7,9-dihydro-1H-purine-6,8-dione (5) (12 g, 36%) as a brown solid. ES+, m/z 206.1 [M+H]$^+$; $C_8H_7N_5O_2$; $^1$H NMR (400 MHz, DMSO-$d_6$): δ 11.32 (s, 1H), 6.74 (s, 2H), 4.53 (s, 2H), 3.14 (s, 1H).

Step-13: N-(6,8-Dioxo-7-(prop-2-yn-1-yl)-6,7,8,9-tetrahydro-1H-purin-2-yl)acetamide (6)

Acetic anhydride (4.85 mL, 47.56 mmol) was added to a solution of 2-amino-7-(prop-2-yn-1-yl)-7,9-dihydro-1H-purine-6,8-dione (5) (6.5 g, 31.70 mmol) in DMF (65 mL) at room temperature under argon atmosphere and the resulting reaction mixture was stirred at room temperature for 18 h under argon atmosphere. The reaction mixture was cooled to 0° C. (solid was formed under stirring) and stirred for 30 minutes. The product was filtered, washed with ethanol and dried under vacuum to afford N-(6,8-dioxo-7-(prop-2-yn-1-yl)-6,7,8,9-tetrahydro-1H-purin-2-yl)acetamide (6) (4 g, 51.2%) as an brown solid. ES+, m/z 248.1 [M+H]$^+$; $C_{10}H_9N_5O_3$; $^1$H NMR (400 MHz, DMSO-d$_6$): δ 11.83 (s, 2H), 4.61 (s, 2H), 3.23 (s, 1H), 2.16 (s, 3H).

Step-14: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)propyl acetate (7A) and (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7B)

To N-(6,8-dioxo-7-(prop-2-yn-1-yl)-6,7,8,9-tetrahydro-1H-purin-2-yl)acetamide (6) (700 mg, 2.834 mmol) and (3R,5S)-5-(1-acetoxypropyl)tetrahydrofuran-2,3-diyl diacetate (7S) (979 mg, 3.40 mmol) dissolved in 1,2-dichloroethane (10 mL) was added bis(trimethylsilyl)acetamide (2.14 mL, 8.502 mmol). The reaction mixture was stirred at 80° C. for 30 min under argon and then allowed to cool to room temperature. The 1,2-dichloroethane was removed under vacuum and the residue was taken up in MeCN (10 mL) whereupon trimethylsilyl trifluoromethanesulfonate (0.08 mL, 0.437 mmol) was added. The reaction mixture was heated to 80° C. and stirred for 16 h, cooled to room temperature, diluted with water and extracted with EtOAc (3×100 mL). The combined organic layers were washed with water (100 mL), brine (100 mL), dried over Na$_2$SO$_4$ and concentrated. The crude compound was purified by reverse phase prep-HPLC (Waters Prep-HPLC (Empower-3 software) (Column: X-SELECT-C18 (250*19), 5 u Mobile phase: 10 mM Ammonium bicarbonate in H$_2$O:MeCN GRADIENT: (T % B): 0/25, 8/45, 12/45, 12.1/98, 14/98, 14.1/25, 17/25 Flow Rate: 15 ml/Min Diluent: MeCN+ H$_2$O+THF+MeOH) to afford (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7A) (90 mg) ES+, m/z 476.2 [M+H]$^+$; $C_{21}H_{25}N_5O_8$ and (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7B) (90 mg) ES+, m/z 476.2 [M+H]$^+$; $C_{21}H_{25}N_5O_8$, both as off-white solids.

Step-15: 2-Amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1

To a solution (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7A) (90 mg, 0.189 mmol) in methanol (10 mL) was added K$_2$CO$_3$ (104 mg, 0.757 mmol) at 0° C. The reaction mixture was stirred at room temperature for 16 h and then concentrated under vacuum. The residue obtained was purified by GRACE FLASH chromatography (Reverse phase using 0.01% of formic acid in acetonitrile as eluent) to afford 2-amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1 (25 mg, 21%), as a white solid. ES$^-$, m/z 348.1 [M−H]; $C_{15}H_{19}N_5O_5$, $^1$H NMR (500 MHz, DMSO-d$_6$): δ 11.38 (brs, 1H), 6.66 (s, 2H), 5.51 (d, J=3.2 Hz, 1H), 5.38 (d, J=4.4 Hz, 1H), 4.76-4.72 (m, 1H), 4.68-4.66 (m, 1H), 4.59 (m, 2H), 4.02-3.98 (m, 1H), 3.27-3.25 (m, 1H), 3.22-3.20 (m, 1H), 2.40-2.33 (m, 1H), 1.80-1.75 (m, 1H), 1.40-1.38 (m, 1H), 1.31-1.25 (m, 1H), 0.95 (t, J=8.0 Hz, 3H).

Step-16: 2-Amino-9-((2R,3R,5S)-3-hydroxy-5-((R)-1-hydroxypropyl)tetrahydrofuran-2-yl)-7-(prop-2-yn-1-yl)-7,9-dihydro-H-purine-6,8-dione, Compound 2 and 2-amino-9-((2R,3R,5S)-3-hydroxy-5-((R)-1-hydroxypropyl)tetrahydrofuran-2-yl)-7-(propa-1,2-dien-1-yl)-7,9-dihydro-1H-purine-6,8-dione, Compound 3

To a solution of (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7B) (90 mg, 0.189 mmol) in methanol (10 mL) was added K$_2$CO$_3$ (104 mg, 0.757 mmol) at 0° C. The reaction mixture was stirred at room temperature for 16 h and then concentrated under vacuum. The residue obtained was purified by GRACE FLASH chromatography (Reverse phase using 0.01% of formic acid in acetonitrile as eluent) to afford 2-amino-9-((2R,3R,5S)-3-hydroxy-5-((R)-1-hydroxypropyl)tetrahydrofuran-2-yl)-7-(prop-2-yn-1-yl)-7,9-dihydro-1H-purine-6,8-dione, Compound 2 (15 mg), as a white solid. ES$^-$, m/z 348.1 [M−H]; $C_{15}H_{19}N_5O_5$, $^1$H NMR (500 MHz, DMSO-d$_6$): δ 10.99 (brs, 1H), 6.54 (s, 2H), 5.49 (d, J=3.6 Hz, 1H), 5.37 (d, J=4.8 Hz, 1H), 4.82-4.78 (m, 1H), 4.63-4.58 (m, 3H), 3.96-3.91 (m, 1H), 3.41-3.36 (m, 1H), 3.23-3.22 (m, 1H), 2.45-2.39 (m, 1H), 1.87-1.81 (m, 1H), 1.45-1.41 (m, 1H), 1.25-1.20 (m, 1H), 0.88 (t, J=8.0 Hz, 3H). The isomerized propargyl biproduct, 2-amino-9-((2R,3R,5S)-3-hydroxy-5-((R)-1-hydroxypropyl)tetrahydrofuran-2-yl)-7-(propa-1,2-dien-1-yl)-7,9-dihydro-1H-purine-6,8-dione, Compound 3 (10 mg) was also isolated as an off-white solid. ES+, m/z 350.1 [M+H]; $C_{15}H_{19}N_5O_5$, $^1$H NMR (500 MHz, DMSO-d$_6$): δ 11.79 (brs, 1H), 7.31 (t, J=6.5 Hz, 1H), 6.58 (s, 1H), 5.48 (d, J=4 Hz, 1H), 5.43 (d, J=6.5 Hz, 2H), 5.34 (d, J=5 Hz, 1H), 4.79 (s, 1H), 4.78-4.77 (m, 1H), 3.96-3.93 (m, 1H), 3.41-3.39 (m, 1H), 2.40-2.36 (m, 1H), 1.85-1.81 (m, 1H), 1.42-1.40 (m, 1H), 1.25-1.21 (m, 2H), 0.87 (t, J=7.5 Hz, 3H).

Alternative Synthetic Procedures for Compound 1.

Example 2: 2-Amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1

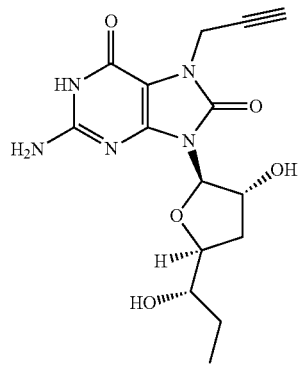 [SMILES: C#CCn1c(=O)n([C@@H]2O[C@H]([C@@H](O)CC)C[C@H]2O)c2nc(N)[nH]c(=O)c21]

Compound 1 was also synthesized according to the following alternative multi-step procedure.

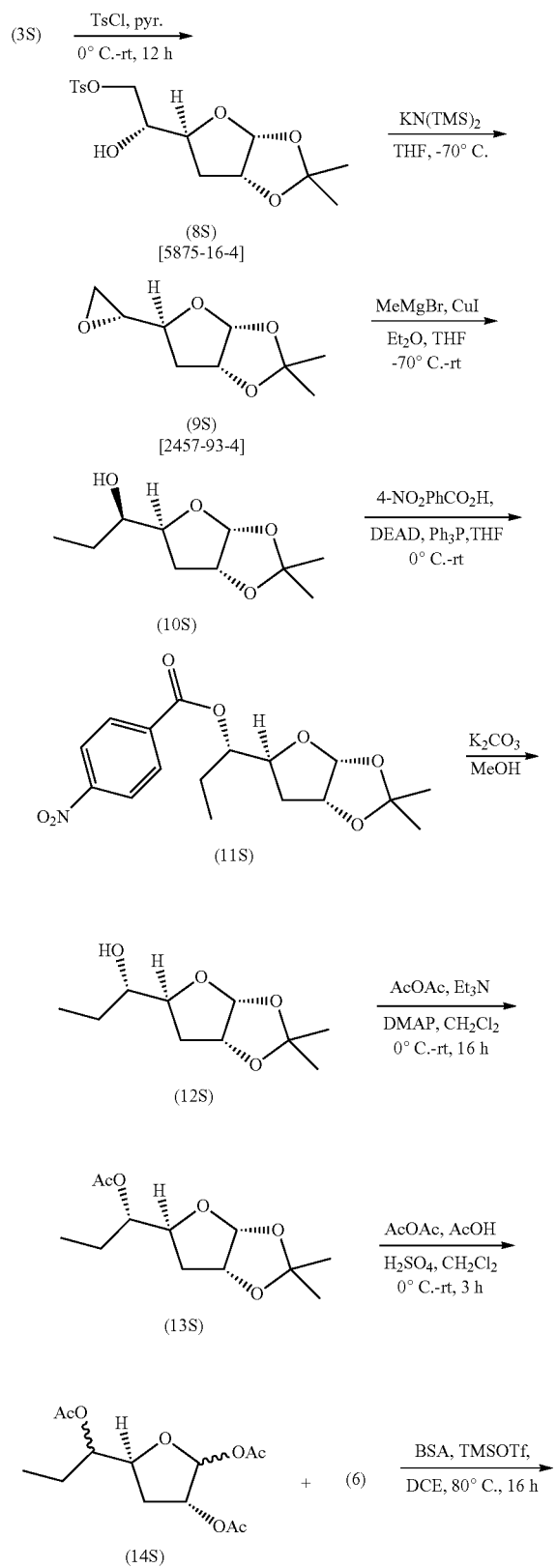

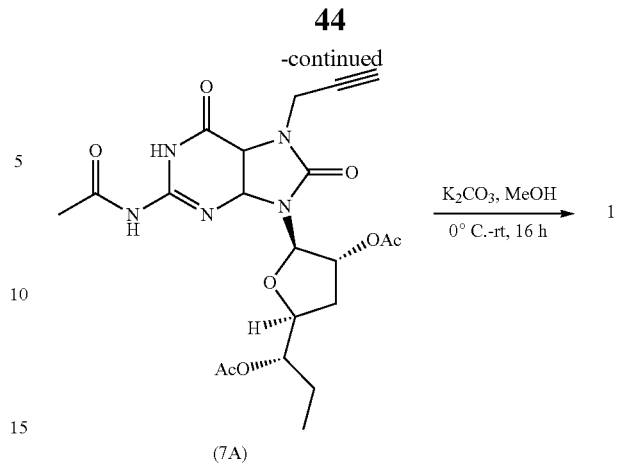

(7A)

Step-1: (R)-2-((3aR,5S,6aR)-2,2-Dimethyltetrahydrofuro[2,3-d][1,3]dioxol-5-yl)-2-hydroxyethyl 4-methylbenzenesulfonate (8S)

To a solution of (R)-1-((3aR,5S,6aR)-2,2-dimethyltetrahydrofuro[2,3-d][1,3]dioxol-5-yl)ethane-1,2-diol (3S) (25 g, 122 mmol) in dry pyridine (250 mL) was added p-toluenesulfonyl chloride (34.7 g, 183 mmol) at 0° C. After being stirred at room temperature for 12 h, pyridine was removed under vacuum. The residue was diluted with water (500 mL), extracted with EtOAc (2×600 mL). The combined EtOAc layer was dried over $Na_2SO_4$ and concentrated. The concentrate was purified by column chromatography on silica gel (100-200 mesh, eluting with 25% EtOAc in petroleum ether) to afford 26.4 g (60%) of (R)-2-((3aR,5S,6aR)-2,2-dimethyltetrahydrofuro[2,3-d][1,3]dioxol-5-yl)-2-hydroxyethyl 4-methylbenzenesulfonate (8S) [5875-16-4] as a light yellow oil. $^1$H NMR (500 MHz, $CDCl_3$): δ 7.80 (d, J=6.5 Hz, 2H), 7.36 (d, J=8.00 Hz, 2H), 5.76 (d, J=4 Hz, 1H), 4.72 (t, J=4.00 Hz, 1H), 4.17-4.14 (m, 2H), 4.01-3.97 (m, 2H), 2.45 (s, 3H), 2.41 (d, J=4 Hz, 1H), 2.10-2.04 (m, 1H), 1.80-1.75 (m, 1H), 1.51 (s, 3H), 1.33 (s, 3H).

Step-2: (3aR,5S,6aR)-2,2-Dimethyl-5-((R)-oxiran-2-yl)tetrahydrofuro[2,3-d][1,3]dioxole (9S)

To a solution of (R)-2-((3aR,5S,6aR)-2,2-dimethyltetrahydrofuro[2,3-d][1,3]dioxol-5-yl)-2-hydroxyethyl 4-methylbenzenesulfonate (3S) (26 g, 72 mmol) in anhydrous THF (260 mL) cooled at −78° C. was added potassium bis(trimethylsilyl)amide (108 mL, 108 mmol, 1 M in THF) under $N_2$ atmosphere. After being stirred at −78° C. for 1 h, the reaction mixture was poured into saturated $NH_4Cl$ solution. The organic layer was separated and the aqueous phase was extracted with EtOAc (2×200 mL). The combined organic layers were dried over $Na_2SO_4$ and concentrated in vacuum. The crude product was purified by column chromatography on silica gel (100-200 mesh, eluting with 25% EtOAc in petroleum ether) to afford 10.5 g (78%) of (3aR,5S,6aR)-2,2-dimethyl-5-((R)-oxiran-2-yl)tetrahydrofuro[2,3-d][1,3]dioxole (9S) [2457-93-4] as a light yellow oil. $^1$H NMR: (400 MHz, $CDCl_3$): δ 5.84 (d, J=5.4 Hz, 1H), 4.75 (t, J=4.4 Hz, 1H), 4.23-4.18 (m, 1H), 3.15-3.13 (m, 1H), 2.83-2.80 (m, 1H), 2.61 (m, 1H), 2.07 (dd, J=13.2, 4.8 Hz, 1H), 1.75-1.68 (m, 1H), 1.50 (s, 3H), 1.32 (s, 3H).

Step-3: (R)-1-((3aR,5S,6aR)-2,2-Dimethyltetrahydrofuro[2,3-d][1,3]dioxol-5-yl)propan-1-ol (10S)

To a suspension of CuI (2 g, 10.7 mmol) in dry THF (300 mL) under $N_2$ atmosphere was added methylmagnesium bromide (3 M in diethyl ether, 53 mL, 159 mmol) at −78° C. After being stirred at −78° C. for 1 hour, a solution of (3aR,5S,6aR)-2,2-dimethyl-5-((R)-oxiran-2-yl)tetrahydrofuro[2,3-d][1,3]dioxole (9S) (10 g, 53 mmol) in THF (40 mL) was added and stirred at −78° C. for an additional 2 hours. The reaction mixture was poured into saturated $NH_4Cl$ solution (200 mL) and the organic layer was separated. The aqueous phase was extracted with EtOAc (2×200 mL) and the organic layers were combined, dried over $Na_2SO_4$ and concentrated in vacuum. The crude product was purified by column chromatography on silica gel (100-200 mesh, eluting with 30% EtOAc in petroleum ether) to afford 8.2 g (75%) of (R)-1-((3aR,5S,6aR)-2,2-dimethyltetrahydrofuro[2,3-d][1,3]dioxol-5-yl)propan-1-ol (10S) as a light yellow oil. $^1$H NMR (500 MHz, $CDCl_3$): δ 5.81 (d, J=3.5 Hz, 1H), 4.75-4.73 (m, 1H), 4.23-4.19 (m, 1H), 3.85-3.84 (m, 1H), 2.04-2.02 (m, 1H), 1.91-1.90 (m, 2H), 1.51 (s, 3H), 1.45-1.39 (m, 2H), 1.32 (s, 3H), 1.01 (t, J=7.5 Hz, 3H).

Step-4: (S)-1-((3aR,5S,6aR)-2,2-Dimethyltetrahydrofuro[2,3-d][1,3]dioxol-5-yl)propyl 4-nitrobenzoate (11S)

To a stirred solution of (R)-1-((3aR,5S,6aR)-2,2-dimethyltetrahydrofuro[2,3-d][1,3]dioxol-5-yl)propan-1-ol (10S) (8 g, 39 mmol), triphenylphosphine (31 g, 118 mmol), 4-nitrobenzoic acid (20 g, 118 mmol) in THF (240 mL) was added diethylazodicarboxylate (18.6 mL, 118 mmol) drop wise at 0° C. under $N_2$ atm. After being stirred at RT for 10 h, the mixture was quenched by addition of saturated $NaHCO_3$ solution (200 mL) and extracted with EtOAc (2×200 mL). The organic layers were combined, dried over $Na_2SO_4$ and concentrated in vacuum. The residue was purified by column chromatography on silica gel (100-200 mesh, eluting with 15% EtOAc in petroleum ether) to afford 9 g (64.7%) of (S)-1-((3aR,5S,6aR)-2,2-dimethyltetrahydrofuro[2,3-d][1,3]dioxol-5-yl)propyl 4-nitrobenzoate (11S) as a light yellow solid. $^1$H NMR (400 MHz, $CDCl_3$): δ 8.34-8.27 (m, 2H), 8.25-8.21 (m, 2H), 5.83 (d, J=3.6 Hz, 1H), 5.20-5.15 (m, 1H), 4.73 (t, J=4.0 Hz, 1H), 4.40-4.38 (m, 1H), 2.12 (dd, J=13.2, 3.6 Hz, 1H), 1.88-1.78 (m, 2H), 1.68-1.62 (m, 1H), 1.55 (s, 3H), 1.32 (s, 3H), 1.01 (t, J=7.2 Hz, 3H).

Step-5: (S)-1-((3aR,5S,6aR)-2,2-Dimethyltetrahydrofuro[2,3-d][1,3]dioxol-5-yl)propan-1-ol (12S)

To a stirred solution of (S)-1-((3aR,5S,6aR)-2,2-dimethyltetrahydrofuro[2,3-d][1,3]dioxol-5-yl)propyl 4-nitrobenzoate (11S) (9 g, 26 mmol) in methanol (180 mL) was added $K_2CO_3$ (7.5 g, 55 mmol). After being stirred at room temperature for 30 minutes, the resultant mixture was filtered and the filtrate was concentrated under vacuum. The crude material was purified by column chromatography on silica gel (100-200 mesh, eluting with 30% EtOAc in petroleum ether) to afford 4.5 g (87%) of (S)-1-((3aR,5S,6aR)-2,2-dimethyltetrahydrofuro[2,3-d][1,3]dioxol-5-yl)propan-1-ol (12S) as a light yellow oil. $^1$H NMR (400 MHz, $CDCl_3$): δ 5.81 (d, J=3.6 Hz, 1H), 4.74 (t, J=4.4 Hz, 1H), 4.17-4.13 (m, 1H), 3.42-3.38 (m, 1H), 2.05-2.00 (m, 2H), 1.80-1.71 (m, 1H), 1.57-1.50 (m, 5H), 1.32 (s, 3H), 1.01 (t, J=7.6 Hz, 3H).

Step-6: (S)-1-((3aR,5S,6aR)-2,2-Dimethyltetrahydrofuro[2,3-d][1,3]dioxol-5-yl)propyl acetate (13S)

To a stirred solution of (S)-1-((3aR,5S,6aR)-2,2-dimethyltetrahydrofuro[2,3-d][1,3]dioxol-5-yl)propan-1-ol (12S) (4.5 g, 22 mmol), TEA (31 mL, 267 mmol) and DMAP (0.538 g, 4.4 mmol) in anhydrous DCM (90 mL) was added acetic anhydride (20 g, 198 mmol). After being stirred at room temperature for 10 h the reaction was quenched with a saturated aq. $NaHCO_3$ solution (100 mL). The organic layer was separated and the aqueous phase was extracted with DCM (2×100 mL). The combined organic layers were dried over $Na_2SO_4$ and concentrated under vacuum. The crude product was purified by column chromatography on silica gel (100-200 mesh, eluting with 20% EtOAc in petroleum ether) to afford 4.4 g (80.5%) of (S)-1-((3aR,5S,6aR)-2,2-dimethyltetrahydrofuro[2,3-d][1,3]dioxol-5-yl)propyl acetate (13S) as a colorless oil. $^1$H NMR (400 MHz, CDCl3): δ 5.80 (d, J=3.6 Hz, 1H), 4.9-4.87 (m, 1H), 4.72 (t, J=4.4 Hz, 1H), 4.30-4.25 (m, 1H), 2.10 (s, 3H), 2.03-1.99 (m, 1H), 1.69-1.55 (m, 3H), 1.51 (s, 3H), 1.32 (s, 3H), 0.91 (t, J=4.0 Hz, 3H). Step-7: (3R,5S)-5-((S)-1-Acetoxypropyl)tetrahydrofuran-2,3-diyl diacetate (14S)

To a solution of (S)-1-((3aR,5S,6aR)-2,2-dimethyltetrahydrofuro[2,3-d][1,3]dioxol-5-yl)propyl acetate (13S) (4.4 g, 18 mmol), acetic acid (10.4 mL, 180 mmol) and acetic anhydride (8.8 mL, 90 mmol) in anhydrous DCM (90 mL) was added concentrated $H_2SO_4$ (0.44 mL) at 0° C. After being stirred at RT for 3 hours, the reaction was quenched by addition of saturated aq·$NaHCO_3$ solution (100 mL). The organic layer was separated and the aqueous phase was extracted with DCM (2×100 mL). The combined organic layers were dried over $Na_2SO_4$ and concentrated under vacuum. The crude product was purified by column chromatography on silica gel (100-200 mesh, eluting with 30% EtOAc in petroleum ether) to afford 2.7 g (52%) of (3R,5S)-5-((S)-1-acetoxypropyl)tetrahydrofuran-2,3-diyl diacetate (14S) as a colorless oil. $^1$H NMR (400 MHz, $CDCl_3$): δ 6.10 (s, 1H), 5.18 (d, J=4.4 Hz, 1H), 4.87-4.82 (m, 1H), 4.44-4.34 (m, 1H), 2.12-2.10 (m, 9H), 1.61-1.54 (m, 4H), 0.94 (m, 3H).

Step-8: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)propyl acetate (7A)

To N-(6,8-dioxo-7-(prop-2-yn-1-yl)-6,7,8,9-tetrahydro-1H-purin-2-yl)acetamide (6) (300 mg, 1.21 mmol), (3R,5S)-5-((S)-1-acetoxypropyl)tetrahydrofuran-2,3-diyl diacetate (14S) (384 mg, 1.33 mmol) dissolved in 1,2-dichloroethane (20 mL) was added bis(trimethylsilyl)acetamide (0.91 mL, 3.63 mmol). The resulting reaction mixture was stirred at 80° C. for 30 min under argon. The reaction mixture was allowed to warm to RT and 1,2-dichloroethane was removed under vacuum. The residue was taken up in ACN (20 mL) and trimethylsilyl trifluoromethanesulfonate (0.335 mL, 1.815 mmol) was added. The reaction mixture was heated at 80° C. for 16 h. The reaction mixture was cooled to room temperature and concentrated under vacuum. The residue was diluted with aq·$NaHCO_3$ (50 mL) and extracted with EtOAc (3×50 mL). The combined EtOAc layers were washed with water (30 mL), brine (30 mL), dried over $Na_2SO_4$ and concentrated under vacuum. The crude compound was purified by GRACE flash chromatography (using 80% EtOAc in pet ether as eluant) to afford 200 mg (34.6%) of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7A) as an off-white solid. ES+, m/z 476.2 [M+H]$^+$; $C_{21}H_{25}N_5O_8$.

Step-9: 2-Amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7A) (200 mg, 0.421 mmol) in MeOH (20 mL) was added $K_2CO_3$ (232 mg, 1.684 mmol) at 0° C. The reaction mixture was stirred at RT for 16 h. Methanol was removed under reduced pressure at 30° C. The residue was purified by normal phase GRACE flash chromatography (using 7% MeOH in DCM as eluant) followed by a reverse phase GRACE flash chromatography (using 0.01% aq. $HCO_2H$ and ACN as eluent). The pure fractions upon lyophilization afforded 32 mg (22%) of 2-amino-9-((2R,3R,5S)-3-hydroxy-5-((S)-1-hydroxypropyl)tetrahydrofuran-2-yl)-7-(prop-2-yn-1-yl)-7,9-dihydro-1H-purine-6,8-dione, Compound 1 as an off white solid. $ES^+$, m/z 350.2 [M+H]; $C_{15}H_{19}N_5O_5$: $^1H$ NMR (400 MHz, DMSO-$d_6$): δ 11.00 (brs, 1H), 6.55 (brs, 2H), 5.51 (d, J=4.0 Hz, 1H), 5.39 (d, J=5.2 Hz, 1H), 4.76-4.72 (m, 1H), 4.58-4.55 (m, 3H), 4.02-3.98 (m, 1H), 3.31-3.30 (m, 1H), 3.23-3.22 (m, 1H), 2.39-2.33 (m, 1H), 1.78-1.75 (m, 1H), 1.45-1.38 (m, 1H), 1.31-1.25 (m, 1H), 0.87 (t, J=7.2 Hz, 3H).

Example 3: 2-Amino-7-(cyclopropylmethyl)-9-((2R,3R,5S)-3-hydroxy-5-((S)-1-hydroxypropyl)tetrahydrofuran-2-yl)-7,9-dihydro-1H-purine-6,8-dione, Compound 4

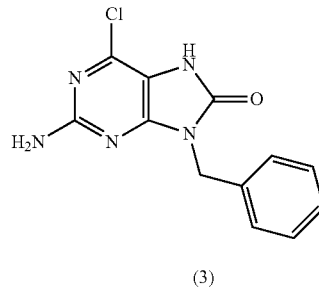

Preparation of Intermediates (12) and (14)

Intermediate compounds (12) and (14) were synthesized according to the following multi-step procedure.

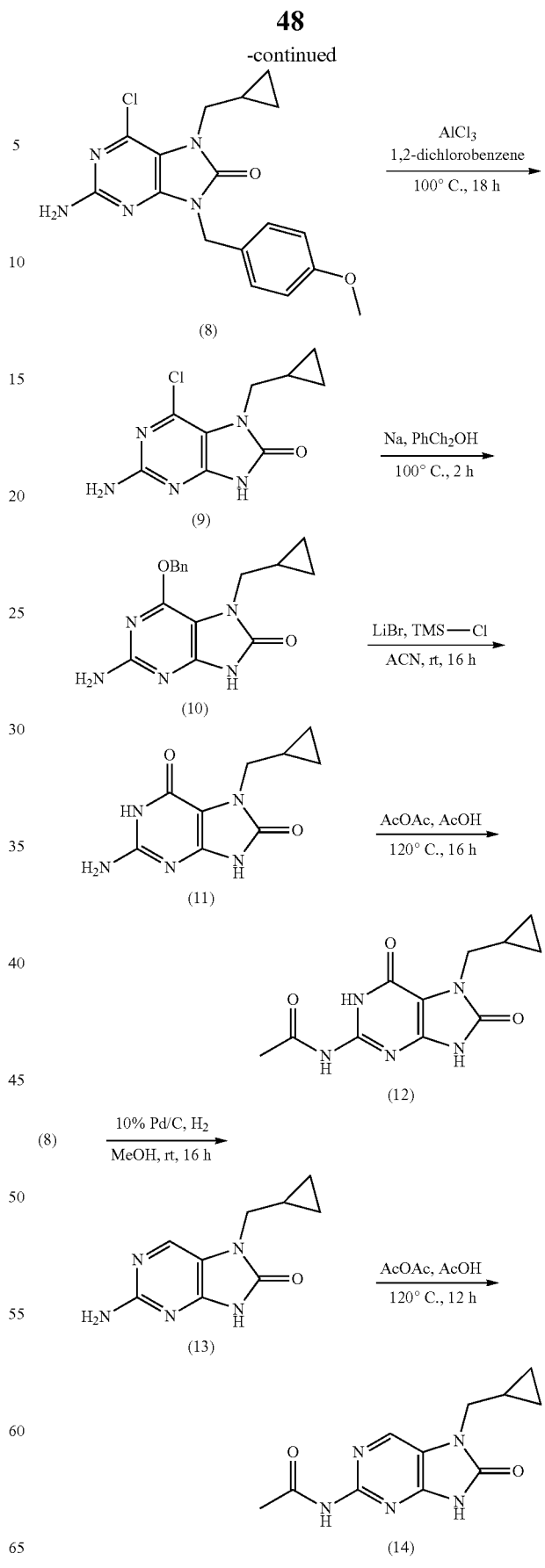

Step-1: 2-Amino-6-chloro-7-(cyclopropylmethyl)-9-(4-methoxybenzyl)-7,9-dihydro-8H-purin-8-one (8)

Cyclopropyl methyl bromide (32.9 g, 24.39 mol) was added to a suspension of 2-amino-6-chloro-9-(4-methoxybenzyl)-7,9-dihydro-8H-purin-8-one (3) (62 g, 20.32 mol), $K_2CO_3$ (42 g, 30.49 mol) in DMF (500 mL) at 0° C. and then stirred at room temperature for 18 h. The reaction mixture was poured on to ice cold water and stirred for 30 mins at room temperature. The precipitated solid product was collected by filtration and dried under vacuum to afford 2-amino-6-chloro-7-(cyclopropylmethyl)-9-(4-methoxybenzyl)-7,9-dihydro-8H-purin-8-one (8) (60 g, 82%) as a brown solid. TLC: 30% Ethyl acetate in hexane; $R_f$: 0.4; ES+, m/z 360.1 $[M+H]^+$; $C_{17}H_{18}ClN_5O_2$; $^1$H NMR (400 MHz, DMSO-$d_6$): δ 7.23 (d, J=8.4 Hz, 2H), 6.89 (d, J=8.8 Hz, 2H), 6.75 (s, 2H), 4.86 (s, 2H), 3.80 (d, J=6.8 Hz, 2H), 3.71 (s, 3H), 1.21-1.17 (m, 1H), 0.50-0.46 (m, 2H), 0.37-0.34 (m, 2H).

Step-2: 2-Amino-6-chloro-7-(cyclopropylmethyl)-7,9-dihydro-8H-purin-8-one (9)

Anhydrous $AlCl_3$ powder (25 g, 187 mmol) was added to a stirred solution of 2-amino-6-chloro-7-(cyclopropylmethyl)-9-(4-methoxybenzyl)-7,9-dihydro-8H-purin-8-one (8) (50 g, 139.2 mmol) in 1,2-dichloro benzene (250 mL) at room temperature under argon atmosphere and the resulting reaction mixture was stirred at 100° C. for 18 h under argon atmosphere. The reaction mixture was cooled to room temperature and quenched with ice cold water, basified with a sat. $NaHCO_3$ solution under vigorous stirring and filtered. The filtered solid was taken into 10% MeOH in dichloromethane, stirred for 30 min and filtered (repeated thrice with volume of 1.0 L solvent). The filtrate was passed through a pad of celite and concentrated under reduced pressure. The solid thus obtained was washed twice with 10% methanol in dichloromethane and filtered. The filtered solid was again washed with twice acetonitrile, filtered and dried to afford 2-amino-6-chloro-7-(cyclopropylmethyl)-7,9-dihydro-8H-purin-8-one (9) (12 g, 36%) as a brown solid. TLC: 50% Ethyl acetate in hexane; $R_f$: 0.3; ES+, m/z 240.1 $[M+H]^+$; $C_9H_{10}ClN_5O$. $^1$H NMR (500 MHz, DMSO-$d_6$): δ 11.81 (s, 1H), 6.58 (s, 2H), 3.73-3.72 (d, J=7.0 Hz, 2H), 1.21-1.17 (m, 1H), 0.50-0.46 (m, 2H), 0.37-0.34 (m, 2H). m.p. 286-290° C.

Step-3: 2-Amino-6-(benzyloxy)-7-(cyclopropylmethyl)-7,9-dihydro-8H-purin-8-one (10)

Sodium metal (1.43 g, 62.6 mmol) was added to benzyl alcohol (25.0 mL) for 1 h (until all the sodium dissolved). The resulting viscous liquid was cooled to rt and 2-amino-6-chloro-7-(cyclopropylmethyl)-7,9-dihydro-8H-purin-8-one (9) (5.0 g, 20.86 mmol) was added. The resulting reaction mixture was stirred at 100° C. for 1 h and quenched with ice water (200 mL). Diethyl ether (150 mL) was added and stirred for 15 min. The resulting precipitated solid was filtered, washed with water and dried. The solid was dissolved in 15% methanol-dichloromethane (500 mL), filtered through celite pad, washed with brine and concentrated. The resulting solid was washed with diethyl ether and filtered to afford 2-amino-6-(benzyloxy)-7-(cyclopropylmethyl)-7,9-dihydro-8H-purin-8-one (10) (3.5 g, 54%) as an off white solid. TLC: 70% Ethyl acetate in pet ether; $R_f$: 0.6; ES+, m/z 312.2 $[M+H]^+$; $C_{16}H_{17}N_5O_2$. $^1$H NMR (500 MHz, DMSO-$d_6$): δ 11.30 (brs, 1H), 7.48-7.46 (m, 2H), 7.41-7.38 (m, 2H), 7.35-7.30 (m, 1H), 6.15 (s, 2H), 5.41 (s, 2H), 3.56 (d, J=7.0 Hz, 2H), 1.14-1.10 (m, 1H), 0.36-0.32 (m, 2H), 0.23-

Step-4: 2-Amino-7-(cyclopropylmethyl)-7,9-dihydro-1H-purine-6,8-dione (11)

A suspension of 2-amino-6-(benzyloxy)-7-(cyclopropylmethyl)-7,9-dihydro-8H-purin-8-one (10) (10.0 g, 32.15 mmol), anhydrous LiBr (3.34 g, 38.58 mmol), chlorotrimethylsilane (4.53 g, 108.6 mmol) in acetonitrile (700 mL) were stirred at room temperature for 16 h. Methanol (60 mL) was added to the reaction mixture and stirred for 30 min. The solvent was distilled off to a reduced volume of ~100 mL and filtered. The filter cake was washed with acetonitrile and dried. The solid was taken into a sat. $NaHCO_3$ solution (200 mL), stirred for 1 h, filtered, washed with water and dried. The solid was stirred in 10% methanol/dichloromethane (50 mL), filtered and dried to afford 2-amino-7-(cyclopropylmethyl)-7,9-dihydro-1H-purine-6,8-dione (11) (8.5 g, 80%) as a pale brown solid. TLC: 10% methanol in dichloromethane; $R_f$: 0.4; ES+, m/z 222.1 $[M+H]^+$; $C_9H_{11}N_5O_2$. $^1$H NMR (500 MHz, DMSO-$d_6$): δ 11.06 (s, 1H), 10.68 (s, 1H), 6.36 (s, 2H), 3.58 (d, J=7.0 Hz, 2H), 1.19-1.14 (m, 1H), 0.40-0.36 (m, 2H), 0.33-0.30 (m, 2H). m.p. 364-368° C.

Step-5: N-(7-(Cyclopropylmethyl)-6,8-dioxo-6,7,8,9-tetrahydro-1H-purin-2-yl)acetamide (12)

Acetic anhydride (0.13 mL, 1.3574 mmol) was added to a solution of 2-amino-7-(cyclopropylmethyl)-7,9-dihydro-1H-purine-6,8-dione (11) (200 mg, 0.9049 mmol) in acetic acid (5 mL) at ambient temperature under argon atmosphere and the resulting reaction mixture was heated at 140° C. for 6 h. The reaction mixture was cooled down to 0° C. (solid was formed under stirring) and stirred for 30 minutes. The product was filtered, and dried under vacuum to afford N-(7-(cyclopropylmethyl)-6,8-dioxo-6,7,8,9-tetrahydro-1H-purin-2-yl)acetamide (12) (180 mg, 75.6%) as an brown solid: $C_{11}H_{13}N_5O_3$: LC-MS indicated 98% of desired m/z (M+H; 264.1). $^1$H NMR (400 MHz, DMSO-$d_6$): δ 12.01 (s, 1H), 11.68 (s, 1H), 11.65 (s, 1H), 3.66 (d, J=7.2 Hz, 2H), 2.15 (s, 3H), 2.21-2.15 (m, 1H), 043-0.38 (m, 2H), 0.36-0.32 (m, 2H).

Step-6: 2-Amino-7-(cyclopropylmethyl)-7,9-dihydro-8H-purin-8-one (13)

10% Pd—C (5.0 g) was added to a solution of 2-amino-6-chloro-7-(cyclopropylmethyl)-9-(4-methoxybenzyl)-7,9-dihydro-8H-purin-8-one (8) (20 g, mmol) in methanol (500 mL). The reaction mixture was hydrogenated with $H_2$ gas at 80 psi of pressure in a Parr shaker vial at room temperature for 24 h. The reaction mixture was filtered through a celite pad and the filtrate was evaporated to give crude product. To the crude compound was added acetonitrile with stirred for 15 min, filtered. This step was repeated and the solid was dried under vacuum to afford 2-amino-7-(cyclopropylmethyl)-7,9-dihydro-8H-purin-8-one (13) (11 g, 64%) as an off white solid. TLC: 70% Ethyl acetate in hexane; $R_f$: 0.2; ES+, m/z 206.2 $[M+H]^+$; $C_9H_{11}N_5O$. $^1$H NMR (500 MHz, DMSO-$d_6$): δ 12.68 (s, 1H), 8.11 (s, 1H), 7.87 (s, 2H), 3.60-3.59 (d, J=7.5 Hz, 2H), 1.18-1.12 (m, 1H), 0.50-0.46 (m, 2H), 0.37-0.34 (m, 2H). m.p. 245-249° C.

Step-7: N-(7-(cyclopropylmethyl)-8-oxo-8,9-dihydro-7H-purin-2-yl)acetamide (14)

To a stirred solution of 2-amino-7-(cyclopropylmethyl)-7,9-dihydro-8H-purin-8-one (13) (2 g, 9.75 mmol) in AcOH (50 mL) was added Ac₂O (3.68 mL, 39.02 mmol). The resulting solution was heated at 120° C. for 12 h. The reaction mixture was cooled to RT and resulting solid was collected by filtration, washed with diethyl ether (100 mL) and dried to obtain 1.6 g (51%) of N-(7-(cyclopropylmethyl)-8-oxo-8,9-dihydro-7H-purin-2-yl)acetamide (14) as an orange solid. ES+, m/z 248.2 [M+H]⁺; $C_{11}H_{13}N_5O_2$: ¹H NMR (400 MHz, DMSO-$d_6$): δ 12.97 (s, 1H), 11.71 (s, 1H), 8.31 (s, 1H), 3.74, (d, J=7.2 Hz, 2H), 2.22 (s, 3H), 1.45-1.13 (m, 1H), 0.53 (t, J=3.6 Hz, 2H), 0.48 (t, J=3.6 Hz, 2H).

Step-8: (S)-1-((2S,4R,5R)-5-(2-Acetamido-7-(cyclopropylmethyl)-6,8-dioxo-1,6,7,8-tetrahydro-9H-purin-9-yl)-4-acetoxytetrahydrofuran-2-yl)propyl acetate (15)

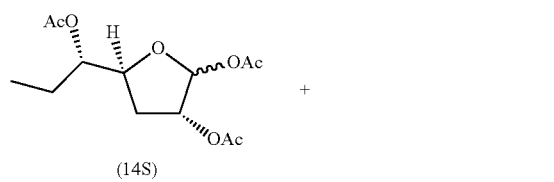

(14S)

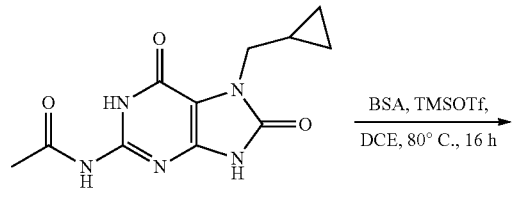

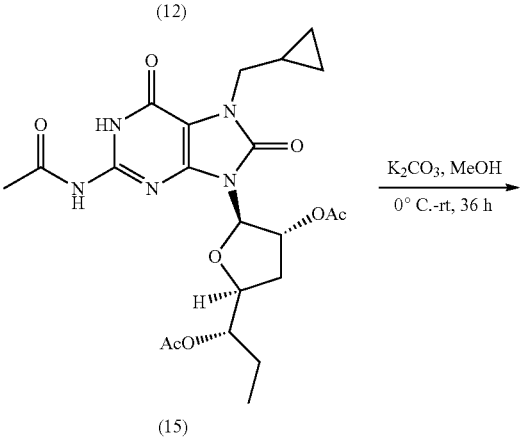

N-(7-(cyclopropylmethyl)-6,8-dioxo-6,7,8,9-tetrahydro-1H-purin-2-yl)acetamide (12) (200 mg, 0.7604 mmol), (3R,5S)-5-((S)-1-acetoxypropyl)tetrahydrofuran-2,3-diyl diacetate (14S) (219 mg, 0.7604 mmol) and bis(trimethylsilyl)acetamide (0.58 mL, 2.2812 mmol) were dissolved in 1,2-dichloroethane (10 mL). The reaction mixture was stirred at 80° C. for 30 min under argon followed by concentration under reduced pressure. The resultant residue was diluted with ACN (50 mL), charged with TMSOTf (0.212 mL, 1.1406 mmol), placed into a preheated oil bath at 80° C., and stirred for 16 h. The reaction was cooled to room temperature and the solvent was removed by rotary evaporation. The resultant solid was dissolved in ethyl acetate (100 mL) and extracted with saturated aqueous NaHCO₃ (2×30 mL). The organic phase was dried over Na₂SO₄ and concentrated. The crude product was purified by flash chromatography (SiO₂, 0 to 80% EtOAc-pet-ether) to afford (S)-1-((2S,4R,5R)-5-(2-acetamido-7-(cyclopropylmethyl)-6,8-dioxo-1,6,7,8-tetrahydro-9H-purin-9-yl)-4-acetoxytetrahydrofuran-2-yl)propyl acetate (15) (175 mg, 46.9%) as an light yellow solid: $C_{22}H_{29}N_5O_8$: ES+, m/z 492.2 [M+H]⁺. This compound was used further without any further purification.

Step-9: 2-Amino-7-(cyclopropylmethyl)-9-((2R,3R,5S)-3-hydroxy-5-((S)-1-hydroxypropyl)tetrahydrofuran-2-yl)-7,9-dihydro-1H-purine-6,8-dione, Compound 4

To a solution of (S)-1-((2S,4R,5R)-5-(2-acetamido-7-(cyclopropylmethyl)-6,8-dioxo-1,6,7,8-tetrahydro-9H-purin-9-yl)-4-acetoxytetrahydrofuran-2-yl)propyl acetate (15) (175 mg, 0.3564 mmol) in methanol (10 mL) was added K₂CO₃ (20 mg, 0.1424 mmol) at 0° C. The reaction mixture was stirred at room temperature for 36 h, concentrated and purified by prep-HPLC (Column: X-SELECT-C18 (250*19), 5 u Mobile phase: 0.1% TFA in H₂O:ACN gradient: (T % B):—0/5, 1/5, 8/40, 9/40, 9.1/98, 11/98, 11.1/5, 14/5 Flow Rate: 20 m). Pure fractions were collected and lyophilized to afford 2-amino-7-(cyclopropylmethyl)-9-((2R,3R,5S)-3-hydroxy-5-((S)-1-hydroxypropyl)tetrahydrofuran-2-yl)-7,9-dihydro-1H-purine-6,8-dione, Compound 4 (60 mg, 47.6%), as a white solid. $C_{16}H_{23}N_5O_5$: ES⁺, m/z 366.2 [M+H]⁺. ¹H NMR (500 MHz, DMSO-$d_6$): δ 10.87 (s, 1H), 6.45 (s, 2H), 5.52 (s, 1H), 4.76-4.75 (m, 1H), 4.01-3.97 (m, 1H), 3.64 (d, J=7 Hz, 2H), 3.27-3.25 (m, 1H), 2.39-2.35 (m, 1H), 1.79-1.74 (m, 1H), 1.41-1.37 (m, 1H), 1.28-1.17 (m, 2H), 0.88-0.85 (t, J=7 Hz, 3H), 0.40 (d, J=7.5 Hz, 2H), 0.34 (d, J=3.5 Hz, 2H).

Example 4: 2-Amino-7-(cyclopropylmethyl)-9-((2R,3R,5S)-3-hydroxy-5-((S)-1-hydroxypropyl)tetrahydrofuran-2-yl)-7,9-dihydro-8H-purin-8-one, Compound 5

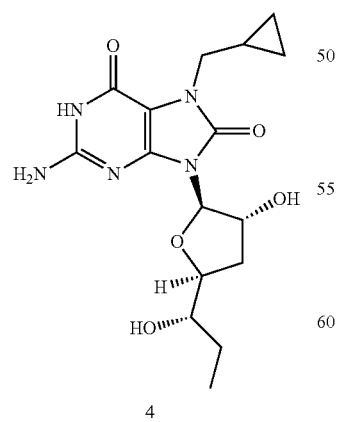

4

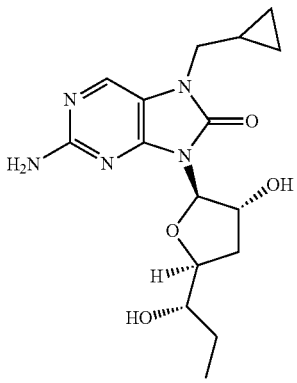 [SMILES: CC[C@H](O)[C@@H]1C[C@@H](O)[C@H](n2c(=O)n(CC3CC3)c3cnc(N)nc32)O1]

Compound 5 was prepared according to the following 2 step procedure.

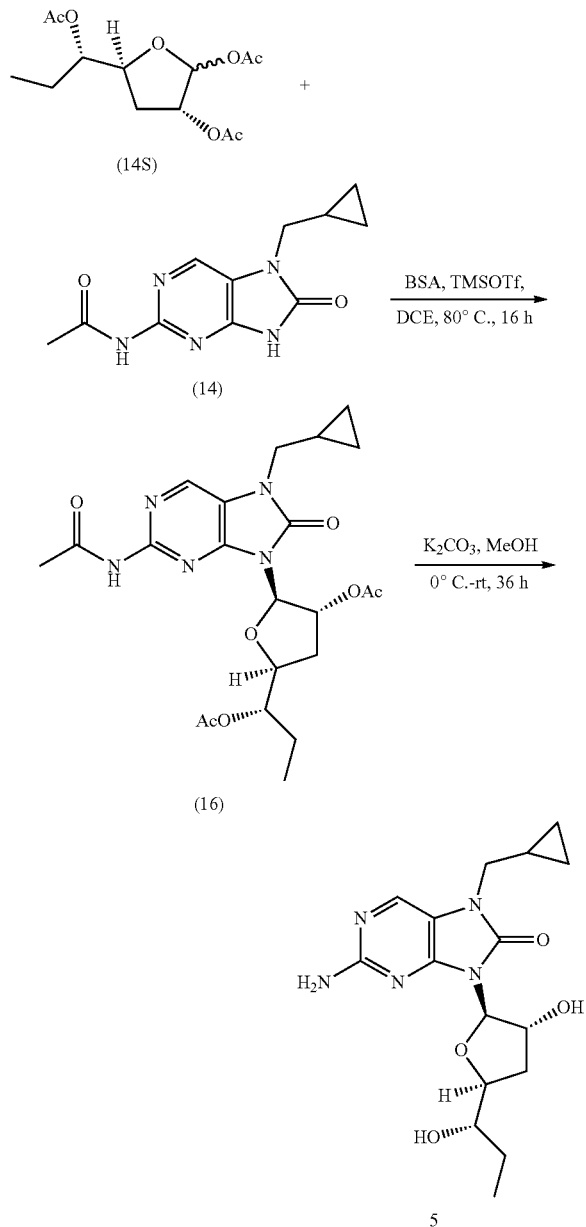

Step-1: (S)-1-((2S,4R,5R)-5-(2-Acetamido-7-(cyclopropylmethyl)-8-oxo-7,8-dihydro-9H-purin-9-yl)-4-acetoxytetrahydrofuran-2-yl)propyl acetate (16)

A stirred solution of N-(7-(Cyclopropylmethyl)-8-oxo-8,9-dihydro-7H-purin-2-yl)acetamide (14) (300 mg, 1.21 mmol), (3R,5S)-5-((S)-1-acetoxypropyl)tetrahydrofuran-2,3-diyl diacetate (14S) (384.7 mg, 1.33 mmol), bis(trimethylsilyl)acetamide (0.73 mL, 3.64 mmol) in 1,2-dichloroethane (25 mL) was heated to 80° C. for 30 min under argon. The reaction mixture was cooled to RT and 1,2-dichloroethane was removed under vacuum. The residue was dissolved in ACN (30 mL), TMSOTf (0.40 mL, 1.82 mmol) was added and the reaction mixture was maintained at 80° C. for 16 h. The mixture was then cooled to room temperature and concentrated under vacuum. The residue was diluted with aqueous sat·NaHCO₃ (50 mL) and extracted with EtOAc (3×50 mL). The combined EtOAc layers were washed with water (30 mL), brine (30 mL), dried over Na₂SO₄ and concentrated under vacuum. The crude compound was purified by column chromatography over silica gel (100-200 mesh) using 3% MeOH/DCM as eluant to afford 250 mg (53.6%) of (S)-1-((2S,4R,5R)-5-(2-acetamido-7-(cyclopropylmethyl)-8-oxo-7,8-dihydro-9H-purin-9-yl)-4-acetoxytetrahydrofuran-2-yl)propyl acetate (16) as a pale yellow solid. $C_{22}H_{29}N_5O_7$: ES⁺, m/z 476.1 [M+H]⁺.

Step 2: 2-Amino-7-(cyclopropylmethyl)-9-((2R,3R,5S)-3-hydroxy-5-((S)-1-hydroxypropyl)tetrahydrofuran-2-yl)-7,9-dihydro-8H-purin-8-one, Compound 5

To a stirred solution of (S)-1-((2S,4R,5R)-5-(2-acetamido-7-(cyclopropylmethyl)-8-oxo-7,8-dihydro-9H-purin-9-yl)-4-acetoxytetrahydrofuran-2-yl)propyl acetate (16) (250 mg, 0.526 mmol) in MeOH (15 mL) was added K₂CO₃ (145 mg, 1.052 mmol) at 0° C. The reaction mixture was stirred at RT for 16 h and acetic acid (0.05 mL, 0.815 mmol) was added. The solution was stirred for an additional 20 min and concentrated under reduced pressure at 30° C. The residue was purified by Prep HPLC (X-SELECT-C18 (250*19), 5 u Mobile phase: 10 mM ammonium bicarbonate in H₂O:MeCN Gradient: (T % B):—0/20, 8/35, 11/35, 11/98, 13/98, 13.1/20, 16/20 Flow Rate: 18 ml) to afford 35 mg (46%) of 2-amino-7-(cyclopropylmethyl)-9-((2R,3R,5S)-3-hydroxy-5-((S)-1-hydroxypropyl)tetrahydrofuran-2-yl)-7,9-dihydro-8H-purin-8-one, Compound 5 as an off white solid. $C_{16}H_{23}N_5O_4$: ES⁺, m/z 350.1 [M+H]⁺. ¹H NMR (500 MHz, DMSO-d₆): δ 8.06 (s, 1H), 6.24 (brs, 2H), 5.64-5.60 (m, 1H), 5.44 (bs, 1H), 4.82-4.79 (m, 1H), 4.61 (bs, 1H), 4.03-4.02 (m, 1H), 4.03-4.01 (m, 1H), 3.62 (d, J=7.0 Hz, 2H), 3.31 (s, 1H), 2.49 (m, 1H), 1.80-1.78 (m, 1H), 1.41-1.31 (m, 1H), 1.28-1.27 (m, 1H), 0.87 (t, J=7.0 Hz, 3H), 0.51-0.46 (m, 2H), 0.36-0.33 (m, 2H).

Example 5: 2-Amino-9-((2R,3R,5S)-3-hydroxy-5-((S)-1-hydroxypropyl)tetrahydrofuran-2-yl)-7-(prop-2-yn-1-yl)-7,9-dihydro-8H-purin-8-one, Compound 6

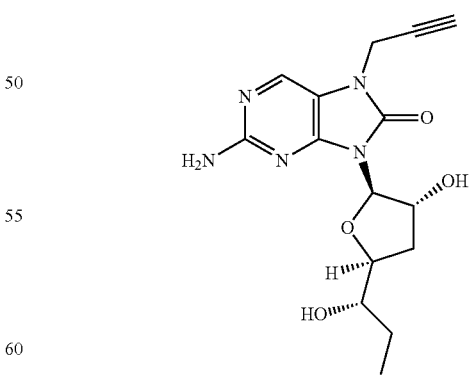

Preparation of Intermediate (21)

Intermediate compound (21) was synthesized according to the following multi-step procedure.

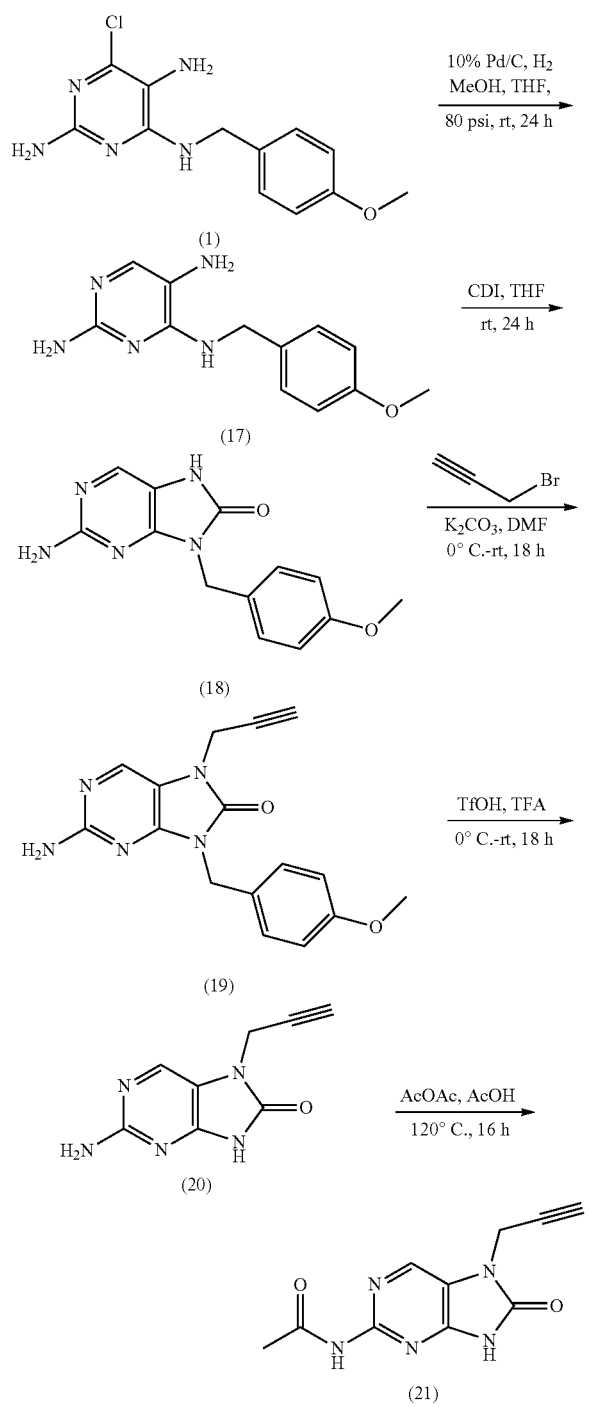

Step-1:
N4-(4-Methoxybenzyl)pyrimidine-2,4,5-triamine (17)

10% Pd—C (10 g) was added to a solution of 6-chloro-N4-(4-methoxy-benzyl)-pyrimidine-2,4,5-triamine (1) (2.5 g, 0.072 mol) in methanol (50 mL) and THF (150 mL). The reaction mixture was hydrogenated with $H_2$ gas at 80 psi of pressure in a Parr shaker vial at room temperature for 24 h. The reaction mixture was filtered through celite pad and the filtrate was evaporated. The crude compound was stirred in ethyl acetate (100 mL) for 15 min, the solid compound was collected by filtration and dried under vacuum to afford N4-(4-methoxybenzyl)pyrimidine-2,4,5-triamine (17) (21.0 g, 95.8%), ES+, m/z 246.2 [M+H]$^+$; $C_{12}H_{15}N_5O$; $^1$H NMR (400 MHz, DMSO-d$_6$): δ 11.71 (bs, 1H), 8.75-8.68 (m, 1H), 7.31 (d, J=8.4 Hz, 2H), 7.25 (bs, 2H), 7.07 (s, 1H), 6.90 (d, J=8 Hz, 2H), 4.77 (bs, 2H), 4.56 (d, J=5.6 Hz, 2H), 3.73 (s, 3H).

Step-2: 2-Amino-9-(4-methoxybenzyl)-7,9-dihydro-8H-purin-8-one (18)

A mixture of N4-(4-methoxybenzyl)pyrimidine-2,4,5-triamine (17) (23.0 g, 9.39 mol) and 1,1'-carbonyldiimidazole (18.3 g, 11.27 mol) in THF (250 mL) was stirred at room temperature for 18 h. The reaction mixture was concentrated under reduced pressure. To the resulting residue was added ice cold water and stirred for 30 min at room temperature. The precipitated solid was filtered, washed with water and dried under vacuum to afford (22.0 g, 86.6%) of 2-amino-9-(4-methoxybenzyl)-7,9-dihydro-8H-purin-8-one (18) as a light brown solid. ES+, m/z 272.2 [M+H]$^+$; $C_{13}H_{13}N_5O_2$; $^1$H NMR (400 MHz, DMSO-d$_6$): δ 10.81 (s, 1H), 7.73 (s, 1H), 7.23 (d, J=8.0 Hz, 2H), 6.88 (d, J=8.4 Hz, 2H), 6.19 (s, 2H), 4.80 (s, 2H), 3.72 (s, 3H).

Step-3: 2-Amino-9-(4-methoxybenzyl)-7-(prop-2-yn-1-yl)-7,9-dihydro-8H-purin-8-one (19)

Propargyl bromide (87 mL, 77.49 mol) was added to a suspension of 2-amino-9-(4-methoxybenzyl)-7,9-dihydro-8H-purin-8-one (18) (17.5 g, 6.46 mol) and $K_2CO_3$ (13.4 g, 9.69 mol) in DMF (175 mL) at 0° C. and stirred at room temperature for 18 h. The reaction mixture was quenched with ice water (400 mL) and stirred for 30 min. The resulting precipitated solid was filtered, washed with water and dried under vacuum to afford 2-amino-9-(4-methoxybenzyl)-7-(prop-2-yn-1-yl)-7,9-dihydro-8H-purin-8-one (19) (17.5 g, 86.68%) as a brown solid. ES$^+$, m/z 310.1 [M+H]$^+$; $C_{16}H_{15}N_5O_2$; $^1$H NMR (400 MHz, DMSO-d$_6$): δ 7.97 (s, 1H), 7.24 (d, J=8.4 Hz, 2H), 6.89 (dd, J=8.8 Hz, J=4.8 Hz, 2H), 6.36 (s, 2H), 4.84 (s, 2H), 4.64 (d, J=2.4 Hz, 2H), 3.71 (s, 3H), 3.37 (s, 1H).

Step-4: 2-Amino-7-(prop-2-yn-1-yl)-7,9-dihydro-8H-purin-8-one (20)

Trifluoromethanesulfonic acid (21.84 g, 14.56 mol) was added to a suspension of 2-amino-9-(4-methoxybenzyl)-7-(prop-2-yn-1-yl)-7,9-dihydro-8H-purin-8-one (19) (15.0 g, 4.854 mol) in trifluoroacetic acid (16.65 g, 14.56 mol) at 0° C. under argon atmosphere and the resulting reaction mixture was stirred at room temperature for 18 h. The reaction mixture was quenched with ice cold water, made basic with excess sat. NaHCO$_3$ solution under vigorous stirring and filtered. The residual solid was taken into ethyl acetate, stirred for 30 min. and filtered. The solid residue was dried under vacuum to afford 2-amino-7-(prop-2-yn-1-yl)-7,9-dihydro-8H-purin-8-one (20) (6.50 g, 70.85%) as a light yellow solid. ES+, m/z 190.1 [M+H]$^+$; $C_8H_7N_5O$; $^1$H NMR (400 MHz, DMSO-d$_6$): δ 11.32 (s, 1H), 7.57 (s, 1H), 5.60 (s, 2H), 4.46 (s, 2H), 3.22 (s, 1H).

Step-5: N-(8-Oxo-7-(prop-2-yn-1-yl)-8,9-dihydro-7H-purin-2-yl)acetamide (21)

Acetic anhydride (4.86 mL, 4.76 mol) was added to a solution of 2-amino-7-(prop-2-yn-1-yl)-7,9-dihydro-8H-purin-8-one (20) (6.0 g, 3.17 mol) in DMF (60 mL) at room temperature under argon atmosphere and the resulting reaction mixture was stirred at 140° C. for 10 h. The reaction mixture was cooled to 0° C., whereupon a solid was formed under stirring for 1 h. The product was filtered, washed with water and dried under vacuum to afford N-(8-oxo-7-(prop-2-yn-1-yl)-8,9-dihydro-7H-purin-2-yl)acetamide (21) (5.8 g, 79%) as a light yellow solid. ES+, m/z 232.1 [M+H]$^+$; $C_{10}H_9N_5O_2$; $^1$H NMR (500 MHz, DMSO-d$_6$): δ 9.80 (s, 1H), 7.76 (s, 1H), 6.17 (s, 1H), 4.53 (s, 2H), 3.24 (s, 1H), 2.11 (s, 3H).

Step-6: (S)-1-((2S,4R,5R)-5-(2-Acetamido-8-oxo-7-(prop-2-yn-1-yl)-7,8-dihydro-9H-purin-9-yl)-4-acetoxytetrahydrofuran-2-yl)propyl acetate (22)

Compound 6 was prepared according to the following 2 step procedure.

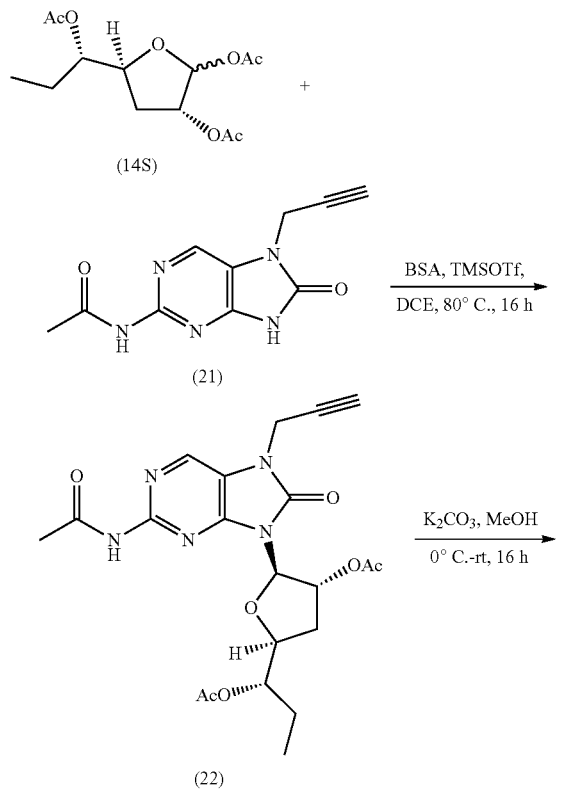

A stirred mixture of N-(8-oxo-7-(prop-2-yn-1-yl)-8,9-dihydro-7H-purin-2-yl)acetamide (21) (300 mg, 1.298 mmol), (3R,5S)-5-((S)-1-acetoxypropyl)tetrahydrofuran-2,3-diyl diacetate (14S) (411 mg, 1.428 mmol), bis(trimethylsilyl)acetamide (0.87 mL, 3.894 mmol) in 1,2-dichloroethane (30 mL) was heated to 80° C. for 30 min under argon. The reaction mixture was cooled to RT and 1,2-dichloroethane was removed under vacuum. The residue was dissolved in ACN (30 mL) and TMSOTf (0.36 mL, 1.945 mmol) was added. The stirred reaction mixture was heated to 80° C. for 16 h. The reaction mixture was cooled to room temperature and concentrated under vacuum. The residue was diluted with aqueous sat. NaHCO$_3$ (50 mL) and extracted with EtOAc (3×50 mL). The combined EtOAc layer were washed with water (30 mL), brine (30 mL), dried over Na$_2$SO$_4$ and concentrated under vacuum. The crude compound was purified by column chromatography over silica gel (100-200 mesh) using 3% MeOH/DCM as eluent to afford 320 mg (53.6%) of (S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)propyl acetate (22) as a pale yellow solid. ES+, m/z 460.2 [M+H]$^+$; $C_{21}H_{25}N_5O_7$.

Step-7: 2-Amino-9-((2R,3R,5S)-3-hydroxy-5-((S)-1-hydroxypropyl)tetrahydrofuran-2-yl)-7-(prop-2-yn-1-yl)-7,9-dihydro-8H-purin-8-one, Compound 6

To a stirred solution of (S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)propyl acetate (22) (150 mg, 0.326 mmol) in MeOH (15 mL) was added K$_2$CO$_3$ (90 mg, 0.653 mmol) at 0° C. Stirring was continued at RT for 16 h. Acetic acid (0.05 mL, 0.815 mmol) was added to this solution, stirred for 20 min. and concentrated under reduced pressure at 30° C. The residue was purified by normal phase GRACE flash chromatography (5% MeOH in DCM) to afford 50 mg (46%) of 2-amino-9-((2R,3R,5S)-3-hydroxy-5-((S)-1-hydroxypropyl)tetrahydrofuran-2-yl)-7-(prop-2-yn-1-yl)-7,9-dihydro-8H-purin-8-one, Compound 6 as an off white solid. ES+, m/z 334.2 [M+H]$^+$; $C_{15}H_{19}N_5O_4$; $^1$H NMR (500 MHz, DMSO-d$_6$): δ 8.01 (s, 1H), 6.34 (brs, 2H), 5.60 (d, J=3.0 Hz, 1H), 5.42 (d, J=4.5 Hz, 1H), 4.80 (t, J=3.5 Hz, 1H), 4.63 (d, J=2.5 Hz, 2H), 4.54 (d, J=6.5 Hz, 1H), 4.03-4.01 (m, 1H), 3.39 (t, J=2.5 Hz, 1H), 3.29-3.28 (m, 1H), 2.45-2.42 (m, 1H), 1.81-1.78 (m, 1H), 1.45-1.41 (m, 1H), 1.28-1.26 (m, 1H), 0.87 (t, J=7.5 Hz, 3H).

Example 6: 2-Amino-9-((2R,3R,5S)-3-hydroxy-5-((S)-1-hydroxypropyl)tetrahydrofuran-2-yl)-7-(propa-1,2-dien-1-yl)-7,9-dihydro-8H-purin-8-one, Compound 7

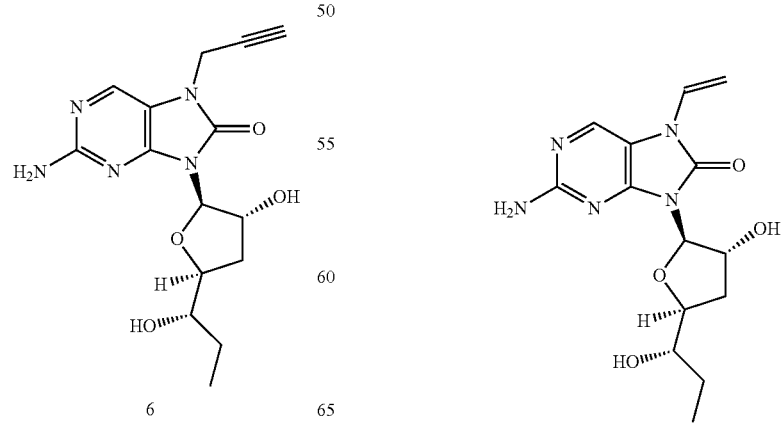

To a stirred solution of (S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)propyl acetate (22) (150 mg, 0.326 mmol) in MeOH (15 mL) was added K$_2$CO$_3$ (135 mg, 0.980 mmol) at 0° C. The reaction mixture was stirred at RT for 16 h, whereupon it was concentrated under reduced pressure. The residue was purified by normal phase GRACE flash chromatography (5% MeOH in DCM) and further purified by reverse phase GRACE flash chromatography (0.01% HCO$_2$H in ACN). The compound thus obtained was washed with acetonitrile (10 mL) and dried to afford 40 mg (36.6%) of 2-amino-9-((2R,3R,5S)-3-hydroxy-5-((S)-1-hydroxypropyl)tetrahydrofuran-2-yl)-7-(propa-1,2-dien-1-yl)-7,9-dihydro-8H-purin-8-one, Compound 7. ES+, m/z 334.1 [M+H]$^+$; C$_{15}$H$_{19}$N$_5$O$_4$: $^1$H NMR (500 MHz, DMSO-d$_6$): δ 8.12 (s, 1H), 7.20 (t, J=6.5 Hz, 1H), 6.47 (brs, 2H), 5.82 (d, J=6.5 Hz, 2H), 5.63 (d, J=3.0 Hz, 1H), 5.42 (d, J=7.5 Hz, 1H), 4.81-4.78 (m, 1H), 4.50 (d, J=6.5 Hz, 1H), 4.04-4.02 (m, 1H), 3.31-3.28 (m, 1H), 2.50-2.42 (m, 1H), 1.79-1.78 (m, 1H), 1.47-1.39 (m, 1H), 1.28-1.23 (m, 1H), 0.87 (t, J=7.5 Hz, 3H).

Example 7: 2-Amino-9-((2R,3R,5S)-3-hydroxy-5-((S)-1-hydroxypropyl)tetrahydrofuran-2-yl)-7-(propa-1,2-dien-1-yl)-7,9-dihydro-1H-purine-6,8-dione, Compound 8

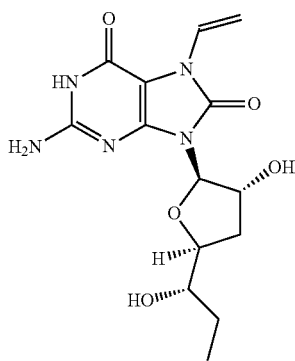 [SMILES: C=Cn1c(=O)n([C@@H]2O[C@H]([C@@H](O)CC)C[C@H]2O)c2nc(N)[nH]c(=O)c21]

To a stirred solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propyl acetate (7A) (200 mg, 0.421 mmol) in MeOH (10 mL) was added K$_2$CO$_3$ (290 mg, 2.10 mmol) at 0° C. The reaction mixture was stirred at rt for 16 h and methanol was concentrated under reduced pressure at rt. The residue obtained was directly purified by GRACE reverse phase 0.1% FA:ACN (performed twice) and pure fraction was lyophilized to afford 2-amino-9-((2R,3R,5S)-3-hydroxy-5-((S)-1-hydroxypropyl)tetrahydrofuran-2-yl)-7-(propa-1,2-dien-1-yl)-7,9-dihydro-1H-purine-6,8-dione as an off white solid. C$_{15}$H$_{19}$N$_5$O$_5$: $^1$H NMR (500 MHz, DMSO-d$_6$): δ 10.96 (brs, 1H), 7.18 (t, J=6.5 Hz, 1H), 6.60 (brs, 2H), 5.56 (d, J=3.0 Hz, 1H), 5.51 (d, J=3.0 Hz, 2H), 5.45 (d, J=8.0 Hz, 1H), 4.74-4.72 (m, 1H), 4.48 (d, J=6.5 Hz, 1H), 3.98 (q, J=3.0 Hz, 1H), 3.29-3.26 (m, 1H), 2.36-2.33 (m, 1H), 1.76-1.73 (m, 1H), 1.39-1.38 (m, 1H), 1.27-1.24 (m, 1H), 0.87 (t, J=7.5 Hz, 3H).

Example 8: 2-Amino-9-((2R,3R,5S)-3-hydroxy-5-((S)-1-hydroxyethyl)tetrahydrofuran-2-yl)-7-(prop-2-yn-1-yl)-7,9-dihydro-1H-purine-6,8-dione, Compound 9

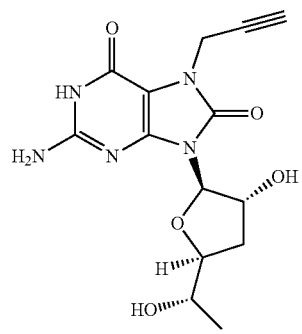 [SMILES: C#CCn1c(=O)n([C@@H]2O[C@H]([C@H](C)O)C[C@H]2O)c2nc(N)[nH]c(=O)c21]

Compound 9 was also synthesized according to the following multi-step procedure.

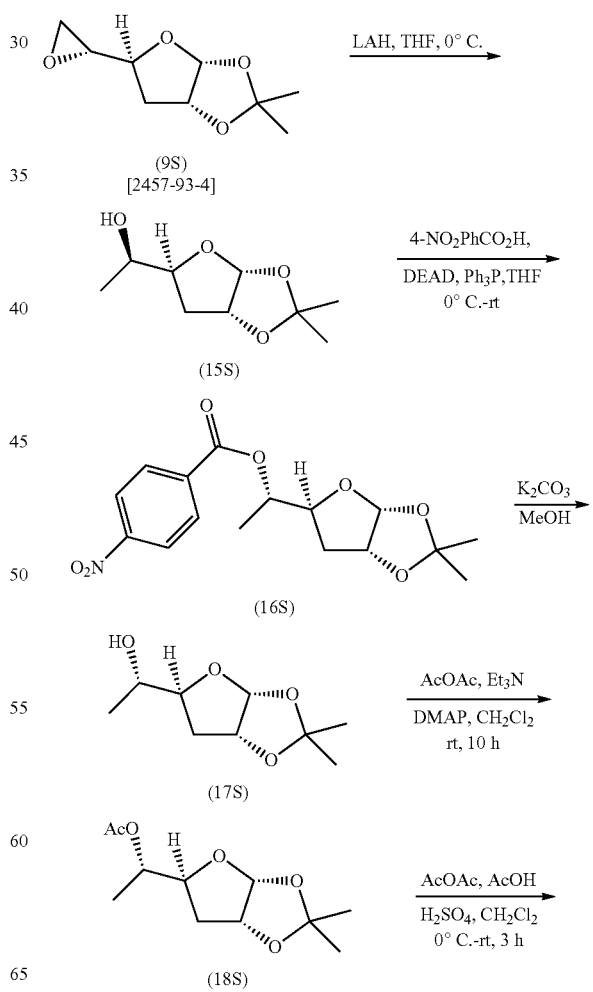

-continued

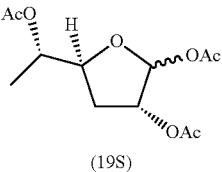

(19S)

(6) + (19S) $\xrightarrow[\text{80° C., 16 h}]{\text{BSA, TMSOTf} \atop \text{DCE, MeCN,}}$

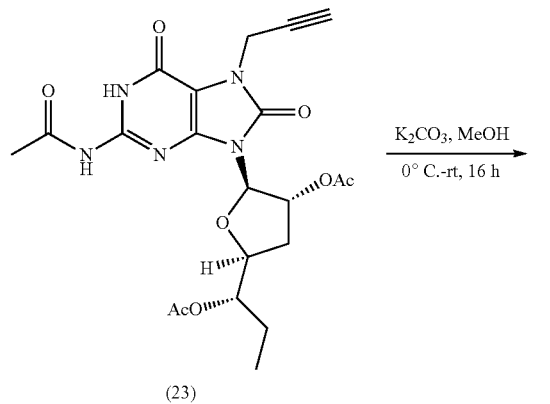

(23)

$\xrightarrow[\text{0° C.-rt, 16 h}]{\text{K}_2\text{CO}_3\text{, MeOH}}$ 9

Step-1: (R)-1-((3aR,5S,6aR)-2,2-Dimethyltetrahydrofuro[2,3-d][1,3]dioxol-5-yl)ethan-1-ol (15S)

To a stirred solution of (3aR,5S,6aR)-2,2-dimethyl-5-((R)-oxiran-2-yl)tetrahydrofuro[2,3-d][1,3]dioxole (9S) in dry THF (3 g, 15.9 mmol) under N$_2$ atmosphere was added LAH (1 M in THF, 53 mL, 159 mmol) at 0° C. After being stirred at 0° C. for 2 hrs, the reaction mixture was quenched with saturated NH$_4$Cl solution (50 mL). The organic layer was separated and the aqueous phase was extracted with EtOAc (2×200 mL). The combined organic layer was dried over Na$_2$SO$_4$ and concentrated in vacuum. The crude was purified by column chromatography on silica gel (100-200 mesh, eluting with 40% EtOAc in petroleum ether) to afford 2.7 g (89%) of (R)-1-((3aR,5S,6aR)-2,2-dimethyltetrahydrofuro[2,3-d][1,3]dioxol-5-yl)ethan-1-ol as a colorless liquid. C$_9$H$_{16}$O$_4$: $^1$H NMR (400 MHz, CDCl$_3$): δ 5.82 (d, J=3.6 Hz, 1H), 4.75 (t, J=4.0 Hz, 1H), 4.19-4.08 (m, 2H), 2.05 (brs, 1H), 2.04-1.88 (m, 2H), 1.51 (s, 3H), 1.32 (s, 3H), 1.14 (d, J=6.4 Hz, 3H).

Step-2: (S)-1-((3aR,5S,6aR)-2,2-Dimethyltetrahydrofuro[2,3-d][1,3]dioxol-5-yl)ethyl 4-nitrobenzoate (16S)

To a stirred solution of (R)-1-((3aR,5S,6aR)-2,2-dimethyltetrahydrofuro[2,3-d][1,3]dioxol-5-yl)ethan-1-ol (15S) (2.7 g, 39 mmol) in THF (30 mL) was added triphenylphosphine (7.5 g, 28.7 mmol), 4-nitrobenzoic acid (4.7 g, 28.7 mmol) followed by addition of diethylazodicarboxylate (4.5 mL, 28.7 mmol) dropwise at 0° C. under N$_2$ atmosphere. After being stirred at 25° C. for 10 h, the mixture was quenched by addition of saturated NaHCO$_3$ solution (50 mL) and extracted with EtOAc (2×100 mL). The organic layers were combined, dried over Na$_2$SO$_4$ and concentrated in vacuum. The residue was purified by column chromatography on silica gel (100-200 mesh, eluting with 15% EtOAc in petroleum ether) to afford 3 g (62%) of (S)-1-((3aR,5S,6aR)-2,2-dimethyltetrahydrofuro[2,3-d][1,3]dioxol-5-yl) ethyl 4-nitrobenzoate as a light yellow liquid. C$_{16}$H$_{19}$NO$_7$: ES+, m/z 338.2 [M+H]$^+$. $^1$H NMR (400 MHz, CDCl$_3$): δ 8.30-8.20 (m, 4H), 5.86 (d, J=3.6 Hz, 1H), 5.23 (quintet, J=6.4 Hz, 1H), 4.76 (t, J=4.4 Hz, 1H), 4.38 (ddd, J=10.8, 6.0, 4.8 Hz, 1H), 2.10 (dd, J=13.2, 4.4 Hz, 1H), 1.68 (m, 1H), 1.63 (s, 3H), 1.41 (d, J=6.4 Hz, 3H), 1.33 (s, 3H).

Step-3: (S)-1-((3aR,5S,6aR)-2,2-Dimethyltetrahydrofuro[2,3-d][1,3]dioxol-5-yl)ethan-1-ol (17S)

To a stirred solution of (R)-1-((3aR,5S,6aR)-2,2-dimethyltetrahydrofuro[2,3-d][1,3]dioxol-5-yl)ethan-1-ol (16S) (5.5 g, 16.3 mmol) in methanol (50 mL) was added K$_2$CO$_3$ (4.5 g, 32.6 mmol). After being stirred at room temperature for 30 minutes, the resulted reaction mixture was filtered and the filtrate was concentrated in vacuum. The crude was purified by column chromatography on silica gel (100-200 mesh, eluting with 30% EtOAc in petroleum ether) to afford 2.7 g (88%) of (S)-1-((3aR,5S,6aR)-2,2-dimethyltetrahydrofuro[2,3-d][1,3]dioxol-5-yl)ethan-1-ol as a light yellow solid. C$_9$H$_{16}$O$_4$: $^1$H NMR (400 MHz, CDCl$_3$): δ 5.81 (d, J=3.6 Hz, 1H), 4.76 (t, J=4.2 Hz, 1H), 4.12-4.05 (m, 1H), 3.68-3.65 (m, 1H), 2.19 (d, J=4.0 Hz, 1H), 2.05-2.01 (m, 2H), 1.68-1.62 (m, 2H), 1.32 (s, 3H), 1.20 (s, 3H).

Step-4: (S)-1-((3aR,5S,6aR)-2,2-Dimethyltetrahydrofuro[2,3-d][1,3]dioxol-5-yl)ethyl acetate (18S)

To a stirred solution of (S)-1-((3aR,5S,6aR)-2,2-dimethyltetrahydrofuro[2,3-d][1,3]dioxol-5-yl)ethan-1-ol (17S) (2.7 g, 14.0 mmol), TEA (3.9 mL, 28.0 mmol), DMAP (0.122 g, 2.0 mmol) in anhydrous DCM (30 mL) was added acetic anhydride (2.1 mL, 21.0 mmol). After being stirred at 25° C. for 10 h the reaction mixture was quenched with saturated aq. NaHCO$_3$ solution (30 mL). The organic layer was separated and the aqueous phase was extracted with CH$_2$C$_2$ (2×100 mL). The combined organic layers were dried over Na$_2$SO$_4$ and concentrated in vacuum. The crude was purified by column chromatography on silica gel (100-200 mesh, eluting with 20% EtOAc in petroleum ether) to afford 3.2 g (96%) of (S)-1-((3aR,5S,6aR)-2,2-dimethyltetrahydrofuro[2,3-d][1,3]dioxol-5-yl)ethyl acetate as a colorless oil. C$_{11}$H$_{18}$O$_5$: $^1$H NMR (400 MHz, CDCl$_3$): δ 5.83 (d, J=4.0 Hz, 1H), 4.97-4.92 (m, 1H), 4.73 (t, J=3.2 Hz, 1H), 4.25-4.20 (m, 1H), 2.07-2.01 (m, 4H), 1.67-1.60 (m, 1H), 1.52 (s, 3H), 1.32 (s, 3H), 1.25 (d, J=4.0 Hz, 3H).

Step-5: (3R,5S)-5-((S)-1-Acetoxyethyl)tetrahydrofuran-2,3-diyl diacetate (19S)

To a solution of (S)-1-((3aR,5S,6aR)-2,2-dimethyltetrahydrofuro[2,3-d][1,3]dioxol-5-yl)ethyl acetate (18S) (3.2 g, 13.9 mmol), acetic acid (7.9 mL, 139.1 mmol) and acetic anhydride (6.9 mL, 69.5 mmol) in anhydrous DCM (30 mL) was added concentrated H$_2$SO$_4$ (0.3 mL) at 0° C. After being stirred at 25° C. for 3 hours, the reaction was quenched by addition of saturated aq. NaHCO$_3$ solution (100 mL). The organic layer was separated and the aqueous phase was extracted with EtOAc (2×100 mL). The combined organic layers was dried over anhydrous Na$_2$SO$_4$ and concentrated in vacuum. The crude mixture was purified by column chromatography on silica gel (100-200 mesh, eluting with 30% EtOAc in petroleum ether) to afford 1.3 g (47%) of (3R,5S)-5-((S)-1-acetoxypropyl)tetrahydrofuran-2,3-diyl diacetate as a colorless oil. C$_{12}$H$_{18}$O$_7$: $^1$H NMR (500 MHz, CDCl$_3$): δ 6.39 (s, 1H), 5.18 (d, J=3.6 Hz, 1H), 4.95-4.90 (m, 1H), 4.35-4.31 (m, 1H), 2.11-2.01 (m, 11H), 1.21 (d, J=5.2 Hz, 3H).

Step-6: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)ethyl acetate (23)

N-(6,8-Dioxo-7-(prop-2-yn-1-yl)-6,7,8,9-tetrahydro-1H-purin-2-yl)acetamide (6) (200 mg, 0.8 mmol) (3R,5S)-5-((S)-1-acetoxypropyl)tetrahydrofuran-2,3-diyl diacetate (19S) (265 mg, 0.96 mmol), BSA (0.61 mL, 2.4 mmol) were dissolved in 1,2-dichloroethane (20 mL) and the resulting reaction mixture was stirred at 80° C. for 30 min under argon. The reaction mixture was allowed to warm to RT and 1,2-dichloro ethane was removed by vacuum. The residue was re-dissolved in ACN (20 mL) followed by addition of TMSOTf (0.22 mL, 1.2 mmol). The reaction mixture was heated at 80° C. for 16 h. Then the reaction mixture was cooled to room temperature and concentrated under vacuum and the residue was diluted with aq·NaHCO$_3$ (50 mL) and extracted with EtOAc (3×50 mL). The combined EtOAc layer was washed with water (30 mL), brine (30 mL), dried over anhydrous Na$_2$SO$_4$ and concentrated under vacuum. The crude compound was purified by GRACE (80% EtOAc in pet ether) to afford 200 mg (53%) of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)ethyl acetate as an off-white solid. C$_{20}$H$_{23}$N$_5$O$_8$: ES+, m/z 462.2 [M+H]$^+$.

Step-6: 2-Amino-9-((2R,3R,5S)-3-hydroxy-5-((S)-1-hydroxyethyl)tetrahydrofuran-2-yl)-7-(prop-2-yn-1-yl)-7,9-dihydro-1H-purine-6,8-dione, Compound 9

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)ethyl acetate (23) (200 mg, 0.43 mmol) in MeOH (10 mL) was added K$_2$CO$_3$ (59.6 mg, 0.43 mmol) at 0° C. The resultant reaction mixture was stirred at RT for 16 h. Then methanol was concentrated under reduced pressure at RT and the residue obtained was purified by Prep-HPLC. Upon lyophilization of the pure fractions afforded 35 mg (24%) of 2-amino-9-((2R,3R,5S)-3-hydroxy-5-((S)-1-hydroxyethyl)tetrahydrofuran-2-yl)-7-(prop-2-yn-1-yl)-7,9-dihydro-1H-purine-6,8-dione, Compound 9 as an off white solid. C$_{14}$H$_{17}$N$_5$O$_5$: ES+, m/z 336.1 [M+H]$^+$; $^1$H NMR (400 MHz, DMSO-d$_6$): δ 10.93 (brs, 1H), 6.54 (brs, 2H), 5.22 (d, J=4.0 Hz, 1H), 5.39 (d, J=2.8 Hz, 1H), 5.39 (d, J=4.4 Hz, 1H), 4.75-4.71 (m, 1H), 4.63-4.57 (m, 2H), 3.94-3.88 (m, 1H), 3.58-3.54 (m, 1H), 3.22 (s, 1H), 2.38-2.33 (m, 1H), 1.75-1.70 (m, 1H), 1.06 (d, J=6.4 Hz, 3H).

Example 9: Compounds 10 and 11

2-Amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-1H-purine-6,8-dione, Compound 10

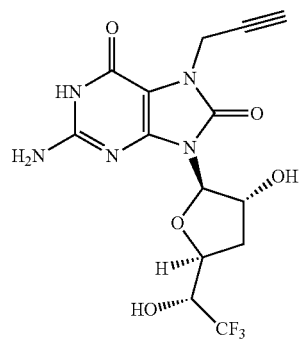 [SMILES: C#CCn1c(=O)n([C@@H]2O[C@H]([C@@H](O)C(F)(F)F)C[C@H]2O)c2nc(N)[nH]c(=O)c21]

2-Amino-9-((2R,3R,5S)-3-hydroxy-5-((S)-2,2,2-trifluoro-1-hydroxyethyl)tetrahydrofuran-2-yl)-7-(prop-2-yn-1-yl)-7,9-dihydro-1H-purine-6,8-dione, Compound 11

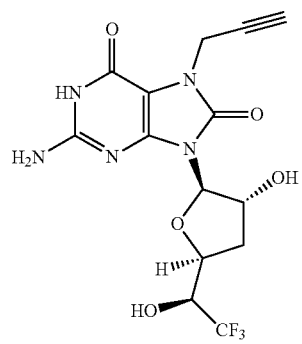 [SMILES: C#CCn1c(=O)n([C@@H]2O[C@H]([C@H](O)C(F)(F)F)C[C@H]2O)c2nc(N)[nH]c(=O)c21]

Compounds 10 and 11 were prepared according to the following multi-step procedures.

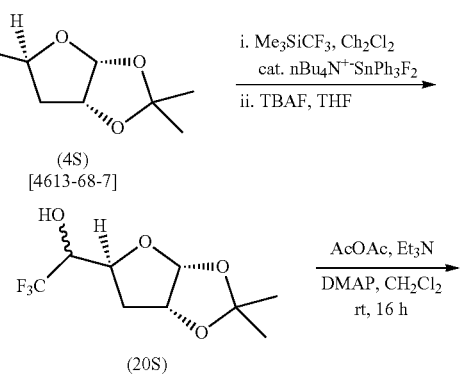

-continued

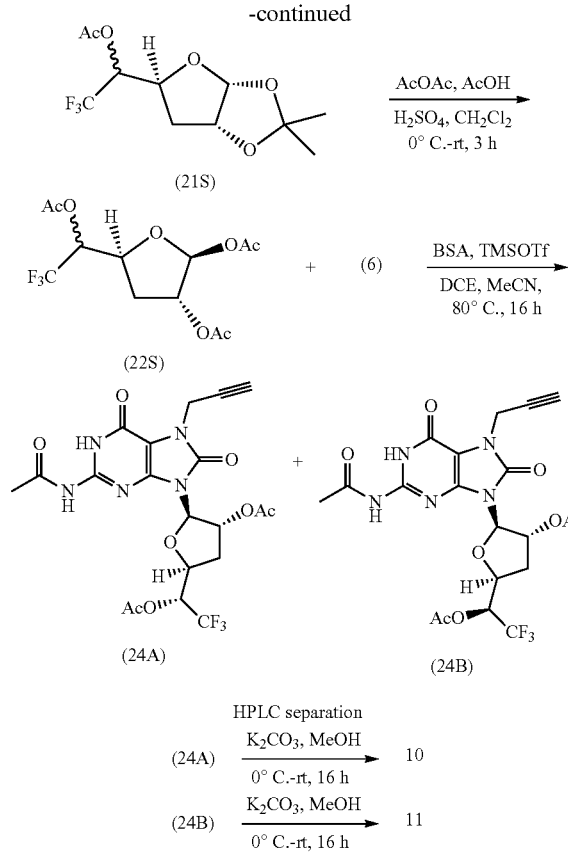

Step-1: 1-((3aR,5S,6aR)-2,2-Dimethyltetrahydrofuro[2,3-d][1,3]dioxol-5-yl)-2,2,2-trifluoroethan-1-ol (20S)

To a stirred solution of (3aR,5S,6aR)-2,2-dimethyltetrahydrofuro[2,3-d][1,3]dioxole-5-carbaldehyde (4S) (4.2 g, 24.41 mmol) in anhydrous dichloromethane (60 mL) was cooled to 0° C. and trifluoromethyltrimethylsilane (3.81 g, 26.86 mmol) was added followed by addition of a catalytic amount of tetra-n-butylammonium difluorotriphenylstannate (1.53 g, 2.44 mmol). The reaction mixture was warmed to room temperature and stirred for 10 h. The reaction mixture was then treated with one equivalent of TBAF (1M in THF) (24.4 mL) and stirred for 1 h and was then quenched with aqueous $NH_4Cl$ and dichloromethane. The organic layer was separated, dried over $Na_2SO_4$ and concentrated in vacuum. The crude product was purified by column chromatography on silica gel (100-200 mesh, eluting with 30% EtOAc in petroleum ether) to afford 1-((3aR,5S,6aR)-2,2-dimethyltetrahydrofuro[2,3-d][1,3]dioxol-5-yl)-2,2,2-trifluoroethan-1-ol (20S) (2 g, 33%, as a diastereomeric mixture) as a colourless oil. $C_9H_{13}F_3O_4$ (diastereomeric mixture): $^1$H NMR (400 MHz, $CDCl_3$): δ 5.86-5.81 (m, 2H), 4.79-4.75 (m, 2H), 4.50-4.43 (m, 2H), 4.38-4.34 (m, 1H), 3.88-3.83 (m, 1H), 2.92 (d, J=9.2 Hz, 1H), 2.79 (bs, 1H), 2.20-2.15 (m, 1H), 2.09-2.06 (m, 2H), 1.98-1.91 (m, 1H), 1.52 (s, 6H), 1.34 (s, 6H).

Step-2: 1-((3aR,5S,6aR)-2,2-Dimethyltetrahydrofuro[2,3-d][1,3]dioxol-5-yl)-2,2,2-trifluoroethyl acetate (21S)

To a stirred solution of 1-((3aR,5S,6aR)-2,2-dimethyltetrahydrofuro[2,3-d][1,3]dioxol-5-yl)-2,2,2-trifluoroethan-1-ol (20S) (2 g, 8.26 mmol), TEA (2.37 mL, 16.52 mmol), DMAP (0.201 g, 1.65 mmol) in anhydrous DCM (30 mL) was added acetic anhydride (1.22 mL, 12.39 mmol). After being stirred at 25° C. for 10 h, the reaction was quenched by saturated aq. $NaHCO_3$ solution (50 mL). The organic layer was separated and the aqueous phase was extracted with DCM (2×50 mL). The combined organic layers were dried over anhydrous $Na_2SO_4$ and concentrated in vacuum. The crude mixture was purified by column chromatography on silica gel (100-200 mesh, eluting with 30% EtOAc in petroleum ether) to afford 1-((3aR,5S,6aR)-2,2-dimethyltetrahydrofuro[2,3-d][1,3]dioxol-5-yl)-2,2,2-trifluoroethyl acetate (21S) (1.6 g, 69% as a diastereomeric mixture) as a colourless oil. $C_{11}H_{15}F_3O_5$ (as a diastereomeric mixture): $^1$H NMR (500 MHz, $CDCl_3$): δ 5.82 (d, J=3.5 Hz, 1H), 4.77 (d, J=4.0 Hz, 1H), 5.67-5.65 (m, 1H), 5.36-5.33 (m, 1H), 4.76-4.74 (m, 2H), 4.53-4.44 (m, 2H), 2.21-2.20 (m, 1H), 2.20 (s, 3H), 2.16 (s, 3H), 2.15-2.12 (m, 1H), 1.98-1.90 (m, 1H), 1.75-1.67 (m, 1H), 1.52 (s, 6H), 1.34 (s, 6H).

Step-3: (2S,3R,5S)-5-(1-Acetoxy-2,2,2-trifluoroethyl)tetrahydrofuran-2,3-diyl diacetate (22S)

To a solution of 1-((3aR,5S,6aR)-2,2-dimethyltetrahydrofuro[2,3-d][1,3]dioxol-5-yl)-2,2,2-trifluoroethyl acetate (1.6 g, 4.87 mmol), acetic acid (2.92 mL, 48.7 mmol) and acetic anhydride (2.32 mL, 24.39 mmol) in anhydrous DCM (30 mL) was added concentrated $H_2SO_4$ (0.1 mL) at 0° C. After being stirred at 25° C. for 3 hours, the reaction was quenched by addition of saturated aq·$NaHCO_3$ solution (100 mL). The organic layer was separated and the aqueous phase was extracted with DCM (2×70 mL). The combined organic layers were dried over anhydrous $Na_2SO_4$ and concentrated in vacuum. The crude was purified by column chromatography on silica gel (100-200 mesh, eluting with 20% EtOAc in petroleum ether) to afford (2S,3R,5S)-5-(1-acetoxy-2,2,2-trifluoroethyl)tetrahydrofuran-2,3-diyl diacetate (22S) (700 mg, 38%, as a diastereomeric mixture) as a colourless oil. $C_{12}H_{15}F_3O_7$ (as a diastereomeric mixture): $^1$H NMR (400 MHz, $CDCl_3$): δ 6.14 (d, J=9.6 Hz, 2H), 5.61-5.58 (m, 1H), 5.33-5.27 (m, 1H), 5.22-5.19 (m, 2H), 4.71-4.66 (m, 1H), 4.61-4.55 (m, 1H), 2.44-2.37 (m, 1H), 2.36-2.20 (s, 2H), 2.19 (s, 3H), 2.17 (s, 3H), 2.12-2.09 (m, 4H), 2.06 (s, 9H).

Step-4: (R)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24A) and (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24B)

To N-(6,8-dioxo-7-(Prop-2-yn-1-yl)-6,7,8,9-tetrahydro-1H-purin-2-yl)acetamide (6) (400 mg, 1.61 mmol), (2S,3R,5S)-5-(1-acetoxy-2,2,2-trifluoroethyl)tetrahydrofuran-2,3-diyl diacetate (22S) (637 mg, 1.94 mmol) dissolved in 1,2-dichloroethane (20 mL) was added BSA (1.2 mL, 4.85 mmol). The resulting reaction mixture was stirred at 80° C. for 30 min under argon and then cooled to room temperature and 1,2-dichloroethane was removed under vacuum. The residue was dissolved in acetonitrile (20 mL) followed by the addition of TMSOTf (0.44 mL, 2.42 mmol). The reaction mixture was heated at 80° C. for 16 h, cooled to room temperature and concentrated under vacuum and to the residue obtained was added aq. $NaHCO_3$ (50 mL) and extracted with EtOAc (3×50 mL). The combined EtOAc layer was washed with water (30 mL), brine (30 mL), dried over Na$_2$SO$_4$ and concentrated under vacuum. The crude compound was purified by GRACE flash chromatography (using 80% EtOAc in pet ether as eluent) to afford 250 mg (LC/MS: 55%-25% of diastereomeric mixture) of (R,S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24A, 24B) as a brown solid. Further purification by Prep-HPLC (X-SELECT-C18 (250*19), 5 u Mobile phase: 10 mM ammonium bicarbonate in H$_2$O:MeCN GRADIENT: (T % B):—0/20, 8/58, 16/98, 16.1/20, 19/20 Flow Rate: 18 ml/min Diluent: MeCN+H$_2$O+THF) gave 130 mg of (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24A); C$_{20}$H$_{20}$F$_3$N$_5$O$_8$: ES+, m/z 516.2 [M+H]$^+$ and 80 mg (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24B); C$_{20}$H$_{20}$F$_3$N$_5$O$_8$: ES+, m/z 516.1 [M+H]$^+$.

Step-5: 2-Amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-1H-purine-6,8-dione, Compound 10

To a solution of (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24A) (130 mg, 0.252 mmol) in MeOH (20 mL) was added K$_2$CO$_3$ (34 mg, 0.252 mmol) at 0° C. and the reaction mixture was stirred at RT for 16 h. Methanol was removed under reduced pressure at 30° C. The residue was directly purified by a reverse phase GRACE flash chromatography (using 10 mM ammonium bicarbonate in H$_2$O as eluent). Lyophilization of the pure fractions afforded 30 mg (50%) of 2-amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-1H-purine-6,8-dione, Compound 10 as a white solid. C$_{14}$H$_{14}$F$_3$N$_5$O$_5$: ES-, m/z 388.0 [M-H]$^-$. $^1$H NMR (400 MHz, DMSO-d$_6$): δ 11.21 (brs, 1H), 6.62 (brs, 2H), 6.53 (d, J=6.4 Hz, 1H), 5.58 (d, J=6.4 Hz, 1H), 5.10 (d, J=4.4 Hz, 1H), 4.833-4.79 (m, 1H), 4.59 (d, J=2.0 Hz, 2H), 4.26 (q, J=14.4 Hz, 14.8 Hz, 1H), 4.13 (q, J=14.0 Hz, 14.0 Hz, 1H), 3.21 (t, J=2.4 Hz, 1H), 2.72-2.65 (m, 1H), 1.96-1.90 (m, 1H).

Step-6: 2-Amino-9-((2R,3R,5S)-3-hydroxy-5-((S)-2,2,2-trifluoro-1-hydroxyethyl)tetrahydrofuran-2-yl)-7-(prop-2-yn-1-yl)-7,9-dihydro-1H-purine-6,8-dione, Compound 11

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2,2,2-trifluoroethyl acetate (24B) (80 mg, 0.155 mmol) in MeOH (20 mL) was added K$_2$CO$_3$ (21 mg, 0.155 mmol) at 0° C. and the reaction mixture was stirred at RT for 16 h. Methanol was removed under reduced pressure at 30° C. and the residue obtained was directly purified by reverse phase GRACE flash chromatography (using 10 mM ammonium bicarbonate in H$_2$O as eluent). Lyophilization of the pure fractions afforded 30 mg (81%) of 2-amino-9-((2R,3R,5S)-3-hydroxy-5-((S)-2,2,2-trifluoro-1-hydroxyethyl)tetrahydrofuran-2-yl)-7-(prop-2-yn-1-yl)-7,9-dihydro-1H-purine-6,8-dione, Compound 11 as a white solid. C$_{14}$H$_{14}$F$_3$N$_5$O$_5$: ES+, m/z 390.1 [M+H]$^+$. $^1$H NMR (400 MHz, DMSO-d$_6$): δ 11.02 (brs, 1H), 6.57 (brs, 2H), 6.30 (d, J=8.4 Hz, 1H), 5.57-5.54 (m, 2H), 4.76-4.72 (m, 1H), 4.60 (d, J=2.4 Hz, 2H), 4.34-4.29 (m, 1H), 4.05-4.00 (m, 1H), 3.24 (t, J=2.4 Hz, 1H), 2.56-2.52 (m, 1H), 1.97-1.91 (m, 1H).

Example 10: Compounds 12 and 13

2-Amino-9-((2R,3S,4R,5R)-4-fluoro-3-hydroxy-5-((R)-1-hydroxypropyl)tetrahydrofuran-2-yl)-7-(prop-2-yn-1-yl)-7,9-dihydro-1H-purine-6,8-dione, Compound 12

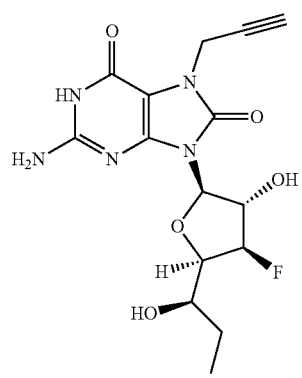 [SMILES: C#CCn1c(=O)n([C@@H]2O[C@H]([C@H](O)CC)[C@H](F)[C@H]2O)c2nc(N)[nH]c(=O)c21]

2-Amino-9-((2R,3S,4R,5S)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13

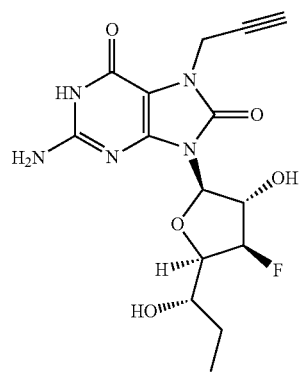 [SMILES: C#CCn1c(=O)n([C@@H]2O[C@H]([C@@H](O)CC)[C@H](F)[C@H]2O)c2nc(N)[nH]c(=O)c21]

Compounds 12 and 13 were prepared according to the following multi-step procedures.

The synthesis of (27S) was carried out according to the procedures described in U.S. Pat. No. 9,708,607B2.

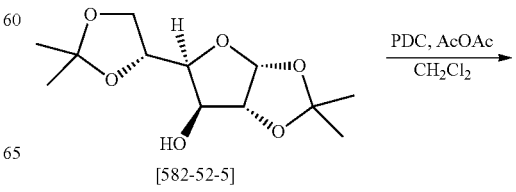

-continued

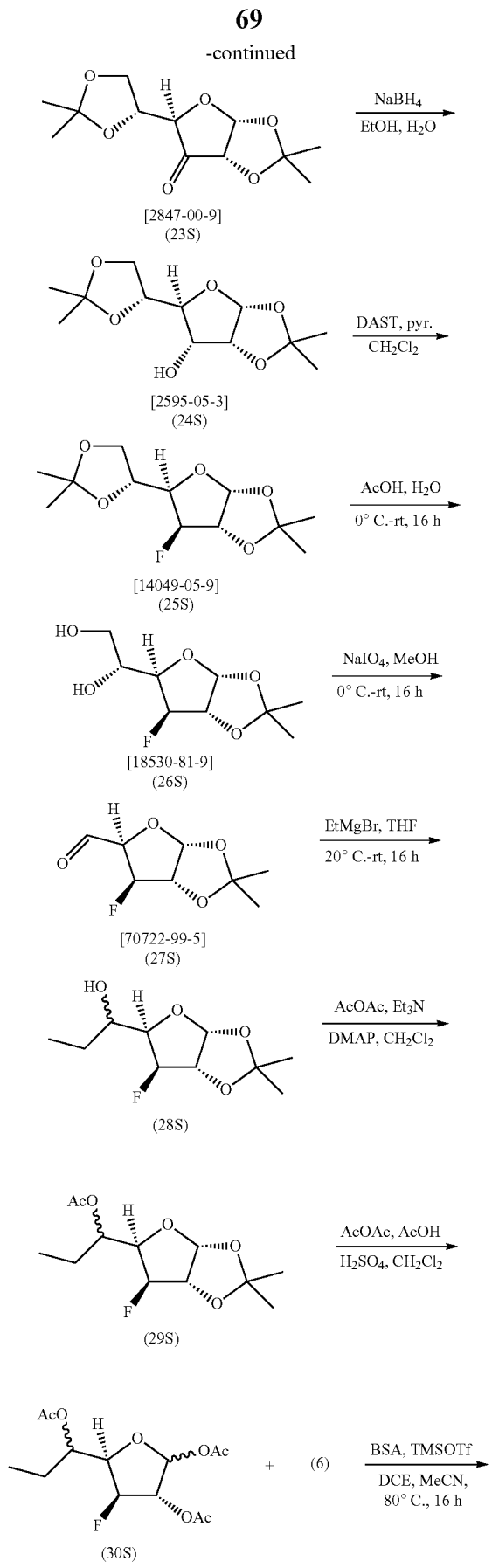

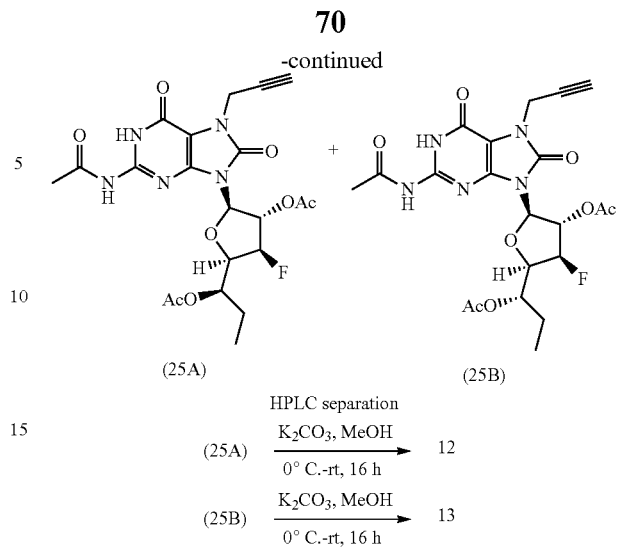

HPLC separation (25A) $\xrightarrow[0°\text{C.-rt, 16 h}]{K_2CO_3, \text{MeOH}}$ 12

(25B) $\xrightarrow[0°\text{C.-rt, 16 h}]{K_2CO_3, \text{MeOH}}$ 13

Step-1: (3aR,5R,6aS)-5-((R)-2,2-Dimethyl-1,3-dioxolan-4-yl)-2,2-dimethyldihydrofuro[2,3-d][1,3]dioxol-6(5H)-one (23S)

To a stirred solution of (3aR,5S,6S,6aR)-5-((R)-2,2-dimethyl-1,3-dioxolan-4-yl)-2,2-dimethyltetrahydrofuro[2,3-d][1,3]dioxol-6-ol [582-52-5] (2 g, 7.68 mmol) and Ac$_2$O (2 mL) in CH$_2$Cl$_2$ (20 mL) was added pyridinium dichromate (3.5 g, 9.30 mmol). The reaction mixture stirred at room temperature for 16 h. At this time the reaction mixture was concentrated under vacuum and EtOAc (3×100 mL) was added with stirring. The residual mixture was filtered through silica-gel and concentrated in vacuum. The crude product was used in next step without further purification, to afford (1.1 g, 55.44%) of (3aR,5R,6aS)-5-((R)-2,2-dimethyl-1,3-dioxolan-4-yl)-2,2-dimethyldihydrofuro[2,3-d][1,3]dioxol-6(5H)-one (23S) [2847-00-9] as an off white solid. C$_{12}$H$_{18}$O$_6$: $^1$H NMR (400 MHz, CDCl$_3$): δ 6.14 (d, J=4.8 Hz, 1H), 4.39-4.35 (m, 3H), 4.02 (d, J=0.8 Hz, 1H), 2.10 (s, 1H), 1.49 (s, 3H), 1.36 (s, 3H), 1.34 (s, 6H).

Step-2: (3aR,5S,6R,6aR)-5-((R)-2,2-Dimethyl-1,3-dioxolan-4-yl)-2,2-dimethyltetrahydrofuro[2,3-d][1,3]dioxol-6-ol (24S)

To a solution of (3aR,5R,6aS)-5-((R)-2,2-dimethyl-1,3-dioxolan-4-yl)-2,2-dimethyldihydrofuro[2,3-d][1,3]dioxol-6(5H)-one (23S) (1.9 g, 7.36 mmol) in EtOH:water (10 mL: 3 mL) was added NaBH$_4$ (292 mg, 8.83 mmol). The reaction mixture stirred at room temperature for 16 h and concentrated under vacuum. To the residue was added EtOAc (3×100 mL) with stirring. The mixture was then passed through silica-gel and concentrated in vacuum. The crude product was used in next step without any further purification to afford (1 g, 52.2%) of (3aR,5S,6R,6aR)-5-((R)-2,2-dimethyl-1,3-dioxolan-4-yl)-2,2-dimethyltetrahydrofuro[2,3-d][1,3]dioxol-6-ol (24S) [2595-05-3] as an off white solid. C$_{12}$H$_{20}$O$_6$: $^1$H NMR (500 MHz, CDCl$_3$): δ 5.65 (d, J=3.5 Hz, 1H), 5.09 (d, J=7.0 Hz, 1H), 4.46 (t, J=4.0 Hz, 1H), 4.24-4.21 (m, 1H), 3.93 (t, J=8.0 Hz, 1H), 3.85-3.73 (m, 3H), 1.44 (s, 3H), 1.32 (s, 3H), 1.27 (s, 3H), 1.26 (s, 3H).

Step-3: (3aR,5R,6S,6aS)-5-((R)-2,2-Dimethyl-1,3-dioxolan-4-yl)-6-fluoro-2,2-dimethyltetrahydrofuro[2,3-d][1,3]dioxole (25S)

To a solution of (3aR,5S,6R,6aR)-5-((R)-2,2-dimethyl-1,3-dioxolan-4-yl)-2,2-dimethyltetrahydrofuro[2,3-d][1,3]dioxol-6-ol (24S) (22 g, 84.61 mmol) in pyridine (10 ml, 126.92 mmol) and anhydrous $CH_2Cl_2$ (200 mL) was slowly added DAST (16.8 mL, 126.92 mmol). The reaction mixture and stirred at room temperature for 48 h, cooled to 0° C. and poured into saturated cold aqueous $NaHCO_3$ (100 mL). The aqueous layer was extracted with $CH_2Cl_2$ (3×300 mL). The combined organic layers were dried over $Na_2SO_4$, filtered and evaporated under reduced pressure. The crude residue was purified by column chromatography (silica gel; hexane: ethyl acetate 7:3) to afford 15 g (67.7%) of (3aR,5R,6S,6aS)-5-((R)-2,2-dimethyl-1,3-dioxolan-4-yl)-6-fluoro-2,2-dimethyltetrahydrofuro[2,3-d][1,3]dioxole (25S) [14049-05-9] as a thick yellow mass. $C_{12}H_{19}FO_5$: $^1H$ NMR (400 MHz, $CDCl_3$): δ 5.95 (d, J=3.6 Hz, 1H), 5.07 (dd, J=2.0 Hz, 1H), 4.71-4.68 (dd, J=4 Hz, 1H), 4.31-4.26 (m, 1H), 4.16-4.10 (m, 3H), 1.50 (s, 3H), 1.45 (s, 3H), 1.36 (s, 3H), 1.32 (s, 3H).

Step-4: (R)-1-((3aR,5R,6S,6aS)-6-Fluoro-2,2-dimethyltetrahydrofuro[2,3-d][1,3]dioxol-5-yl)ethane-1,2-diol (26S)

A solution of (3aR,5R,6S,6aS)-5-((R)-2,2-dimethyl-1,3-dioxolan-4-yl)-6-fluoro-2,2-dimethyltetrahydrofuro[2,3-d][1,3]dioxole (25S) (2.0 g, 7.66 mmol) in 60% AcOH/water (12 mL) was stirred at room temperature for 24 h. The mixture was concentrated under vacuum to afford 1.6 g (94%) of (R)-1-((3aR,5R,6S,6aS)-6-fluoro-2,2-dimethyltetrahydrofuro[2,3-d][1,3]dioxol-5-yl)ethane-1,2-diol (26S) [18530-81-9] as a colorless oil. The crude product was used without purification. $C_9H_{15}FO$: $^1H$ NMR (400 MHz, DMSO-$d_6$): δ 5.94 (d, J=3.6 Hz, 1H), 5.01 (dd, J=30.0, 2.0 Hz, 1H), 4.72 (dd, J=10.8, 4.0 Hz, 1H), 4.99 (ddd, 1H, J=30.0, 9.2, 2.0 Hz), 3.60-3.54 (m, 2H), 3.40-3.30 (m, 1H), 1.90 (s, 2H), 1.39 (s, 3H), 1.26 (s, 3H).

Step-5: (3aR,5R,6S,6aS)-6-Fluoro-2,2-dimethyltetrahydrofuro[2,3-d][1,3]dioxole-5-carbaldehyde (27S)

To a solution of (R)-1-((3aR,5R,6S,6aS)-6-fluoro-2,2-dimethyltetrahydrofuro[2,3-d][1,3]dioxol-5-yl)ethane-1,2-diol (26S) (2 g, 9.0 mmol) in methanol (20 mL) cooled in an ice bath was added sodium metaperiodate (2.3 g, 10.81 mmol). After being stirred at room temperature for 16 h, the resulting suspension was filtered. The filtrate was concentrated in vacuum. The residue was purified by column chromatography on silica gel (EtOAc) to afford 1.4 g (81.53%) of (3aR,5R,6S,6aS)-6-fluoro-2,2-dimethyltetrahydrofuro[2,3-d][1,3]dioxole-5-carbaldehyde (27S) [70722-99-5] as an colourless oil, $C_8H_{11}FO_4$, and was used in next step without further purification.

Step-6: 1-((3aR,5R,6S,6aS)-6-Fluoro-2,2-dimethyltetrahydrofuro[2,3-d][1,3]dioxol-5-yl)propan-1-ol (28S)

To a solution of (3aR,5R,6S,6aS)-6-fluoro-2,2-dimethyltetrahydrofuro[2,3-d][1,3]dioxole-5-carbaldehyde (27S) (1 g, 5.26 mmol) in THF (20 mL) was added ethyl magnesium bromide (1M in THF, 5.26 mL, 5.26 mmol) at −20° C. under argon. After being stirred at room temperature for 16 h the reaction mixture was quenched by saturated $NH_4Cl$ solution and extracted with EtOAc (3×50 mL). The combined organic layers were filtered and concentrated in vacuum. The residue was purified by column chromatography on silica gel (eluting with 1:4 EtOAc in Pet-ether) to afford 800 mg (69.14%) of a diastereomeric mixture of 1-((3aR,5R,6S,6aS)-6-fluoro-2,2-dimethyltetrahydrofuro[2,3-d][1,3]dioxol-5-yl)propan-1-ol (28S) as a colorless oil and used without further purification.

Step-7: 1-((3aR,5R,6S,6aS)-6-Fluoro-2,2-dimethyltetrahydrofuro[2,3-d][, 3]dioxol-5-yl)propyl acetate (29S)

To a stirred solution of 1-((3aR,5R,6S,6aS)-6-fluoro-2,2-dimethyltetrahydrofuro[2,3-d][1,3]dioxol-5-yl)propan-1-ol (28S) (1.2 g, 5.42 mmol), TEA (1.52 mL, 10.85 mmol) and DMAP (133 mg, 1.08 mmol) in anhydrous DCM (20 mL) was added acetic anhydride (830 mg, 8.14 mmol). The resultant reaction mixture was stirred at 22° C. for 18 h, then quenched with saturated aq. $NaHCO_3$ solution (20 mL). The organic layer was separated and the aqueous phase was extracted with DCM (2×50 mL). The combined organic layers were dried over $Na_2SO_4$, filtered and concentrated in vacuum. The crude product was purified by column chromatography on silica gel (100-200 mesh, 20% EtOAc in petroleum ether) to afford 700 mg (49%) of 1-((3aR,5R,6S,6aS)-6-fluoro-2,2-dimethyltetrahydrofuro[2,3-d][1,3]dioxol-5-yl)propyl acetate (29S) as a colorless oil (diastereomeric mixture). $C_{12}H_{19}FO_5$: $^1H$ NMR (400 MHz, $CDCl_3$): δ 5.96 (d, J=3.6 Hz, 1H), 5.13-5.07 (m, 1H), 4.90 (dd, J=50.0, 2.4 Hz, 1H), 4.68 (dd, J=10.6, 4.0 Hz, 1H), 4.24-4.01 (m, 2H), 2.04 (s, 3H), 1.92-1.85 (m, 1H), 1.71-1.64 (m, 1H), 1.51 (s, 3H), 1.32 (s, 3H), 0.95 (t, J=7.6 Hz, 3H).

Step-8: (3S,4S,5R)-5-(1-Acetoxypropyl)-4-fluorotetrahydrofuran-2,3-diyl diacetate (30S)

To a stirred solution of 1-((3aR,5R,6S,6aS)-6-fluoro-2,2-dimethyltetrahydrofuro[2,3-d][1,3]dioxol-5-yl)propyl acetate (29S) (600 mg, 2.28 mmol), acetic acid (1.3 mL, 22.81 mmol) and acetic anhydride (1.08 mL, 11.46 mmol) in anhydrous DCM (10 mL) was added concentrated $H_2SO_4$ (0.10 mL) at 0° C. After stirring at RT for 3 hours, the reaction mixture was quenched by addition of saturated aq. $NaHCO_3$ solution (10 mL). The organic layer was separated and the aqueous phase was extracted with DCM (2×50 mL). The combined organic layers were dried over $Na_2SO_4$ and concentrated in vacuum. The crude product was purified by column chromatography on silica gel (100-200 mesh, 30% EtOAc in petroleum ether) to afford a mixture of diastereomers (300 mg, 42.85%) of (3S,4S,5R)-5-(1-acetoxypropyl)-4-fluorotetrahydrofuran-2,3-diyl diacetate (30S) as a colorless oil. $C_{13}H_{19}FO_7$: $^1H$ NMR (400 MHz, $CDCl_3$): δ 6.13 (s, 1H), 5.30-5.15 (m, 1H), 5.12-5.04 (m, 1H), 4.37-4.29 (m, 2H), 4.44-4.34 (m, 1H), 2.10-2.08 (m, 9H), 1.88-1.69 (m, 1H), 1.68-1.59 (m, 1H), 0.95-0.88 (m, 3H).

Step-9: (R)-1-((2R,3S,4S,5R)-5-(2-Acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25A) and (S)-1-((2R,3S,4S,5R)-5-(2-Acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25B)

To N-(6,8-dioxo-7-(prop-2-yn-1-yl)-6,7,8,9-tetrahydro-1H-purin-2-yl)acetamide (6) (340 mg, 1.28 mmol), (3S,4S,5R)-5-(1-acetoxypropyl)-4-fluorotetrahydrofuran-2,3-diyl diacetate (30S) (504 mg, 1.66 mmol) dissolved in 1,2-dichloroethane (10 mL) was added bis(trimethylsilyl)acetamide (77 mg, 3.84 mmol). The reaction mixture was stirred at 80° C. for 30 min under argon, cooled to RT whereupon 1,2-dichloroethane was removed under vacuum. The residue was then dissolved in MeCN (20 mL) followed by addition of TMSOTf (0.43 mL, 1.92 mmol). The reaction mixture was heated at 80° C. for 16 h, cooled to room temperature and concentrated under vacuum. The residue was diluted with aq. NaHCO$_3$ (50 mL) and extracted with EtOAc (3×50 mL). The combined EtOAc layer was washed with water (30 mL), brine (30 mL), dried over Na$_2$SO$_4$, filtered and concentrated under vacuum. The crude compound was purified by Prep HPLC using KROMOSIL C18 column (150*25 MM), 10 u Mobile phase: 0.1% HCO$_2$H in H$_2$O:MeOH Gradient: (T % B): —0/50, 1/50, 8/70, 10/70, 10.1/98, 13/98, 13.1/50, 15/50 Flow Rate: 20 mL/min; Diluent: MeCN+H$_2$O+THF to afford 50 mg of (R)-1-((2R,3S,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25A); C$_{21}$H$_{24}$FN$_5$O$_8$: ES+, m/z 494.2 [M+H]$^+$ and 50 mg of (S)-1-((2R,3S,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25B); C$_{21}$H$_{24}$FN$_5$O$_8$: ES+, m/z 494.2 [M+H]$^+$ both as a yellow solids.

Step-10: 2-Amino-9-((2R,3S,4R,5R)-4-fluoro-3-hydroxy-5-((R)-1-hydroxypropyl)tetrahydrofuran-2-yl)-7-(prop-2-yn-1-yl)-7,9-dihydro-H-purine-6,8-dione, Compound 12

To a solution of (R)-1-((2R,3S,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25A) (50 mg, 0.10 mmol) in MeOH (4 mL) was added K$_2$CO$_3$ (14 mg, 0.10 mmol) at 0° C. The reaction mixture was stirred at RT for 16 h. Methanol was removed under reduced pressure at 30° C. The residue was directly purified by a reverse phase GRACE flash chromatography (using 0.01% aq. HCO$_2$H and MeCN as eluent). The pure fractions were lyophilized to afford 20 mg (53.7%) of 2-amino-9-((2R,3S,4R,5R)-4-fluoro-3-hydroxy-5-((R)-1-hydroxypropyl)tetrahydrofuran-2-yl)-7-(prop-2-yn-1-yl)-7,9-dihydro-1H-purine-6,8-dione, Compound 12 as a white solid. C$_{15}$H$_{18}$FN$_5$O$_5$: ES+, m/z 368.2 [M+H]$^+$. $^1$H NMR (400 MHz, DMSO-d$_6$): δ 11.04 (brs, 1H), 6.63 (brs, 2H), 5.91 (d, J=5.6 Hz, 1H), 5.33-5.32 (m, 1H), 5.28-5.25 (m, 1H), 5.00 (d, J=3.6 Hz, 1H), 4.85 (d, J=6.0 Hz, 1H), 4.59 (d, J=2.4 Hz, 2H), 3.71-3.60 (m, 2H), 3.24-3.23 (t, J=2.4 Hz, 1H), 1.59-1.53 (m, 1H), 1.32-1.25 (m, 1H), 0.88 (t, J=7.2 Hz, 3H).

Step-11: 2-Amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13

To a solution of (S)-1-((2R,3S,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25B) (50 mg, 0.11 mmol) in MeOH (4 mL) was added K$_2$CO$_3$ (16 mg, 0.11 mmol) at 0° C. The reaction mixture was stirred at RT for 16 h whereupon methanol was removed under reduced pressure at 30° C. The residue was purified by reverse phase GRACE flash chromatography (using 0.01% aq. HCO$_2$H and MeCN as eluent). The pure fractions were lyophilized to afford (15 mg, 40.3%) of 2-amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13 as a white solid. C$_{15}$H$_{18}$FN$_5$O$_5$: ES+, m/z 368.1 [M+H]$^+$. $^1$H NMR (400 MHz, DMSO-d$_6$): δ 11.0 (brs, 1H), 6.58 (brs, 2H), 5.94 (d, J=5.6 Hz, 1H), 5.36 (m, 1H), 5.29 (m, 1H), 4.97 (ddd, 1H, J=53.7, 4.6, 2.2 Hz, 1H), 4.82 (d, J=6.8 Hz, 1H), 4.61 (d, J=2.4 Hz, 2H), 3.80 (ddd, J=23.6, 7.0, 4.6 Hz, 1H), 3.54 (m, 1H), 3.25 (t, J=2.4 Hz, 1H), 1.49 (m, 1H), 1.33 (m, 1H), 0.92 (t, J=7.4 Hz, 3H).

Alternative Synthetic Procedure for Compound 13

Example 11: 2-Amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13

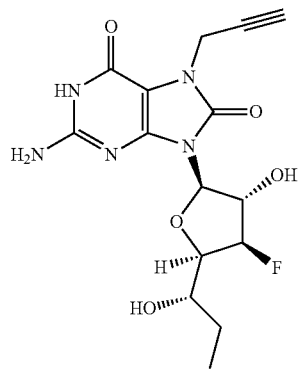 [SMILES: C#CCn1c(=O)n([C@@H]2O[C@H]([C@@H](O)CC)[C@H](F)[C@H]2O)c2nc(N)[nH]c(=O)c21]

Compound 13 was also prepared according to the following stereoselective multi-step synthesis.

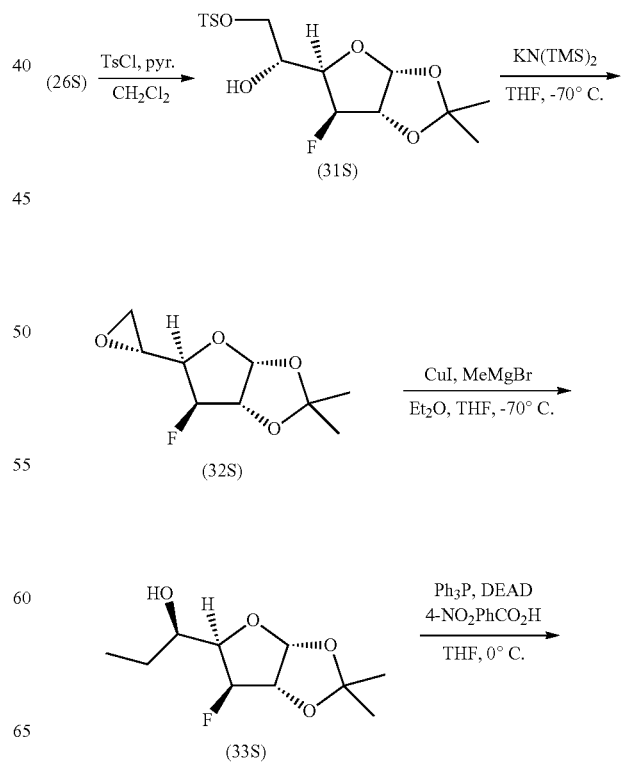

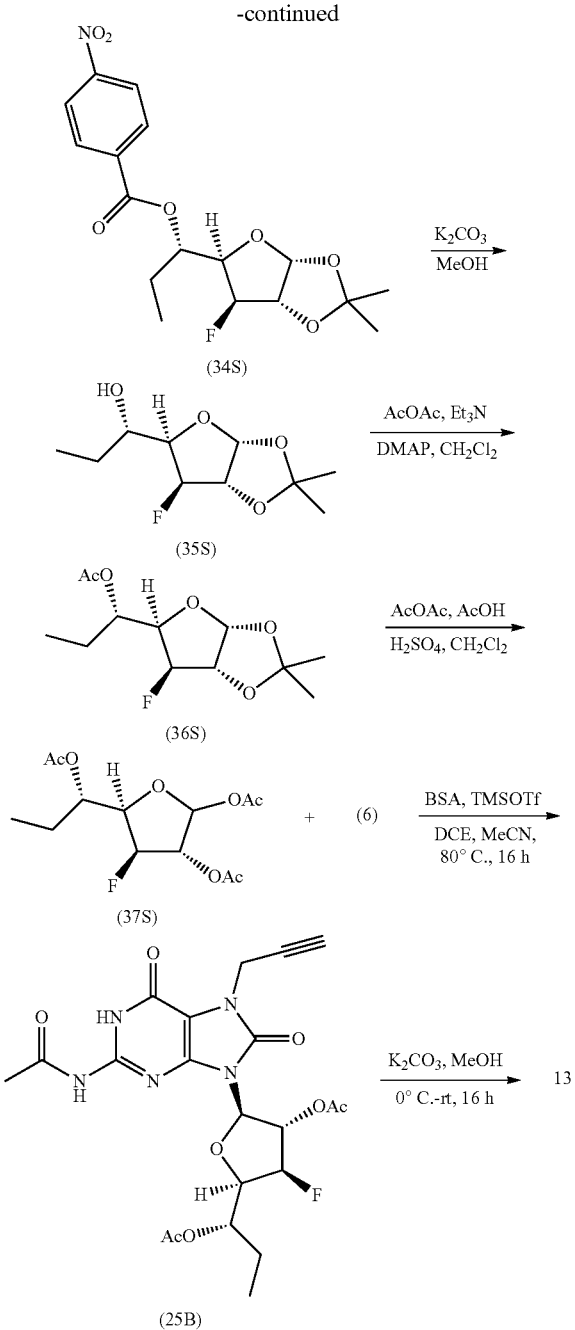

ing with 25% EtOAc in Pet-ether) to afford (2 g, 29.5%) of (R)-2-((3aR,5R,6S,6aS)-6-fluoro-2,2-dimethyltetrahydrofuro[2,3-d][1,3]dioxol-5-yl)-2-hydroxyethyl 4-methylbenzenesulfonate (31S) as a light yellow oil. $C_{16}H_{21}FO_7S$: ES+, m/z 394.2 [M+H$_2$O]$^+$. $^1$H NMR (400 MHz, CDCl$_3$): δ 7.81 (d, J=6.4 Hz, 2H), 7.37 (d, J=8.00 Hz, 2H), 5.90 (d, J=3.6 Hz, 1H), 5.13 (dd, J=2.4 Hz, 1H), 4.69 (dd, J=3.6 Hz, 1H), 4.32 (d, J=7.2 Hz, 1H), 4.13-4.04 (m, 3H), 2.47 (d, J=4.8 Hz, 1H), 2.45 (s, 3H), 1.46 (s, 3H), 1.31 (s, 3H).

Step-2: (3aR,5R,6S,6aS)-6-Fluoro-2,2-dimethyl-5-((R)-oxiran-2-yl)tetrahydrofuro[2,3-d][1,3]dioxole (32S)

To a solution of (R)-2-((3aR,5R,6S,6aS)-6-fluoro-2,2-dimethyltetrahydrofuro[2,3-d][1,3]dioxol-5-yl)-2-hydroxyethyl 4-methylbenzenesulfonate (31S) (2 g, 5.31 mmol) in anhydrous THF (10 mL) cooled at −78° C. was added potassium bis(trimethylsilyl)amide (6.43 mL, 6.43 mmol, 1 M in THF) under N$_2$ atmosphere. After being stirred at −78° C. for 1 h, the reaction mixture was poured into a saturated NH$_4$Cl solution. The organic layer was separated and the aqueous phase was extracted with EtOAc (2×100 mL). The combined organic layer was dried over Na$_2$SO$_4$, filtered and concentrated in vacuum. The crude product was purified by column chromatography over silica gel (100-200 mesh; 25% EtOAc in petroleum ether) to afford (900 mg, 82.9%) of (3aR,5R,6S,6aS)-6-fluoro-2,2-dimethyl-5-((R)-oxiran-2-yl) tetrahydrofuro[2,3-d][1,3]dioxole (32) as a light yellow oil. $C_9H_{13}FO_4$: $^1$H NMR: (400 MHz, CDCl$_3$): δ 6.00 (d, J=3.6 Hz, 1H), 5.06 (dd, J=50.0, 2.0 Hz, 1H), 4.73 (dd, J=10.8, 3.6 Hz, 1H), 3.80 (ddd, J=28.6, 6.8, 2.2 Hz, 1H), 3.22 (m, 1H), 2.93 (dd, J=5.0, 3.6 Hz, 1H), 2.80 (dd, J=5.0, 2.6 Hz, 1H), 1.45 (s, 3H), 1.33 (s, 3H).

Step-3: (R)-1-((3aR,5R,6S,6aS)-6-Fluoro-2,2-dimethyltetrahydrofuro[2,3-d][1,3]dioxol-5-yl)propan-1-ol (33S)

To a stirred suspension of CuI (186 mg, 0.980 mmol) in dry THF (20 mL) under N$_2$ atmosphere was added methylmagnesium bromide (1.0 M in diethyl ether, 14.7 mL, 14.70 mmol) at −78° C. After being stirred at −78° C. for 1 hour a solution of (3aR,5R,6S,6aS)-6-fluoro-2,2-dimethyl-5-((R)-oxiran-2-yl)tetrahydrofuro[2,3-d][1,3]dioxole (32S) (1.0 g, 4.90 mmol) in THF (10 mL) was added and stirred at −78° C. for an additional 2 hours. The reaction mixture was poured into a saturated NH$_4$Cl solution (200 mL), the organic layer was separated and the aqueous phase was extracted with EtOAc (2×200 mL). The combined organic layers were dried over Na$_2$SO$_4$, filtered and concentrated in vacuum. The crude product was purified by column chromatography on silica gel (100-200 mesh, 30% EtOAc in petroleum ether) to afford 1.0 g (92.3%) of (R)-1-((3aR,5R,6S,6aS)-6-fluoro-2,2-dimethyltetrahydrofuro[2,3-d][1,3]dioxol-5-yl)propan-1-ol (33S) as a light yellow oil. $C_{10}H_{17}FO_4$: $^1$H NMR (400 MHz, CDCl$_3$): δ 5.98 (d, J=3.6 Hz, 1H), 5.08 (dd, J=50.0, 2.4 Hz, 1H), 4.69 (dd, J=11.2, 3.6 Hz, 1H), 4.01 (dd, J=29.8, 2.4 Hz, 1H), 3.85 (m, 1H), 1.86-1.80 (m, 1H), 1.75 (d, J=6.0 Hz, 1H), 1.52 (s, 3H), 1.32 (s, 3H), 1.05 (t, J=7.2 Hz, 3H).

Step-4: (S)-1-((3aR,5R,6S,6aS)-6-Fluoro-2,2-dimethyltetrahydrofuro[2,3-d][1,3]dioxol-5-yl)propyl 4-nitrobenzoate (34S)

To a stirred solution of (R)-1-((3aR,5R,6S,6aS)-6-fluoro-2,2-dimethyltetrahydrofuro[2,3-d][1,3]dioxol-5-yl)propan- Step-1: (R)-2-((3aR,5R,6S,6aS)-6-Fluoro-2,2-dimethyltetrahydrofuro[2,3-d][1,3]dioxol-5-yl)-2-hydroxyethyl 4-methylbenzenesulfonate (31S)

To a solution of (R)-1-((3aR,5R,6S,6aS)-6-fluoro-2,2-dimethyltetrahydrofuro[2,3-d][1,3]dioxol-5-yl)ethane-1,2-diol (26S) (4 g, 18.01 mmol) in dry pyridine (40 mL) was added p-toluenesulfonyl chloride (4.79 g, 25.22 mmol) at 0° C. After stirring the reaction mixture at room temperature for 12 h, pyridine was removed under vacuum. The residue was diluted with water (100 mL) and extracted with EtOAc (2×200 mL). The combined EtOAc layer was dried over Na$_2$SO$_4$ and concentrated. The residue was purified by column chromatography on silica gel (100-200 mesh, elut- 1-ol (33S) (1.0 g, 4.52 mmol), triphenylphosphine (2.3 g, 9.04 mmol), 4-nitrobenzoic acid (1.51 g, 9.04 mmol) in THF (240 mL) was added diethylazodicarboxylate (1.57 mL, 9.04 mmol) dropwise at 0° C. under $N_2$ atm. After being stirred at RT for 10 h, the mixture was quenched by addition of a saturated $NaHCO_3$ solution (50 mL) and extracted with EtOAc (2×50 mL). The organic layers were combined, dried over $Na_2SO_4$, filtered and concentrated in vacuum. The residue was purified by column chromatography on silica gel (100-200 mesh, 15% EtOAc in pet ether) to afford (650 mg, 38.9%) of (S)-1-((3aR,5R,6S,6aS)-6-fluoro-2,2-dimethyltetrahydrofuro[2,3-d][1,3]dioxol-5-yl)propyl 4-nitrobenzoate (34S) as a light yellow solid. $C_{17}H_{20}FNO_7$: ES+, m/z 370.2 $[M+H]^+$. $^1H$ NMR (400 MHz, $CDCl_3$): δ 8.30-8.21 (m, 4H), 6.00 (d, J=3.6 Hz, 1H), 5.51 (m, 1H), 4.97 (dd, J=50.0, 2.4 Hz, 1H), 4.73 (dd, J=11.4, 3.6 Hz, 1H), 4.35 (ddd, J=29.2, 8.2, 2.4 Hz, 1H), 1.89-1.80 (m, 2H), 1.51 (s, 3H), 1.33 (s, 3H), 1.03 (t, J=7.2 Hz, 3H).

Step-5: (S)-1-((3aR,5R,6S,6aS)-6-Fluoro-2,2-dimethyltetrahydrofuro[2,3-d][1,3]dioxol-5-yl)propan-1-ol (35S)

To a stirred solution of (S)-1-((3aR,5R,6S,6aS)-6-fluoro-2,2-dimethyltetrahydrofuro[2,3-d][1,3]dioxol-5-yl)propyl 4-nitrobenzoate (34S) (650 mg, 1.76 mmol) in methanol (10 mL) was added $K_2CO_3$ (486 mg, 3.52 mmol). After being stirred at room temperature for 3 h, the resultant reaction mixture was filtered and the filtrate was concentrated in vacuum. The crude material was purified by column chromatography on silica gel (100-200 mesh, 30% EtOAc in petroleum ether) to afford (389 mg, 100%) of (S)-1-((3aR,5R,6S,6aS)-6-fluoro-2,2-dimethyltetrahydrofuro[2,3-d][1,3]dioxol-5-yl)propan-1-ol (35S) as a light yellow oil. $C_{10}H_{17}FO_4$: $^1H$ NMR (500 MHz, $CDCl_3$): δ 6.00 (d, J=4.0 Hz, 1H), 4.90 (dd, J=50.0, 2.4 Hz, 1H), 4.71 (dd, J=11.2, 3.6 Hz, 1H), 4.05 (ddd, J=30.4, 8.0, 2.4 Hz, 1H), 3.85 (m, 1H), 2.17 (d, J=1.6 Hz, 1H), 1.61-1.56 (m, 1H), 1.49 (s, 3H), 1.33 (s, 3H), 1.06 (t, J=7.6 Hz, 3H).

Step-6: (S)-1-((3aR,5R,6S,6aS)-6-Fluoro-2,2-dimethyltetrahydrofuro[2,3-d][1,3]dioxol-5-yl)propyl acetate (36S)

To a stirred solution of (S)-1-((3aR,5R,6S,6aS)-6-fluoro-2,2-dimethyltetrahydrofuro[2,3-d][1,3]dioxol-5-yl)propan-1-ol (35S) (400 mg, 1.80 mmol), TEA (0.51 mL, 3.61 mmol) and DMAP (44 mg, 0.36 mmol) in anhydrous $CH_2Cl_2$ (10 mL) was added acetic anhydride (277 mg, 2.71 mmol). After being stirred at 25° C. for 10 h, the reaction was quenched with a saturated aq. $NaHCO_3$ solution (20 mL). The organic layer was separated and the aqueous phase was extracted with $CH_2Cl_2$ (2×50 mL). The combined organic layers were dried over $Na_2SO_4$, filtered and concentrated in vacuum. The crude product was purified by column chromatography on silica gel (100-200 mesh, 20% EtOAc in petroleum ether) to afford (400 mg, 84%) of (S)-1-((3aR,5R,6S,6aS)-6-fluoro-2,2-dimethyltetrahydrofuro[2,3-d][1,3]dioxol-5-yl) propyl acetate (36S) as a colorless oil. $C_{12}H_9FO_5$: $^1H$ NMR (500 MHz, $CDCl_3$): δ 5.98 (d, J=3.5 Hz, 1H), 5.23 (m, 1H), 4.89 (dd, J=49.8, 2.5 Hz, 1H), 4.69 (dd, J=11.5, 4.0 Hz, 1H), 4.19 (ddd, J=29.8, 8.0, 2.5 Hz, 1H), 2.10 (s, 3H), 1.74 (m, 1H), 1.63 (m, 1H), 1.50 (s, 3H), 1.32 (s, 3H), 0.96 (t, J=4.0 Hz, 3H).

Step-7: (3S,4S,5R)-5-((S)-1-Acetoxypropyl)-4-fluorotetrahydrofuran-2,3-diyl diacetate (37S)

To a solution of (S)-1-((3aR,5R,6S,6aS)-6-fluoro-2,2-dimethyltetrahydrofuro[2,3-d][1,3]dioxol-5-yl)propyl acetate (36S) (400 mg, 1.52 mmol), acetic acid (0.86 mL, 15.2 mmol) and acetic anhydride (0.72 mL, 7.60 mmol) in anhydrous $CH_2Cl_2$ (10 mL) was added concentrated $H_2SO_4$ (0.010 mL) at 0° C. After being stirred at RT for 3 h, the reaction was quenched by addition of a saturated aq. $NaHCO_3$ solution (10 mL). The organic layer was separated and the aqueous phase was extracted with $CH_2Cl_2$ (2×50 mL). The combined organic layers were dried over $Na_2SO_4$, filtered and concentrated in vacuum. The crude product was purified by column chromatography on silica gel (100-200 mesh, 30% EtOAc in petroleum ether) to afford (200 mg, 42.8%) of (3S,4S,5R)-5-((S)-1-acetoxypropyl)-4-fluorotetrahydrofuran-2,3-diyl diacetate (37S) as a colorless oil. $C_{13}H_{19}FO_7$: (2.4:1 mixture of α, β anomers by $^1H$ NMR); $^1H$ NMR (400 MHz, $CDCl_3$): δ 6.47 (d, J=4.8 Hz, 0.294H), 6.12 (s, 0.706H), 5.37-4.94 (m, 3H), 4.35-4.25 (m, 1H), 2.12-2.08 (m, 9H), 1.74-1.57 (m, 2H), 0.96 (t, J=7.2 Hz, 3H).

Step-8: (S)-1-((2R,3S,4S,5R)-5-(2-Acetamido-6,8-dioxo-7-(prop-2-yn-1-yl)-1,6,7,8-tetrahydro-9H-purin-9-yl)-4-acetoxy-3-fluorotetrahydrofuran-2-yl) propyl acetate (25B)

Using the procedure described in Example 11, Step-9, replacing (3R,5S)-5-(1-acetoxy-2,2,2-trifluoroethyl)tetrahydrofuran-2,3-diyl diacetate (22S) with (3S,4S,5R)-5-((S)-1-acetoxypropyl)-4-fluorotetrahydrofuran-2,3-diyl diacetate (37S), (S)-1-((2R,3S,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propyl acetate (25B) in 32% yield after reverse phase GRACE purification (0.1% $HCO_2H$ in water and acetonitrile). $C_{21}H_{24}FN_5O_8$: ES+, m/z 494.2 $[M+H]^+$. $^1H$ NMR (400 MHz, $CDCl_3$): δ 11.95 (brs, 1H), 9.30 (s, 1H), 5.84 (m, 2H), 5.72 (m, 1H), 5.05 (ddd, J=50.5, 3.4, 1.2 Hz, 1H), 4.84 (m, 2H), 4.24 (ddd, J=28.7, 8.9, 3.4 Hz, 1H), 2.30 (s, 3H), 2.28 (m, 1H), 2.14 (s, 3H), 2.13 (s, 3H), 1.78 (m, 1H), 1.65 (m, 1H), 0.98 (t, J=7.4, 3H).

Step-9: 2-Amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13

Using the procedure described in Example 11, Step-11, 2-amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-1H-purine-6,8-dione, Compound 13 was prepared in 31% yield as a white solid. $C_{15}H_{18}FN_5O_5$: ES+, m/z 368.3 $[M+H]^+$. $^1H$ NMR (500 MHz, DMSO-$d_6$): δ 11.16 (brs, 1H), 6.65 (brs, 2H), 5.95 (bs, 1H), 5.36 (m, 1H), 5.33 (m, 1H), 4.97 (ddd, 1H, J=53.3, 4.5, 2.5 Hz, 1H), 4.84 (d, J=6.5 Hz, 1H), 4.61 (d, J=2.5 Hz, 2H), 3.80 (ddd, J=23.5, 6.8, 4.8 Hz, 1H), 3.54 (m, 1H), 3.25 (t, J=2.5 Hz, 1H), 1.49 (m, 1H), 1.34 (m, 1H), 0.91 (t, J=7.3 Hz, 3H).

Example 12: 2-Amino-9-((2R,3R,5S)-5-((S)-1,2-dihydroxyethyl)-3-hydroxytetrahydrofuran-2-yl)-7-(prop-2-yn-1-yl)-7,9-dihydro-1H-purine-6,8-dione, Compound 14

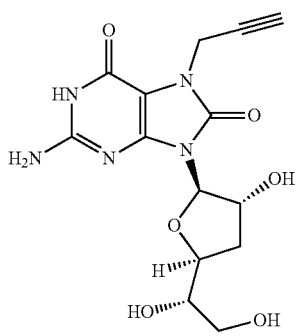 [SMILES: C#CCn1c(=O)n([C@@H]2O[C@H]([C@@H](O)CO)C[C@H]2O)c2nc(N)[nH]c(=O)c21]

Compound 14 was prepared according to the following multi-step procedure.

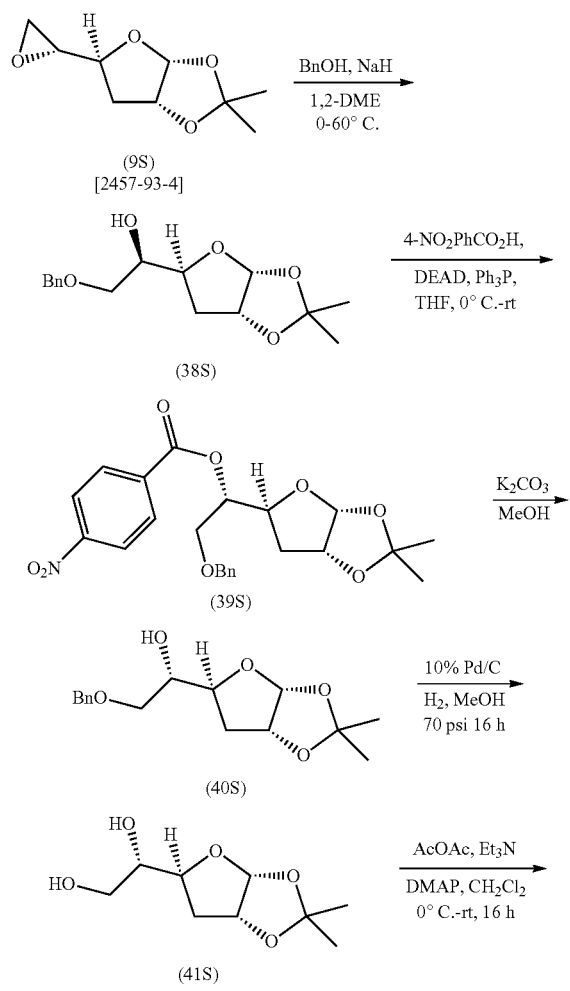

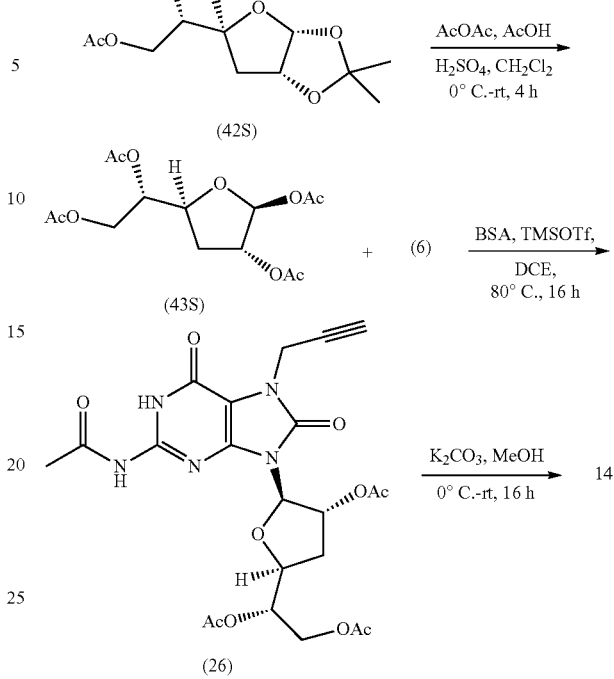

Step-1: (R)-2-(Benzyloxy)-1-((3aR,5S,6aR)-2,2-dimethyltetrahydrofuro[2,3-d][1,3]dioxol-5-yl)ethan-1-ol (38S)

To a suspension of NaH (60% mineral oil dispersion; 3.4 g, 86.2 mmol) in 1,2-dimethoxyethane (40 mL) was added benzyl alcohol (31.2 mL) at 0° C. This was followed by addition of a solution of (3aR,5S,6aR)-2,2-dimethyl-5-((R)-oxiran-2-yl)tetrahydrofuro[2,3-d][1,3]dioxole (9S) (8 g, 43.0 mmol) in 1,2-dimethoxyethane (40 mL) under $N_2$ atmosphere was at 0° C. The reaction mixture was stirred at 60° C. for 4 h and then quenched with a saturated $NH_4Cl$ solution (100 mL) and extracted with $CHCl_3$ (2×300 mL). The combined organic layer was washed with water (100 mL) dried over $Na_2SO_4$, filtered and concentrated in vacuum. The crude mixture was purified by column chromatography on silica gel (100-200 mesh, 60% EtOAc in petroleum ether) to afford 10.0 g (79%) of (R)-2-(benzyloxy)-1-((3aR,5S,6aR)-2,2-dimethyltetrahydrofuro[2,3-d][1,3]dioxol-5-yl)ethan-1-ol (38S) as a colourless liquid. $C_{16}H_{22}O_5$: $^1H$ NMR (400 MHz, $CDCl_3$): δ 7.32 (m, 5H), 5.80 (d, J 3.6 Hz, 1H), 4.74 (t, J 4.0 Hz, 1H), 4.56 (q, $J_{a,b}$=12.2 Hz, 2H), 4.23 (dt, J=10.8, 5.0 Hz, 1H), 4.00 (m, 1H), 3.60 (dd, J=9.6, 3.6 Hz, 1H), 3.48 (dd, J=10.0, 6.8 Hz, 1H), 2.37 (d, J 3.6 Hz, 1H), 2.07 (dd, J=13.4, 4.8 Hz, 1H), 1.85 (m, 1H), 1.57 (s, 3H), 1.27 (s, 3H).

Step-2: (S)-2-(Benzyloxy)-1-((3aR,5S,6aR)-2,2-dimethyltetrahydrofuro[2,3-d][1,3]dioxol-5-yl)ethyl 4-nitrobenzoate (39S)

To a stirred solution of (R)-2-(benzyloxy)-1-((3aR,5S,6aR)-2,2-dimethyltetrahydrofuro[2,3-d][1,3]dioxol-5-yl)ethan-1-ol (38S) (10.0 g, 32.4 mmol), triphenylphosphine (10.2 g, 38.9 mmol), 4-nitrobenzoic acid (5.9 g, 35.7 mmol) in THF (100 mL) was added diethylazodicarboxylate (6.1 mL, 38.9 mmol) dropwise at 0° C. under $N_2$ atm. The reaction mixture was stirred at 18° C. for 10 h. Then the resultant mixture was quenched by addition of a saturated NaHCO$_3$ solution (100 mL) and extracted with EtOAc (2×300 mL). The organic layers were combined, dried over anhydrous Na$_2$SO$_4$, filtered and concentrated in vacuum. The residue was purified by column chromatography on silica gel (100-200 mesh, 30% EtOAc in petroleum ether) to afford 11.5 g (76%) of (S)-2-(benzyloxy)-1-((3aR,5S,6aR)-2,2-dimethyltetrahydrofuro[2,3-d][1,3]dioxol-5-yl)ethyl 4-nitrobenzoate (39S) as a light yellow liquid. C$_{23}$H$_{25}$NO$_8$: $^1$H NMR (400 MHz, CDCl$_3$): δ 8.26 (m, 4H), 7.28 (m, 5H), 5.82 (d, J=3.6 Hz, 1H), 5.40 (m, 1H), 4.72 (t, J=4.2 Hz, 1H), 4.61-4.52 (m, 3H), 3.77 (d, J=5.2 Hz, 2H), 2.12 (dd, J=13.2, 4.4 Hz, 1H), 1.69-1.66 (m, 1H), 1.53 (s, 3H), 1.32 (s, 3H).

Step-3: (S)-2-(Benzyloxy)-1-((3aR,5S,6aR)-2,2-dimethyltetrahydrofuro[2,3-d][1,3]dioxol-5-yl)ethan-1-ol (40S)

To a stirred solution of (S)-2-(benzyloxy)-1-((3aR,5S,6aR)-2,2-dimethyltetrahydrofuro[2,3-d][1,3]dioxol-5-yl)ethyl 4-nitrobenzoate (39S) (11.5 g, 25.9 mmol) in methanol (100 mL) was added K$_2$CO$_3$ (4.1 g, 51.9 mmol). After being stirred at room temperature for 30 minutes, the resultant reaction mixture was filtered and the filtrate was concentrated in vacuum. The crude was purified by column chromatography on silica gel (100-200 mesh, 30% EtOAc in petroleum ether) affording 7.0 g (92%) (S)-2-(benzyloxy)-1-((3aR,5S,6aR)-2,2-dimethyltetrahydrofuro[2,3-d][1,3]dioxol-5-yl)ethan-1-ol (40S). C$_{16}$H$_{22}$O$_5$: $^1$H NMR (500 MHz, CDCl$_3$): δ 7.33 (m, 5H), 5.81 (d, J=3.5 Hz, 1H), 4.73 (t, J=4.3 Hz, 1H), 4.57 (s, 2H), 4.29 (dt, J=10.5, 4.3 Hz, 1H), 3.77 (m, 1H), 3.57 (m, 2H), 2.37 (d, J=5.0 Hz, 1H), 2.02 (dd, J=13.5, 4.5 Hz, 1H), 1.90 (dddd, J=15.5, 9.8, 5.0, 2.5 Hz, 1H), 1.51 (s, 3H), 1.32 (s, 3H).

Step-4: (S)-1-((3aR,5S,6aR)-2,2-Dimethyltetrahydrofuro[2,3-d][1,3]dioxol-5-yl)ethane-1,2-diol (41S)

To a stirred solution of (S)-2-(benzyloxy)-1-((3aR,5S,6aR)-2,2-dimethyltetrahydrofuro[2,3-d][1,3]dioxol-5-yl)ethan-1-ol (40S). (5.5 g, 18.7 mmol) in methanol (50 mL) was added 10% Pd/C (2.5 g, 50 mol %). The reaction mixture was stirred in a Parr shaker at rt under H$_2$ at 70 psi for 16 h. Then the reaction mixture was filtered through a celite pad. The celite pad was washed with additional methanol and the filtrate was concentrated under vacuum. The crude mixture was purified by column chromatography on silica gel (100-200 mesh, 10% MeOH in CH$_2$Cl$_2$) to afford 3.0 g (78%) of (S)-1-((3aR,5S,6aR)-2,2-dimethyltetrahydrofuro[2,3-d][1,3]dioxol-5-yl)ethyl acetate (41S) as a colorless oil. C$_9$H$_{16}$O$_5$: $^1$H NMR (400 MHz, CDCl$_3$): δ 5.82 (d, J=3.6 Hz, 1H), 4.75 (t, J=4.2 Hz, 1H), 4.29 (dt, J=10.4, 4.2 Hz, 1H), 3.74 (d, J=5.2 Hz, 2H), 3.64 (brs, 1H), 2.50 (s, 1H), 2.27 (s, 1H), 2.06 (dd, J=13.4, 4.6 Hz, 1H), 1.93 (dddd, J=15.4, 9.7, 4.6, 2.8 Hz, 1H), 1.52 (s, 3H), 1.32 (m, 3H).

Step-5: (S)-1-((3aR,5S,6aR)-2,2-Dimethyltetrahydrofuro[2,3-d][1,3]dioxol-5-yl)ethane-1,2-diyl diacetate (42S)

To a stirred solution of (S)-1-((3aR,5S,6aR)-2,2-dimethyltetrahydrofuro[2,3-d][1,3]dioxol-5-yl)ethyl acetate (41S) (2.0 g, 9.8 mmol), TEA (5.4 mL, 39.2 mmol), DMAP (239.2 mg, 1.9 mmol) in anhydrous CH$_2$Cl$_2$ (20 mL) cooled to 0° C. was added acetic anhydride (2.9 mL, 29.4 mmol). The reaction mixture was stirred at 25° C. for 16 h and quenched with saturated aq. NaHCO$_3$ solution (30 mL). The organic layer was separated and the aqueous phase was extracted with CH$_2$Cl$_2$ (2×100 mL). The combined organic layers were dried over Na$_2$SO$_4$, filtered and concentrated in vacuum. The crude was purified by column chromatography on silica gel (100-200 mesh, 20% EtOAc in petroleum ether) to afford 2.0 g (71%) of (S)-1-((3aR,5S,6aR)-2,2-dimethyltetrahydrofuro[2,3-d][1,3]dioxol-5-yl)ethane-1,2-diyldiacetate (42S) as a colourless oil. C$_{13}$H$_{20}$O$_7$: $^1$H NMR (500 MHz, CDCl$_3$): δ 5.81 (d, J=3.5 Hz, 1H), 5.18 (dt, J=8.0, 3.8 Hz, 1H), 4.73 (t, J=4.3 Hz, 1H), 4.38 (m, 2H), 4.15 (dd, J=12.0, 7.5 Hz, 1H), 2.12 (s, 3H), 2.08 (m, 1H), 2.05 (s, 3H), 1.65 (m, 1H), 1.52 (s, 3H), 1.34 (s, 3H).

Step-6: (2S,3R,5S)-5-((S)-1,2-diacetoxyethyl)tetrahydrofuran-2,3-diyl diacetate (43S)

To a solution of (S)-1-((3aR,5S,6aR)-2,2-dimethyltetrahydrofuro[2,3-d][1,3]dioxol-5-yl)ethane-1,2-diyldiacetate (42S) (1.3 g, 4.5 mmol), acetic acid (2.58 mL, 45.1 mmol) and acetic anhydride (2.2 mL, 22.5 mmol) in anhydrous CH$_2$Cl$_2$ (20 mL) was added concentrated H$_2$SO$_4$ (0.04 mL) at 0° C. After being stirred at 22° C. for 4 hours, the reaction was quenched by addition of a saturated aq. NaHCO$_3$ solution (100 mL). The organic layer was separated and the aqueous phase was extracted with CH$_2$Cl$_2$ (2×100 mL). The combined organic layers were dried over Na$_2$SO$_4$, filtered and concentrated in vacuum. The crude residue was purified by column chromatography on silica gel (100-200 mesh, 30% EtOAc in petroleum ether) to afford 1.0 g (67%) of (2S,3R,5S)-5-((S)-1,2-diacetoxyethyl)tetrahydrofuran-2,3-diyl diacetate (43S) as a colorless oil. C$_{14}$H$_{20}$O$_9$: $^1$H NMR (500 MHz, CDCl$_3$): δ 6.12 (s, 1H), 5.19 (d, J=3.5 Hz, 1H), 5.13 (m, 1H), 4.50 (m, 1H), 4.32 (dd, J=12.0, 4.0 Hz, 1H), 4.10 (dd, J=12.0, 6.5 Hz, 1H), 2.10-2.06 (m, 14H).

Step-7: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)ethane-1,2-diyl diacetate (26)

N-(6,8-dioxo-7-(prop-2-yn-1-yl)-6,7,8,9-tetrahydro-1H-purin-2-yl)acetamide (6) (300 mg, 1.2 mmol), (2S,3R,5S)-5-((S)-1,2-diacetoxyethyl)tetrahydrofuran-2,3-diyl diacetate (43S) (483.8 mg, 1.4 mmol), BSA (0.92 mL, 3.6 mmol) were dissolved in 1,2-dichloroethane (20 mL) and the resulting reaction mixture was stirred at 80° C. for 30 min under argon. The reaction mixture was allowed to warm to RT and 1,2-dichloro ethane was removed under vacuum. The residue was taken up in MeCN (20 mL), followed by addition of TMSOTf (0.33 mL, 1.8 mmol). The stirred reaction mixture was heated at 80° C. for 16 h., cooled to room temperature and concentrated under vacuum. The residue obtained was diluted with aq. NaHCO$_3$ (50 mL) and extracted with EtOAc (3×50 mL). The combined EtOAc layer was washed with water (30 mL), brine (30 mL), dried over Na$_2$SO$_4$, filtered and concentrated under vacuum The crude product was purified by column chromatography on silica gel (100-200 mesh, 80% EtOAc in petroleum ether) to afford 300 mg (47%) of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)ethane-1,2-diyl diacetate (26) as an off-white solid. C$_{22}$H$_{25}$N$_5$O$_{10}$: ES+, m/z 520.2 [M+H]$^+$.

Step-8: 2-Amino-9-((2R,3R,5S)-5-((S)-1,2-dihydroxyethyl)-3-hydroxytetrahydrofuran-2-yl)-7-(prop-2-yn-1-yl)-7,9-dihydro-1H-purine-6,8-dione, Compound 14

To a solution of (S)-1-((2S,4R,5R)-5-(2-acetamido-6,8-dioxo-7-(prop-2-yn-1-yl)-1,6,7,8-tetrahydro-9H-purin-9- yl)-4-acetoxytetrahydrofuran-2-yl)ethane-1,2-diyl diacetate (26) (300 mg, 0.57 mmol) in MeOH (10 mL) was added $K_2CO_3$ (119.6 mg, 0.86 mmol) at 0° C. The reaction mixture was stirred at RT for 16 h followed by removal of methanol under reduced pressure at RT. The residue obtained was purified by Prep HPLC Column: X-SELECT-C18 (150*19), 5 u Mobile phase: 10 mM $NH_4HCO_3$ in $H_2O$:MeCN GRADIENT: (T % B): —0/2, 3/2, 8/20, 10/40, 10/0.1/98, 12/98, 13.1/2, 16/2; Flow Rate: 20 mL/min. The pure fractions were lyophilized to afford 35 mg (17%) of 2-amino-9-((2R,3R,5S)-5-((S)-1,2-dihydroxyethyl)-3-hydroxytetrahydrofuran-2-yl)-7-(prop-2-yn-1-yl)-7,9-dihydro-1H-purine-6,8-dione, Compound 14 as an off white solid. $C_{14}H_{17}N_5O_6$: ES+, m/z 352.2 [M+H]+. $^1H$ NMR (400 MHz, DMSO-$d_6$): δ 11.76 (brs, 1H), 6.71 (s, 2H), 5.50 (d, J 3.6 Hz 1H), 5.38 (d, J=4.4 Hz, 1H), 4.90 (bs, 1H), 4.75 (m, 1H), 4.60 (s, 2H), 4.47 (m, 1H), 4.17 (m, 1H), 3.37-3.32 (m, 3H), 3.20 (t, J 2.2 Hz, 1H), 2.40 (m, 1H), 1.85 (m, 1H).

Example 13: 2-Amino-9-((2R,3R,5S)-5-((S)-2-amino-1-hydroxyethyl)-3-hydroxytetrahydrofuran-2-yl)-7-(prop-2-yn-1-yl)-7,9-dihydro-1H-purine-6,8-dione, Compound 15

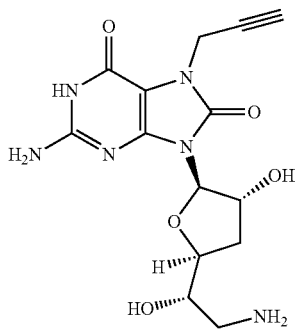 [SMILES: C#CCn1c(=O)n([C@@H]2O[C@H]([C@@H](O)CN)C[C@H]2O)c2nc(N)[nH]c(=O)c21]

Compound 15 was prepared according to the following multi-step procedure.

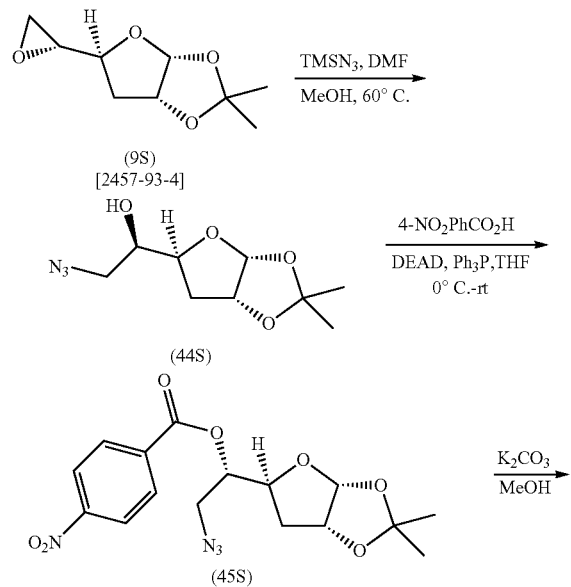

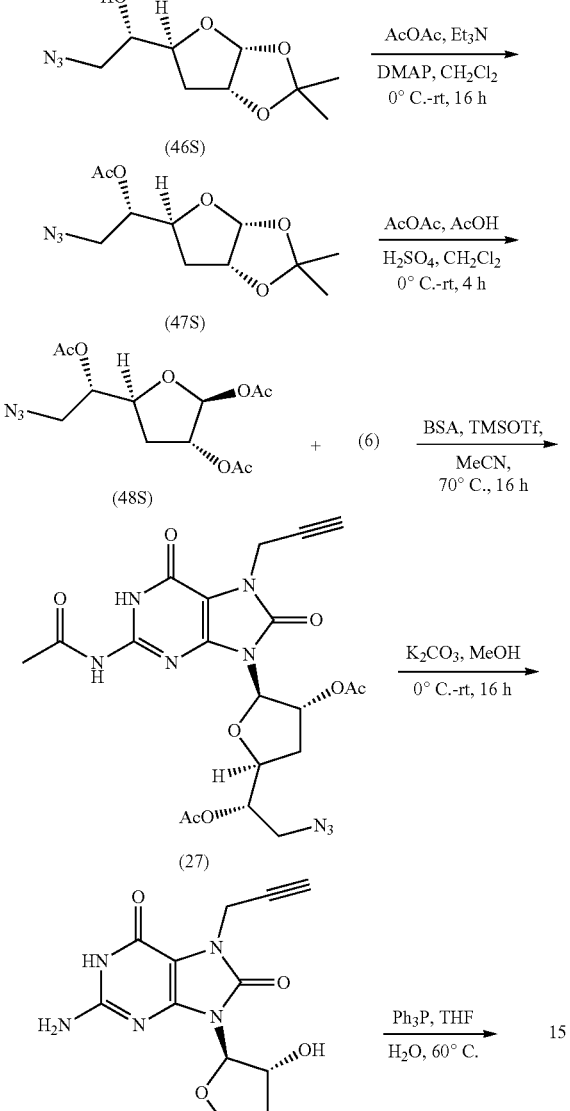

Step-1: (R)-2-Azido-1-((3aR,5S,6aR)-2,2-dimethyl-tetrahydrofuro[2,3-d][1,3]dioxol-5-yl)ethan-1-ol (44S)

To a solution of (3aR,5S,6aR)-2,2-dimethyl-5-((R)-oxiran-2-yl)tetrahydrofuro[2,3-d][1,3]dioxole (9S) (4.0 g, 21.71 mmol) in DMF (40 mL) was added $TMSN_3$ (8 mL, 2 vol) and methanol (8 mL, 2 vol) at 60° C. The reaction was monitored by TLC. After stirring at 60° C. for 48 h. the reaction mixture was poured into 400 mL of ice-water and extracted with EtOAc (2×300 mL). The solution was further washed with a sat. brine solution (2×100 mL) and the organic layer was separated, dried over anhydrous $Na_2SO_4$, filtered and concentrated to afford crude (R)-2-azido-1-((3aR,5S,6aR)-2,2-dimethyltetrahydrofuro[2,3-d][1,3]dioxol-5-yl)ethan-1-ol (44S) (~4.0 g crude, 80%) as a liquid.

$C_9H_{15}N_3O_4$: The crude product was directly used in next step reaction. $^1H$ NMR (400 MHz, CDCl$_3$): δ 5.80 (d, J=3.2 Hz, 1H), 4.77 (t, J=4.0 Hz, 1H), 4.19 (dt, J 10.3, 4.6 Hz, 1H), 3.99 (m, 1H), 3.37 (m, 2H), 2.30 (m, 1H), 2.08 (dd, J=13.2, 4.6 Hz, 1H), 1.86 (ddd, J=15.4, 9.7, 4.8 Hz, 1H), 1.55 (s, 3H), 1.33 (s, 3H).

Step-2: (S)-2-Azido-1-((3aR,5S,6aR)-2,2-dimethyl-tetrahydrofuro[2,3-d][, 3]dioxol-5-yl)ethyl 4-nitrobenzoate (45S)

To a solution of (R)-2-azido-1-((3aR,5S,6aR)-2,2-dimethyltetrahydrofuro[2,3-d][1,3]dioxol-5-yl)ethan-1-ol (44S) (4 g, 17.44 mmol) in THF (60 mL) was added 4-nitrobenzoic acid (5.8 g, 34.8 mmol) and triphenylphosphine (9.1 g, 34.89 mmol) and DEAD (5.4 mL, 34.8 mmol) at 0° C. The reaction was stirred at RT and monitored by TLC. After 16 h the reaction mixture was poured into 200 mL of water and extracted with EtOAc (2×200 mL). The organic layer was further washed with a sat. brine solution (2×60 mL), dried over anhydrous Na$_2$SO$_4$, filtered and concentrated to afford the crude product. The crude product was purified by column chromatography on silica gel (100-200 mesh, 30% EtOAc in petroleum ether) to afford (S)-2-azido-1-((3aR,5S,6aR)-2,2-dimethyltetrahydrofuro[2,3-d][1,3]dioxol-5-yl) ethyl 4-nitrobenzoate (45S) (4.0 g, 60%) as a semi solid. $C_{16}H_{18}N_4O_7$: ES−, m/z 377.1 [M−H]$^-$. $^1H$ NMR (400 MHz, CDCl$_3$): δ 8.33-8.24 (m, 4H), 5.84 (d, J=3.6 Hz, 1H), 5.37 (m, 1H), 4.75 (t, J=4.2 Hz, 1H), 4.51 (dt, J=10.7, 4.6 Hz, 1H), 3.67 (d, J=4.8 Hz, 2H), 2.16 (dd, J=13.2, 4.8 Hz, 1H), 1.66 (ddd, J=15.6, 9.6, 3.6 Hz 1H), 1.55 (s, 3H), 1.33 (s, 3H).

Step-3: (S)-2-Azido-1-((3aR,5S,6aR)-2,2-dimethyl-tetrahydrofuro[2,3-d][1,3]dioxol-5-yl)ethan-1-ol (46S)

To a solution of (S)-2-azido-1-((3aR,5S,6aR)-2,2-dimethyltetrahydrofuro[2,3-d][1,3]dioxol-5-yl)ethyl 4-nitrobenzoate (45S) (4.0 g, 10.572 mmol) in methanol (40 mL, 10 vol), was added K$_2$CO$_3$ (2.9 g, 21.1 mmol) at rt. The reaction was monitored by TLC. After stirring at rt for 1 h the reaction mixture was filtered through a plug of silica gel, and the filtrate was concentrated under vacuum to afford (S)-2-azido-1-((3aR,5S,6aR)-2,2-dimethyltetrahydrofuro[2,3-d] [1,3]dioxol-5-yl)ethan-1-ol (46S) (2.2 g, 83%) as a liquid that was used without further purification. $C_9H_{15}N_3O_4$: $^1H$ NMR (400 MHz, CDCl$_3$): δ 5.81 (m, 1H), 4.75 (t, J=3.8 Hz, 1H), 4.24-4.13 (m, 2H), 3.85 (m, 1H), 3.40 (m, 1H), 2.02 (m, 1H), 1.88 (m, 1H), 1.74 (m, 1H), 1.53 (s, 3H), 1.36 (s, 3H).

Step-4: (S)-2-Azido-1-((3aR,5S,6aR)-2,2-dimethyl-tetrahydrofuro[2,3-d][1,3]dioxol-5-yl)ethyl acetate (47S)

To a stirred solution of (S)-2-azido-1-((3aR,5S,6aR)-2,2-dimethyltetrahydrofuro[2,3-d][1,3]dioxol-5-yl)ethan-1-ol (46S) (2.2 g, 9.59 mmol), TEA (2.67 mL, 19.19 mmol), DMAP (0.23 g, 1.91 mmol) in anhydrous dichloromethane (22 mL) was added acetic anhydride (1.37 mL, 14.39 mmol). After being stirred at 25° C. for 10 h, the reaction was quenched by the saturated aq. NaHCO$_3$ solution (50 mL). The organic layer was separated and the aqueous phase was extracted with DCM (2×50 mL). The combined organic layers were dried over Na$_2$SO$_4$ and concentrated in vacuum. The crude was purified by column chromatography on silica gel (100-200 mesh, eluting with 20% EtOAc in Petroleum ether) to afford (S)-2-azido-1-((3aR,5S,6aR)-2,2-dimethyl-tetrahydrofuro[2,3-d][1,3]dioxol-5-yl)ethyl acetate (47S) (2 g, 86%) as a colourless oil. $C_{11}H_{17}N_3O_5$: $^1H$ NMR (500 MHz, CDCl3): δ 5.81 (d, J=4.0 Hz, 1H), 5.09 (q, J=2.3 Hz, 1H), 4.74 (t, J=4.5 Hz, 1H), 4.36 (dt, J=6.0, 4.5 Hz, 1H), 4.27 (m, 1H), 3.50 (dd, J=6.5, 4.0 Hz, 2H), 2.15 (s, 3H), 1.64-1.58 (m, 1H), 1.57 (s, 3H), 1.32 (s, 3H).

Step-5: (2S,3R,5S)-5-((S)-1-Acetoxy-2-azidoethyl) tetrahydrofuran-2,3-diyl diacetate (48S)

To a solution of (S)-2-azido-1-((3aR,5S,6aR)-2,2-dimethyltetrahydrofuro[2,3-d][1,3]dioxol-5-yl)ethyl acetate (47S) (2.0 g, 7.3 mmol), acetic acid (4.21 mL, 73.72 mmol) and acetic anhydride (3.48 mL, 36.86 mmol) in anhydrous CH$_2$Cl$_2$ (40 mL) was added concentrated H$_2$SO$_4$ (0.1 mL) at 0° C. After being stirred at 25° C. for 3 h, the reaction was quenched by addition of saturated aq. NaHCO$_3$ solution (100 mL). The organic layer was separated and the aqueous phase was extracted with CH$_2$Cl$_2$ (2×100 mL). The combined organic layers were dried over Na$_2$SO$_4$, filtered and concentrated in vacuum. The crude oil was purified by column chromatography on silica gel (100-200 mesh, 30% EtOAc in petroleum ether) to afford (2S,3R,5S)-5-((S)-1-acetoxy-2-azidoethyl)tetrahydrofuran-2,3-diyl diacetate (48S) (1.1 g, 45%) as a colourless oil. $C_{12}H_{17}N_3O_7$: $^1H$ NMR (500 MHz, CDCl$_3$): δ 6.12 (s, 1H), 5.18 (d, J=5.0 Hz, 1H), 5.04 (m, 1H), 4.52 (m, 1H), 3.46 (m, 2H), 2.15 (m, 2H), 2.09-2.07 (s, 9H).

Step-6: (S)-1-((2S,4R,5R)-5-(2-Acetamido-6,8-di-oxo-7-(prop-2-yn-1-yl)-1,6,7,8-tetrahydro-9H-purin-9-yl)-4-acetoxytetrahydrofuran-2-yl)-2-azidoethyl acetate (27)

To a suspension of N-(6,8-dioxo-7-(prop-2-yn-1-yl)-6,7,8,9-tetrahydro-1H-purin-2-yl)acetamide (6) (700 mg, 2.83 mmol) and (2S,3R,5S)-5-((S)-1-acetoxy-2-azidoethyl)tetrahydrofuran-2,3-diyl diacetate (48S) (1.07 g, 3.40 mmol) in acetonitrile (30 mL) was added BSA (2.15 mL, 8.49 mmol). The reaction mixture was stirred at 70° C. for 1 h under argon to form a clear solution. TMSOTf (0.78 mL, 4.24 mmol) was added at 0° C. After being heated with stirring at 70° C. for 16 h, the reaction was quenched with water (60 mL), extracted with EA (2×70 mL). The combined organic layers were dried over Na$_2$SO$_4$, filtered and concentrated in vacuum. The residue was purified by column on silica gel (80% EtOAc in petroleum ether) to afford (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-azidoethyl acetate (27) (0.50 g, 40%) as an off-white solid. $C_{20}H_{22}N_8O_8$: ES+, m/z 503.3 [M+H]$^+$.

Step-7: 2-Amino-9-((2R,3R,5S)-5-((S)-2-azido-1-hydroxyethyl)-3-hydroxytetrahydrofuran-2-yl)-7-(prop-2-yn-1-yl)-7,9-dihydro-1H-purine-6,8-dione (28)

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-azidoethyl acetate (27) (500 mg, 0.99 mmol) in methanol (30 mL), was added K$_2$CO$_3$ (138 mg, 0.99 mmol) at rt. The reaction mixture was stirred at room temperature and monitored by LC/MS. After 16 h the starting material was consumed. The reaction mixture was concentrated under vacuum to afford crude 2-amino-9-((2R,3R,5S)-5-((S)-2-azido-1-hydroxyethyl)-3-hydroxytetrahydrofuran-2-yl)-7-(prop-2-yn-1-yl)-7,9-dihydro-1H-purine-6,8-dione (28) (370 mg, 55%) as a crude solid material that was used in the next step without purification. $C_{14}H_{16}N_8O_5$: ES+, m/z 377.3 [M+H]+.

Step-8: 2-2-Amino-9-((2R,3R,5S)-5-((S)-2-amino-1-hydroxyethyl)-3-hydroxytetrahydrofuran-2-yl)-7-(prop-2-yn-1-yl)-7,9-dihydro-1H-purine-6,8-dione, Compound 15

To a stirred solution of 2-amino-9-((2R,3R,5S)-5-((S)-2-azido-1-hydroxyethyl)-3-hydroxytetrahydrofuran-2-yl)-7-(prop-2-yn-1-yl)-7,9-dihydro-1H-purine-6,8-dione (28) (350 mg, 0.930 mmol) in THF at rt (7 mL, 20 vol), was added triphenyphosphine (487 mg, 1.86 mmol) and water (3.5 mL, 1 vol). The mixture was stirred at 60° C. The reaction was monitored by LCMS and after 16 h the starting material was consumed. The reaction mixture was concentrated under vacuum to afford a thick solid that was subjected to GRACE reverse phase chromatography (10 mmol $NH_4HCO_3$:MeCN) to afford 2-amino-9-((2R,3R,5S)-5-((S)-2-amino-1-hydroxyethyl)-3-hydroxytetrahydrofuran-2-yl)-7-(prop-2-yn-1-yl)-7,9-dihydro-1H-purine-6,8-dione (Compound 15) (30 mg, 20%) as an off-white solid. $C_{14}H_{18}N_6O_5$: 1H NMR (500 MHz, DMSO-$d_6$): δ 6.66 (bs, 2H), 5.50 (d, J=3.0 Hz, 1H), 5.38 (d, J=4.0 Hz, 1H), 4.95 (bs, 1H), 4.74 (d, J=3.0 Hz, 1H), 4.64 (s, 2H), 4.09 (q, J=6.7 Hz, 1H), 3.31 (s, 1H), 3.20 (t, J=2.3 Hz, 1H), 2.59-2.54 (m, 1H), 2.46-2.37 (m, 2H), 1.91-1.71 (m, 1H). ES+, m/z 351.2 [M+H]+.

Example 14: 2-Amino-9-((2R,3R,5S)-3-hydroxy-5-((S)-1-hydroxy-2-(methylamino)ethyl)tetrahydrofuran-2-yl)-7-(prop-2-yn-1-yl)-7,9-dihydro-1H-purine-6,8-dione, Compound 16

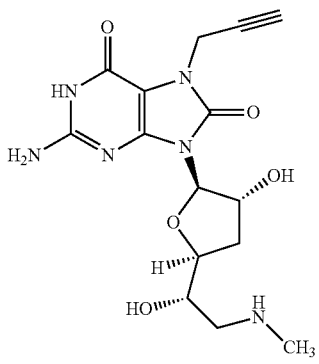 [SMILES: C#CCn1c(=O)n([C@@H]2O[C@H]([C@@H](O)CNC)C[C@H]2O)c2nc(N)[nH]c(=O)c21]

Compound 16 was prepared according to the following multi-step procedure.

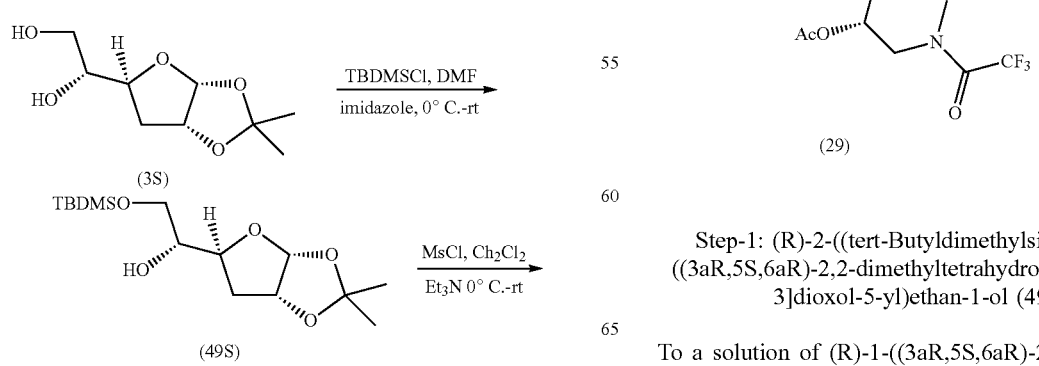

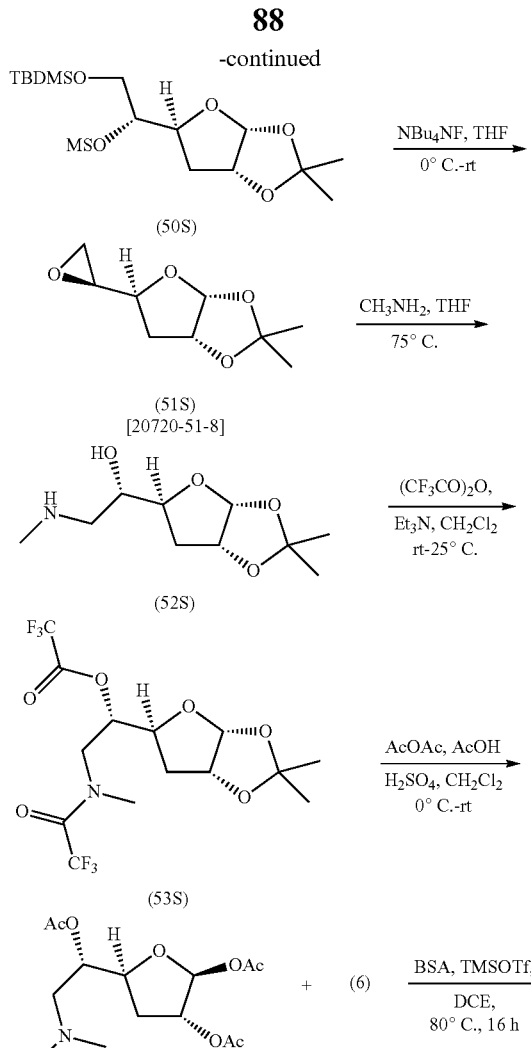

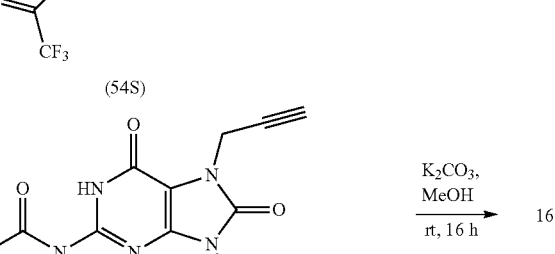

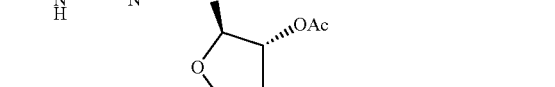

Step-1: (R)-2-((tert-Butyldimethylsilyl)oxy)-1-((3aR,5S,6aR)-2,2-dimethyltetrahydrofuro[2,3-d][1,3]dioxol-5-yl)ethan-1-ol (49S)

To a solution of (R)-1-((3aR,5S,6aR)-2,2-dimethyltetrahydrofuro[2,3-d][1,3]dioxol-5-yl)ethane-1,2-diol (3S) (10.0 g, 49.01 mmol) in DMF (100 mL), was added TBDMS-Cl (7.35 g, 49.01 mmol) and imidazole (4.29 g, 63.21 mmol) at 0° C. The reaction mixture was stirred at 25° C. and monitored by TLC. After 8 h the reaction mixture was poured into 600 mL of ice-water and extracted with EtOAc (2×500 mL). It was further washed with brine solution (2×200 mL) and all organic layers were collected, dried over anhydrous $Na_2SO_4$, filtered and concentrated. The crude product was filtered through a pad of silica to afford (R)-2-((tert-butyldimethylsilyl)oxy)-1-((3aR,5S,6aR)-2,2-dimethyltetrahydrofuro[2,3-d][1,3]dioxol-5-yl)ethan-1-ol (49S) (10.0 g, 65%) as a semi-solid and used as is. $C_{15}H_{30}O_5Si$: $^1H$ NMR (400 MHz, $CDCl_3$): δ 5.80 (d, J=3.6 Hz, 1H), 4.74 (t, J=4.0 Hz, 1H), 4.20 (m, 1H), 3.75 (m, 2H), 3.71-3.65 (m, 1H), 2.15 (m, 1H), 1.83 (m, 1H), 1.56-1.53 (m, 1H), 1.51 (s, 3H), 1.36 (s, 3H), 0.91 (s, 9H), 0.08 (s, 6H).

Step-2: (R)-2-((tert-Butyldimethylsilyl)oxy)-1-((3aR,5S,6aR)-2,2-dimethyltetrahydrofuro[2,3-d][1,3]dioxol-5-yl)ethyl methanesulfonate (50S)

To a solution of (R)-2-((tert-butyldimethylsilyl)oxy)-1-((3aR,5S,6aR)-2,2-dimethyltetrahydrofuro[2,3-d][1,3]dioxol-5-yl)ethan-1-ol (49S) (10.0 g, 31.446 mmol) in $CH_2Cl_2$ (100 mL) cooled to 0° C. was added TEA (14.24 mL, 110.06 mmol) and mesyl chloride (3.63 mL, 47.16 mmol). The stirred reaction mixture was warmed to rt and monitored by TLC. After 16 hrs the reaction mixture was poured into 500 mL of water and extracted with $CH_2Cl_2$ (2×500 mL). The mixture was washed with brine solution (2×200 mL), the organic layers were collected, dried over anhydrous $Na_2SO_4$, filtered and concentrated to afford crude (R)-2-((tert-butyldimethylsilyl)oxy)-1-((3aR,5S,6aR)-2,2-dimethyltetrahydrofuro[2,3-d][1,3]dioxol-5-yl)ethyl methanesulfonate (50S) (11 g, 80%) as a liquid and used as is. $C_{16}H_{32}O_7SSi$: $^1H$ NMR (500 MHz, CDCl3): δ 5.78 (d, J=3.5 Hz, 1H), 4.76 (d, J=4.0 Hz, 1H), 4.42 (m, 1H), 3.83 (d, J=5.0 Hz, 2H), 3.07 (s, 3H), 2.19 (m, 1H), 1.93 (m, 1H), 1.51 (s, 3H), 1.45-1.33 (m, 1H), 1.32 (s, 3H), 0.90 (s, 9H), 0.08 (s, 6H).

Step-3: (3aR,5S,6aR)-2,2-Dimethyl-5-((S)-oxiran-2-yl)tetrahydrofuro[2,3-d][1,3]dioxole (51S)

To a solution of (R)-2-((tert-butyldimethylsilyl)oxy)-1-((3aR,5S,6aR)-2,2-dimethyltetrahydrofuro[2,3-d][1,3]dioxol-5-yl)ethyl methanesulfonate (50S) (11 g, 27.7 mmol) in THF (55 mL) was added 1M TBAF in THF (83.3 mL, 83.3 mmol) at 0° C. The reaction mixture was concentrated to afford crude that was subjected to column chromatography on silica gel (100-200 mesh, eluting with 25% EtOAc in petroleum ether) to afford (3aR,5S,6aR)-2,2-dimethyl-5-((S)-oxiran-2-yl)tetrahydrofuro[2,3-d][1,3]dioxole [20720-51-8] (51S) (3.0 g, 57%) as a liquid. $C_9H_{14}O_4$: $^1H$ NMR (400 MHz, $CDCl_3$): δ 5.81 (d, J=3.6 Hz, 1H), 4.75 (t, J=4.2 Hz, 1H), 4.18 (dt, J=10.8, 4.6 Hz, 1H), 3.04 (q, J=3.6 Hz, 1H), 2.81 (d, J=5.6 Hz, 2H), 2.16 (dd, J=13.4, 4.6 Hz, 1H), 1.85 (ddd, J=15.4, 9.8, 3.6 Hz, 1H), 1.50 (s, 3H), 1.36 (s, 3H).

Step-4: (S)-1-((3aR,5S,6aR)-2,2-Dimethyltetrahydrofuro[2,3-d][1,3]dioxol-5-yl)-2-(methylamino)ethan-1-ol (52S)

To a stirred solution of (3aR,5S,6aR)-2,2-dimethyl-5-((S)-oxiran-2-yl)tetrahydrofuro[2,3-d][1,3]dioxole (51S) (3.0 g, 15.9 mmol) was added methyl amine in THF (2M, 45 mL, 15 vol), in anhydrous THF (30 mL). The reaction mixture was stirred at 75° C. in a sealed tube. After 24 hrs, TLC indicated consumption of (51S). The mixture was concentrated in vacuum to afford crude (S)-1-((3aR,5S,6aR)-2,2-dimethyltetrahydrofuro[2,3-d][1,3]dioxol-5-yl)-2-(methylamino)ethan-1-ol) (52S) (3.1 g, 86%) as a semi solid that was used in the next step without purification. $C_{10}H_{19}NO_4$: $^1H$ NMR (500 MHz, $CDCl_3$): δ 5.81 (d, J=3.5 Hz, 1H), 4.75 (m, 1H), 4.08-4.21 (m, 1H), 3.67-3.81 (m, 1H), 2.79-2.91 (m, 2H), 2.53 (s, 3H), 2.27-2.44 (b, 2H), 1.97-2.04 (m, 2H), 1.51 (s, 3H), 1.32 (s, 3H).

Step-5: (S)-1-((3aR,5S,6aR)-2,2-Dimethyltetrahydrofuro[2,3-d][1,3]dioxol-5-yl)-2-(2,2,2-trifluoro-N-methylacetamido)ethyl 2,2,2-trifluoroacetate (53S)

To a stirred solution of (S)-1-((3aR,5S,6aR)-2,2-dimethyltetrahydrofuro[2,3-d][1,3]dioxol-5-yl)-2-(methylamino)ethan-1-ol) (52S) (3.1 g, 14.28 mmol), TEA (7.4 mL, 57.142 mmol), DMAP (0.234 g, 2.85 mmol) in anhydrous $CH_2Cl_2$ (31 mL) was added trifluro acetic anhydride (3.99 mL, 28.57 mmol). The reaction mixture was heated at 25° C. for 16 h, and then quenched with a saturated aq. $NaHCO_3$ solution (60 mL). Then the organic layer was separated and the aqueous phase was extracted with $CH_2Cl_2$ (2×60 mL). The combined organic layers were dried over anhydrous $Na_2SO_4$, filtered and concentrated in vacuum. The crude product was purified by column chromatography on silica gel (100-200 mesh, 20% EtOAc in petroleum ether) to afford (S)-1-((3aR,5S,6aR)-2,2-dimethyltetrahydrofuro[2,3-d][1,3]dioxol-5-yl)-2-(2,2,2-trifluoro-N-methylacetamido)ethyl 2,2,2-trifluoroacetate (53S) (2 g, 86%) as a viscous liquid. $C_{14}H_{17}F_6NO_6$: ($^1H$ NMR indicates $NEt_3$ salt impurities)$^1H$ NMR (400 MHz, $CDCl_3$): δ 5.82 (d, J=3.6 Hz, 1H), 4.76 (t, J=4.2 Hz, 1H), 4.18 (m, 1H), 3.88 (m, 1H), 3.62 (dd, J=13.8, 3.6 Hz, 1H), 3.49 (dd, J=9.0, 2.4 Hz, 1H), 3.26 (m, 3H), 2.09 (dd, J=13.4, 4.6 Hz, 1H), 1.88-1.95 (m, 1H), 1.51 (s, 3H), 1.30 (s, 3H).

Step-6: (2S,3R,5S)-5-((S)-1-Acetoxy-2-(2,2,2-trifluoro-N-methylacetamido)ethyl)tetrahydrofuran-2,3-diyl diacetate (54S)

To a solution of (S)-1-((3aR,5S,6aR)-2,2-dimethyltetrahydrofuro[2,3-d][1,3]dioxol-5-yl)-2-(2,2,2-trifluoro-N-methylacetamido)ethyl 2,2,2-trifluoroacetate (53S) (2.0 g, 4.8 mmol), acetic acid (1.78 mL, 29.33 mmol) and acetic anhydride (3.01 mL, 29.34 mmol) in anhydrous $CH_2Cl_2$ (40 mL) was added concentrated $H_2SO_4$ (0.1 mL) at 0° C. The resulting reaction mixture was stirred at 22° C. for 3 hrs and was quenched by addition of saturated aq. $NaHCO_3$ solution (200 mL). The organic layer was separated and the aqueous phase was extracted with $CH_2Cl_2$ (2×200 mL). The combined organic layers were dried over $Na_2SO_4$, filtered and concentrated in vacuum. The crude was purified by column chromatography on silica gel (100-200 mesh, 15% EtOAc in petroleum ether) to afford (2S,3R,5S)-5-((S)-1-acetoxy-2-(2,2,2-trifluoro-N-methylacetamido)ethyl)tetrahydrofuran-2,3-diyl diacetate (1.1 g, 47%) as a viscous liquid that was used without further purification. $C_{15}H_{20}F_3NO_8$: ($^1H$ NMR indicates $NEt_3$ salt impurities)$^1H$ NMR (400 MHz, $CDCl_3$): δ 6.11 (s, 1H), 5.32 (m, 1H), 5.25 (m, 1H), 5.19 (d, J=4.4 Hz, 1H), 4.41 (m, 1H), 3.68 (m, 1H), 3.60 (m, 1H), 3.18 (s, 3H), 3.04 (s, 1H), 2.09 (m, 9H).

Step-7: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2-(2,2,2-trifluoro-N-methylacetamido)ethyl acetate (29)

To a mixture of N-(6,8-dioxo-7-(prop-2-yn-1-yl)-6,7,8,9-tetrahydro-1H-purin-2-yl)acetamide (6) (400 mg, 1.619 mmol) and (2S,3R,5S)-5-((S)-1-acetoxy-2-(2,2,2-trifluoro-N-methylacetamido)ethyl)tetrahydrofuran-2,3-diyl diacetate (54S) (840 mg, 2.10 mmol) in 1,2-dichloroethane (40 mL) was added BSA (1.23 mL, 4.8 mmol). The reaction mixture was stirred at 80° C. for 30 min under argon at which time the resulting solution was allowed to cool to RT and 1,2-dichloroethane was removed under vacuum. The residue was taken up in MeCN (40 mL) followed by addition of TMSOTf (0.449 mL, 2.4 mmol). The reaction mixture was heated at 80° C. for 16 h, cooled to room temperature and concentrated under vacuum. The residue was diluted with sat. aq. NaHCO$_3$ (60 mL) and extracted with EtOAc (3×80 mL). The combined EtOAc layers were washed with water (50 mL), brine (40 mL), dried over anhydrous Na$_2$SO$_4$, filtered and concentrated under vacuum. The crude compound was purified by flash column chromatography on silica gel (100-200 mesh, 80% EtOAc in Pet ether) to afford (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-(2,2,2-trifluoro-N-methylacetamido)ethyl acetate (29) (260 mg, 28%) as an off-white solid. C$_{23}$H$_{25}$F$_3$N$_6$O$_9$: $^1$H NMR (400 MHz, DMSO-d$_6$): δ 11.20-11.80 (b, 1H), 5.71 (s, 1H), 5.66 (d, J=6.0 Hz, 1H), 5.26-5.37 (m, 1H), 4.68 (s, 2H), 4.32 (m, 1H), 3.78 (m, 1H), 3.55 (m, 1H), 3.08 (s, 3H), 2.89 (m, 2H), 2.81 (m, 1H), 2.17 (s, 3H), 2.07 (s, 3H), 2.02 (m, 1H), 1.93 (s, 3H). ES+, m/z 586.9 [M+H]$^+$.

Step-8: 2-Amino-9-((2R,3R,5S)-3-hydroxy-5-((S)-1-hydroxy-2-(methylamino)ethyl)tetrahydrofuran-2-yl)-7-(prop-2-yn-1-yl)-7,9-dihydro-1H-purine-6,8-dione Compound 16

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-(2,2,2-trifluoro-N-methylacetamido)ethyl acetate (29) (260 mg, 0.443 mmol) in methanol (10 mL) was added K$_2$CO$_3$ (91.8 mg, 0.665 mmol) at rt. The resultant reaction mixture was stirred at room temperature and monitored by LC/MS. After 16 hrs the starting material was consumed. The reaction mixture was concentrated under vacuum, to afford a thick slurry that was subjected to GRACE reverse phase chromatography (10 mM aq. (NH$_4$)HCO$_3$:MeCN) to afford 2-amino-9-(2R,3R,5S)-3-hydroxy-5-((S)-1-hydroxy-2-(methylamino)ethyl)tetrahydrofuran-2-yl)-7-(prop-2-yn-1-yl)-7,9-dihydro-1H-purine-6,8-dione (Compound 16) (71 mg, 44%) as an off-white solid. C$_{15}$H$_{20}$N$_6$O$_5$: $^1$H NMR (400 MHz, DMSO-d$_6$; D20): δ 5.53 (d, J=3.6 Hz, 1H), 4.74 (m, 1H), 4.62 (s, 2H), 4.12 (m, 1H), 3.58 (m, 1H), 3.16 (t, J=2.4 Hz, 1H), 2.36-2.48 (m, 3H), 2.96 (s, 3H), 1.86 (m, 1H). ES+, m/z 365.3 [M+H]$^+$.

Example 15: 2-Amino-7-(cyclopropylmethyl)-9-((2R,3S,4R,5R)-4-fluoro-3-hydroxy-5-((S)-1-hydroxypropyl)tetrahydrofuran-2-yl)-7,9-dihydro-1H-purine-6,8-dione, Compound 17

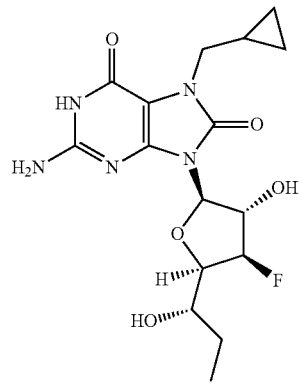 [SMILES: CC[C@H](O)[C@H]1O[C@@H](n2c(=O)n(CC3CC3)c3c(=O)[nH]c(N)nc32)[C@H](O)[C@H]1F]

Using the methods described in Examples 3 and 11, Compound 17 was prepared according to the following procedure from (12) and (37S).

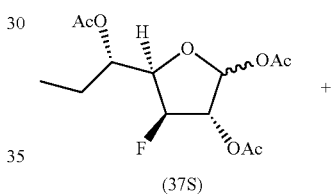

(37S)

+

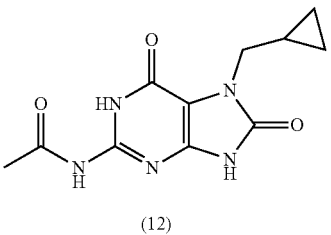

(12)

BSA, TMSOTf
DCE, MeCN
80° C., 16 h

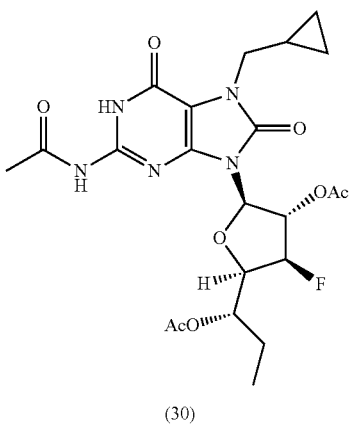

(30)

K$_2$CO$_3$, MeOH
rt, 16 h

-continued

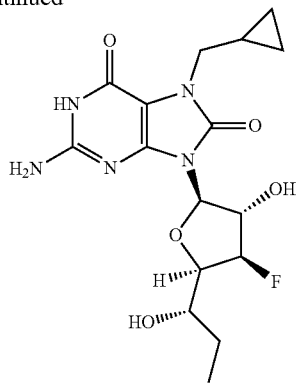

17

Step-1: (S)-1-((2R,3S,4S,5R)-5-(2-Acetamido-7-(cyclopropylmethyl)-6,8-dioxo-1,6,7,8-tetrahydro-9H-purin-9-yl)-4-acetoxy-3-fluorotetrahydrofuran-2-yl)propyl acetate (30)

N-(7-(Cyclopropylmethyl)-6,8-dioxo-6,7,8,9-tetrahydro-1H-purin-2-yl)acetamide (12) (300 mg, 1.1 mmol), (3S,4S,5R)-5-((S)-1-acetoxypropyl)-4-fluorotetrahydrofuran-2,3-diyl diacetate (37S) (523.5 mg, 1.7 mmol) and BSA (0.86 mL, 3.42 mmol) were dissolved in 1,2-dichloroethane (20 mL) and the resulting reaction mixture was stirred at 80° C. for 30 min under argon. The reaction mixture was allowed to cool to RT and 1,2-dichloroethane was removed by vacuum. The residue was dissolved in MeCN (20 mL) followed by addition of TMSOTf (0.31 mL, 1.71 mmol). The reaction mixture was heated at 80° C. for 16 h, cooled to room temperature and concentrated under vacuum. The residue was diluted with sat. aq. NaHCO$_3$ (60 mL) and extracted with EtOAc (3×60 mL). The combined EtOAc layers were washed with water (30 mL), brine (30 mL), dried over anhydrous Na$_2$SO$_4$, filtered and concentrated under vacuum. The crude compound was purified by flash column chromatography (silica gel, 100-200 mesh, 80% EtOAc in pet ether) to afford 230 mg (39%) of (S)-1-((2R,3S,4S,5R)-5-(2-acetamido-7-(cyclopropylmethyl)-6,8-dioxo-1,6,7,8-tetrahydro-9H-purin-9-yl)-4-acetoxy-3-fluorotetrahydrofuran-2-yl)propyl acetate (30) as a pale yellow solid. $C_{22}H_{28}FN_5O_5$: ES+, m/z 510.8 [M+H]$^+$.

Step-2: 2-Amino-7-(cyclopropylmethyl)-9-((2R,3S,4R,5R)-4-fluoro-3-hydroxy-5-((S)-1-hydroxypropyl)tetrahydrofuran-2-yl)-7,9-dihydro-1H-purine-6,8-dione, Compound 17

To a solution of (S)-1-((2R,3S,4S,5R)-5-(2-acetamido-7-(cyclopropylmethyl)-6,8-dioxo-1,6,7,8-tetrahydro-9H-purin-9-yl)-4-acetoxy-3-fluorotetrahydrofuran-2-yl)propyl acetate (30) (230 mg, 0.45 mmol) in methanol (10 mL) was added K$_2$CO$_3$ (62.3 mg, 0.45 mmol) at rt. The reaction mixture was stirred at room temperature for 16 h and concentrated under vacuum to afford a solid mass. The crude product was purified by Prep-HPLC, Column Luna@omega (250*21.2), 5 u Mobile phase: 0.1% HCO$_2$H in H$_2$O:MeCN Gradient: (T % B):—0/5, 8/50, 10.5/50, 10.6/98, 12/98, 12.1/5, 15/5 Flow Rate: 17 mL/min to afford 16 mg (9%) of 2-amino-7-(cyclopropylmethyl)-9-((2R,3S,4R,5R)-4-fluoro-3-hydroxy-5-((S)-1-hydroxypropyl)tetrahydrofuran-2-yl)-7,9-dihydro-1H-purine-6,8-dione (Compound 17) as a white solid. $C_{16}H_{22}FN_5O_5$: The $^1$H NMR spectrum indicated the product to be a formic acid salt; $^1$H NMR (400 MHz, DMSO-d$_6$, D$_2$O): δ 8.48 (s, 1H), 5.39 (d, J=6.4 Hz, 1H), 5.38-5.29 (m, 1H), 5.00 (ddd, J=52.8, 4.8, 2.6 Hz, 1H), 3.85 (dt, J=22.0, 5.7 Hz, 1H), 3.67 (d, J 5.6 Hz, 2H), 3.52 (m, 1H), 1.51 (m, 1H), 1.36 (m, 1H), 1.19 (m, 1H), 0.91 (t, J 7.2 Hz, 3H), 0.43 (m, 2H), 0.38 (m, 2H). ES+, m/z 384.2 [M+H]$^+$.

Example 16: 2-Amino-9-((2R,3R,5S)-3-hydroxy-5-(2-hydroxypropan-2-yl)tetrahydrofuran-2-yl)-7-(prop-2-yn-1-yl)-7,9-dihydro-1H-purine-6,8-dione, Compound 18

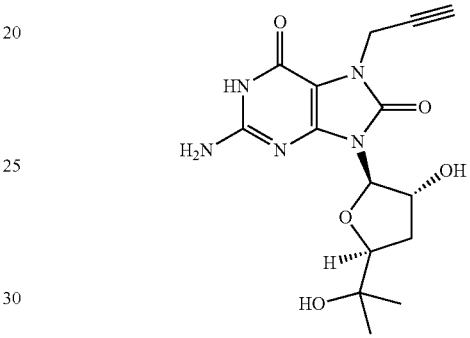

Compound 18 was prepared according to the following multi-step procedure.

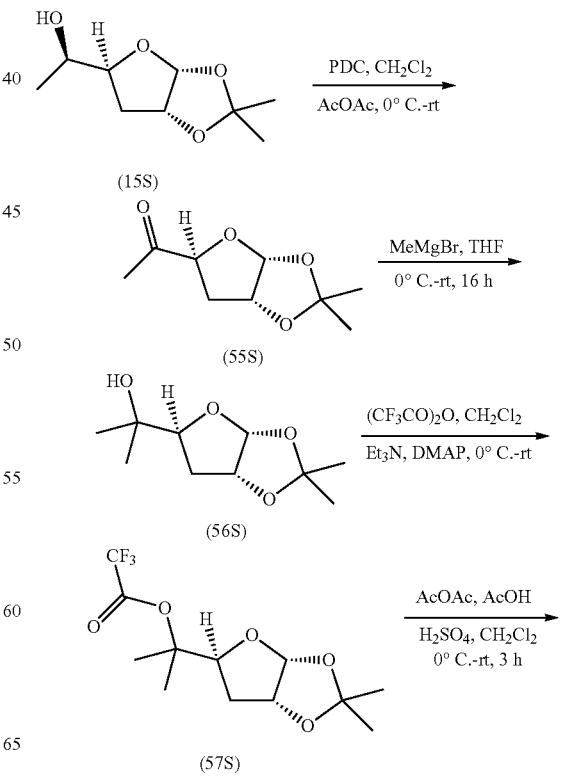

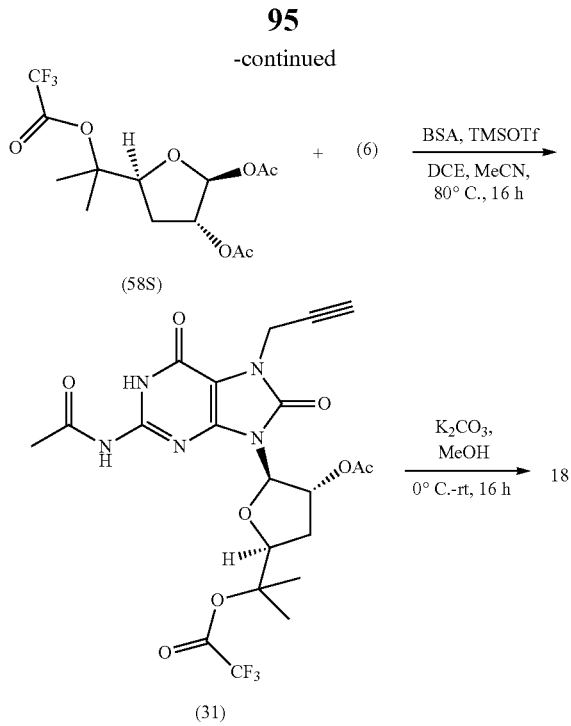
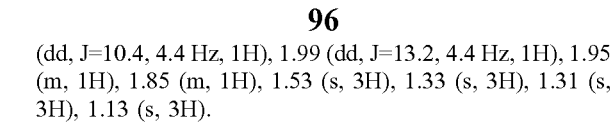

Step-1: 1-((3aR,5S,6aR)-2,2-Dimethyltetrahydrofuro[2,3-d][1,3]dioxol-5-yl)ethan-1-one (55S)

To a stirred solution of (R)-1-((3aR,5S,6aR)-2,2-dimethyltetrahydrofuro[2,3-d][1,3]dioxol-5-yl)ethan-1-ol (15S) (7 g, 37.2 mmol) in CH$_2$Cl$_2$ (70 mL) at 0° C. under N$_2$ atm were added pyridinium dichromate (16.7 g, 44.6 mmol) followed by the dropwise addition of acetic anhydride (7 mL, 1 vol). The reaction mixture was stirred at rt for 16 h, concentrated under reduced pressure and the residue was purified by column chromatography on silica gel (100-200 mesh, 50% EtOAc in petroleum ether) to afford 5 g (66%) of 1-((3aR,5S,6aR)-2,2-dimethyltetrahydrofuro[2,3-d][1,3]dioxol-5-yl)ethan-1-one (55S) as a light yellow liquid. C$_9$H$_{14}$O$_4$: $^1$H NMR (400 MHz, CDCl$_3$): δ 5.93 (d, J=3.2 Hz, 1H), 4.76 (t, J=4.0 Hz 1H), 4.61 (dd, J=11.2, 5.2 Hz, 1H), 2.37 (dd, J=13.4, 5.0 Hz, 1H), 2.24 (s, 3H), 1.77 (m, 1H), 1.52 (s, 3H), 1.34 (s, 3H).

Step-2: 2-((3aR,5S,6aR)-2,2-Dimethyltetrahydrofuro[2,3-d][1,3]dioxol-5-yl)propan-2-ol (56S)

To a stirred solution of 1-((3aR,5S,6aR)-2,2-dimethyltetrahydrofuro[2,3-d][1,3]dioxol-5-yl)ethan-1-one (55S) (5.0 g, 26.8 mmol) in diethyl ether (50 mL) at 0° C. was added methyl magnesium bromide (3.0 M) (22.4 mL 67.20 mmol). After the reaction mixture was stirred at room temperature for 3 h it was quenched with an aqueous saturated ammonium chloride solution. The organic layer was separated and the aqueous phase was extracted with EtOAc (2×200 mL). The combined organic layer were dried over Na$_2$SO$_4$, filtered and concentrated under vacuum. The crude oil was purified by column chromatography on silica gel (100-200 mesh, 50% EtOAc in petroleum ether) to afford 2 g (37%) of 2-((3aR,5S,6aR)-2,2-dimethyltetrahydrofuro[2,3-d][1,3]dioxol-5-yl)propan-2-ol (56S). C$_{10}$H$_{18}$O$_4$: $^1$H NMR (400 MHz, CDCl$_3$): δ 5.81 (d, J=2.4 Hz, 1H), 4.72 (s, 1H), 4.07 (dd, J=10.4, 4.4 Hz, 1H), 1.99 (dd, J=13.2, 4.4 Hz, 1H), 1.95 (m, 1H), 1.85 (m, 1H), 1.53 (s, 3H), 1.33 (s, 3H), 1.31 (s, 3H), 1.13 (s, 3H).

Step-3: 2-((3aR,5S,6aR)-2,2-Dimethyltetrahydrofuro[2,3-d][1,3]dioxol-5-yl)propan-2-yl 2,2,2-trifluoroacetate (57S)

To a stirred ice cold solution of 2-((3aR,5S,6aR)-2,2-dimethyltetrahydrofuro[2,3-d][1,3]dioxol-5-yl)propan-2-ol (56S) (2.0 g, 9.9 mmol) in anhydrous CH$_2$Cl$_2$ (30 mL) was added TEA (4.1 mL, 29.70 mmol), DMAP (0.24 g, 1.9 mmol) and trifluoroacetic anhydride (3.4 mL, 24.7 mmol). The reaction mixture was stirred at rt for 16 h and was then quenched with a saturated aq. NaHCO$_3$ solution (30 mL). The organic layer was separated and the aqueous phase was extracted with CH$_2$Cl$_2$ (2×100 mL). The combined organic layers were dried over Na$_2$SO$_4$, filtered and concentrated under vacuum. The crude product was purified by column chromatography on silica gel (100-200 mesh, 20% EtOAc in petroleum ether) to afford 1.5 g (51%) of 2-((3aR,5S,6aR)-2,2-dimethyltetrahydrofuro[2,3-d][1,3]dioxol-5-yl)propan-2-yl 2,2,2-trifluoroacetate (57S) as a colorless oil. C$_{12}$H$_{17}$F$_3$O$_5$: $^1$H NMR (400 MHz, CDCl$_3$): δ 5.82 (d, J 3.6 Hz, 1H), 4.76 (t, J=4.2 Hz, 1H), 4.26 (dd, J=10.8, 4.8 Hz, 1H), 2.10 (dd, J=13.6, 4.8 Hz, 1H), 1.84 (ddd, J=15.4, 9.5, 4.0 Hz, 1H), 1.65 (s, 3H), 1.57 (s, 3H), 1.52 (s, 3H), 1.33 (s, 3H).

Step-4: (2S,3R,5S)-5-(2-(2,2,2-Trifluoroacetoxy)propan-2-yl)tetrahydrofuran-2,3-diyl diacetate (58S)

To a solution of 2-((3aR,5S,6aR)-2,2-dimethyltetrahydrofuro[2,3-d][1,3]dioxol-5-yl)propan-2-yl 2,2,2-trifluoroacetate (57S) (1.5 g, 5.03 mmol), acetic acid (1.4 mL, 25.1 mmol) and acetic anhydride (2.5 mL, 25.1 mmol) in anhydrous CH$_2$Cl$_2$ (15 mL) was added concentrated H$_2$SO$_4$ (0.1 mL) at 0° C. The reaction mixture was stirred at 25° C. for 3 hours and then was quenched by addition of a saturated aq. NaHCO$_3$ solution (100 mL). The organic layer was separated and the aqueous phase was extracted with CH$_2$Cl$_2$ (2×100 mL). The combined organic layers were dried over anhydrous Na$_2$SO$_4$, filtered and concentrated under vacuum. The crude oil was purified by column chromatography on silica gel (100-200 mesh, 30% EtOAc in petroleum ether) to afford 0.7 g (41%) of (2S,3R,5S)-5-(2-(2,2,2-trifluoroacetoxy)propan-2-yl)tetrahydrofuran-2,3-diyl diacetate (58S). C$_{13}$H$_{17}$F$_3$O$_7$: $^1$H NMR (400 MHz, CDCl$_3$): δ 6.16 (s, 1H), 5.20 (d, J=4.8 Hz, 1H), 4.38 (dd, J=10.4, 6.0 Hz, 1H), 2.25-2.21 (m, 2H), 2.10 (s, 3H), 2.07 (s, 3H), 1.65 (s, 3H), 1.57 (s, 3H).

Step-5: 2-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)propan-2-yl 2,2,2-trifluoroacetate (31)

N-(6,8-dioxo-7-(prop-2-yn-1-yl)-6,7,8,9-tetrahydro-1H-purin-2-yl)acetamide (6) (350 mg, 1.4 mmol), (2S,3R,5S)-5-(2-(2,2,2-trifluoroacetoxy)propan-2-yl)tetrahydrofuran-2,3-diyl diacetate (58S) (726.9 mg, 2.12 mmol) and BSA (1.07 mL, 4.25 mmol) were dissolved in 1,2-dichloroethane (15 mL). The resulting reaction mixture was stirred at 80° C. for 30 min under argon, allowed to cool to room temperature and the solvent was removed by vacuum. The residue was dissolved in MeCN (20 mL) followed by addition of TMSOTf (0.39 mL, 2.1 mmol). The reaction mixture was heated at 70° C. for 16 h, cooled to room temperature and concentrated under vacuum. The residue was diluted with sat. aq. NaHCO₃ (50 mL) and extracted with EtOAc (3×50 mL). The combined EtOAc layer were washed with water (30 mL), brine (20 mL), dried over Na₂SO₄, filtered and concentrated under vacuum. The crude compound was purified by GRACE chromatography (80% EtOAc in pet. ether) to afford 270 mg (49%) of 2-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propan-2-yl 2,2,2-trifluoroacetate (31) as an off-white solid. $C_{21}H_{22}F_3N_5O_8$: ES+, m/z 529.9 [M+H]⁺.

Step-6: 2-Amino-9-((2R,3R,5S)-3-hydroxy-5-(2-hydroxypropan-2-yl)tetrahydrofuran-2-yl)-7-(prop-2-yn-1-yl)-7,9-dihydro-1H-purine-6,8-dione, Compound 18

To a solution of 2-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)propan-2-yl 2,2,2-trifluoroacetate (31) (270 mg, 0.51 mmol) in MeOH (10 mL) was added K₂CO₃ (105.6 mg, 0.76 mmol) at 0° C. The reaction mixture was stirred at RT for 16 h and neutralized with acetic acid at 0° C. Methanol was removed under reduced pressure at RT and the residue obtained was purified by Prep-HPLC. Column: X-SELECT-C18 (250*19), 5 u Mobile phase: 0.1% HCO₂H in H₂O:MeOH gradient: (T % B):—0/20, 8/,50, 10.5/50, 10.6/98, 13/98, 13.1/20, 16/20 Flow Rate: 18 mL/min. The pure fractions were subjected to lyophilization having 45 mg (25%) of 2-amino-9-((2R,3R,5S)-3-hydroxy-5-(2-hydroxypropan-2-yl)tetrahydrofuran-2-yl)-7-(prop-2-yn-1-yl)-7,9-dihydro-1H-purine-6,8-dione (Compound 18) as an off white solid. $C_{15}H_{19}N_5O_5$: ¹H NMR (500 MHz, DMSO-d₆): δ 10.80 (brs, 1H), 6.53 (brs, 2H), 6.51 (brs, 1H), 5.49 (d, J=3.5 Hz, 1H), 5.37 (d, J=4.5 Hz, 1H), 4.76 (m, 1H), 4.59 (d, J=1.5 Hz, 2H), 4.38 (s, 1H), 3.91 (t, J=7.3 Hz, 1H), 3.23 (s, 1H), 2.46-2.41 (m, 1H), 1.75 (m, 1H), 1.03 (d, J=6.0 Hz, 6H). ES+, m/z 350.0 [M+H]⁺.

Example 17: 2-Amino-9-((2R,3S,4R,5R)-4-fluoro-3-hydroxy-5-(2-hydroxypropan-2-yl)tetrahydrofuran-2-yl)-7-(prop-2-yn-1-yl)-7,9-dihydro-1H-purine-6,8-dione, Compound 19

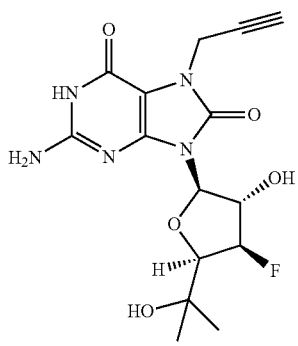 [SMILES: C#CCn1c(=O)n([C@@H]2O[C@H](C(C)(C)O)[C@H](F)[C@H]2O)c2nc(N)[nH]c(=O)c21]

Compound 19 was prepared according to the following multi-step procedure.

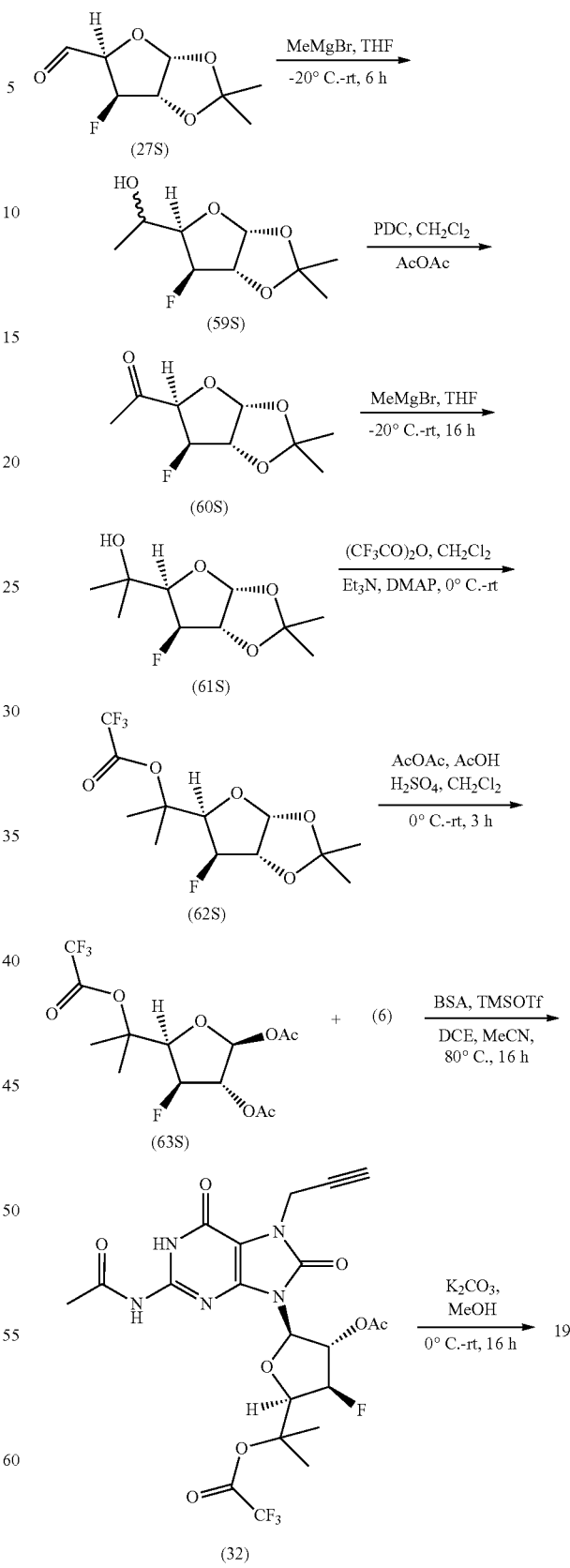

Step-1: 1-((3aR,5R,6S,6aS)-6-Fluoro-2,2-dimethyltetrahydrofuro[2,3-d][1,3]dioxol-5-yl)ethan-1-ol (59S)

To a solution of (3aR,5R,6S,6aS)-6-fluoro-2,2-dimethyltetrahydrofuro[2,3-d][1,3]dioxole-5-carbaldehyde (27S) (1 g, 5.26 mmol) in THF (20 mL) was added methyl magnesium bromide (1M in THF, 15.8 mL, 15.78 mmol) at −20° C. under argon. The reaction mixture was stirred at room temperature for 6 h and then it was quenched with a saturated aq. NH$_4$Cl solution and extracted with EtOAc (3×100 mL). The combined organic layers were dried over anh. Na$_2$SO$_4$, filtered and concentrated in vacuum to afford the crude product that was purified by column chromatography on silica gel (1:4 EtOAc in Pet-ether). 1-((3aR,5R,6S,6aS)-6-fluoro-2,2-dimethyltetrahydrofuro[2,3-d][1,3]dioxol-5-yl)ethan-1-ol (59S) (600 mg, 55.35%), as a thick mass: C$_9$H$_{15}$FO$_4$: $^1$H NMR indicates one enantiomer selectively formed; C-1 stereochemistry not determined: $^1$H NMR (500 MHz, CDCl$_3$): δ 5.98 (d, J=3.5 Hz, 1H), 5.08 (dd, J=50.3, 2.3 Hz, 1H), 4.70 (dd, J=13.5, 4.0 Hz, 1H), 4.10 (m, 1H), 3.97 (ddd, J=29.8, 8.0, 2.3 Hz, 1H), 1.77 (d, J=5.0 Hz, 1H), 1.50 (s, 3H), 1.38 (d, J=6.5 Hz, 3H), 1.33 (s, 3H).

Step-2: 1-((3aR,5R,6R,6aS)-6-Fluoro-2,2-dimethyltetrahydrofuro[2,3-d][1,3]dioxol-5-yl)ethan-1-one (60S)

To a solution of 1-((3aR,5R,6S,6aS)-6-fluoro-2,2-dimethyltetrahydrofuro[2,3-d][1,3]dioxol-5-yl)ethan-1-ol (59S) (100 mg, 0.48 mmol) and Ac$_2$O (0.1 mL) in CH$_2$Cl$_2$ (10 mL) was added pyridinium dichromate (219 mg, 0.58 mmol). The reaction mixture was stirred at room temperature for 16 h, concentrated under vacuum and EtOAc was added portionwise (3×100 mL) with vigorous stirring. The organic layers was passed through a silica-gel plug and concentrated in vacuum to afford (80 mg, 80.88%) of 1-((3aR,5R,6R,6aS)-6-fluoro-2,2-dimethyltetrahydrofuro[2,3-d][1,3]dioxol-5-yl)ethan-1-one (60S) as an colorless oil that was used without any further purification. C$_9$H$_{13}$FO$_4$: $^1$H NMR (400 MHz, CDCl$_3$): δ 6.13 (d, J=4.0 Hz, 1H), 5.18 (dd, J=49.8, 2.6 Hz, 1H), 4.72 (dd, J=9.8, 3.8 Hz, 1H), 4.64 (dd, J=33.0, 2.6 Hz, 1H), 2.28 (d, J=0.4 Hz, 3H), 1.49 (s, 3H), 1.35 (s, 3H).

Step-3: 2-((3aR,5R,6S,6aS)-6-Fluoro-2,2-dimethyltetrahydrofuro[2,3-d][1,3]dioxol-5-yl)propan-2-ol (61S)

To a solution of 1-((3aR,5R,6R,6aS)-6-fluoro-2,2-dimethyltetrahydrofuro[2,3-d][1,3]dioxol-5-yl)ethan-1-one (60S) (100 mg, 0.49 mmol) in THF (10 mL) was added methyl magnesium bromide (1M in THF, 0.75 mL, 0.73 mmol) at −20° C. under argon. The reaction was then stirred at room temperature for 16 h. The reaction mixture was quenched with a saturated aq. NH$_4$Cl solution and extracted with EtOAc (3×50 mL). The combined organic layers were dried over anh. Na$_2$SO$_4$, filtered and concentrated in vacuo to afford the crude product which was purified by column chromatography on silica gel (1:4 EtOAc in pet-ether) to afford (50 mg, 46.4%) of 2-((3aR,5R,6S,6aS)-6-fluoro-2,2-dimethyltetrahydrofuro[2,3-d][1,3]dioxol-5-yl)propan-2-ol (61S), as an colourless oil. C$_{10}$H$_{17}$FO$_4$: $^1$H NMR (500 MHz, CDCl$_3$): δ 6.04 (d, J=4.0 Hz, 1H), 5.03 (dd, J=50.3, 2.3 Hz, 1H), 4.68 (dd, J=12.3, 3.8 Hz, 1H), 3.99 (dd, J=34.0, 2.5 Hz, 1H), 2.18 (d, J=5.0 Hz, 1H), 1.50 (s, 3H), 1.37 (s, 3H) 1.35 (s, 3H), 1.34 (s, 3H).

Step-4: 2-((3aR,5R,6S,6aS)-6-Fluoro-2,2-dimethyltetrahydrofuro[2,3-d][1,3]dioxol-5-yl)propan-2-yl 2,2,2-trifluoroacetate (62S)

To a solution of 2-((3aR,5R,6S,6aS)-6-fluoro-2,2-dimethyltetrahydrofuro[2,3-d][1,3]dioxol-5-yl)propan-2-ol (61S) (1.0 g, 4.54 mmol) in CH$_2$Cl$_2$ (20 mL) was added Et$_3$N (1.28 mL, 9.09 mmol) at 0° C. After stirring for 10 min trifluoroacetic anhydride (1.43 mL, 6.81 mmol) was added at 0° C. and the reaction mixture was stirred at room temperature for an additional 16 h. Then the reaction mixture was quenched with sat. aq. NaHCO$_3$ solution and extracted with CH$_2$Cl$_2$ (3×100 mL). The combined organic layers were dried over Na$_2$SO$_4$, filtered and concentrated in vacuo to afford a residue that was purified by column chromatography on silica gel (1:4 EtOAc in pet-ether) to afford (500 mg, 34.8%) of 2-((3aR,5R,6S,6aS)-6-fluoro-2,2-dimethyltetrahydrofuro[2,3-d][1,3]dioxol-5-yl)propan-2-yl 2,2,2-trifluoroacetate (62S), as a colorless oil. C$_{12}$H$_{16}$F$_4$O$_5$: $^1$H NMR (400 MHz, CDCl$_3$): δ 6.03 (d, J=4.0 Hz, 1H), 5.01 (dd, J=50.4, 2.4 Hz, 1H), 4.67 (dd, J=11.8, 3.8 Hz, 1H), 4.43 (dd, J=32.4, 2.4 Hz, 1H), 1.72 (s, 3H), 1.69 (s, 3H), 1.50 (s, 3H), 1.34 (s, 3H).

Step-5: (2S,3S,4S,5R)-4-Fluoro-5-(2-(2,2,2-trifluoroacetoxy)propan-2-yl)tetrahydrofuran-2,3-diyl diacetate (63S)

To 2-((3aR,5R,6S,6aS)-6-fluoro-2,2-dimethyltetrahydrofuro[2,3-d][1,3]dioxol-5-yl)propan-2-yl 2,2,2-trifluoroacetate (62S) (800 mg, 2.53 mmol) dissolved in CH$_2$Cl$_2$ (20 mL) was added AcOH (1.46 mL, 25.32 mmol), Ac$_2$O (1.20 mL, 12.65 mmol) and conc. H$_2$SO$_4$ (0.1 mL) at 0° C. The resulting reaction mixture was stirred at room temperature for 3 h, quenched with sat. aq. NaHCO$_3$ and extracted with CH$_2$Cl$_2$ (3×100 mL). The combined organic layers were dried over Na$_2$SO$_4$, filtered and concentrated in vacuum. The residue was purified by flash chromatography (SiO$_2$, 0-15% EtOAc-pet. ether) to afford (150 mg, 22.6%) of (2S,3S,4S,5R)-4-fluoro-5-(2-(2,2,2-trifluoroacetoxy)propan-2-yl)tetrahydrofuran-2,3-diyl diacetate (63S) as a colorless oil. C$_{13}$H$_{16}$F$_4$O$_7$: $^1$H NMR (400 MHz, CDCl$_3$): δ 6.20 (s, 1H), 5.31 (d, J=11.6 Hz, 1H), 5.06 (d, J=50.4 Hz, 1H), 4.54 (d, J=31.6 Hz, 1H), 2.14 (s, 3H), 2.10 (s, 3H), 1.74 (s, 3H), 1.69 (s, 3H).

Step-6: 2-((2R,3S,4S,5R)-5-(2-Acetamido-6,8-dioxo-7-(prop-2-yn-1-yl)-1,6,7,8-tetrahydro-9H-purin-9-yl)-4-acetoxy-3-fluorotetrahydrofuran-2-yl)propan-2-yl 2,2,2-trifluoroacetate (32)

N-(6,8-dioxo-7-(prop-2-yn-1-yl)-6,7,8,9-tetrahydro-1H-purin-2-yl)acetamide (6) (300 mg, 1.21 mmol), (2S,3S,4S,5R)-4-fluoro-5-(2-(2,2,2-trifluoroacetoxy)propan-2-yl)tetrahydrofuran-2,3-diyl diacetate (63S) (654 mg, 1.82 mmol) and BSA (0.61 mL, 3.03 mmol) were dissolved in 1,2-dichloroethane (10 mL) and the reaction mixture was stirred at 80° C. for 30 min under argon. The reaction mixture was allowed to cool to room temperature followed by addition of TMSOTf (0.40 mL, 1.82 mmol). The resulting reaction mixture was stirred at 80° C. for 30 min under argon, allowed to cool to room temperature and the solvent was removed by vacuum. The residue was dissolved in MeCN (15 mL) followed by addition of TMSOTf (0.40 mL, 1.82 mmol). The reaction mixture was heated at 80° C. for 16 h, cooled to room temperature, diluted with water and extracted with EtOAc (3×100 mL). The combined organic layer was washed with water (100 mL), brine (100 mL), dried over Na$_2$SO$_4$, filtered and concentrated. The crude product was purified by GRACE reverse phase flash chromatography (Column: FLASH PURE-C18 (40 m irregular), Mobile phase: 0.1% HCO$_2$H in H$_2$O:MeCN T % B):—30 mins; Flow Rate: 12 mL/min.) to afford (160 mg, 24.1%) of 2-((2R,3R,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propan-2-yl 2,2,2-trifluoroacetate (32) as a yellow solid. C$_{21}$H$_2$F$_4$N$_5$O$_8$: $^1$H NMR (400 MHz, CDCl$_3$): δ 11.97 (bs, 1H), 8.18 (s, 1H), 6.19 (dd, J=22.8, 5.2 Hz, 1H), 5.77 (d, J=5.6 Hz, 1H), 5.17 (d, J=51.4, 3.8 Hz, 1H), 4.86 (d, J=2.4 Hz, 2H), 4.27 (dd, J=29.6, 4.0 Hz, 1H), 2.32 (t, J=2.4 Hz, 1H), 2.21 (s, 3H), 2.13 (s, 3H), 1.76 (s, 3H), 1.72 (s, 3H). ES+, m/z 548.40 [M+H]$^+$.

Step-7: 2-Amino-9-((2R,3S,4R,5R)-4-fluoro-3-hydroxy-5-(2-hydroxypropan-2-yl)tetrahydrofuran-2-yl)-7-(prop-2-yn-1-yl)-7,9-dihydro-1H-purine-6,8-dione, Compound 19

To a solution of 2-((2R,3R,4S,5R)-5-(2-acetamido-6,8-dioxo-7-(prop-2-yn-1-yl)-1,6,7,8-tetrahydro-9H-purin-9-yl)-4-acetoxy-3-fluorotetrahydrofuran-2-yl)propan-2-yl 2,2,2-trifluoroacetate (32) (160 mg, 0.29 mmol) in methanol (10 mL) was added K$_2$CO$_3$ (48 mg, 0.35 mmol) at 0° C. The reaction mixture was stirred at room temperature for 16 h, concentrated and subjected to GRACE FLASH chromatography (Reverse phase using 0.01% of formic acid in acetonitrile). The pure fractions were concentrated to yield 2-amino-9-((2R,3S,4S,5R)-4-fluoro-3-hydroxy-5-(2-hydroxypropan-2-yl)tetrahydrofuran-2-yl)-7-(prop-2-yn-1-yl)-7,9-dihydro-1H-purine-6,8-dione, Compound 19 (53 mg, 49.4%) as a white solid. C$_{15}$H$_{18}$FN$_5$O$_5$: $^1$H NMR (400 MHz, DMSO-d$_6$): δ 10.96 (brs, 1H), 6.56 (s, 2H), 5.93 (d, J=5.6 Hz, 1H), 5.35-5.32 (m, 1H), 5.26 (m, 1H), 5.01 (ddd, J=53.8, 4.8, 2.6 Hz, 1H), 4.64 (s, 1H), 4.60 (d, J=2.0 Hz, 2H), 3.75 (dd, J=26.2, 4.6 Hz, 1H), 3.24 (t, J=2.2 Hz, 1H), 1.17 (s, 6H). ES+, m/z 368.0 [M+H]$^+$.

Example 18: 2-Amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-8H-purin-8-one, Compound 20 and 2-Amino-9-((2R,3S,4R,5R)-4-fluoro-3-hydroxy-5-((S)-1-hydroxypropyl)tetrahydrofuran-2-yl)-7-(propa-1,2-dien-1-yl)-7,9-dihydro-8H-purin-8-one, Compound 21

20

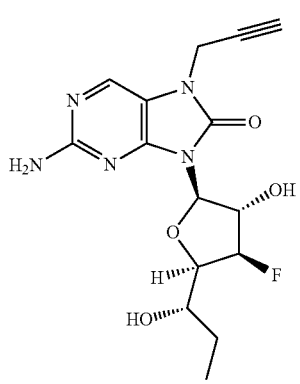

21

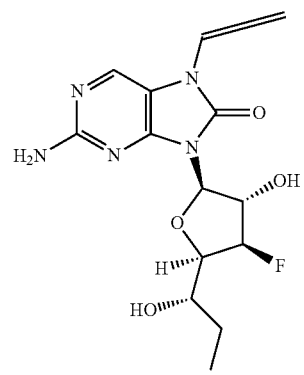

Using the procedures described in Example 5, Compounds 20 and 21 were synthesized from (21) and (37S) as follows:

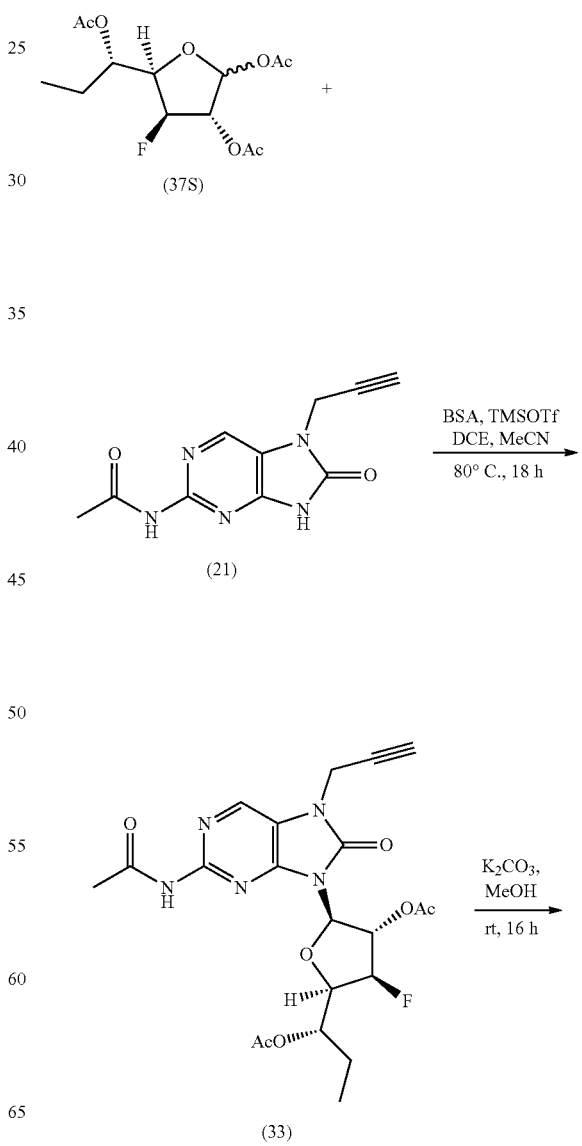

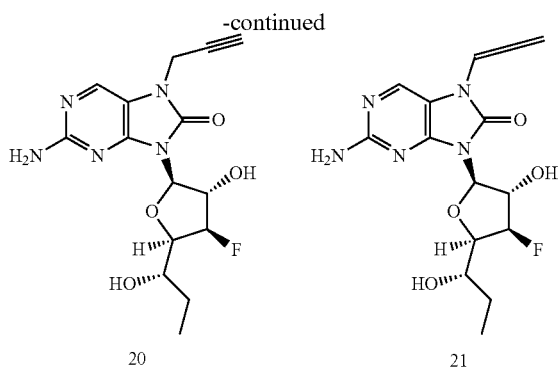

Step-1: (S)-1-((2R,3S,4S,5R)-5-(2-Acetamido-8-oxo-7-(prop-2-yn-1-yl)-7,8-dihydro-9H-purin-9-yl)-4-acetoxy-3-fluorotetrahydrofuran-2-yl)propyl acetate (33)

N-(8-oxo-7-(prop-2-yn-1-yl)-8,9-dihydro-7H-purin-2-yl) acetamide (21) (400 mg, 1.731 mmol), (3S,4S,5R)-5-((S)-1-acetoxypropyl)-4-fluorotetrahydrofuran-2,3-diyl diacetate (37S) (627 mg, 2.079 mmol) and BSA (1.049 g, 5.194 mmol) were dissolved in dichloroethane (20 mL). The reaction mixture was stirred at 80° C. for 30 min under argon. Then the reaction mixture was concentrated under reduced pressure and the residue was taken up in MeCN (50 mL). The reaction flask was charged with TMSOTf (577 mg, 2.594 mmol) and placed into a preheated oil bath at 80° C. After 18 h the reaction was cooled to room temperature and the solvent was removed by rotary evaporation. The resultant solid was dissolved in ethyl acetate (50 mL) and washed with saturated aqueous $NaHCO_3$ (2×30 mL). The organic phase was dried over $Na_2SO_4$, filtered and concentrated. The crude product was purified by column chromatography ($SiO_2$, 0 to 80% ethyl acetate-Pet ether), to yield (400 mg, 48.43%) of (S)-1-((2R,3S,4S,5R)-5-(2-acetamido-8-oxo-7-(prop-2-yn-1-yl)-7,8-dihydro-9H-purin-9-yl)-4-acetoxy-3-fluorotetrahydrofuran-2-yl)propyl acetate (33) as a light yellow solid. $C_{21}H_{24}FN_5O_7$: ES+, m/z 477.8 [M+H]+. LC/MS also indicated loss of one Ac group (ES+, m/z 435.8 [M+H]+). The product was used without further purification.

Step-2: 2-Amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-8H-purin-8-one, Compound 20 and 2-Amino-9-((2R,3S,4R,5R)-4-fluoro-3-hydroxy-5-((S)-1-hydroxypropyl)tetrahydrofuran-2-yl)-7-(propa-1,2-dien-1-yl)-7,9-dihydro-8H-purin-8-one, Compound 21

(S)-1-((2R,3S,4S,5R)-5-(2-acetamido-8-oxo-7-(prop-2-yn-1-yl)-7,8-dihydro-9H-purin-9-yl)-4-acetoxy-3-fluorotetrahydrofuran-2-yl)propyl acetate (33) (400 mg, 0.8385 mmol) was dissolved in methanol (10 mL) followed by addition of $K_2CO_3$ (173 mg, 1.257 mmol) at 0° C. The reaction mixture was stirred at room temperature for 16 h and concentrated. The residue was purified by GRACE FLASH chromatography (Reverse phase; 0.01% of formic acid in acetonitrile) to afford (53 mg, 38.93%) of 2-amino-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-8H-purin-8-one (Compound 20) as an off white solid and (20 mg, 14.69%) of 2-amino-9-((2R,3S,4R,5R)-4-fluoro-3-hydroxy-5-((S)-1-hydroxypropyl)tetrahydrofuran-2-yl)-7-(propa-1,2-dien-1-yl)-7,9-dihydro-8H-purin-8-one (Compound 21) as an off white solid.

Compound 20: $C_{15}H_{18}FN_5O_4$: ES+, m/z 352.2 [M+H]+; $^1$H NMR (500 MHz, DMSO-$d_6$): δ 8.06 (s, 1H), 6.39 (s, 2H), 5.97 (d, J=5.5 Hz, 1H), 5.46 (d, J=6.5 Hz, 1H), 5.40 (m, 1H), 5.00 (ddd, J=53.3, 4.3, 2.0 Hz, 1H), 4.80 (d, J=6.5 Hz, 1H), 4.66 (d, J=5.5 Hz, 2H), 3.85 (ddd, J=24.3, 7.0, 4.8 Hz, 1H), 3.56 (m, 1H), 3.41 (t, J=2.5 Hz, 1H), 1.49 (m, 1H), 1.35 (m, 1H), 0.91 (t, J=7.3 Hz, 3H).

Compound 21: $C_{15}H_{18}FN_5O_4$: ES+, m/z 352.1 [M+H]+; $^1$H NMR (500 MHz, DMSO-$d_6$): δ 8.18 (s, 1H), 7.23 (t, J=6.8 Hz, 1H), 6.52 (s, 2H), 5.95 (brs, 1H), 5.83 (d, J=6.5 Hz, 2H), 5.48 (d, J=6.0 Hz, 1H), 5.33 (ddd, J=25.0, 6.0, 2.0 Hz, 1H), 5.01 (ddd, J=53.0, 4.5, 2.0 Hz, 1H), 4.77 (s, 1H), 3.85 (ddd, J=24.3, 7.3, 4.5 Hz, 1H), 3.57 (m, 1H), 1.51 (m, 1H), 1.34 (m, 1H), 0.92 (t, J=7.3 Hz, 3H).

Example 19: 2-Amino-9-((2R,3R,5S)-3-hydroxy-5-((S)-1-hydroxypropyl)tetrahydrofuran-2-yl)-7-(2-(methylthio)ethyl)-7,9-dihydro-1H-purine-6,8-dione, Compound 22

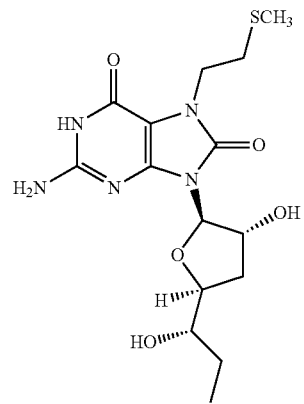 [SMILES: CC[C@H](O)[C@@H]1C[C@@H](O)[C@H](n2c(=O)n(CCSC)c3c(=O)[nH]c(N)nc32)O1]

Compound 22 was prepared according to the following multi-step procedure.

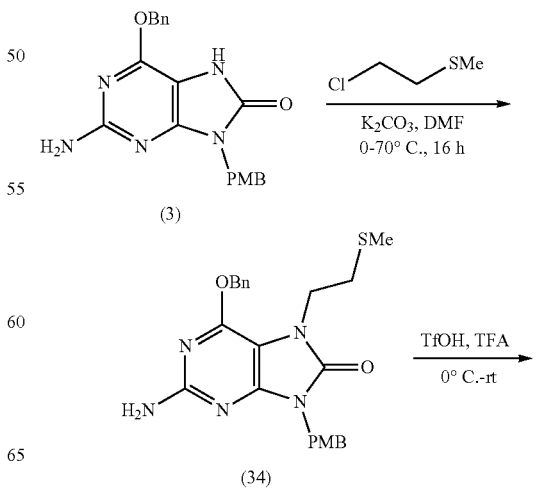

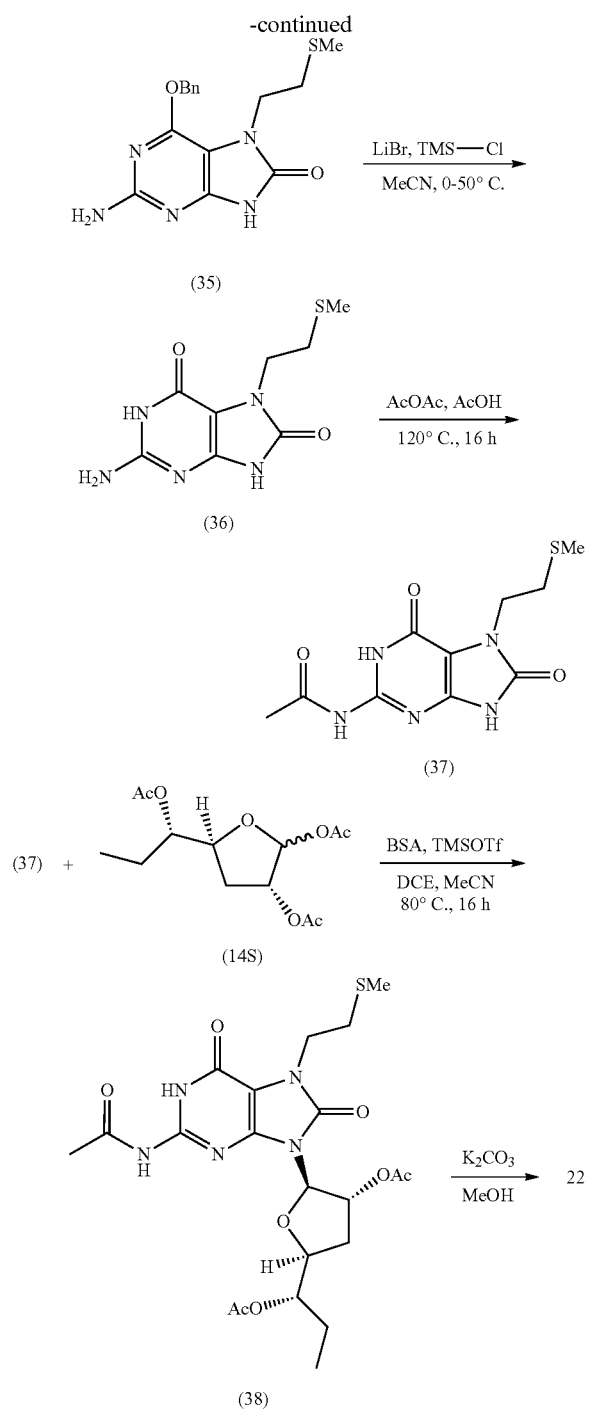

with water and dried to give 2-amino-6-(benzyloxy)-9-(4-methoxybenzyl)-7-(2-(methylthio)ethyl)-7,9-dihydro-8H-purin-8-one (34) (4.0 g, 85%) as an off-white solid. $C_{23}H_{25}N_5O_3S$: $^1$H NMR (400 MHz, DMSO-$d_6$): δ 7.47 (d, J=7.2 Hz, 1H), 7.40 (d, J=6.8 Hz, 2H), 7.39-7.22 (m, 2H), 7.19 (d, J=6.8 Hz, 2H), 6.87 (d, J=8.8 Hz, 2H), 6.42 (s, 2H), 5.42 (s, 2H), 4.83 (s, 2H), 3.93 (t, J=7.0 Hz, 2H), 3.71 (s, 3H), 2.68 (t, J=7.0 Hz, 2H), 1.90 (s, 3H). ES+, m/z 452.3 [M+H]$^+$.

Step-2: 2-Amino-6-(benzyloxy)-7-(2-(methylthio)ethyl)-7,9-dihydro-8H-purin-8-one (35)

Trifluoromethane sulfonic acid (3.56 mL, 35.47 mmol) was added to a suspension of 2-amino-6-(benzyloxy)-9-(4-methoxybenzyl)-7-(2-(methylthio)ethyl)-7,9-dihydro-8H-purin-8-one (34) (4.0 g, 8.86 mmol) in TFA (2.71 mL, 35.47 mmol) at room temperature under argon atmosphere and the resulting reaction mixture was stirred at room temperature for 16 h under argon atmosphere. The reaction mixture was quenched with ice cold water (200 mL) and made basic with sat. aq. NaHCO$_3$ solution (300 mL) under vigorous stirring and filtered. The filtered solid was taken up in ethyl acetate, stirred for 30 min., filtered and dried to afford 2-amino-6-(benzyloxy)-7-(2-(methylthio)ethyl)-7,9-dihydro-8H-purin-8-one (35) (1.8 g, 62%) as a brown solid. $C_{15}H_{17}N_5O_2S$; $^1$H NMR (400 MHz, DMSO-$d_6$): δ 10.87 (s, 1H), 7.47 (s, 5H), 6.48 (s, 2H), 4.84 (d, J=12.8 Hz, 1H), 4.64 (d, J=12.8 Hz, 1H), 4.23 (m, 2H), 3.67-3.58 (m, 2H), 2.81 (s, 3H). ES+, m/z 332.2 [M+H]$^+$.

Step-3: 2-Amino-7-(2-(methylthio)ethyl)-7,9-dihydro-1H-purine-6,8-dione (36)

LiBr (0.701 g, 8.15 mmol) and TMSCl (2.7 mL g, 21.7 mmol) were added to a suspension of 2-amino-6-(benzyloxy)-7-(2-(methylthio)ethyl)-7,9-dihydro-8H-purin-8-one (35) (1.8 g, 5.4 mmol) in acetonitrile (36 mL) at 0° C. under argon atmosphere. The reaction mixture was stirred at 50° C. for 16 h under argon atmosphere, quenched with ice cold water (200 mL), made basic with sat. aq. NaHCO$_3$ solution (300 mL) with vigorous stirring. The solid formed was filtered and EtOAc was added, stirred for 30 min, filtered off and dried to afford 2-amino-7-(2-(methylthio)ethyl)-7,9-dihydro-1H-purine-6,8-dione (36) (1.0 g, 76%) as a brown solid. $C_8H_{11}N_5O_2S$: $^1$H NMR (400 MHz, DMSO-$d_6$): δ 11.09 (s, 1H), 10.66 (s, 1H), 6.37 (s, 2H), 3.90 (t, J=6.8 Hz, 2H), 2.76 (t, J=6.8 Hz, 2H), 2.07 (s, 3H). ES+, m/z 242.0 [M+H]$^+$.

Step-4: N-(7-(2-(Methylthio)ethyl)-6,8-dioxo-6,7,8,9-tetrahydro-1H-purin-2-yl)acetamide (37)

Acetic anhydride (2.53 mL, 24.89 mmol) was added to a solution of 2-amino-7-(2-(methylthio)ethyl)-7,9-dihydro-1H-purine-6,8-dione (36) (1 g, 4.14 mmol) in AcOH (10 mL) at ambient temperature under argon atmosphere and the resulting reaction mixture was heated at 120° C. for 16 h under argon atmosphere. The reaction mixture was stirred and cooled to 0° C. for 30 minutes whereupon a dark solid precipitated. The product was filtered, washed with diethyl ether and dried under vacuum to afford N-(7-(2-(methylthio)ethyl)-6,8-dioxo-6,7,8,9-tetrahydro-1H-purin-2-yl)acetamide (37) (1.0 g, 85%) as an brown solid. The dried product was directly used in the next step. $C_{10}H_{13}N_5O_3S$: $^1$H NMR (500 MHz, DMSO-$d_6$): δ 12.01 (s, 1H), 11.69 (s, 1H), 11.64

Step-1: 2-Amino-6-(benzyloxy)-9-(4-methoxybenzyl)-7-(2-(methylthio)ethyl)-7,9-dihydro-8H-purin-8-one (34)

To a suspension of 2-amino-6-(benzyloxy)-9-(4-methoxybenzyl)-7,9-dihydro-8H-purin-8-one (3) in DMF (60 mL) was added (2-chloroethyl)(methyl)sulfane (2.56 g, 23.34 mmol), K$_2$CO$_3$ (4.39 g, 31.83 mmol) at 0° C. The reaction mixture was stirred at 70° C. for 16 h. The reaction mixture was quenched with ice water (200 mL), diethyl ether (100 mL) was added and stirred for 15 min. The resulting precipitated solid was filtered, washed (s, 1H), 3.99 (t, J=7.0 Hz, 2H), 2.79 (t, J=7.0 Hz, 2H), 2.18 (s, 3H), 2.08 (s, 3H). ES+, m/z 283.8 [M+H]⁺.

Step-5: (S)-1-((2S,4R,5R)-5-(2-Acetamido-7-(2-(methylthio)ethyl)-6,8-dioxo-1,6,7,8-tetrahydro-9H-purin-9-yl)-4-acetoxytetrahydrofuran-2-yl)propyl acetate (38)

N-(7-(2-(methylthio)ethyl)-6,8-dioxo-6,7,8,9-tetrahydro-1H-purin-2-yl)acetamide (37) (760 mg, 2.663 mmol), (3R,5S)-5-((S)-1-acetoxypropyl)tetrahydrofuran-2,3-diyl diacetate (14S) (923 mg, 3.20 mmol) and BSA (1.33 mL, 5.28 mmol) were dissolved in 1,2-dichloroethane (35 mL) and the resulting reaction mixture was stirred at 80° C. for 30 min under argon. The reaction mixture was allowed to cool to rt and 1,2-dichloroethane was removed under vacuum. The residue was dissolved in MeCN (35 mL) followed by addition of TMSOTf (0.488 mL, 2.64 mmol). The reaction mixture was heated at 80° C. for 16 h, cooled to room temperature and concentrated under vacuum. The residue was diluted with sat. aq. NaHCO₃ (60 mL) and extracted with EtOAc (3×80 mL). The combined EtOAc layer was washed with water (50 mL), brine (40 mL), dried over Na₂SO₄, filtered and concentrated under vacuum. The crude compound was purified by flash column chromatography on silica gel (80% EtOAc in pet. ether) to afford (S)-1-((2S,4R,5R)-5-(2-acetamido-7-(2-(methylthio)ethyl)-6,8-dioxo-1,6,7,8-tetrahydro-9H-purin-9-yl)-4-acetoxytetrahydrofuran-2-yl)propyl acetate (38) (250 mg, 28%) as an off-white solid and taken on directly to the final step as is.

Step-6: 2-Amino-9-((2R,3R,5S)-3-hydroxy-5-((S)-1-hydroxypropyl)tetrahydrofuran-2-yl)-7-(2-(methylthio)ethyl)-7,9-dihydro-1H-purine-6,8-dione, Compound 22

To a solution of (S)-1-((2S,4R,5R)-5-(2-acetamido-7-(2-(methylthio)ethyl)-6,8-dioxo-1,6,7,8-tetrahydro-9H-purin-9-yl)-4-acetoxytetrahydrofuran-2-yl)propyl acetate (38) (250 mg, 0.4892 mmol) in methanol (10 mL), was added K₂CO₃ (135 mg, 0.978 mmol) at room temperature. The reaction was monitored by LC/MS until (38) was consumed. After stirring at room temperature for 16 h. the reaction mixture was concentrated under vacuum to afford a crude solid that was purified by GRACE reverse phase chromatography (0.1% aq. HCO₂H:MeCN) to give 2-amino-9-((2R,3R,5S)-3-hydroxy-5-((S)-1-hydroxypropyl)tetrahydrofuran-2-yl)-7-(2-(methylthio)ethyl)-7,9-dihydro-1H-purine-6,8-dione (Compound 22) (25 mg, 14%) as an off-white solid. $C_{15}H_{23}N_5O_5S$: ¹H NMR (500 MHz, DMSO-d₆): δ 11.6 (s, 1H), 6.62 (s, 2H), 5.52 (d, J=3.5 Hz, 1H), 5.35 (d, J=4.5 Hz, 1H), 4.75 (m, 2H), 4.00 (m, 1H), 3.95 (t, J=7.0 Hz, 2H), 3.25 (m, 1H), 2.78 (t, J=7.0 Hz, 2H), 2.38 (m, 1H), 2.08 (s, 3H), 1.78 (m, 1H), 1.39 (m, 1H), 1.28 (m, 1H), 0.87 (t, J=7.5 Hz, 3H). ES+, m/z 386.2 [M+H]⁺.

Example 20:2-Amino-9-((2R,3R,5S)-5-((S)-2-fluoro-1-hydroxyethyl)-3-hydroxytetrahydrofuran-2-yl)-7-(prop-2-yn-1-yl)-7,9-dihydro-1H-purine-6,8-dione, Compound 23

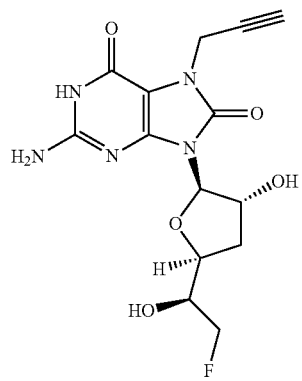 [SMILES: C#CCn1c(=O)n([C@@H]2O[C@H]([C@H](O)CF)C[C@H]2O)c2nc(N)[nH]c(=O)c21]

Compound 23 was prepared according to the following multi-step procedure.

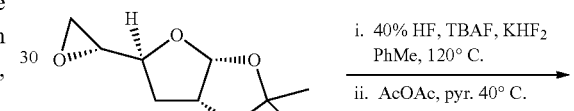

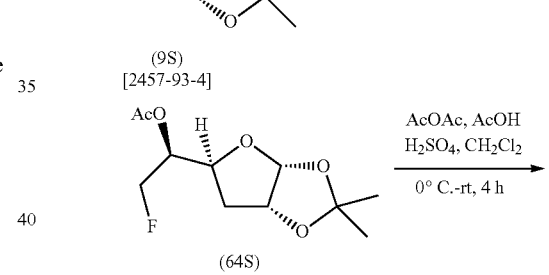

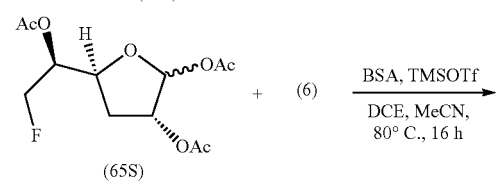

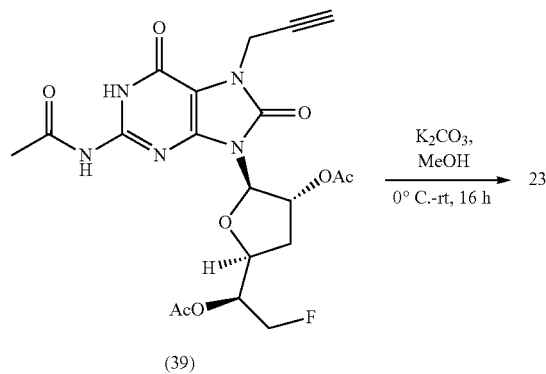

Step-1: (S)-1-((3aR,5S,6aR)-2,2-Dimethyltetrahydrofuro[2,3-d][1,3]dioxol-5-yl)-2-fluoroethyl acetate (64S)

A 40% HF solution (0.69 mL, 16.1 m·mol) was added to TBAF (1M in THF) (16 mL, 16.1 mmol) and after 5 min the solution was concentrated under reduced pressure (1 mbar, 100° C.). To this concentrated mixture, (3aR,5S,6aR)-2,2-dimethyl-5-((R)-oxiran-2-yl)tetrahydrofuro[2,3-d][1,3]dioxole (9S) (1 g, 5.3 mmol), and a solution of KHF$_2$ (125.8 mg, 1.61 mmol) in dry toluene (20 ml) were added and the mixture was maintained at 120° C. for 18 h. The reaction mixture was cooled to rt, Ac$_2$O (1.6 mL, 16.1 mmol) and dry pyridine (3.5 mL, 16.1 mmol) were added and the mixture was maintained under stirring at 40° C. for 2 h. The reaction mixture was quenched with water and extracted with EtOAc (2×75 mL). The organic phase was washed with 2M HCl and saturated aq. NaHCO$_3$ solution (50 mL), dried over anhydrous Na$_2$SO$_4$, filtered and concentrated under vacuum. The crude product was purified by column chromatography on silica gel (100-200 mesh, 20% EtOAc in petroleum ether) to afford 1 g (76%) of (S)-1-((3aR,5S,6aR)-2,2-dimethyltetrahydrofuro[2,3-d][1,3]dioxol-5-yl)-2-fluoroethyl acetate (64S). C$_{11}$H$_{17}$FO$_5$: $^1$H NMR (400 MHz, CDCl3): δ 5.80 (d, J=3.6 Hz, 1H), 5.11 (m, 1H), 4.74 (t, J=4.2 Hz, 1H), 4.61 (ddd, J=47.6, 10.6, 3.0 Hz, 1H), overlapping with 4.56 (ddd, J=46.8, 10.6, 4.8 Hz, 1H), 4.36 (ddd, J=10.6, 6.2, 4.8 Hz, 1H), 2.17 (dd, J=13.6, 4.4 Hz, 1H), 2.11 (s, 3H), 1.80 (dd, J=13.4, 10.6, 4.8 Hz, 1H), 1.51 (s, 3H), 1.32 (s, 3H).

Step-2: (3R,5S)-5-((S)-1-Acetoxy-2-fluoroethyl)tetrahydrofuran-2,3-diyl diacetate (65S)

To a solution of (S)-1-((3aR,5S,6aR)-2,2-dimethyltetrahydrofuro[2,3-d][1,3]dioxol-5-yl)-2-fluoroethyl acetate (64S) (1 g, 4.03 mmol), acetic acid (2.3 mL, 40.3 mmol) and acetic anhydride (2 mL, 20.1 mmol) in anhydrous CH$_2$Cl$_2$ (30 mL) was added concentrated H$_2$SO$_4$ (0.1 mL) at 0° C. After being stirred at 25° C. for 4 h, the reaction was quenched by the addition of ice cold water. The organic layer was separated and the aqueous phase was extracted with CH$_2$Cl$_2$ (2×75 mL). The combined organic layer was washed with saturated aq·NaHCO$_3$ solution (50 mL), dried over Na$_2$SO$_4$, filtered and concentrated under vacuum. The crude product was purified by column chromatography on silica gel (100-200 mesh, 30% EtOAc in petroleum ether) to afford 0.4 g (36%) of (3R,5S)-5-((S)-1-acetoxypropyl)tetrahydrofuran-2,3-diyl diacetate (64S) as a colorless oil. C$_{12}$H$_{17}$FO$_7$: $^1$H NMR indicated an α (minor), β (major) anomeric mixture; $^1$H NMR (400 MHz, CDCl$_3$): δ 6.16 (s, 1H), 5.18 (m, 1H), 5.08-5.02 (m, 1H), 4.66-4.64 (m, 1H), 4.55-4.51 (m, 2H), 2.23-2.12 (m, 2H), 2.10-2.08 (m, 9H).

Step-3: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2-fluoroethyl acetate (39)

N-(6,8-Dioxo-7-(prop-2-yn-1-yl)-6,7,8,9-tetrahydro-1H-purin-2-yl)acetamide (6) (250 mg, 1.01 mmol), (3R,5S)-5-((S)-1-acetoxypropyl)tetrahydrofuran-2,3-diyl diacetate (64S) (354.6 mg, 1.2 mmol), and BSA (0.76 mL, 3.03 mmol) were dissolved in 1,2-dichloroethane (15 mL) and the solution was stirred at 80° C. for 30 min under argon. The reaction mixture was then cooled to rt and 1,2-dichloroethane was removed under vacuum. The residue was dissolved in MeCN (20 mL) followed by the addition of TMSOTf (0.28 mL, 1.5 mmol). The reaction mixture was heated at 80° C. for 16 h., cooled to room temperature and concentrated under vacuum. The residue was diluted with sat. aq. NaHCO$_3$ (50 mL) and extracted with EtOAc (3×50 mL). The combined EtOAc layer was washed with water (30 mL), brine (30 mL), dried over Na$_2$SO$_4$, filtered and concentrated under vacuum. The crude compound was purified by GRACE flash chromatography (80% EtOAc in Pet ether) to afford 190 mg (39%) of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-fluoroethyl acetate (39) as an off-white solid. C$_{20}$H$_{22}$FN$_5$O$_8$: ES+, m/z 480.2 [M+H]$^+$.

Step-4: 2-Amino-9-((2R,3R,5S)-5-((S)-2-fluoro-1-hydroxyethyl)-3-hydroxytetrahydrofuran-2-yl)-7-(prop-2-yn-1-yl)-7,9-dihydro-1H-purine-6,8-dione, Compound 23

To a solution of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-fluoroethyl acetate (39) (190 mg, 0.39 mmol) in MeOH (10 mL) was added K$_2$CO$_3$ (54.7 mg, 0.43 mmol) at 0° C., and the reaction mixture was stirred at RT for 16 h. The solvent was removed under reduced pressure at RT and the residue was purified by Prep-HPLC (Column: X-select-C18 (250*19), 5 u Mobile phase: 10 mM ammonium bicarbonate in H$_2$O:MeCN Gradient: (T % B):—0/5, 1/5, 8/50, 8.1/98, 11/98, 11.1/5, 14/5 Flow rate: 18 mL/min Diluent: MeCN+H$_2$O+THF). The pure fractions were lyophilized to afford 55 mg (39%) of 2-amino-9-((2R,3R,5S)-5-((S)-2-fluoro-1-hydroxyethyl)-3-hydroxytetrahydrofuran-2-yl)-7-(prop-2-yn-1-yl)-7,9-dihydro-1H-purine-6,8-dione (Compound 23) as an off white solid. C$_{14}$H$_{16}$FN$_5$O$_5$: $^1$H NMR (400 MHz, DMSO-d$_6$): δ 11.09 (brs, 1H), 6.59 (bs, 2H) 5.52 (d, J=3.6 Hz, 1H), 5.43 (d, J=4.8 Hz, 1H), 5.28 (d, J=5.6 Hz, 1H), 4.80 (m, 1H), 4.58 (d, J 2.4 Hz, 2H), 4.49-4.36 (m, 1H), 4.38-4.22 (m, 1H), 4.05 (q, J=7.2 Hz, 1H), 3.77-3.70 (m, 1H), 3.22 (t, J=2.2 Hz, 1H), 2.55 (m, 1H), 1.93 (m, 1H). ES+, m/z 354.1 [M+H]$^+$.

Example 21: 2-Amino-9-((2R,3R,5S)-5-((R)-2-fluoro-1-hydroxyethyl)-3-hydroxytetrahydrofuran-2-yl)-7-(prop-2-yn-1-yl)-7,9-dihydro-1H-purine-6,8-dione, Compound 24

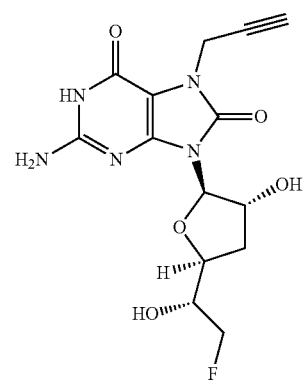 [SMILES: C#CCn1c(=O)n([C@@H]2O[C@H]([C@@H](O)CF)C[C@H]2O)c2nc(N)[nH]c(=O)c21]

Similar to the procedure used to synthesize Compound 23, Compound 24 was prepared according to the following multi-step procedure.

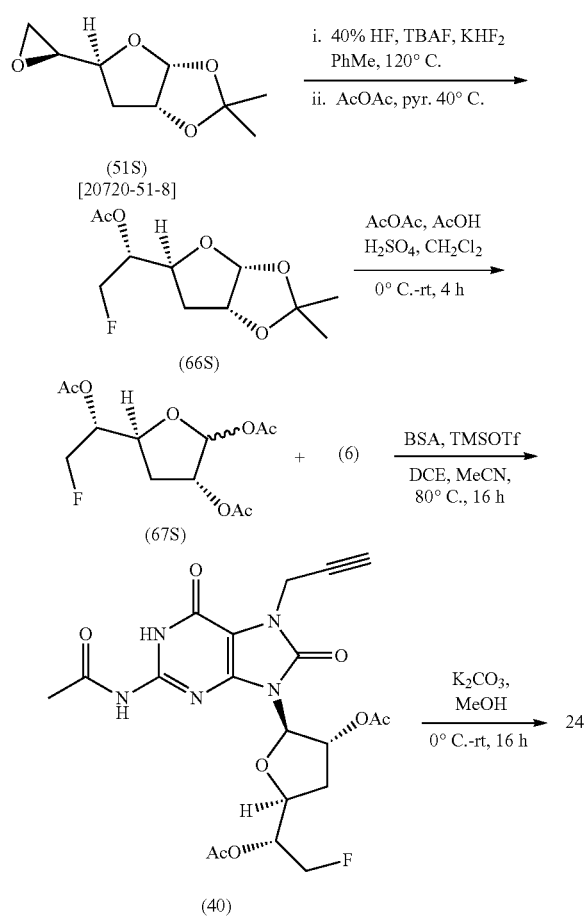

Step-1: (R)-1-((3aR,5S,6aR)-2,2-Dimethyltetrahydrofuro[2,3-d][1,3]dioxol-5-yl)-2-fluoroethyl acetate (66S)

A 40% HF solution (1.38 mL, 32.2 mmol) was added to TBAF (32 mL, 32.2 mmol 1M in THF) and after 5 min the solution was concentrated under reduced pressure (1 mbar, 100° C.). To this concentrated mixture a solution of (3aR, 5S,6aR)-2,2-dimethyl-5-((S)-oxiran-2-yl)tetrahydrofuro[2, 3-d][1,3]dioxole (51S) (2 g, 10.7 mmol) and KHF$_2$ (251.6 mg, 3.2 mmol) in dry toluene (20 mL) were added and the mixture was maintained at 120° C. for 18 h. The reaction mixture was then cooled to room temperature and Ac$_2$O (3.2 mL, 32.2 mmol) and dry pyridine (6.1 mL, 86.0 mmol) were added. The reaction mixture was stirred at 40° C. for 2 h and then quenched with water and EtOAc (2×75 mL). The combined organic phase was washed with 2M HCl, a saturated aq. NaHCO$_3$ solution (50 mL), dried over Na$_2$SO$_4$, filtered and concentrated under vacuum. The crude mixture was purified by column chromatography over silica gel (100-200 mesh, 20% EtOAc in petroleum ether) to give 1.6 g (61%) of (R)-1-((3aR,5S,6aR)-2,2-dimethyltetrahydrofuro[2,3-d][1,3]dioxol-5-yl)-2-fluoroethyl acetate (66S). C$_{11}$H$_{17}$FO$_5$: $^1$H NMR (400 MHz, CDCl$_3$): δ 5.82 (d, J=3.6 Hz, 1H), 5.19-5.14 (m, 1H), 4.74 (t, J 4.2 Hz, 1H), 4.63 (m, 1H), 4.51 (m, 1H), 4.41 (dt, J=10.8, 4.6 Hz, 1H), 2.14 (s, 3H), 2.11 (m, 1H) 1.66 (ddd, J=13.2, 10.8, 4.8 Hz, 1H), 1.51 (s, 3H), 1.32 (s, 3H).

Step-2: (3R,5S)-5-((R)-1-Acetoxy-2-fluoroethyl)tetrahydrofuran-2,3-diyl diacetate (67S)

To a solution of (R)-1-((3aR,5S,6aR)-2,2-dimethyltetrahydrofuro[2,3-d][1,3]dioxol-5-yl)-2-fluoroethyl acetate (66S) (1.6 g, 4.03 mmol), acetic acid (3.6 mL, 64.5 mmol) and acetic anhydride (3.2 mL, 32.2 mmol) in anhydrous CH$_2$Cl$_2$ (20 mL) was added concentrated H$_2$SO$_4$ (0.1 mL) at 0° C. The resultant reaction mixture was stirred at 22° C. for 4 h and was then quenched by the addition of ice cold water. The organic layer was separated and the aqueous phase was extracted with CH$_2$Cl$_2$ (2×75 mL). The combined organic layer was washed with saturated aq. NaHCO$_3$ solution (50 mL), dried over Na$_2$SO$_4$, filtered and concentrated under vacuum. The crude product was purified by column chromatography over silica gel (100-200 mesh, 30% EtOAc in petroleum ether) to give 0.8 g (44%) of (3R,5S)-5-((R)-1-acetoxy-2-fluoroethyl)tetrahydrofuran-2,3-diyl diacetate (67S) as a colorless oil. C$_{12}$H$_{17}$FO$_7$: $^1$H NMR indicated an α (minor), β (major) anomeric mixture; $^1$H NMR (400 MHz, CDCl$_3$): δ 6.13 (s, 1H), 5.20 (d, J=4.4 Hz, 2H), 5.12 (ddd, J=20.4, 4.4, 1.3 Hz, 1H), 4.61-4.47 (m, 4H), 2.14 (s, 3H), 2.10 (s, 3H), 2.08 (s, 3H).

Step-3: (R)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2-fluoroethyl acetate (40)

N-(6,8-dioxo-7-(prop-2-yn-1-yl)-6,7,8,9-tetrahydro-1H-purin-2-yl)acetamide (6) (300 mg, 1.2 mmol), (3R,5S)-5-((R)-1-acetoxy-2-fluoroethyl)tetrahydrofuran-2,3-diyl diacetate (67S) (425.5 mg, 1.4 mmol) and BSA (0.9 mL, 3.6 mmol) were dissolved in 1,2-dichloroethane (15 mL) and stirred at 80° C. for 30 min under argon. The reaction mixture was allowed to cooled to RT and 1,2-dichloroethane was removed in vacuo. The residue was dissolved in MeCN (20 mL) and to the solution was added TMSOTf (0.33 mL, 1.5 mmol). The reaction mixture was stirred at 80° C. for 16 h, cooled to room temperature and concentrated under vacuum. To the residue was added sat. aq·NaHCO$_3$ (50 mL) and extracted with EtOAc (3×50 mL). The combined EtOAc layer was washed with water (30 mL), brine (30 mL), dried over anhydrous Na$_2$SO$_4$, filtered and concentrated under vacuum. The crude compound was purified by GRACE flash chromatography (80% EtOAc in pet ether) to afford 120 mg (20%) of (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-fluoroethyl acetate (40) as an off-white solid. C$_2$H$_{22}$FN$_5$O$_8$: ES+, m/z 480.2 [M+H]$^+$.

Step-4: 2-amino-9-((2R,3R,5S)-5-((R)-2-Fluoro-1-hydroxyethyl)-3-hydroxytetrahydrofuran-2-yl)-7-(prop-2-yn-1-yl)-7,9-dihydro-1H-purine-6,8-dione, (Compound 24)

To a solution of (R)-1-((2S,4R,5R)-5-(2-acetamido-6,8-dioxo-7-(prop-2-yn-1-yl)-1,6,7,8-tetrahydro-9H-purin-9- yl)-4-acetoxytetrahydrofuran-2-yl)-2-fluoroethyl acetate (40) (120 mg, 0.25 mmol) in MeOH (10 mL) was added K$_2$CO$_3$ (34.5 mg, 0.43 mmol) at 0° C. The reaction mixture was stirred at RT for 16 h and then the solvent was removed under reduced pressure at RT. The residue was purified by Prep HPLC (Column: X-Select-C18 (150*19), 5 u Mobile phase: 0.1% HCO$_2$H in H$_2$O:MeCN Gradient: (T % B):—0/5, 8/40, 8.1/98, 10/98, 10.1/5, 12/5 Flow Rate: 17 mL/min; Diluent: MeOH+H$_2$O+THF) and the pure fractions were lyophilized to afford 35 mg (39%) of 2-amino-9-((2R,3R,5S)-5-((R)-2-fluoro-1-hydroxyethyl)-3-hydroxytetrahydrofuran-2-yl)-7-(prop-2-yn-1-yl)-7,9-dihydro-1H-purine-6,8-dione (Compound 24) as an off white solid. C$_{14}$H$_{16}$FN$_5$O$_5$: $^1$H NMR (400 MHz, DMSO-d$_6$): δ 11.36 (brs, 1H), 6.69 (s, 2H), 5.53 (d, J=2.8 Hz, 1H), 5.46 (brs, 1H), 5.24 (m, 1H), 4.73 (m, 1H), 4.59 (brs, 2H), 4.48-4.39 (m, 1H), 4.36-4.27 (m, 1H), 4.16 (m, 1H), 3.71-3.67 (m, 1H), 3.22 (s, 1H), 2.45 (m, 1H), 1.83 (m, 1H). $^{19}$F NMR (376 MHz, DMSO-d$_6$): δ-228.9 (ddd, J=47.4, 46.2, 19.4 Hz). ES+, m/z 354.1 [M+H]$^+$.

Example 22:2-Amino-9-((2R,3R,5S)-3-hydroxy-5-((R)-2,2,2-trifluoro-1-hydroxyethyl)tetrahydrofuran-2-yl)-7-propyl-7,9-dihydro-1H-purine-6,8-dione, Compound 25

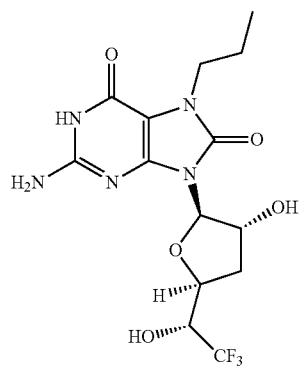 [SMILES: CCCn1c(=O)n([C@@H]2O[C@H]([C@@H](O)C(F)(F)F)C[C@H]2O)c2nc(N)[nH]c(=O)c21]

Compound 25 was prepared according to the following multi-step procedure.

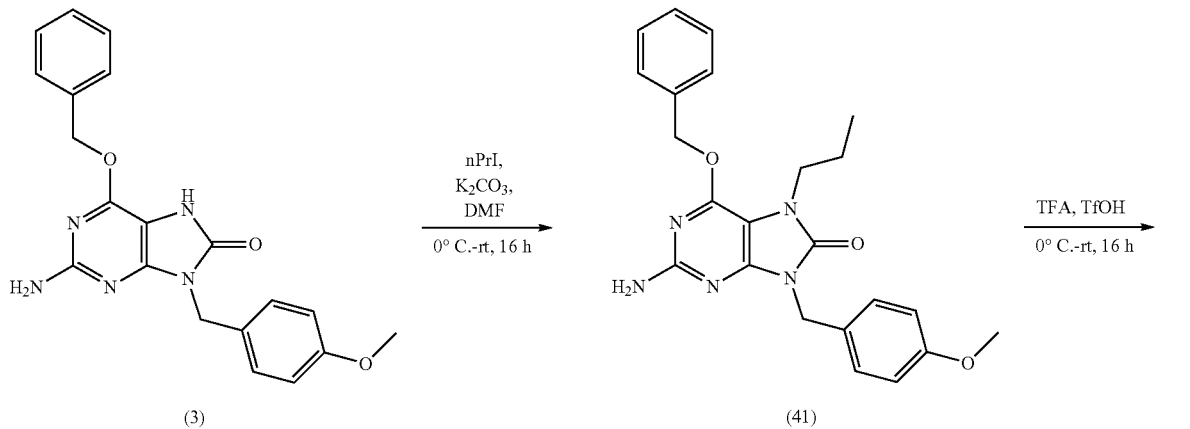

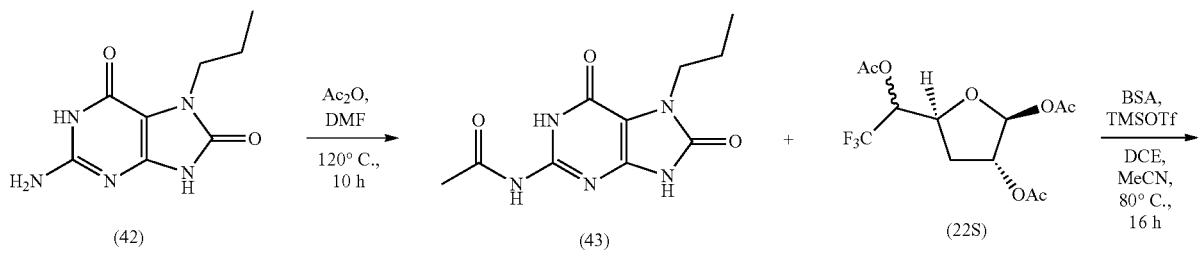

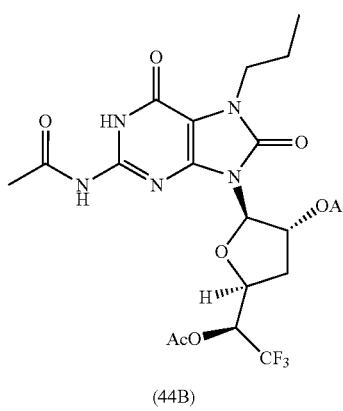 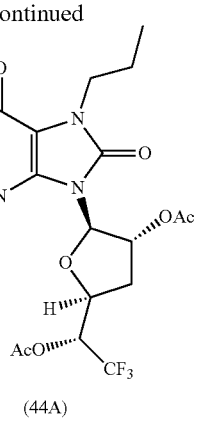 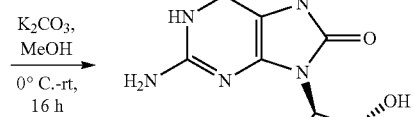 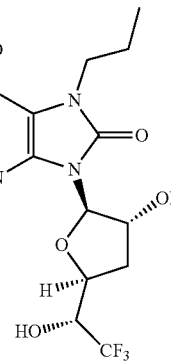

(44B)  (44A)  (25)

HPLC separation

Step-1: 2-Amino-6-(benzyloxy)-9-(4-methoxybenzyl)-7-propyl-7,9-dihydro-8H-purin-8-one (41)

1-Iodopropane (1.59 mL, 15.91 mmol) was added to a suspension of 2-amino-6-(benzyloxy)-9-(4-methoxybenzyl)-7,9-dihydro-8H-purin-8-one (3) (4 g, 10.61 mmol), $K_2CO_3$ (3.66 g, 26.52 mmol) in DMF (50 mL) at 0° C. and stirred at room temperature for 16 h. The reaction mixture was quenched with ice water (100 mL), diluted with diethyl ether (80 mL) and stirred for 15 min. The resulting precipitate was collected by filtration, washed with water and dried to afford 2-amino-6-(benzyloxy)-9-(4-methoxybenzyl)-7-propyl-7,9-dihydro-8H-purin-8-one (41) (3.5 g, 75%) as an brown solid; $C_{23}H_{25}N_5O_3$: $^1H$ NMR (400 MHz, DMSO-$d_6$): δ 7.48-7.34 (m, 5H), 7.20 (d, J=8.8 Hz, 2H), 6.87 (d, J=8.8 Hz, 2H), 6.39 (s, 2H), 5.41 (s, 2H), 4.82 (s, 2H), 3.73-3.69 (m, 2H), 3.71 (s, 3H), 1.58 (m, 2H), 0.73 (t, J=7.4 Hz, 3H). ES+, m/z 420.2 [M+H]+.

Step-2: 2-Amino-7-propyl-7,9-dihydro-1H-purine-6,8-dione (42)

Trifluoromethanesulfonic acid (4 mL, 50.11 mmol) was added to a suspension of 2-amino-6-(benzyloxy)-9-(4-methoxybenzyl)-7-propyl-7,9-dihydro-8H-purin-8-one (41) (3.5 g, 8.35 mmol) in trifluoroacetic acid (4.4 mL, 50.11 mmol) at 0° C. under an argon atmosphere and the resulting reaction mixture was slowly warmed to room temperature and stirred for 3 h. The reaction mixture was quenched with ice cold water, the pH was made basic with excess sat. aq. $NaHCO_3$ under vigorous stirring and filtered. The residual solid was taken into diethyl ether (150 mL), stirred for 30 min, filtered and dried to afford 2-amino-7-propyl-7,9-dihydro-1H-purine-6,8-dione (42) (1.6 g; 91%) as a pale yellow solid; $C_8H_{11}N_5O_2$: $^1H$ NMR (400 MHz, DMSO-$d_6$): δ 11.04 (s, 1H), 10.64 (s, 1H), 6.33 (s, 2H), 3.67 (t, J=7.2 Hz, 2H), 1.62 (sextet, J=7.2 Hz, 2H), 0.81 (t, J=7.6 Hz, 3H). ES+, m/z 210.1 [M+H]+.

Step-3: N-(6,8-Dioxo-7-propyl-6,7,8,9-tetrahydro-1H-purin-2-yl)acetamide (43)

Acetic anhydride (2.27 mL, 22.96 mmol) was added to a solution of 2-amino-7-propyl-7,9-dihydro-1H-purine-6,8-dione (42) (1.6 g, 7.65 mmol) in AcOH (20 mL) at ambient temperature under argon atmosphere and the resulting reaction mixture was heated at 120° C. for 10 h. With vigourous stirring reaction mixture was cooled to 0° C. whereupon a solid was formed. After stirring at 0° C. for an additional 30 minutes, the solids were filtered and dried under vacuum to afford N-(6,8-dioxo-7-propyl-6,7,8,9-tetrahydro-1H-purin-2-yl)acetamide (43) (1.3 g, 68%) as a pale yellow solid: $C_{10}H_{13}N_5O_3$: $^1H$ NMR (400 MHz, DMSO-$d_6$): δ 11.98 (s, 1H), 11.65 (s, 1H), 11.64 (s, 1H), 3.76 (t, J=7.0 Hz, 2H), 2.15 (s, 3H), 1.67-1.62 (m, 2H), 0.83 (t, J=7.4 Hz, 3H). ES+, m/z 252.1 [M+H]+.

Step-4: (R)-1-((2S,4R,5R)-5-(2-Acetamido-6,8-dioxo-7-propyl-1,6,7,8-tetrahydro-9H-purin-9-yl)-4-acetoxytetrahydrofuran-2-yl)-2,2,2-trifluoroethyl acetate (44A)

N-(6,8-Dioxo-7-propyl-6,7,8,9-tetrahydro-1H-purin-2-yl)acetamide (43) (500 mg, 1.99 mmol), (2S,3R,5S)-5-(1-acetoxy-2,2,2-trifluoroethyl)tetrahydrofuran-2,3-diyl diacetate (22S) (784 mg, 2.39 mmol), BSA (1.5 mL, 5.97 mmol) were dissolved in 1,2-dichloroethane (20 mL) and the resulting reaction mixture was stirred at 80° C. for 30 min under argon. The reaction mixture was allowed to cool to RT and 1,2-dichloroethane was removed under vacuum. The residue was dissolved in MeCN (20 mL) followed by the addition of TMSOTf (0.54 mL, 2.98 mmol). With stirring, the reaction mixture was heated at 80° C. for 16 h, cooled to room temperature and concentrated under vacuum. To the residue was added sat. aq·$NaHCO_3$ (50 mL) and extracted with EtOAc (3×50 mL). The combined EtOAc layers were washed with water (30 mL), brine (30 mL), dried over $Na_2SO_4$, filtered and concentrated under vacuum. The crude compound was purified by GRACE flash chromatography (80% EtOAc in pet ether) to afford 400 mg of diastereomeric mixture as indicated by LC/MS (estimated to be ~3:1 44A:44B) Further purification by Prep-HPLC (KROMOSIL-C18 (150*25 MM), 7 u Mobile phase: 10 mM ammonium bicarbonate in $H_2O$:MeCN gradient: (T % B):—0/20, 8/50, 13/50, 13.1/98, 15/98, 15.1/20, 17/20; Flow Rate: 22 mL/min; Diluent: (MeCN+$H_2O$+THF) gave ~100 mg of (R)-1-((2S,4R,5R)-5-(2-acetamido-6,8-dioxo-7-propyl-1,6,7,8-tetrahydro-9H-purin-9-yl)-4-acetoxytetrahydrofuran-2-yl)-2,2,2-trifluoroethyl acetate (44A) and ~50 mg of (S)-1-((2S,4R,5R)-5-(2-acetamido-6,8-dioxo-7-propyl-1,6,7,8-tetrahydro-9H-purin-9-yl)-4-acetoxytetrahydrofuran-2-yl)-2,2,2-trifluoroethyl acetate (44B), both as pale yellow solids after lyophilization. (44A): $C_{20}H_{24}F_3N_5O_8$: $^1H$ NMR (500 MHz, DMSO-$d_6$): δ 12.15 (brs, 1H), 11.75 (brs, 1H), 5.75

(d, J=1.5 Hz, 1H), 5.66 (m, 2H), 4.51 (m, 1H), 3.82 (t, J=7.0 Hz, 2H), 2.84 (m, 1H), 2.17 (s, 3H), 2.13 (m, 1H), 2.08 (s, 6H), 1.67 (m, 2H), 0.85 (t, J=7.5 Hz, 3H). ES+, m/z 520.1 [M+H]$^+$. (44B): $^1$H NMR (500 MHz, CDCl$_3$): δ 11.96 (brs, 1H), 9.50 (brs, 1H), 6.16 (s, 1H), 6.02 (t, J=7.0 Hz, 1H), 5.41 (d, J=4.5 Hz, 1H), 4.65 (m, 1H), 3.97 (t, J=7.3 Hz, 2H), 2.94 (m, 1H), 2.29 (s, 3H), 2.25 (s, 3H), 2.16 (m, 1H), 2.14 (s, 6H) 1.77 (m, 2H), 0.94 (t, J=7.0 Hz, 3H).

Step-5: 2-Amino-9-((2R,3R,5S)-3-hydroxy-5-((R)-2,2,2-trifluoro-1-hydroxyethyl)tetrahydrofuran-2-yl)-7-propyl-7,9-dihydro-1H-purine-6,8-dione (Compound 25)

To a solution of (R)-1-((2S,4R,5R)-5-(2-acetamido-6,8-dioxo-7-propyl-1,6,7,8-tetrahydro-9H-purin-9-yl)-4-acetoxytetrahydrofuran-2-yl)-2,2,2-trifluoroethyl acetate (44A) (100 mg, 0.192 mmol) in MeOH (20 mL) was added K$_2$CO$_3$ (40 mg, 0.289 mmol) at 0° C. and the reaction mixture was stirred at rt for 16 h. Methanol was removed under reduced pressure at 30° C. The residue was purified by reverse phase GRACE flash chromatography (using 10 mM ammonium bicarbonate in H$_2$O as eluent). The pure fractions were lyophilized to afford 60 mg (80%) of 2-amino-9-((2R,3R,5S)-3-hydroxy-5-((R)-2,2,2-trifluoro-1-hydroxyethyl) tetrahydrofuran-2-yl)-7-propyl-7,9-dihydro-1H-purine-6,8-dione (Compound 25) as a white solid. C$_{14}$H$_{18}$F$_3$N$_5$O$_5$: $^1$H NMR (500 MHz, DMSO-d$_6$): δ 11.06 (brs, 1H), 6.53 (brs, 2H), 6.39 (d, J=8.0 Hz, 1H), 5.58 (d, J=3.50 Hz, 1H), 5.52 (d, J=4.5 Hz, 1H), 4.76 (m, 1H), 4.34 (m, 1H), 4.02 (m, 1H), 3.74 (t, J=7.3 Hz, 2H), 2.54 (m, 1H), 1.97 (m, 1H), 1.63 (sextet, J=7.3 Hz, 2H), 0.82 (t, J=7.3 Hz, 3H). ES+, m/z 394.0 [M+H]$^+$.

Example 23: 2-Amino-9-((2R,3S,4R,5R)-4-fluoro-3-hydroxy-5-((S)-1-hydroxypropyl)tetrahydrofuran-2-yl)-7-propyl-7,9-dihydro-1H-purine-6,8-dione, Compound 26

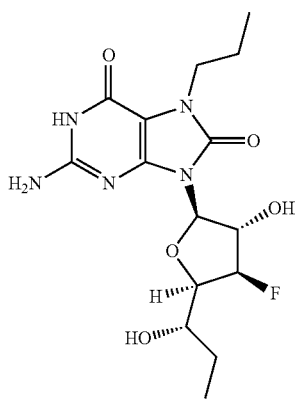 [SMILES: CCCn1c(=O)n([C@@H]2O[C@H]([C@@H](O)CC)[C@H](F)[C@H]2O)c2nc(N)[nH]c(=O)c21]

Compound 26 was prepared according to the following 2 step procedure.

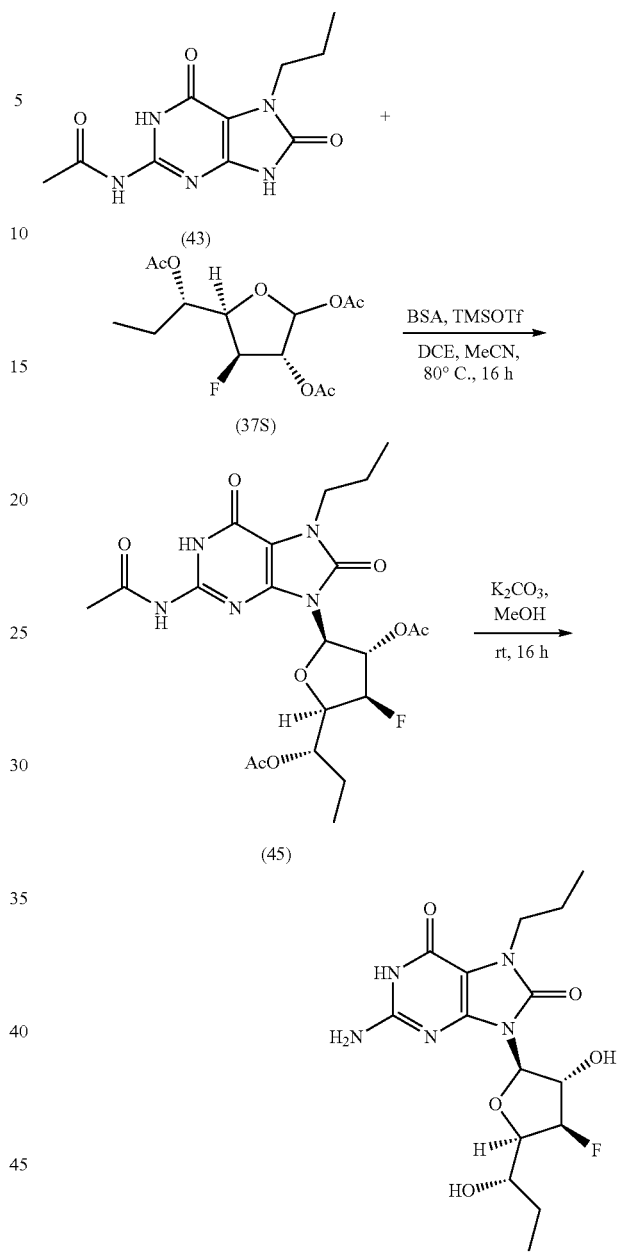

Step-1: (S)-1-((2R,3S,4S,5R)-5-(2-Acetamido-6,8-dioxo-7-propyl-1,6,7,8-tetrahydro-9H-purin-9-yl)-4-acetoxy-3-fluorotetrahydrofuran-2-yl)propyl acetate (45)

N-(6,8-Dioxo-7-propyl-6,7,8,9-tetrahydro-1H-purin-2-yl)acetamide (43) (300 mg, 1.1 mmol), (3S,4S,5R)-5-((S)-1-acetoxypropyl)-4-fluorotetrahydrofuran-2,3-diyl diacetate (37S) (548.6 mg, 1.7 mmol) and BSA (0.9 mL, 3.58 mmol) were dissolved in 1,2-dichloroethane (20 mL) and the resulting reaction mixture was stirred at 80° C. for 30 min under argon. The reaction mixture was allowed to cool to RT and 1,2-dichloroethane was removed under vacuum. The residue was dissolved in MeCN (20 mL) followed by addition of TMSOTf (0.33 mL, 1.79 mmol). The reaction mixture was heated at 80° C. for 16 h, was cooled to room temperature and concentrated under vacuum. To the residue was added sat. aq. NaHCO$_3$ (60 mL) and extracted with EtOAc (3×60 mL). The combined EtOAc layer were washed with water (30 mL), brine (30 mL), dried over Na$_2$SO$_4$, filtered and concentrated under vacuum. The crude product was purified by flash column chromatography (80% EtOAc in pet ether) to afford 200 mg (33%) (S)-1-((2R,3S,4S,5R)-5-(2-acetamido-6,8-dioxo-7-propyl-1,6,7,8-tetrahydro-9H-purin-9-yl)-4-acetoxy-3-fluorotetrahydrofuran-2-yl)propyl acetate (45) as an off-white solid. C$_{21}$H$_{28}$FN$_5$O$_8$: ES+, m/z 498.2 [M+H]$^+$.

Step-2: 2-Amino-9-((2R,3S,4R,5R)-4-fluoro-3-hydroxy-5-((S)-1-hydroxypropyl)tetrahydrofuran-2-yl)-7-propyl-7,9-dihydro-1H-purine-6,8-dione (Compound 26)

To a solution of (S)-1-((2R,3S,4S,5R)-5-(2-acetamido-6,8-dioxo-7-propyl-1,6,7,8-tetrahydro-9H-purin-9-yl)-4-acetoxy-3-fluorotetrahydrofuran-2-yl)propyl acetate (45) (200 mg, 0.4 mmol) in methanol (10 mL) was added K$_2$CO$_3$ (111 mg, 0.80 mmol) at rt. The stirred reaction mixture was monitored by LC/MS. After 16 h. the mixture was concentrated under vacuum to afford a thick mass that was subjected to Prep-HPLC (Column: LUNA@ OMEGA (250*21.2), 5 u Mobile phase: 0.1% HCO$_2$H in H$_2$O:MeCN GRADIENT: (T % B):—0/10, 8/50, 9/50, 9.1/98, 12/98, 12.1/10, 15/10 Flow Rate: 17 mL/min) to afford 30 mg (21%) of 2-amino-9-((2R,3S,4R,5R)-4-fluoro-3-hydroxy-5-((S)-1-hydroxypropyl)tetrahydrofuran-2-yl)-7-propyl-7,9-dihydro-1H-purine-6,8-dione (Compound 26) as an off-white solid; C$_{15}$H$_{22}$FN$_5$O$_5$: $^1$H NMR indicated the product to be the formic acid salt. $^1$H NMR (500 MHz, DMSO-d$_6$): δ 11.59 (brs, 1H), 8.48 (s, 1H), 6.79 (s, 2H), 5.95 (m, 1H), 5.37 (d, J=6.5 Hz, 1H) 5.32 (ddd, J=24.8, 6.5, 2.8 Hz, 1H), 5.00 (dd, J=50.5, 4.5 Hz, 1H), 4.91 (m, 1H), 3.82 (dt, J=21.5, 5.8 Hz, 1H), 3.75 (t, J 7.0 Hz, 2H), 3.51 (brs, 1H), 1.64 (m, 2H), 1.50-1.43 (m, 1H), 1.36-1.31 (m, 1H), 0.91 (t, J 7.3 Hz, 3H), 0.84 (t, J 7.3 Hz, 3H). ES+, m/z 372.2 [M+H]$^+$.

Example 24: 2-Amino-9-((2R,3S,4R,5R)-4-fluoro-3-hydroxy-5-((S)-1-hydroxypropyl)tetrahydrofuran-2-yl)-7-(3,3,3-trifluoropropyl)-7,9-dihydro-1H-purine-6,8-dione, Compound 27

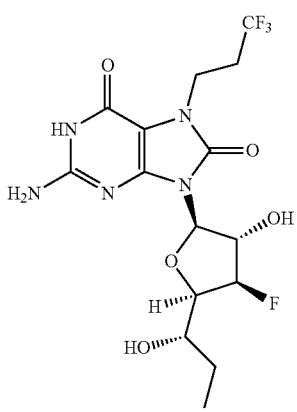 [SMILES: CC[C@H](O)[C@H]1O[C@@H](n2c(=O)n(CCC(F)(F)F)c3c(=O)[nH]c(N)nc32)[C@H](O)[C@H]1F]

Compound 27 was prepared according to the following multistep procedure.

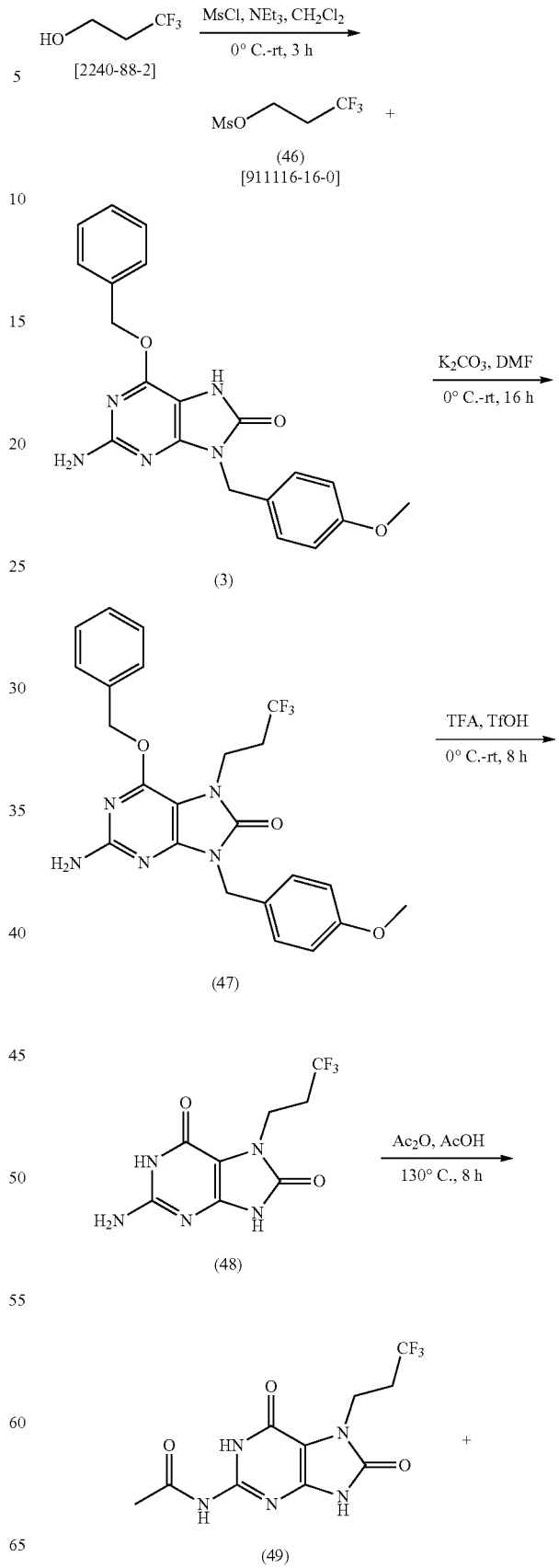

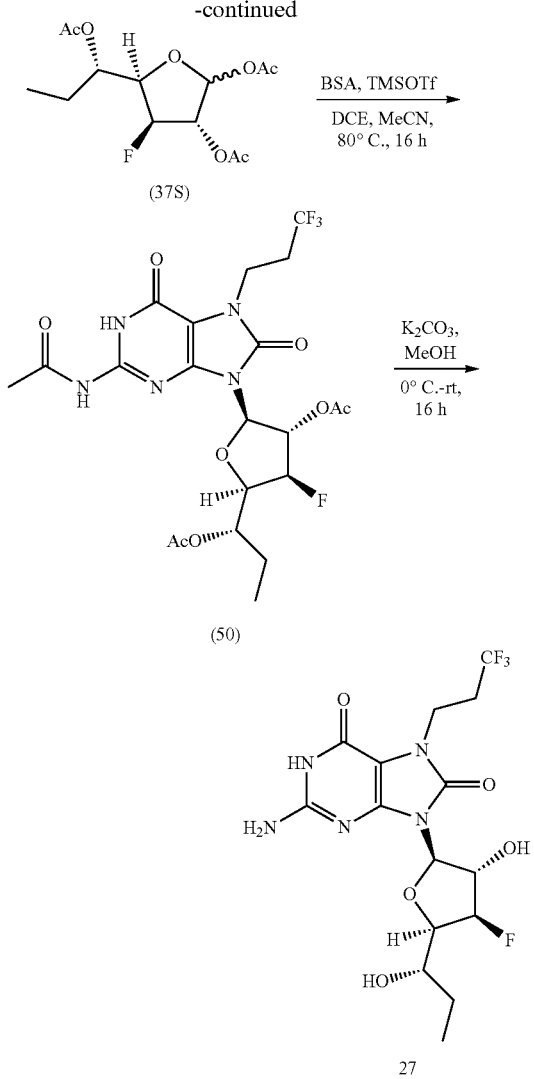

Step-1: 3,3,3-Trifluoropropyl methanesulfonate (46)

To a solution of 3,3,3-trifluoropropan-1-ol [2240-88-2] (5.0 g, 43.8 mmol) in $CH_2Cl_2$ (10 mL) was added TEA (12.3 mL, 87.7 mmol) followed by the dropwise addition of methanesulfonyl chloride (5 mL, 65.8 mmol) at 0° C. The resulting mixture was stirred at room temperature for 3 h. The reaction mixture was diluted with $CH_2C_2$ and the organic phase was washed with brine, dried over $Na_2SO_4$, filtered and concentrated to give the crude product that was purified by silica gel chromatography eluting with petroleum ether/ethyl acetate (30%) to give 3,3,3-trifluoropropyl methanesulfonate [911116-16-0] (46) (7.0 g, 83% yield) as light yellow oil. $C_4H_7F_3O_3S$: $^1H$ NMR (400 MHz, $CDCl_3$): 4.43 (t, J=5.6 Hz, 2H), 3.05 (s, 3H), 2.66-2.55 (m, 2H).

Step-2: 2-Amino-6-(benzyloxy)-9-(4-methoxybenzyl)-7-(3,3,3-trifluoropropyl)-7,9-dihydro-8H-purin-8-one (47)

To a stirred suspension of 2-amino-6-(benzyloxy)-9-(4-methoxybenzyl)-7,9-dihydro-8H-purin-8-one (3) (8.0 g, 21.22 mmol), $K_2CO_3$ (5.85 g, 42.44 mmol) in DMF (100 mL) at 0° C. was added 3,3,3-trifluoropropyl methanesulfonate (46) (6.11 g, 31.83 mmol). The reaction mixture was warmed to room temperature, stirred for 16 h. and quenched with ice water (200 mL) and diethyl ether (80 mL) was added and stirred for 15 min. The resulting precipitate was collected by filtration, washed with water and dried to afford 2-amino-6-(benzyloxy)-9-(4-methoxybenzyl)-7-(3,3,3-trifluoropropyl)-7,9-dihydro-8H-purin-8-one (47) (6.5 g, 75%) as a brown solid; $C_{23}H_{22}F_3N_5O_3$: $^1H$ NMR (400 MHz, DMSO-$d_6$): 7.48 (d, J=6.8 Hz, 2H), 7.40 (d, J=6.8 Hz, 2H), 7.37 (m, 1H), 7.20 (d, J=8.4 Hz, 2H), 6.87 (d, J=8.4 Hz, 2H), 6.46 (s, 2H), 5.42 (s, 2H), 4.82 (s, 2H), 4.02 (t, J=6.8 Hz, 2H), 3.71 (s, 3H), 2.62 (m, 2H). ES+, m/z 474.1 $[M+H]^+$.

Step-3: 2-Amino-7-(3,3,3-trifluoropropyl)-7,9-dihydro-1H-purine-6,8-dione (48)

Trifluoromethane sulfonic acid (2.06 mL, 25.36 mmol) was added to a suspension of 2-amino-6-(benzyloxy)-9-(4-methoxybenzyl)-7-(3,3,3-trifluoropropyl)-7,9-dihydro-8H-purin-8-one (47) (3.0 g, 6.3424 mmol) in trifluoroacetic acid (2.12 mL, 25.36 mmol) at room temperature under argon atmosphere and the resulting reaction mixture was stirred at room temperature for 8 h. The reaction mixture was quenched with ice cold water. The pH of the reaction mixture was made basic with a sat. aq. $NaHCO_3$ solution under vigorous stirring and filtered. The filtered solid was taken into ethyl acetate, stirred for 30 min., filtered and dried to afford 2-amino-7-(3,3,3-trifluoropropyl)-7,9-dihydro-1H-purine-6,8-dione (48) (1.2 g, 75%) as a brown solid. $C_8H_8F_3N_5O_2$: $^1H$ NMR (400 MHz, DMSO-$d_6$): δ 11.17 (s, 1H), 10.74 (s, 1H), 6.41 (s, 2H), 3.97 (t, J=6.8 Hz, 2H), 2.73-2.70 (m, 2H). ES+, m/z 264.1 $[M+H]^+$.

Step-4: N-(6,8-Dioxo-7-(3,3,3-trifluoropropyl)-6,7,8,9-tetrahydro-1H-purin-2-yl)acetamide (49)

Acetic anhydride (0.69 mL, 6.844 mmol) was added to a solution of 2-amino-7-(3,3,3-trifluoropropyl)-7,9-dihydro-1H-purine-6,8-dione (48) (1.2 g, 4.562 mmol) in AcOH (15 mL) at room temperature under an argon atmosphere and the resulting reaction mixture was stirred at 130° C. for 8 h. The reaction mixture was cooled to 0° C., and the solids formed were stirred for 30 minutes. The product was filtered, washed with EtOH and dried under vacuum to afford N-(6,8-dioxo-7-(3,3,3-trifluoropropyl)-6,7,8,9-tetrahydro-1H-purin-2-yl)acetamide (49) (800 mg, 61%) as a brown solid. $C_{10}H_{10}F_3N_5O_3$: $^1H$ NMR (400 MHz, DMSO-$d_6$): δ 12.05 (s, 1H), 11.77 (s, 1H), 11.68 (s, 1H), 4.06 (t, J=6.8 Hz, 2H), 2.75 (m, 2H), 2.15 (s, 3H). ES+, m/z 306.1 $[M+H]^+$.

Step-5: (S)-1-((2R,3S,4S,5R)-5-(2-Acetamido-6,8-dioxo-7-(3,3,3-trifluoropropyl)-1,6,7,8-tetrahydro-9H-purin-9-yl)-4-acetoxy-3-fluorotetrahydrofuran-2-yl)propyl acetate (50)

N-(6,8-dioxo-7-(3,3,3-trifluoropropyl)-6,7,8,9-tetrahydro-1H-purin-2-yl)acetamide (49) (350 mg, 1.147 mmol), (3S,4S,5R)-5-((S)-1-acetoxypropyl)-4-fluorotetrahydrofuran-2,3-diyl diacetate (37S) (450 mg, 1.491 mmol) and BSA (0.873 mL, 3.441 mmol) were dissolved in 1,2-dichloroethane (20 mL) and the reaction mixture was stirred at 80° C. for 30 min under argon. The reaction mixture was cooled to rt and 1,2-dichloroethane was removed by vacuum. The residue was dissolved in MeCN (20 mL) followed by addition of TMSOTf (0.318 mL, 1.720 mmol). The stirred reaction mixture was heated at 80° C. for 16 h, cooled to room temperature and concentrated under vacuum. To the residue was added sat. aq. NaHCO₃ (60 mL) and then extracted with EtOAc (3×60 mL). The combined EtOAc layers were washed with water (30 mL), brine (30 mL), dried over Na₂SO₄, filtered and concentrated under vacuum. The crude compound was purified by flash column (80% EtOAc in pet ether) to afford (S)-1-((2R,3S,4S,5R)-5-(2-acetamido-6,8-dioxo-7-(3,3,3-trifluoropropyl)-1,6,7,8-tetrahydro-9H-purin-9-yl)-4-acetoxy-3-fluorotetrahydrofuran-2-yl)propyl acetate (50) (210 mg, 33%) as an off-white solid. $C_{21}H_{25}F_4N_5O_8$: ES+, m/z 552.3 [M+H]⁺.

Step-6: 2-Amino-9-((2R,3S,4R,5R)-4-fluoro-3-hydroxy-5-((S)-1-hydroxypropyl)tetrahydrofuran-2-yl)-7-(3,3,3-trifluoropropyl)-7,9-dihydro-1H-purine-6,8-dione (Compound 27)

To a solution of (S)-1-((2R,3S,4S,5R)-5-(2-acetamido-6,8-dioxo-7-(3,3,3-trifluoropropyl)-1,6,7,8-tetrahydro-9H-purin-9-yl)-4-acetoxy-3-fluorotetrahydrofuran-2-yl)propyl acetate (50) (210 mg, 0.381 mmol) in methanol (6 mL) was added K₂CO₃ (79 mg, 0.571 mmol) at room temperature. The reaction mixture was stirred at room temperature for 16 h., and then concentrated under vacuum to afford a thick mass. The crude product was purified by GRACE reverse phase chromatography (0.1% HCO₂H:MeCN) to afford 2-amino-9-((2R,3S,4R,5R)-4-fluoro-3-hydroxy-5-((S)-1-hydroxypropyl)tetrahydrofuran-2-yl)-7-(3,3,3-trifluoropropyl)-7,9-dihydro-1H-purine-6,8-dione (Compound 27) (30 mg, 19%) as an off-white solid. $C_{15}H_{19}F_4N_5O_5$: ¹H NMR indicated the compound exist as the formic acid salt. ¹H NMR (500 MHz, DMSO-d₆): δ 11.25 (brs, 1H), 8.42 (s, 1H), 6.69 (s, 2H), 5.91 (s, 1H), 5.39 (d, J=6.5 Hz, 1H), 5.32-5.25 (m, 1H), 4.98 (dt, J=48.5, 3.5 Hz, 1H), 4.84 (d, J=6.0 Hz, 1H), 4.04 (t, J=7.0 Hz, 2H), 3.81 (dt, J=23.0, 5.8 Hz, 1H), 3.52 (m, 1H), 2.75 (m, 2H), 1.49 (m, 1H), 1.34 (m, 1H), 0.91 (t, J=7.5 Hz, 3H). ES+, m/z 426.2 [M+H]⁺.

Example 25: 2-Amino-9-((2R,3R,5S)-3-hydroxy-5-((R)-2,2,2-trifluoro-1-hydroxyethyl)tetrahydrofuran-2-yl)-7-(3,3,3-trifluoropropyl)-7,9-dihydro-1H-purine-6,8-dione, Compound 28

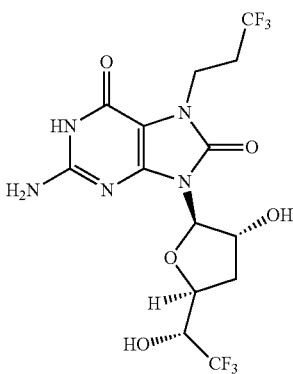 [SMILES: Nc1nc2c(c(=O)[nH]1)n(CCC(F)(F)F)c(=O)n2[C@@H]1O[C@H]([C@@H](O)C(F)(F)F)C[C@H]1O]

Compound 28 was prepared according to the following two step procedure.

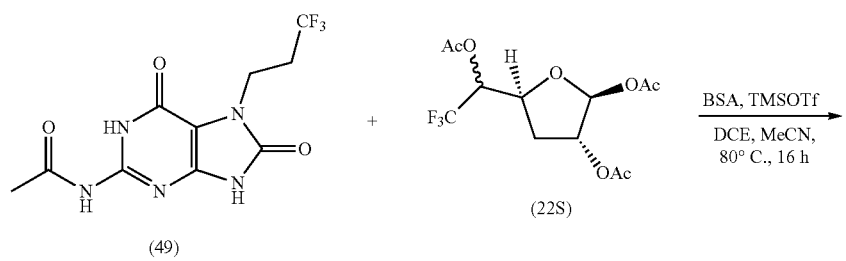

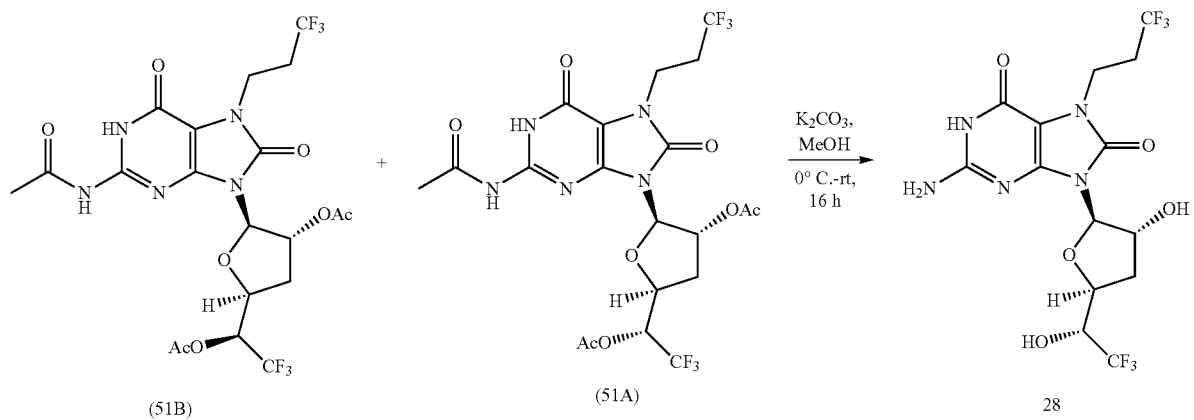

HPLC separation

Step-1: (R)-1-((2S,4R,5R)-5-(2-Acetamido-6,8-di-oxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51A) and (S)-1-((2S,4R,5R)-5-(2-Acetamido-6,8-dioxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51B)

To a suspension of N-(6,8-dioxo-7-(3,3,3-trifluoropropyl)-6,7,8,9-tetrahydro-1H-purin-2-yl)acetamide (49) (500 mg, 1.63 mmol) and (2S,3R,5S)-5-(1-acetoxy-2,2,2-trifluoroethyl)tetrahydrofuran-2,3-diyl diacetate (22S) (645 mg, 1.96 mmol) in 1,2-dichloroethane (20 mL) was added BSA (1.24 mL, 4.91 mmol). The reaction mixture was stirred at 80° C. for 30 min under argon and then cooled to RT. The 1,2-dichloroethane was removed under vacuum and the residue was dissolved in MeCN (20 mL) followed by addition of TMSOTf (0.44 mL, 2.45 mmol). The reaction mixture was heated at 80° C. for 16 h, cooled to room temperature and concentrated under vacuum. To the concentrate was added sat. aq. NaHCO$_3$ (50 mL) and extracted with EtOAc (3×50 mL). The combined EtOAc layer were washed with water (30 mL), brine (30 mL), dried over anhydrous Na$_2$SO$_4$, filtered and concentrated under vacuum. The crude products were purified by GRACE flash chromatography (80% EtOAc in pet. ether) to afford 350 mg (~62:38 of a diastereomeric mixture by LC/MS) of (R,S)-1-((2S,4R,5R)-5-(2-acetamido-6,8-dioxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51A:51B) as an off-white solid. Further purification by prep-HPLC (LUNA OMEGA C18(250*21.2), 5 u mobile phase: 10 mM ammonium bicarbonate in H$_2$O:MeCN gradient: (T % B):— 0/40, 8/65, 10/65, 10.1/98, 14/98, 14.1/40, 17/40; Flow rate: 17 mL/min; Diluent: MeCN+H$_2$O+THF) gave 60 mg of (R)-1-((2S,4R,5R)-5-(2-acetamido-6,8-dioxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51A) and 40 mg of (S)-1-((2S,4R,5R)-5-(2-acetamido-6,8-dioxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51A) both as off-white solids after lyophilization. (51A): C$_2$H$_{21}$F$_6$N$_5$O$_8$: ES+, m/z 574.4 [M+H]$^+$. (51B): C$_2$H$_{21}$F$_6$N$_5$O$_8$: ES+, m/z 574.4 [M+H]$^+$.

Step-2: 2-Amino-9-((2R,3R,5S)-3-hydroxy-5-((R)-2,2,2-trifluoro-1-hydroxyethyl)tetrahydrofuran-2-yl)-7-(3,3,3-trifluoropropyl)-7,9-dihydro-1H-purine-6,8-dione (Compound 28)

To a solution of (R)-1-((2S,4R,5R)-5-(2-acetamido-6,8-dioxo-7-(3,3,3-trifluoropropyl)-1,6,7,8-tetrahydro-9H-purin-9-yl)-4-acetoxytetrahydrofuran-2-yl)-2,2,2-trifluoroethyl acetate (51A) (60 mg, 0.1 mmol) in MeOH (20 mL) was added K$_2$CO$_3$ (21.6 mg, 1.5 mmol) at 0° C. and the reaction mixture was stirred at RT for 16 h. Methanol was removed under reduced pressure at 30° C. The residue was directly purified by reverse phase GRACE flash chromatography (using 10 mM ammonium bicarbonate in H$_2$O). The pure fractions were lyophilized to afford 25 mg (54%) of 2-amino-9-((2R,3R,5S)-3-hydroxy-5-((R)-2,2,2-trifluoro-1-hydroxyethyl)tetrahydrofuran-2-yl)-7-(3,3,3-trifluoropropyl)-7,9-dihydro-1H-purine-6,8-dione (Compound 28) as a white solid. C$_{14}$H$_{15}$F$_6$N$_5$O$_5$: $^1$H NMR (400 MHz, DMSO-d$_6$): δ 11.07 (brs, 1H), 6.56 (brs, 2H), 6.31 (d, J=8.0 Hz, 1H), 5.58 (d, J=3.2 Hz, 1H), 5.53 (d, J=4.8 Hz, 1H), 4.73 (m, 1H), 4.33 (m, 1H), 4.05 (t, J=6.8 Hz, 2H), 4.02 (m, 1H), 2.74 (m, 2H), 2.55 (m, 1H), 1.96 (m, 1H). ES+, m/z 448.3 [M+H]$^+$.

Example 26: 2-Amino-7-(cyclopropylmethyl)-9-((2R,3R,5S)-3-hydroxy-5-((R)-2,2,2-trifluoro-1-hydroxyethyl)tetrahydrofuran-2-yl)-7,9-dihydro-1H-purine-6,8-dione, Compound 29

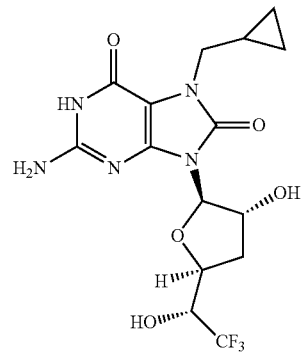 [SMILES: Nc1nc2c(c(=O)[nH]1)n(CC1CC1)c(=O)n2[C@@H]1O[C@H]([C@@H](O)C(F)(F)F)C[C@H]1O]

Compound 29 was prepared according to the following two step procedure.

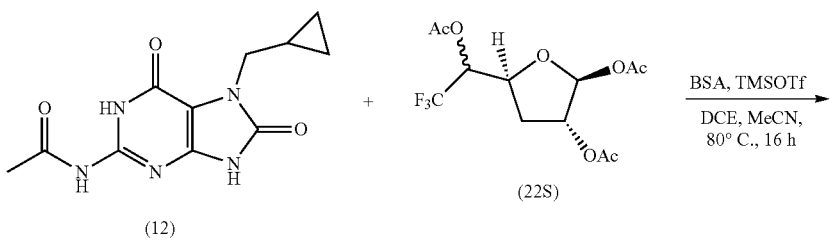

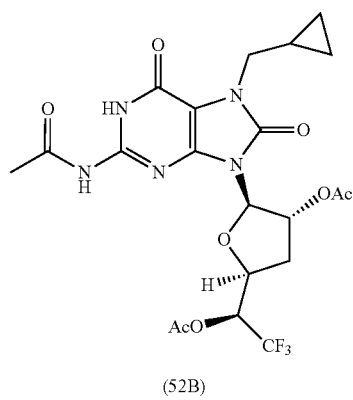

(52B)

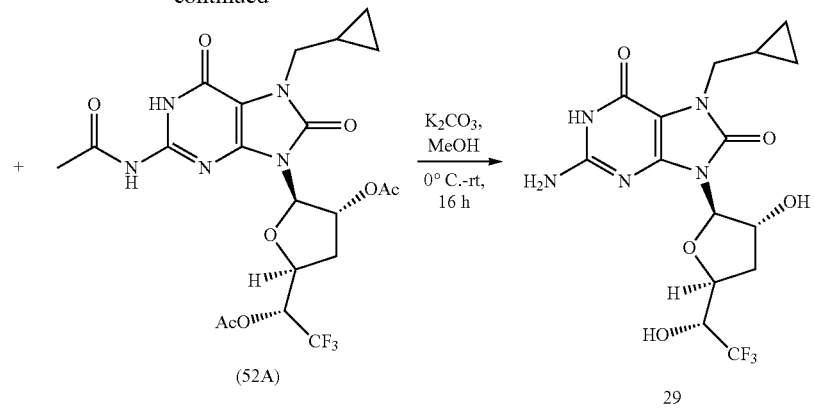

29

HPLC separation

Step 1: (R)-1-((2S,4R,5R)-5-(2-Acetamido-7-(cyclopropylmethyl)-6,8-dioxo-1,6,7,8-tetrahydro-9H-purin-9-yl)-4-acetoxytetrahydrofuran-2-yl)-2,2,2-trifluoroethyl acetate (52A) and (S)-1-((2S,4R,5R)-5-(2-Acetamido-7-(cyclopropylmethyl)-6,8-dioxo-1,6,7,8-tetrahydro-9H-purin-9-yl)-4-acetoxytetrahydrofuran-2-yl)-2,2,2-trifluoroethyl acetate (52B)

2-Amino-7-(cyclopropylmethyl)-7,9-dihydro-1H-purine-6,8-dione (12) (350 mg, 1.33 mmol), (2S,3R,5S)-5-(1-acetoxy-2,2,2-trifluoroethyl)tetrahydrofuran-2,3-diyl diacetate (22S) (567 mg, 1.73 mmol) and BSA (1.0 mL, 3.9 mmol) were dissolved in 1,2-dichloroethane (20 mL) and the mixture was stirred at 80° C. for 30 min under argon. The reaction mixture was allowed to cool to rt and 1,2-dichloroethane was removed under vacuum. The residue was dissolved in MeCN (20 mL) followed by the addition of TMSOTf (0.36 mL, 1.99 mmol). The reaction mixture was heated at 80° C. for 16 h, cooled to room temperature and concentrated under vacuum. To the residue obtained was added sat. aq. NaHCO$_3$ (50 mL) and then extracted with EtOAc (3×50 mL). The combined EtOAc layer were washed with water (30 mL), brine (30 mL), dried over Na$_2$SO$_4$, filtered and concentrated under vacuum. The crude compound was purified by GRACE flash chromatography (using 80% EtOAc in pet ether as eluent) to afford 260 mg (~5:3 mixture of diastereomers) of (R,S)-1-((2S,4R,5R)-5-(2-acetamido-7-(cyclopropylmethyl)-6,8-dioxo-1,6,7,8-tetrahydro-9H-purin-9-yl)-4-acetoxytetrahydrofuran-2-yl)-2,2,2-trifluoroethyl acetate (52A:52B) as an brown solid. Further purification by Prep-HPLC (LUNA OMEGA C18 (250*21.2), 5 u Mobile phase: 10 mM ammonium bicarbonate in H$_2$O:MeCN gradient: (T % B):—0/30, 8/60, 12/60, 12.1/98, 14/98, 14.1/30, 17/30; Flow Rate: 17 mL/min; Diluent: MeCN+H$_2$O+THF) gave 130 mg of (R)-1-((2S,4R,5R)-5-(2-acetamido-7-(cyclopropylmethyl)-6,8-dioxo-1,6,7,8-tetrahydro-9H-purin-9-yl)-4-acetoxytetrahydrofuran-2-yl)-2,2,2-trifluoroethyl acetate (52A) and 60 mg (S)-1-((2S,4R,5R)-5-(2-acetamido-7-(cyclopropylmethyl)-6,8-dioxo-1,6,7,8-tetrahydro-9H-purin-9-yl)-4-acetoxy tetrahydrofuran-2-yl)-2,2,2-trifluoroethyl acetate (52B), both as off-white solids after lyophilization. (52A): C$_{21}$H$_{24}$F$_3$N$_5$O$_8$: ES+, m/z 532.4 [M+H]$^+$. (52B): C$_{21}$H$_{24}$F$_3$N$_5$O$_8$: ES+, m/z 532.4 [M+H]$^+$.

Step 2: 2-Amino-7-(cyclopropylmethyl)-9-((2R,3R,5S)-3-hydroxy-5-((R)-2,2,2-trifluoro-1-hydroxyethyl)tetrahydrofuran-2-yl)-7,9-dihydro-1H-purine-6,8-dione (Compound 29)

To a solution of (R)-1-((2S,4R,5R)-5-(2-acetamido-7-(cyclopropylmethyl)-6,8-dioxo-1,6,7,8-tetrahydro-9H-purin-9-yl)-4-acetoxytetrahydrofuran-2-yl)-2,2,2-trifluoroethylacetate (52A) (130 mg, 0.24 mmol) in MeOH (20 mL) was added K$_2$CO$_3$ (50.6 mg, 0.36 mmol) at 0° C. The reaction mixture was stirred at rt for 16 h whereupon methanol was removed under reduced pressure at 30° C. The residue was purified by reverse phase GRACE flash chromatography (using 0.01% aq. NH$_4$HCO$_3$ and MeCN). The pure fractions were lyophilized to afforded 75 mg (75%) of 2-amino-7-(cyclopropylmethyl)-9-((2R,3R,5S)-3-hydroxy-5-((R)-2,2,2-trifluoro-1-hydroxyethyl)tetrahydrofuran-2-yl)-7,9-dihydro-1H-purine-6,8-dione (Compound 29) as a white solid. C$_{15}$H$_{18}$F$_3$N$_5$O$_5$: $^1$H NMR (400 MHz, DMSO-d$_6$): δ 10.95 (brs, 1H), 6.50 (brs, 2H), 6.33 (d, J=8.4 Hz, 1H), 5.59 (d, J=3.6 Hz, 1H), 5.53 (d, J=4.8 Hz, 1H), 4.77 (m, 1H), 4.34 (m, 1H), 4.03 (m, 1H), 3.65 (d, J=7.2 Hz, 2H), 2.54 (m, 1H), 1.97 (m, 1H), 1.18 (m, 1H), 0.41 (m, 2H), 0.35 (m, 2H). ES+, m/z 406.0 [M+H]$^+$.

Example 27:2-Amino-7-butyl-9-((2R,3S,4R,5R)-4-fluoro-3-hydroxy-5-((S)-1-hydroxypropyl)tetrahydrofuran-2-yl)-7,9-dihydro-1H-purine-6,8-dione, Compound 30

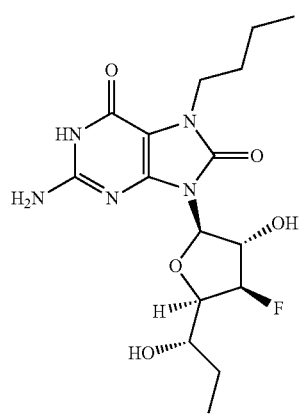 [SMILES: CCCCn1c(=O)n([C@@H]2O[C@H]([C@@H](O)CC)[C@H](F)[C@H]2O)c2nc(N)[nH]c(=O)c21]

Compound 30 was prepared according to the following multi-step procedure.

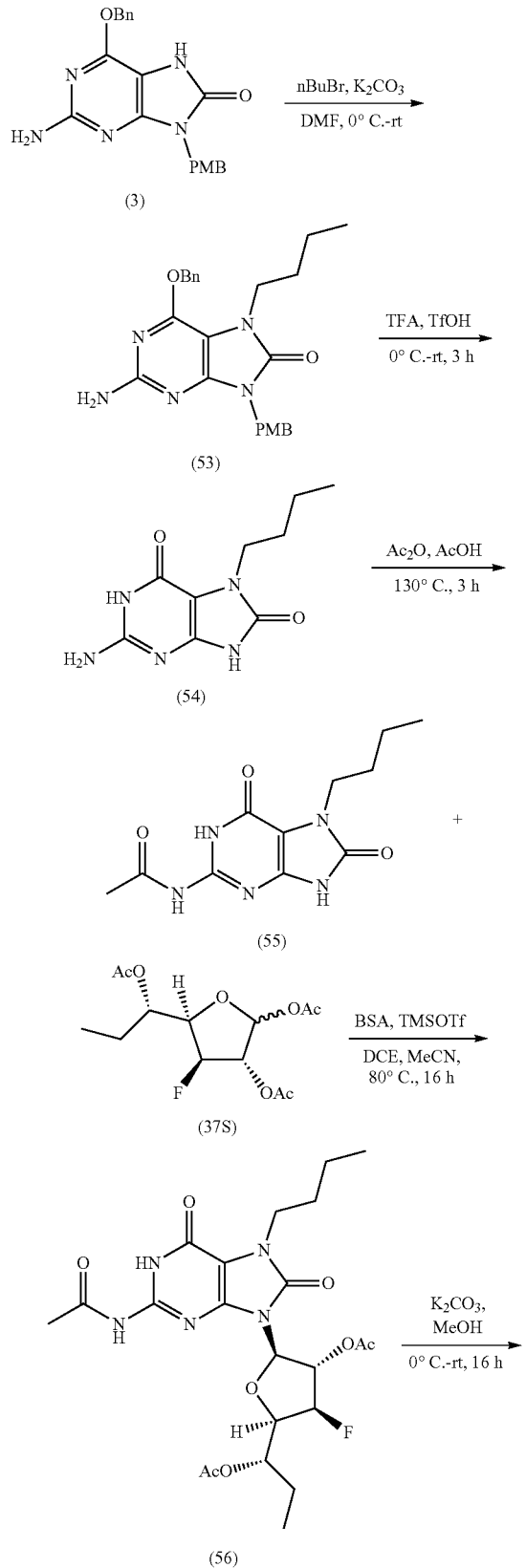

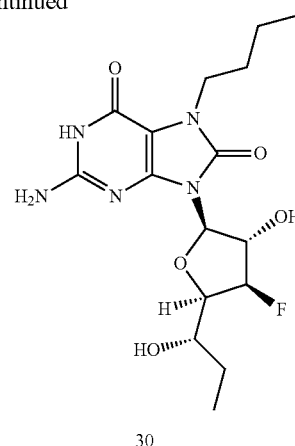

Step 1: 2-Amino-6-(benzyloxy)-7-butyl-9-(4-methoxybenzyl)-7,9-dihydro-8H-purin-8-one (53)

Butyl bromide (2.15 mL, 15.9 mmol) was added to a suspension of 2-amino-6-(benzyloxy)-9-(4-methoxybenzyl)-7,9-dihydro-8H-purin-8-one (3) (5 g, 13.25 mmol), $K_2CO_3$ (2.7 g, 19.85 mmol) in DMF (80 mL) at 0° C. and stirred at room temperature for 18 h. The reaction mixture was quenched with ice water (120 mL), diluted with diethyl ether (80 mL) and stirred for 15 min. The resulting precipitated solid was collected by filtration, washed with water and dried to afford 2-amino-6-(benzyloxy)-7-butyl-9-(4-methoxybenzyl)-7,9-dihydro-8H-purin-8-one (53) (4.9 g, 85%) as a brown solid. $C_{24}H_{27}N_5O_3$: $^1$H NMR (400 MHz, DMSO-$d_6$): δ 7.47 (d, J=6.8 Hz, 2H), 7.40 (d, J=6.8 Hz, 2H), 7.37 (m, 1H), 7.20 (d, J=8.4 Hz, 2H), 6.87 (d, J=8.8 Hz, 2H), 6.39 (s, 2H), 5.41 (s, 2H), 4.82 (s, 2H), 3.74 (m, 2H), 3.71 (s, 3H), 1.53 (m, 2H), 1.15 (m, 2H), 0.77 (t, J=7.4 Hz, 3H). ES+, m/z 434.1 [M+H]$^+$.

Step 2: 2-Amino-7-butyl-7,9-dihydro-1H-purine-6,8-dione (54)

Trifluoromethanesulfonic acid (2.99 mL, 33.9 mmol) was added to a suspension of 2-amino-6-(benzyloxy)-7-butyl-9-(4-methoxybenzyl)-7,9-dihydro-8H-purin-8-one (53) (4.9 g, 11.31 mmol) in triflouroacetic acid (2.59 mL, 33.9 mmol) at 0° C. under argon atmosphere. The reaction mixture was slowly warmed to room temperature and stirred for 3 h. To the reaction mixture was added ice cold water and pH was made basic with a sat. aq. $NaHCO_3$ solution while being stirred vigorously. The resultant solids were filtered off and taken up in ethyl acetate (50 mL), stirred for 30 min. filtered and dried to afford 2-amino-7-butyl-7,9-dihydro-1H-purine-6,8-dione (54) (2.0 g, 79%) as a brown solid. $C_9H_{13}N_5O_2$: $^1$H NMR (400 MHz, DMSO-$d_6$): δ 11.05 (s, 1H), 10.62 (s, 1H), 6.33 (s, 2H), 3.71 (t, J=7.0 Hz, 2H), 1.57 (m, 2H), 1.23 (m, 2H), 0.8 (t, J=7.4 Hz, 3H). ES+, m/z 224.1 [M+H]$^+$.

Step 3: N-(7-Butyl-6,8-dioxo-6,7,8,9-tetrahydro-1H-purin-2-yl)acetamide (55)

Acetic anhydride (2.54 ml, 26.90 mmol) was added to a solution of 2-amino-7-butyl-7,9-dihydro-1H-purine-6,8-dione (54) (2 g, 8.96 mmol) in AcOH (20 mL) at ambient temperature under argon atmosphere. The reaction mixture was stirred at 130° C. for 3 h under argon, cooled down to 0° C. Solids formed and stirring was continued for 30 minutes. The product was filtered, washed with ethanol and dried under vacuum to afford N-(7-butyl-6,8-dioxo-6,7,8,9-tetrahydro-1H-purin-2-yl)acetamide (55) (1.5 g, 66%) as a brown solid. $C_{11}H_{13}N_5O_3$: ES+, m/z 266.3 [M+H]$^+$.

Step 4: (S)-1-((2R,3S,4S,5R)-5-(2-Acetamido-7-butyl-6,8-dioxo-1,6,7,8-tetrahydro-9H-purin-9-yl)-4-acetoxy-3-fluorotetrahydrofuran-2-yl)propyl acetate (56)

To N-(7-butyl-6,8-dioxo-6,7,8,9-tetrahydro-1H-purin-2-yl)acetamide (55) (340 mg, 1.28 mmol), and (3S,4S,5R)-5-((S)-1-acetoxypropyl)-4-fluorotetrahydrofuran-2,3-diyl diacetate (37S) (504 mg, 1.66 mmol) in 1,2-dichloroethane (10 mL) was added BSA (777 mg, 3.84 mmol). The reaction mixture was stirred at 80° C. for 30 min under argon, cooled to RT and 1,2-dichloroethane was removed under vacuum. The residue was dissolved in MeCN (20 mL) and TMSOTf (0.43 mL, 1.92 mmol) was added. The reaction mixture was heated at 80° C. for 16 h, cooled to room temperature and concentrated under vacuum. To the residue was added sat. aq. NaHCO₃ (50 mL) and then extracted with EtOAc (3×50 mL). The combined EtOAc layer were washed with water (30 mL), brine (30 mL), dried over Na₂SO₄, filtered and concentrated under vacuum. The crude product was purified by GRACE flash chromatography (using 80% EtOAc in pet ether) to afford (150 mg, 22.9%) of (S)-1-((2R,3S,4S,5R)-5-(2-acetamido-7-butyl-6,8-dioxo-1,6,7,8-tetrahydro-9H-purin-9-yl)-4-acetoxy-3-fluorotetrahydrofuran-2-yl)propyl acetate (56) as an yellow gummy solid. $C_{22}H_{30}FN_5O_8$: ES+, m/z 512.4 $[M+H]^+$.

Step 5: 2-Amino-7-butyl-9-((2R,3S,4R,5R)-4-fluoro-3-hydroxy-5-((S)-1-hydroxypropyl)tetrahydrofuran-2-yl)-7,9-dihydro-1H-purine-6,8-dione, (Compound 30)

To a solution of (S)-1-((2R,3S,4S,5R)-5-(2-acetamido-7-butyl-6,8-dioxo-1,6,7,8-tetrahydro-9H-purin-9-yl)-4-acetoxy-3-fluorotetrahydrofuran-2-yl)propyl acetate (56) (150 mg, 0.29 mmol) in MeOH (10 mL) was added $K_2CO_3$ (60 mg, 0.44 mmol) at 0° C. and the reaction mixture was stirred at RT for 16 h. Methanol was removed under reduced pressure at 30° C. The residue was added directly to normal phase GRACE flash chromatography (using 7% MeOH in $CH_2Cl_2$) followed by reverse phase GRACE flash chromatography (using 0.01% aq. $HCO_2H$ in MeCN). The pure fractions were collected and lyophilized to afford (20 mg, 17.69%) of 2-amino-7-butyl-9-((2R,3S,4R,5R)-4-fluoro-3-hydroxy-5-((S)-1-hydroxypropyl)tetrahydrofuran-2-yl)-7,9-dihydro-1H-purine-6,8-dione (Compound 30) as a white solid. $C_{16}H_{24}FN_5O_5$: ¹H NMR (500 MHz, DMSO-$d_6$): δ 10.90 (s, 1H), 6.51 (brs, 2H), 5.90 (d, J=5.5 Hz, 1H), 5.37-5.32 (m, 2H), 5.00 (dt, J=55.5, 2.5 Hz, 1H), 4.84 (d, J=7.0 Hz, 1H), 3.83 (m, 1H), 3.78 (t, J=3.5 Hz, 2H), 3.51 (m, 1H), 1.60 (m, 2H), 1.51 (m, 1H), 1.33 (m, 1H), 1.26 (m, 2H), 0.91 (t, J=7.5 Hz, 3H), 0.88 (t, J=7.5 Hz, 3H). ES+, m/z 386.2 $[M+H]^+$.

Example 28: 2-Amino-7-butyl-9-((2R,3R,5S)-3-hydroxy-5-((R)-2,2,2-trifluoro-1-hydroxyethyl)tetrahydrofuran-2-yl)-7,9-dihydro-1H-purine-6,8-dione, Compound 31

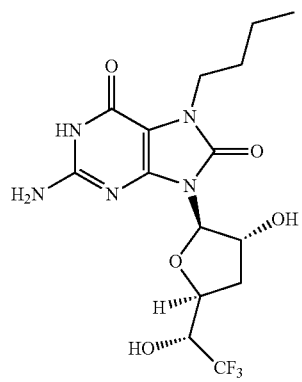 [SMILES: CCCCn1c(=O)n([C@@H]2O[C@H]([C@@H](O)C(F)(F)F)C[C@H]2O)c2nc(N)[nH]c(=O)c21]

Compound 31 was prepared according to the following two step procedure.

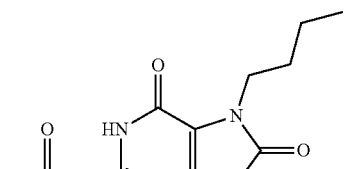
(55)

(22S)

BSA, TMSOTf
DCE, MeCN,
80° C., 16 h

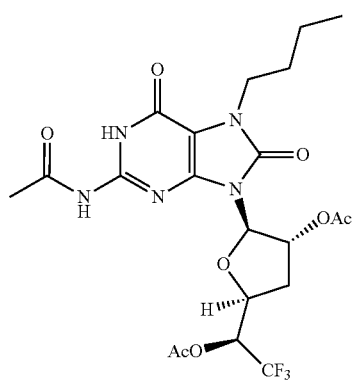
(57B)

(57A)

$K_2CO_3$,
MeOH
0° C.-rt,
16 h

HPLC separation

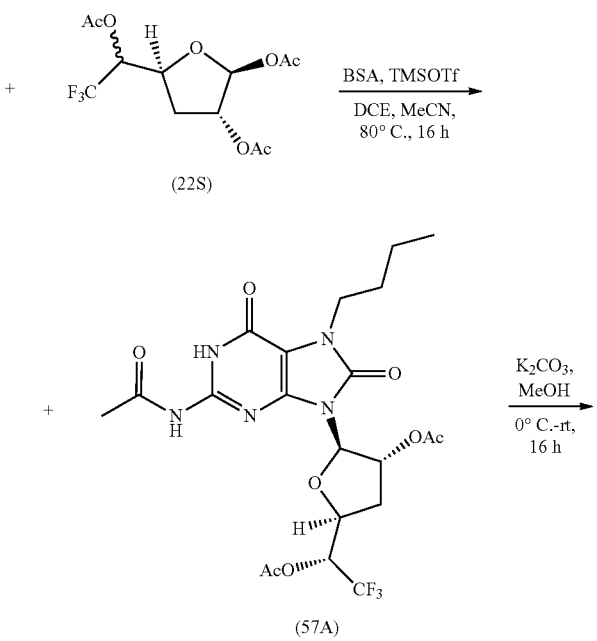

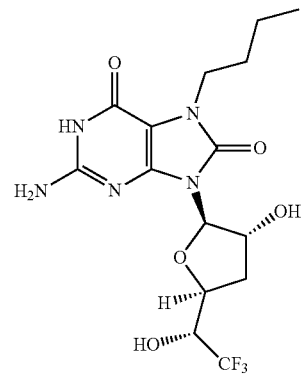

31

Step 1: (R)-1-((2S,4R,5R)-5-(2-Acetamido-7-butyl-6,8-dioxo-1,6,7,8-tetrahydro-9H-purin-9-yl)-4-acetoxytetrahydrofuran-2-yl)-2,2,2-trifluoroethyl acetate (57A) and (S)-1-((2S,4R,5R)-5-(2-Acetamido-7-butyl-6,8-dioxo-1,6,7,8-tetrahydro-9H-purin-9-yl)-4-acetoxytetrahydrofuran-2-yl)-2,2,2-trifluoroethyl acetate (57B)

N-(7-Butyl-6,8-dioxo-6,7,8,9-tetrahydro-1H-purin-2-yl)acetamide (55) (350 mg, 1.32 mmol), (2S,3R,5S)-5-(1-acetoxy-2,2,2-trifluoroethyl)tetrahydrofuran-2,3-diyl diacetate (22S) (563 mg, 1.71 mmol) and BSA (1 mL, 3.9 mmol) were dissolved in 1,2-dichloroethane (20 mL) and the resulting reaction mixture was stirred at 80° C. for 30 min under argon. The reaction mixture was allowed to cool to rt and 1,2-dichloroethane was removed under vacuum. The residue was dissolved in MeCN (20 mL) followed by addition of TMSOTf (0.36 mL, 1.98 mmol), and the reaction mixture was heated at 80° C. for 16 h. At this time the reaction mixture was cooled to room temperature and concentrated under vacuum. A saturated. aq·NaHCO$_3$ (50 mL) solution was added to the residue and extracted with EtOAc (3×50 mL). The combined EtOAc layer was washed with water (30 mL), brine (30 mL), dried over Na$_2$SO$_4$, filtered and concentrated under vacuum. The crude compound was purified by GRACE flash chromatography (80% EtOAc in pet ether) to afford 250 mg (46% and 29% of a diastereomeric mixture by LC/MS) of (R,S)-1-((2S,4R,5R)-5-(2-acetamido-7-butyl-6,8-dioxo-1,6,7,8-tetrahydro-9H-purin-9-yl)-4-acetoxytetrahydrofuran-2-yl)-2,2,2-trifluoroethyl acetate as an brown solid. Further purification by Prep-HPLC (X-SELECT-C18 (250*19 MM), 5 u Mobile phase: 10 mM ammonium bicarbonate in H$_2$O:MeCN gradient: (T % B):—0/30, 8/5, 13/55, 13.1/98, 15/98, 15.1/30, 18/3; Flow Rate: 7 mL/min; Diluent: MeCN+H$_2$O+THF) gave 90 mg of (R)-1-((2S,4R,5R)-5-(2-acetamido-7-butyl-6,8-dioxo-1,6,7,8-tetrahydro-9H-purin-9-yl)-4-acetoxytetrahydrofuran-2-yl)-2,2,2-trifluoroethyl acetate (57A) (peak-1) and 60 mg (S)-1-((2S,4R,5R)-5-(2-acetamido-7-butyl-6,8-dioxo-1,6,7,8-tetrahydro-9H-purin-9-yl)-4-acetoxytetrahydrofuran-2-yl)-2,2,2-trifluoroethyl acetate (57B) (peak-2), both as off-white solids after lyophilization of the pure fractions collected. (57A): C$_{21}$H$_{26}$F$_3$N$_5$O$_8$: $^1$H NMR (500 MHz, DMSO-d$_6$): δ 12.15 (bs, 1H), 11.61 (brs, 1H), 5.75 (s, 1H), 5.65 (m, 2H), 4.53 (m, 1H), 3.86 (t, J=6.8 Hz, 2H), 2.83 (bs, 1H), 2.17 (s, 3H), 2.14 (m, 1H), 2.08 (s, 6H), 1.64 (m, 2H), 1.27 (m, 2H), 0.87 (t, J=7.3 Hz, 3H). ES+, m/z 534.0 [M+H]$^+$. (57B): C$_{21}$H$_{26}$F$_3$N$_5$O$_8$: $^1$H NMR (500 MHz, CDCl$_3$): δ 12.10 (bs, 1H), 9.47 (brs, 1H), 6.19 (s, 1H), 6.04 (m, 1H), 5.38 (d, J=6.0 Hz, 1H), 4.66 (m, 1H), 4.00 (t, J=7.3 Hz, 2H), 2.93 (m, 1H), 2.30 (s, 3H), 2.26 (s, 3H), 2.17 (m, 1H), 2.12 (s, 3H), 1.74 (m, 2H), 1.37 (m, 2H), 0.94 (t, J=7.3 Hz, 3H). ES+, m/z 534.4 [M+H]$^+$.

Step 2: 2-Amino-7-butyl-9-((2R,3R,5S)-3-hydroxy-5-((R)-2,2,2-trifluoro-1-hydroxyethyl)tetrahydrofuran-2-yl)-7,9-dihydro-1H-purine-6,8-dione, (Compound 31)

To a solution of (R)-1-((2S,4R,5R)-5-(2-acetamido-7-butyl-6,8-dioxo-1,6,7,8-tetrahydro-9H-purin-9-yl)-4-acetoxytetrahydrofuran-2-yl)-2,2,2-trifluoroethyl acetate (57A) (90 mg, 0.16 mmol) in MeOH (20 mL) was added K$_2$CO$_3$ (34.9 mg, 0.25 mmol) at 0° C. The reaction mixture was stirred at rt for 16 h. and methanol was removed under reduced pressure at 30° C. The residue was subjected directly to reverse phase GRACE flash chromatography (using 10 mM ammonium bicarbonate in H$_2$O). The pure fractions on lyophilization afforded 50 mg (73%) of 2-amino-7-butyl-9-((2R,3R,5S)-3-hydroxy-5-((R)-2,2,2-trifluoro-1-hydroxyethyl)tetrahydrofuran-2-yl)-7,9-dihydro-1H-purine-6,8-dione (Compound 31) as an off-white solid. C$_{15}$H$_{20}$F$_3$N$_5$O$_5$: $^1$H NMR (500 MHz, DMSO-d$_6$): δ 11.00 (brs, 1H), 6.51 (brs, 2H), 6.35 (d, J=8.5 Hz, 1H), 5.58 (d, J=3.5 Hz, 1H), 5.52 (d, J=5.0 Hz, 1H), 4.74 (m, 1H), 4.34 (dt, J=11.3, 3.6 Hz, 1H), 4.02 (m, 1H), 3.78 (t, J=7.0 Hz, 2H), 2.51 (m, 1H), 1.97 (m, 1H), 1.60 (m, 2H), 1.24 (m, 2H), 0.88 (t, J=7.5 Hz, 3H). ES+, m/z 408.3 [M+H]$^+$.

135

Example 29: 2-Amino-9-((2R,3R,5S)-3-hydroxy-5-((S)-1-hydroxypropyl)tetrahydrofuran-2-yl)-7-(2-hydroxyethyl)-7,9-dihydro-1H-purine-6,8-dione, Compound 32

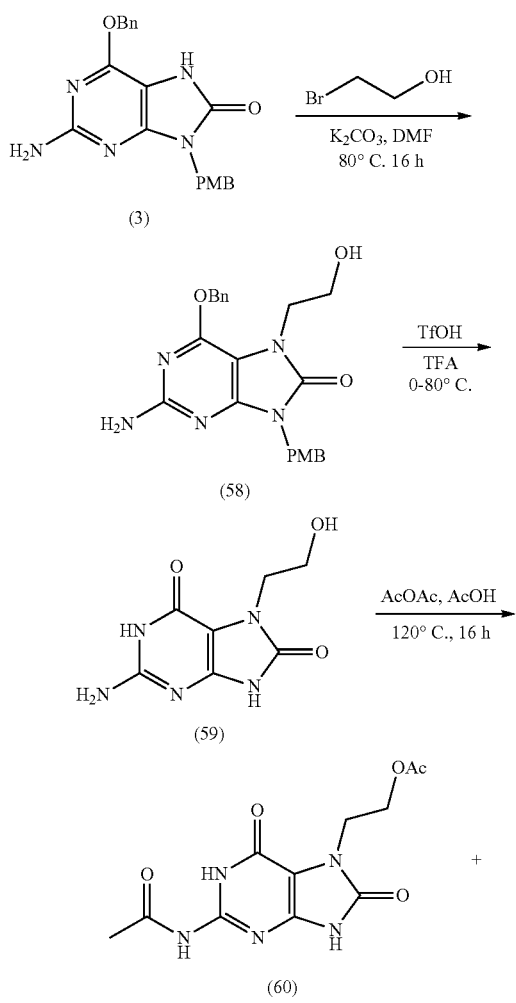

Compound 32 was prepared according to the following multi-step procedure.

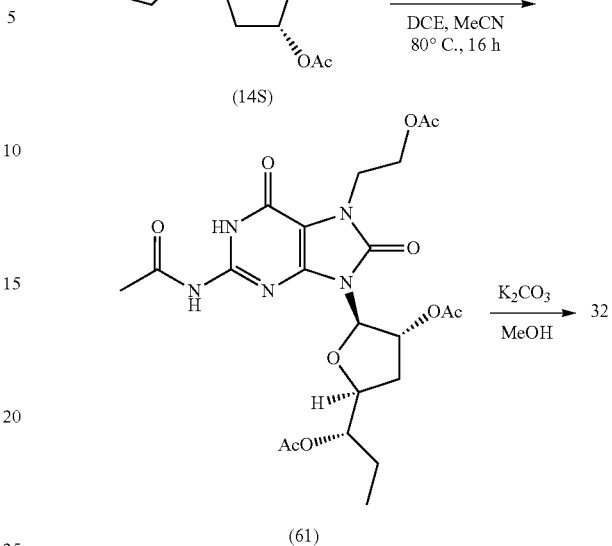

Step 1: 2-Amino-6-(benzyloxy)-7-(2-hydroxyethyl)-9-(4-methoxybenzyl)-7,9-dihydro-8H-purin-8-one (58)

2-Bromoethan-1-ol (2.4 mL, 33.1 mmol) was added to a suspension of 2-amino-6-(benzyloxy)-9-(4-methoxybenzyl)-7,9-dihydro-8H-purin-8-one (3) (5.0 g, 13.2 mmol), $Cs_2CO_3$ (5.4 g, 39.8 mmol) in DMF (50 mL) at 0° C. After the reaction mixture was stirred at 80° C. for 72 h. ice water (100 mL) was added and stirring was continued for 1 h. The resulting precipitated solid was filtered, washed with water, EtOAc and dried to afford 4 g of 2-amino-6-(benzyloxy)-7-(2-hydroxyethyl)-9-(4-methoxybenzyl)-7,9-dihydro-8H-purin-8-one (58) as an off white solid contaminated with 10% starting purine (3) by LC/MS and $^1$H NMR. $C_{22}H_{23}N_5O_4$: ES+, m/z 422.0 [M+H]$^+$ and $C_{20}H_{19}N_5O$: 378.0 [M+H]$^+$. $^1$H NMR (400 MHz, DMSO-d$_6$): δ 10.80 (s, N$^{7H}$(4)), 7.49-7.18 (m, 9H), 6.87 (dd, J=8.4, 1.2 Hz, 2H), 6.36 (s, 1H), 6.39 (s, 1H), 5.42 (d, J=7.2 Hz, 2H), 4.81 (d, J=15.6 Hz, 2H), 4.76 (m, 1H), 3.84 (t, J=6.2 Hz, 1H), 3.71 (s, 3H), 3.57 (q, J=6.0 Hz, 1H).

Step 2: 2-Amino-7-(2-hydroxyethyl)-7,9-dihydro-1H-purine-6,8-dione (59)

Trifluoromethane sulfonic acid (5.0 mL, 57.0 mmol) was added to a suspension 2-amino-6-(benzyloxy)-7-(2-hydroxyethyl)-9-(4-methoxybenzyl)-7,9-dihydro-8H-purin-8-one (58) (4.0 g, 9.5 mmol) in trifluoroacetic acid (4.6 mL, 57.0 mmol) at 0° C. under argon atmosphere. The reaction mixture was slowly warmed to room temperature and stirred for 16 h. whereupon ice cold water was added. With vigorous stirring the pH of the mixture was made basic with conc. aq. NH$_3$. The solids formed were filtered and taken up in ethyl acetate, stirred for 30 min., filtered and dried to afford 1.8 g of 2-amino-6-hydroxy-7-(2-hydroxyethyl)-7,9-dihydro-8H-purin-8-one (59) as a brown solid. $C_7H_9N_5O_3$: ES+, m/z 212.0 [M+H]$^+$. $^1$H NMR (500 MHz, DMSO-d$_6$): δ 10.82 (s, 1H), 10.53 (s, 1H), 6.29 (s, 2H), 4.75 (t, J=5.8 Hz, 1H), 3.78 (t, J=6.0 Hz, 2H), 3.57 (m, 2H).

Step 3: 2-(2-Acetamido-6,8-dioxo-1,6,8,9-tetrahydro-7H-purin-7-yl)ethyl acetate (60)

Acetic anhydride (3.3 mL, 34.1 mmol) was added to a solution of 2-amino-6-hydroxy-7-(2-hydroxyethyl)-7,9-dihydro-8H-purin-8-one (59) (1.8 g, 8.53 mmol) in AcOH (20 mL) at room temperature and the reaction mixture was heated at 120° C. for 16 h under an argon atmosphere. The reaction mixture was cooled to 0° C. and stirred for 30 minutes. The solids that precipitated were filtered, washed with EtOAc and dried under vacuum to afford 1.3 g of 2-(2-acetamido-6-hydroxy-8-oxo-8,9-dihydro-7H-purin-7-yl)ethyl acetate (60) as an brown solid. $C_{11}H_{13}N_5O_5$: ES+, m/z 296.0 [M+H]$^+$. Th crude product was used directly in the next step without purification.

Step 4: (S)-1-((2S,4R,5R)-5-(2-Acetamido-7-(2-acetoxyethyl)-6,8-dioxo-1,6,7,8-tetrahydro-9H-purin-9-yl)-4-acetoxytetrahydrofuran-2-yl)propyl acetate (61)

2-(2-Acetamido-6-hydroxy-8-oxo-8,9-dihydro-7H-purin-7-yl)ethylacetate (60) (1.0 g. 3.3 mmol), (3R,5S)-5-((S)-1-acetoxypropyl)tetrahydrofuran-2,3-diyl diacetate (14S) (1.17 g, 4.06 mmol) and BSA (2.5 mL, 10.1 mmol) were dissolved in 1,2-dichloroethane (20 mL). The reaction mixture was stirred at 800° C. for 30 min under argon and concentrated under reduced pressure. To the remaining residue was added MeCN (20 mL) and to this solution was added TMSOTf (0.94 mL, 5.08 mmol). The reaction mixture was placed into a pre-heated oil bath at 80° C., stirred for 16 h and then cooled to room temperature. The solvent was removed under reduced pressure and solids were dissolved in ethyl acetate (100 mL) and washed with saturated aqueous NaHCO$_3$ (1×30 mL). The organic phase was dried over Na$_2$SO$_4$, filtered and concentrated. The crude compound was purified by column chromatography (SiO$_2$, 0 to 60% EtOAc-Pet-ether) to afford 250 mg (13%) of (S)-1-((2S,4R,5R)-5-(2-acetamido-7-(2-acetoxyethyl)-6,8-dioxo-1,6,7,8-tetrahydro-9H-purin-9-yl)-4-acetoxytetrahydrofuran-2-yl) propyl acetate (61) as a pale yellow solid. $C_{22}H_{29}N_5O_{10}$: ES+, m/z 523.9 [M+H]$^+$.

Step 5: 2-Amino-9-((2R,3R,5S)-3-hydroxy-5-((S)-1-hydroxypropyl)tetrahydrofuran-2-yl)-7-(2-hydroxyethyl)-7,9-dihydro-1H-purine-6,8-dione, (Compound 32)

To a solution of (S)-1-((2S,4R,5R)-5-(2-acetamido-7-(2-acetoxyethyl)-6,8-dioxo-1,6,7,8-tetrahydro-9H-purin-9-yl)-4-acetoxytetrahydrofuran-2-yl)propyl acetate (61) (250 mg, 0.47 mmol) in methanol (15 mL) at room temperature was added K$_2$CO$_3$ (98.9 mg, 0.71 mmol). The reaction mixture was stirred at room temperature for 16 h. After complete consumption of the starting material as indicated by LC/MS, the reaction mixture was concentrated under reduced pressure. The crude product was purified by Prep-HPLC using Column: LUNA OMEGA C18 (250*21.2), 5 u Mobile phase: 10 mM NH$_4$HCO$_3$ in H$_2$O:MeOH gradient: (T % B):—0/10, 8/50, 12/60, 12.1/98, 14/98, 14/10, 18/10; Flow Rate: 16 mL/min; Diluent: MeCN+H$_2$O+THF. Lyophilization of the pure fractions afforded 20 mg of 2-amino-9-((2R, 3R,5S)-3-hydroxy-5-((S)-1-hydroxypropyl)tetrahydrofuran-2-yl)-7-(2-hydroxyethyl)-7,9-dihydro-1H-purine-6,8-dione (Compound 32) as an off-white solid: $C_{14}H_{21}N_5O_6$: $^1$H NMR (400 MHz, DMSO-d$_6$): δ 11.10 (brs, 1H), 6.51 (s, 2H), 5.52 (d, J 3.2 Hz, 1H), 5.34 (d, J 4.8 Hz, 1H), 4.87 (brs, 1H), 4.75 (m, 1H), 4.63 (d, J=6.8 Hz, 1H), 4.01 (m, 1H), 3.83 (t, J=6.0 Hz, 2H), 3.59 (m, 2H), 3.27 (m, 1H), 2.38 (m, 1H), 1.77 (m, 1H), 1.39 (m, 1H), 1.28 (m, 1H), 0.87 (t, J 7.2 Hz, 3H). ES+, m/z 356.0 [M+H]$^+$.

Example 30: Compound 33 and 34

2-Amino-9-((2R,3R,5S)-3-hydroxy-5-((S)-1-hydroxypropyl)tetrahydrofuran-2-yl)-7-((R)-2-hydroxypropyl)-7,9-dihydro-1H-purine-6,8-dione, Compound 33

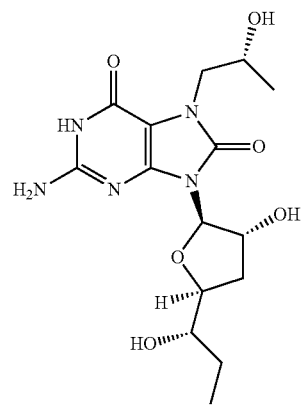 [SMILES: CC[C@H](O)[C@@H]1C[C@@H](O)[C@H](n2c(=O)n(C[C@@H](C)O)c3c(=O)[nH]c(N)nc32)O1]

2-Amino-9-((2R,3R,5S)-3-hydroxy-5-((S)-1-hydroxypropyl)tetrahydrofuran-2-yl)-7-((S)-2-hydroxypropyl)-7,9-dihydro-1H-purine-6,8-dione, Compound 34

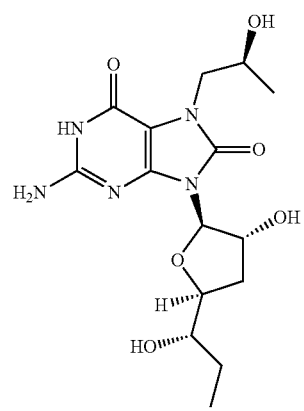 [SMILES: CC[C@H](O)[C@@H]1C[C@@H](O)[C@H](n2c(=O)n(C[C@H](C)O)c3c(=O)[nH]c(N)nc32)O1]

Compounds 33 and 34 were prepared according to the following multi-step procedures.

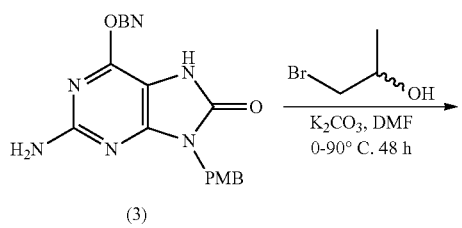

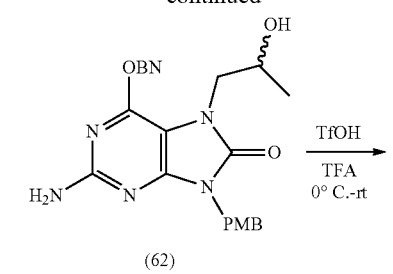

(62)

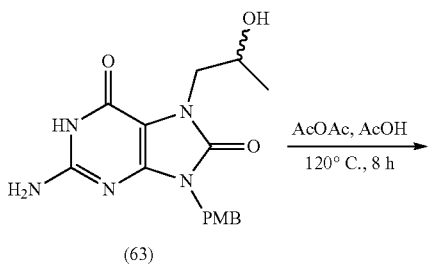

(63)

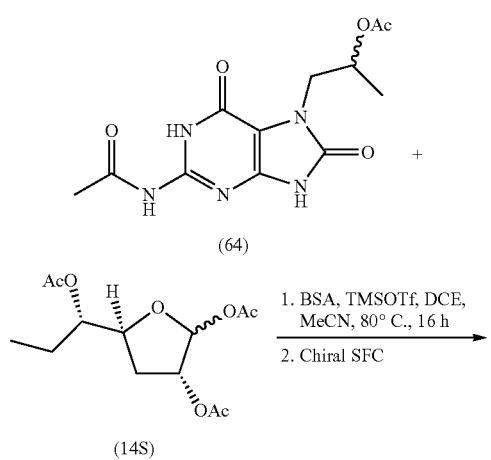

(14S)

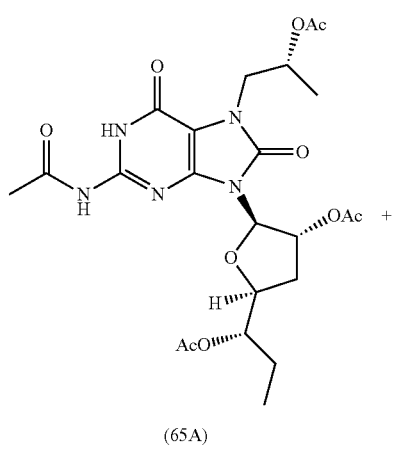

(65A)

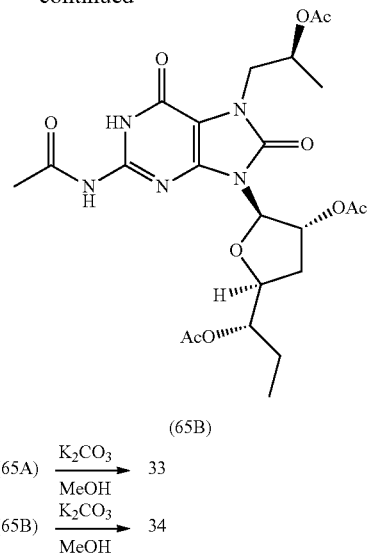

(65B)

(65A) $\xrightarrow{\text{K}_2\text{CO}_3}$ 33
       MeOH (65B) $\xrightarrow{\text{K}_2\text{CO}_3}$ 34
       MeOH Step 1: 2-Amino-6-(benzyloxy)-7-(2-hydroxypropyl)-9-(4-methoxybenzyl)-7,9-dihydro-8H-purin-8-one (62)

To a stirred suspension of 2-amino-6-(benzyloxy)-9-(4-methoxybenzyl)-7,9-dihydro-8H-purin-8-one (3) (5 g, 13.26 mmol), K$_2$CO$_3$ (2.74 g, 19.89 mmol) in DMF (50 mL) at 0° C. was added 1-bromopropan-2-ol (2.765 g, 19.89 mmol). Stirring was continued at 90° C. for 48 h. To the stirred reaction mixture was added ice water (500 mL) followed by diethyl ether (80 mL). After about 15 min. the resulting precipitated solid was filtered, washed with water and dried to afford 2-amino-6-(benzyloxy)-7-(2-hydroxypropyl)-9-(4-methoxybenzyl)-7,9-dihydro-8H-purin-8-one (62) (2 g, 34.66%) as an off-white solid. C$_{23}$H$_{25}$N$_5$O$_4$: $^1$H NMR (400 MHz, DMSO-d$_6$): δ 7.48 (d, J=7.2 Hz, 2H), 7.41-7.32 (m, 3H), 7.21 (d, J=8.8 Hz, 2H), 6.87 (d, J=8.4 Hz, 2H), 6.36 (s, 2H), 5.41 (q, J=12.4 Hz, 2H), 4.82 (s, 2H), 4.74 (s, 1H), 3.90 (m, 1H), 3.77 (m, 1H), 3.71 (s, 3H), 3.57 (dd, J=13.6, 5.2 Hz, 1H), 0.941 (d, J=6.4 Hz, 3H). ES+, m/z 436.4 [M+H]$^+$.

Step 2: 2-Amino-7-(2-hydroxypropyl)-7,9-dihydro-1H-purine-6,8-dione (63)

Trifluoromethanesulfonic acid (1.55 mL, 10.34 mmol) was added to a suspension of 2-amino-6-(benzyloxy)-7-(2-hydroxypropyl)-9-(4-methoxybenzyl)-7,9-dihydro-8H-purin-8-one (62) (1.5 g, 3.44 mmol) in trifluoroacetic acid (1.18 mL, 10.34 mmol) at 0° C. under argon atmosphere with stirring. The reaction mixture was slowly warmed to room temperature and stirred for 16 h. The crude product was purified by reverse phase GRACE flash chromatography using 0.1% of HCO$_2$H in water and MeCN to afford 2-amino-7-(2-hydroxypropyl)-7,9-dihydro-1H-purine-6,8-dione (63) (0.4 g, 47.4%) as an off-white solid. C$_8$H$_{11}$N$_5$O$_3$: $^1$H NMR (400 MHz, DMSO-d$_6$): δ 11.08 (s, 1H), 10.69 (s, 1H), 6.35 (s, 2H), 4.8 (bs, 1H), 3.94 (m, 1H), 3.69 (dd, J=13.4, 6.6 Hz, 1H), 3.59 (dd, J=13.6, 6.0 Hz, 1H), 0.99 (d, J=5.6 Hz, 3H). ES+, m/z 226.0 [M+H]$^+$.

Step 3: 1-(2-Acetamido-6,8-dioxo-1,6,8,9-tetrahydro-7H-purin-7-yl)propan-2-yl acetate (64)

Acetic anhydride (0.79 mL, 7.73 mmol) was added to a solution of 2-amino-7-(2-hydroxypropyl)-7,9-dihydro-1H- purine-6,8-dione (63) (0.58 g, 2.57 mmol) in AcOH (10 mL) at ambient temperature under argon atmosphere and the resulting reaction mixture was stirred at 120° C. for 8 h under argon atmosphere. The reaction mixture was concentrated, EtOAc (20 mL) was added and stirring was continued for 30 minutes. The product was filtered, washed with EtOAc and dried under vacuum to afford 1-(2-acetamido-6,8-dioxo-1,6,8,9-tetrahydro-7H-purin-7-yl)propan-2-yl acetate (64) (500 mg, 62.81%) as a light brown solid. $C_{12}H_{15}N_5O_5$: $^1H$ NMR (400 MHz, DMSO-$d_6$): δ 12.00 (s, 1H), 11.70 (s, 1H), 11.66 (s, 1H), 5.15 (m, 1H), 3.97 (dd, J=14.2, 7.4 Hz, 1H), 3.90 (dd, J=14.0, 4.4 Hz, 1H), 2.15 (s, 3H), 1.88 (s, 3H), 1.17 (d, J=6.4 Hz, 3H). ES+, m/z 310.0 [M+H]$^+$.

Step 4: (S)-1-((2S,4R,5R)-5-(2-acetamido-7-((R)-2-acetoxypropyl)-6,8-dioxo-1,6,7,8-tetrahydro-9H-purin-9-yl)-4-acetoxytetrahydrofuran-2-yl)propyl acetate (65A) and (S)-1-((2S,4R,5R)-5-(2-acetamido-7-((S)-2-acetoxypropyl)-6,8-dioxo-1,6,7,8-tetrahydro-9H-purin-9-yl)-4-acetoxytetrahydrofuran-2-yl)propyl acetate (65B)

1-(2-Acetamido-6,8-dioxo-1,6,8,9-tetrahydro-7H-purin-7-yl)propan-2-yl acetate (64) (400 mg, 1.29 mmol), (3R,5S)-5-((S)-1-acetoxypropyl)tetrahydrofuran-2,3-diyl diacetate (14S) (559 mg, 1.94 mmol) and BSA (1.30 mL, 6.47 mmol) were dissolved in 1,2-dichloromethane (15 mL). The reaction mixture was stirred at 80° C. for 30 min. under argon. At this time the reaction mixture was concentrated under reduced pressure, and the residue was dissolved in MeCN (30 mL) followed by addition of TMSOTf (0.71 mL, 3.2 mmol). The stirred reaction mixture was placed into a pre-heated oil bath at 80° C. After 3 h the reaction mixture was cooled to room temperature and the solvent was removed under reduced pressure. The resultant solid was dissolved in ethyl acetate (80 mL) and to the stirred solution was added saturated aqueous NaHCO$_3$ (2×30 mL). The organic phase was separated, dried over anhydrous Na$_2$SO$_4$, filtered and concentrated. The crude products was purified by column chromatography (SiO$_2$, 0 to 80% ethyl acetate-pet ether) to give a 1:1 mixture of (S)-1-((2S,4R,5R)-5-(2-acetamido-7-((R,S)-2-acetoxypropyl)-6,8-dioxo-1,6,7,8-tetrahydro-9H-purin-9-yl)-4-acetoxytetrahydrofuran-2-yl)propyl acetate (220 mgs). The racemic mixture was further purified by Chiral SFC-150-080 HPLC (Lux; Cellulose-4 OX-H; 250×30×5µ; 75% CO$_2$, 25% MeOH; Total Flow: 60.0 g/min.; Back pressure: 120.0 bar; 30° C.; UV: 214.0 nm; Stack time: 7.0 mins; Load/injection: 14.57 mgs) to afford 50 mg of (S)-1-((2S,4R,5R)-5-(2-acetamido-7-((R)-2-acetoxypropyl)-6,8-dioxo-1,6,7,8-tetrahydro-9H-purin-9-yl)-4-acetoxytetrahydrofuran-2-yl)propyl acetate (65A; 7(R) stereochemistry arbitrarily assigned) and 50 mg of (S)-1-((2S,4R,5R)-5-(2-acetamido-7-((S)-2-acetoxypropyl)-6,8-dioxo-1,6,7,8-tetrahydro-9H-purin-9-yl)-4-acetoxytetrahydrofuran-2-yl)propyl acetate (65B; 7(S) stereochemistry arbitrarily assigned), both as off-white solids after evaporation of methanol. Analytical SFC was used to check diastereomeric purity; (Chiralcel OX-H; 250×4.6×5µ; 75% CO$_2$, 25% MeOH; Total Flow: 3.0 g/min.; Back pressure: 100.0 bar; 30° C.; UV: 214.0 nm) 65A: $C_{23}H_{31}N_5O_{10}$: ES+, m/z 538.0 [M+H]$^+$. 65B: $C_{23}H_{31}N_5O_{10}$: ES+, m/z 537.9 [M+H]$^+$.

Step 5: 2-Amino-9-((2R,3R,5S)-3-hydroxy-5-((S)-1-hydroxypropyl)tetrahydrofuran-2-yl)-7-((R)-2-hydroxypropyl)-7,9-dihydro-1H-purine-6,8-dione (Compound 33)

To a solution of (S)-1-((2S,4R,5R)-5-(2-acetamido-7-((R)-2-acetoxypropyl)-6,8-dioxo-1,6,7,8-tetrahydro-9H-purin-9-yl)-4-acetoxytetrahydrofuran-2-yl)propyl acetate (65A) (50 mg, 0.09 mmol) in methanol (5 mL) at room temperature, was added K$_2$CO$_3$ (19 mg, 0.13 mmol) and the reaction mixture was stirred at room temperature for 16 h. At this time the solvent was removed under reduced pressure and the resulting crude compound was purified by GRACE flash chromatography (0.1% HCO$_2$H in water, acetonitrile) to afford 2-amino-9-((2R,3R,5S)-3-hydroxy-5-((S)-1-hydroxypropyl)tetrahydrofuran-2-yl)-7-((R)-2-hydroxypropyl)-7,9-dihydro-1H-purine-6,8-dione (Compound 33) (24 mg, 69.66%), as a yellow solid. $C_{15}H_{23}N_5O_6$: $^1H$ NMR indicated formation of the formic acid salt. $^1H$ NMR (500 MHz, DMSO-$d_6$): δ 8.52 (s, 1H), 6.70-6.50 (b, 2H), 5.52 (d, J=3.5 Hz, 1H), 5.35 (s, 1H), 4.75 (s, 2H), 4.01 (m, 1H), 3.91 (m, 1H), 3.70 (m, 2H), 3.20 (m, 1H), 2.38 (m, 2H), 1.79 (m, 1H), 1.39 (m, 1H), 1.28 (m, 1H), 1.01 (d, J=6.5 Hz, 3H), 0.87 (t, J=7.5 Hz 3H). ES+, m/z 370.36 [M+H]$^+$.

Step 6: 2-Amino-9-((2R,3R,5S)-3-hydroxy-5-((S)-1-hydroxypropyl)tetrahydrofuran-2-yl)-7-((S)-2-hydroxypropyl)-7,9-dihydro-1H-purine-6,8-dione (Compound 34)

To a solution of (S)-1-((2S,4R,5R)-5-(2-acetamido-7-((S)-2-acetoxypropyl)-6,8-dioxo-1,6,7,8-tetrahydro-9H-purin-9-yl)-4-acetoxytetrahydrofuran-2-yl)propyl acetate (65B) (50 mg, 0.093 mmol) in methanol (5 mL) at room temperature was added K$_2$CO$_3$ (19 mg, 0.13 mmol). After stirring the reaction mixture at room temperature for 16 h. the solvent was removed under reduced pressure. The resulting crude product was purified by GRACE flash chromatography (0.1% HCO$_2$H in water, acetonitrile) to afford 2-amino-9-((2R,3R,5S)-3-hydroxy-5-((S)-1-hydroxypropyl)tetrahydrofuran-2-yl)-7-((S)-2-hydroxypropyl)-7,9-dihydro-1H-purine-6,8-dione (Compound 34) (15 mg, 43.54%), as a white solid. $C_{15}H_{23}N_5O_6$: $^1H$ NMR (400 MHz, DMSO-$d_6$): δ 11.15 (s, 1H), 6.54 (s, 2H), 5.52 (d, J=3.2 Hz, 1H), 5.34 (s, 1H), 4.85 (bs, 1H), 4.75 (s, 1H), 4.57 (d, J=6.4 Hz, 1H), 4.03-3.92 (m, 2H), 3.75 (dd, J=13.6, 6.8 Hz, 1H), 3.64 (dd, J=13.4, 5.8 Hz, 1H), 3.26 (m, 1H), 2.38 (m, 1H), 1.77 (m, 1H), 1.39 (m, 1H), 1.28 (m, 1H), 1.01 (d, J=6.0 Hz, 3H), 0.89 (t, J=7.5 Hz, 3H). ES+, m/z 370.0 [M+H]$^+$.

Example 31: 2-Amino-9-((2R,3R,5S)-3-hydroxy-5-((S)-1-hydroxybut-3-yn-1-yl)tetrahydrofuran-2-yl)-7-(prop-2-yn-1-yl)-7,9-dihydro-1H-purine-6,8-dione, Compound 35

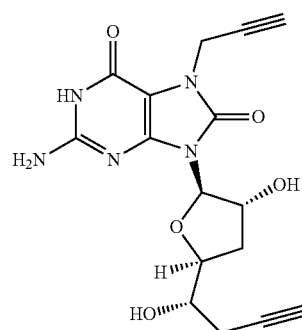

Compound 35 was prepared according to the following multi-step procedure.

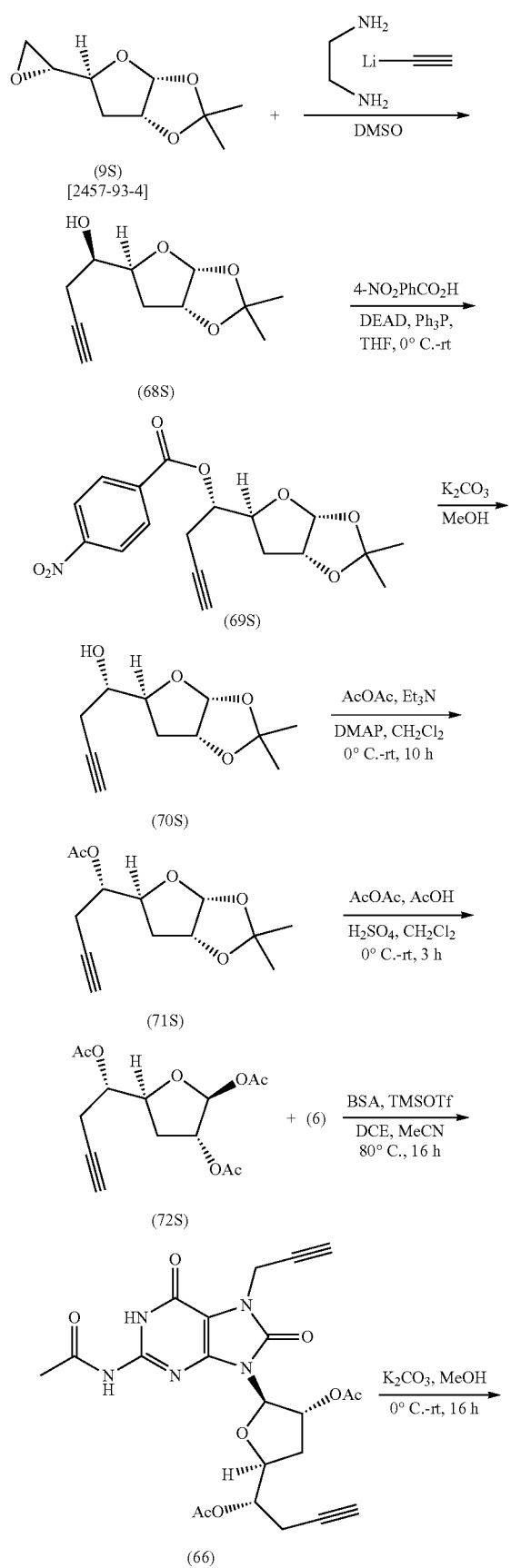

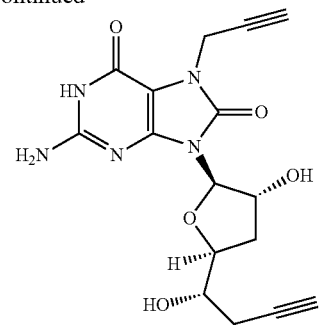

Step 1: (R)-1-((3aR,5S,6aR)-2,2-Dimethyltetrahydrofuro[2,3-d][1,3]dioxol-5-yl)but-3-yn-1-ol (68S)

To a solution of (3aR,5S,6aR)-2,2-dimethyl-5-((R)-oxiran-2-yl)tetrahydrofuro[2,3-d][1,3]dioxole (9S) (4 g, 21.7 mmol) in DMSO (50 mL), was added lithium acetylide-ethylenediamine complex (4.9 g, 53.76 mmol) at rt. The reaction was monitored by TLC and the mixture was stirred for 18 hr. The reaction mixture was poured into 100 mL of ice-water and extracted with diethyl ether (2×100 mL). The organic phase was washed with a brine solution (2×100 mL), separated and dried over $Na_2SO_4$, filtered and concentrated to give the crude product that was purified by silica gel chromatography using a petroleum ether/ethyl acetate gradient (0-30%), to give (R)-1-((3aR,5S,6aR)-2,2-dimethyltetrahydrofuro[2,3-d][1,3]dioxol-5-yl)but-3-yn-1-ol (68S) (2.5 g, 55%) as an orange liquid. $C_{11}H_{16}O_4$: $^1$H NMR (400 MHz, $CDCl_3$): δ 5.81 (d, J=3.6 Hz, 1H), 4.76 (t, J=4.4 Hz, 1H), 4.31 (dt, J=10.6, 4.4 Hz, 1H), 4.00 (ddd, J=10.4, 6.6, 3.8 Hz, 1H), 2.49-2.37 (m, 2H), 2.30 (d, J=6.5 Hz, 1H), 2.09 (dd, J=13.5, 4.6 Hz, 1H), 2.05 (t, J=2.6 Hz, 1H), 1.86 (ddd, J=13.4, 10.6, 4.8 Hz, 1H), 1.52 (s, 3H), 1.35 (s, 3H).

Step 2: (S)-1-((3aR,5S,6aR)-2,2-Dimethyltetrahydrofuro[2,3-d][1,3]dioxol-5-yl)but-3-yn-1-yl 4-nitrobenzoate (69S)

To a solution of (R)-1-((3aR,5S,6aR)-2,2-dimethyltetrahydrofuro[2,3-d][1,3]dioxol-5-yl)but-3-yn-1-ol (68S) (2.5 g, 11.7 mmol) in THF (60 mL) was added 4-nitrobenzoic acid (3.9 g, 23.5 mmol), triphenyl phosphine (3.0 g, 23.5 mmol) and DEAD (3.7 mL, 23.5 mmol) at 0° C. The reaction mixture was monitored by TLC and stirring was continued for 16 hours at rt. At this time the reaction mixture was poured into 200 mL of water and extracted with EtOAc (2×200 mL). The organic phase was washed with a sat. brine solution (2×60 mL), separated, dried over anhydrous $Na_2SO_4$, filtered and concentrated to afford the crude product that was purified by column chromatography with silica and a petroleum ether/ethyl acetate gradient (0-20%) to yield (S)-1-((3aR,5S,6aR)-2,2-dimethyltetrahydrofuro[2,3-d][1,3]dioxol-5-yl)but-3-yn-1-yl 4-nitrobenzoate (69S) (2.5 g, 59%) as a semi-solid. $C_{18}H_{19}NO_7$:

Step 3: (S)-1-((3aR,5S,6aR)-2,2-Dimethyltetrahydrofuro[2,3-d][1,3]dioxol-5-yl)but-3-yn-1-ol (70S)

To a solution of (S)-1-((3aR,5S,6aR)-2,2-dimethyltetrahydrofuro[2,3-d][1,3]dioxol-5-yl)but-3-yn-1-yl 4-nitrobenzoate (69S) (2.5 g, 6.92 mmol) in methanol (25 mL) was added K$_2$CO$_3$ (1.43 g, 10.38 mmol) at rt. The reaction mixture was stirred for 1 hour at rt., filtered and concentrated to give the crude product that was purified by column chromatography (petroleum ether/ethyl acetate; 0-40% gradient) to give (S)-1-((3aR,5S,6aR)-2,2-dimethyltetrahydrofuro[2,3-d][1,3]dioxol-5-yl)but-3-yn-1-ol (70S) (1.4 g, 95%) as an orange liquid. C$_{11}$H$_{16}$O$_4$: $^1$H NMR (500 MHz, CDCl$_3$): δ 5.82 (d, J=3.5 Hz, 1H), 4.76 (t, J=4.5 Hz, 1H), 4.33 (m, 1H), 3.70 (m, 1H), 2.51-2.48 (m, 2H), 2.30 (d, J=6.5 Hz, 1H), 2.09 (dd, J=13.0, 4.5 Hz, 1H), 2.05 (t, J=2.5 Hz, 1H), 1.87 (m, 1H), 1.53 (s, 3H), 1.26 (s, 3H).

Step 4: (S)-1-((3aR,5S,6aR)-2,2-Dimethyltetrahydrofuro[2,3-d][1,3]dioxol-5-yl)but-3-yn-1-yl acetate (71S)

To a stirred solution of ((S)-1-((3aR,5S,6aR)-2,2-dimethyltetrahydrofuro[2,3-d][1,3]dioxol-5-yl)but-3-yn-1-ol (70S) (1.32 g, 6.22 mmol), TEA (1.76 mL, 12.45 mmol), DMAP (0.151 g, 1.24 mmol) in anhydrous CH$_2$Cl$_2$ (22 mL) was added acetic anhydride (0.92 mL, 9.33 mmol). After being stirred at 25° C. for 10 h, the reaction was added to a saturated aq·NaHCO$_3$ solution (50 mL). The organic layer was separated and the aqueous phase was extracted with CH$_2$Cl$_2$ (2×50 mL). The combined organic layers were dried over anhydrous Na$_2$SO$_4$, filtered and concentrated in vacuo. The crude mixture was purified by column chromatography on silica gel (100-200 mesh, 30% EtOAc in petroleum ether) to afford (S)-1-((3aR,5S,6aR)-2,2-dimethyltetrahydrofuro[2,3-d][1,3]dioxol-5-yl)but-3-yn-1-yl acetate (71S) (1.3 g, 83%) as a colorless oil. C$_{13}$H$_{18}$O$_5$: $^1$H NMR (400 MHz, CDCl$_3$): δ 5.82 (d, J=3.6 Hz, 1H), 5.03 (m, 1H), 4.75 (dd, J=8.0, 3.6 Hz, 1H), 4.48 (m, 1H), 2.65-2.52 (m, 2H), 2.12 (s, 3H), 2.09 (m, 1H), 2.07 (m, 1H), 1.65 (m, 1H), 1.52 (s, 3H), 1.33 (s, 3H).

Step 5: (2S,3R,5S)-5-((S)-1-Acetoxybut-3-yn-1-yl)tetrahydrofuran-2,3-diyl diacetate (72S)

To a solution of (S)-1-((3aR,5S,6aR)-2,2-dimethyltetrahydrofuro[2,3-d][1,3]dioxol-5-yl)but-3-yn-1-yl acetate (71S) (1.3 g, 5.11 mmol), acetic acid (3.0 mL, 51.18 mmol) and acetic anhydride (2.43 mL, 25.59 mmol) in anhydrous CH$_2$Cl$_2$ (50 mL) was added concentrated H$_2$SO$_4$ (0.2 mL) at 0° C. After being stirred at 25° C. for 3 hours, the pH of the reaction mixture was made basic by the addition of saturated aq·NaHCO$_3$ solution (100 mL). The organic layer was separated and the aqueous phase was extracted with CH$_2$Cl$_2$ (2×100 mL). The combined organic layers were dried over Na$_2$SO$_4$, filtered and concentrated in vacuum. The crude product was purified by column chromatography on silica gel (100-200 mesh, 30% EtOAc in petroleum ether) to afford (2R,3R,5S)-5-((S)-1-acetoxybut-3-yn-1-yl)tetrahydrofuran-2,3-diyl diacetate (72S) (700 mg, 46%) as a colorless oil. C$_{14}$H$_{18}$O$_7$: $^1$H NMR (400 MHz, CDCl$_3$): δ 6.13 (s, 1H), 5.19 (d, J=4.4 Hz, 1H), 5.00 (m, 1H), 4.59 (m, 1H), 2.62-2.47 (m, 2H), 2.15-2.12 (m, 3H), 2.10 (s, 9H).

Step 6: (S)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)but-3-yn-1-yl acetate (66)

N-(6,8-dioxo-7-(prop-2-yn-1-yl)-6,7,8,9-tetrahydro-1H-purin-2-yl)acetamide (6) (500 mg, 2.02 mmol), (2R,3R,5S)-5-((S)-1-acetoxybut-3-yn-1-yl)tetrahydrofuran-2,3-diyl diacetate (72S) (723 mg, 2.42 mmol), BSA (1.53 mL, 6.07 mmol) were dissolved in 1,2-dichloroethane (20 mL) and the reaction mixture was stirred at 80° C. under argon. After 30 min. the reaction mixture was cooled to RT and 1,2-dichloroethane was removed under vacuum. The residue was dissolved in MeCN (20 mL) followed by addition of TMSOTf (0.55 mL, 3.03 mmol). The reaction mixture was heated at 80° C. for 16 h, cooled to room temperature and concentrated under vacuum. To the residue obtained was added sat. aq. NaHCO$_3$ (50 mL) and then extracted with EtOAc (3×50 mL). The combined EtOAc extracts were washed with water (30 mL), brine (30 mL), dried over Na$_2$SO$_4$, filtered and concentrated under vacuum. The crude product was purified by GRACE flash chromatography (80% EtOAc in pet ether) to afford 230 mg (34.6%) of (S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)but-3-yn-1-yl acetate (66) as a brown solid. C$_{22}$H$_{23}$N$_5$O$_8$: ES+, m/z 486.0 [M+H]$^+$.

Step 7: 2-Amino-9-((2R,3R,5S)-3-hydroxy-5-((S)-1-hydroxybut-3-yn-1-yl)tetrahydrofuran-2-yl)-7-(prop-2-yn-1-yl)-7,9-dihydro-1H-purine-6,8-dione (Compound 35)

To a solution of ((S)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)but-3-yn-1-yl acetate (66) (210 mg, 0.432 mmol) in MeOH (20 mL) was added K$_2$CO$_3$ (90 mg, 0.649 mmol) at 0° C. and the reaction mixture was stirred at RT for 16 h. Methanol was removed under reduced pressure at 30° C. The residue was applied directly to reverse phase GRACE flash chromatography (using 0.01% aq. NH$_4$HCO$_3$ and MeCN). The pure fractions were collected and lyophilized to afford 80 mg (46%) of 2-amino-9-((2R,3R,5S)-3-hydroxy-5-((S)-1-hydroxybut-3-yn-1-yl)tetrahydrofuran-2-yl)-7-(prop-2-yn-1-yl)-7,9-dihydro-1H-purine-6,8-dione (Compound 35) as a white solid. C$_{16}$H$_{17}$N$_5$O$_5$: $^1$H NMR (400 MHz, DMSO-d$_6$): δ 10.95 (brs, 1H), 6.53 (brs, 2H), 5.53 (d, J=3.2 Hz, 1H), 5.42 (d, J=4.4 Hz, 1H), 5.00 (d, J=6.8 Hz, 1H), 4.73 (m, 1H), 4.59 (s, 2H), 4.17 (m, 1H), 3.57 (m, 1H), 3.22 (s, 1H), 2.74 (s, 1H), 2.43 (m, 1H), 2.33-2.26 (m, 2H), 1.82 (m, 1H). ES+, m/z 360.0 [M+H]$^+$.

Example 32: 2-Amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-8H-purin-8-one, Compound 36

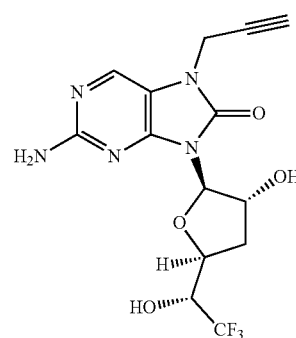

Compound 36 was prepared according to the following two step procedure.

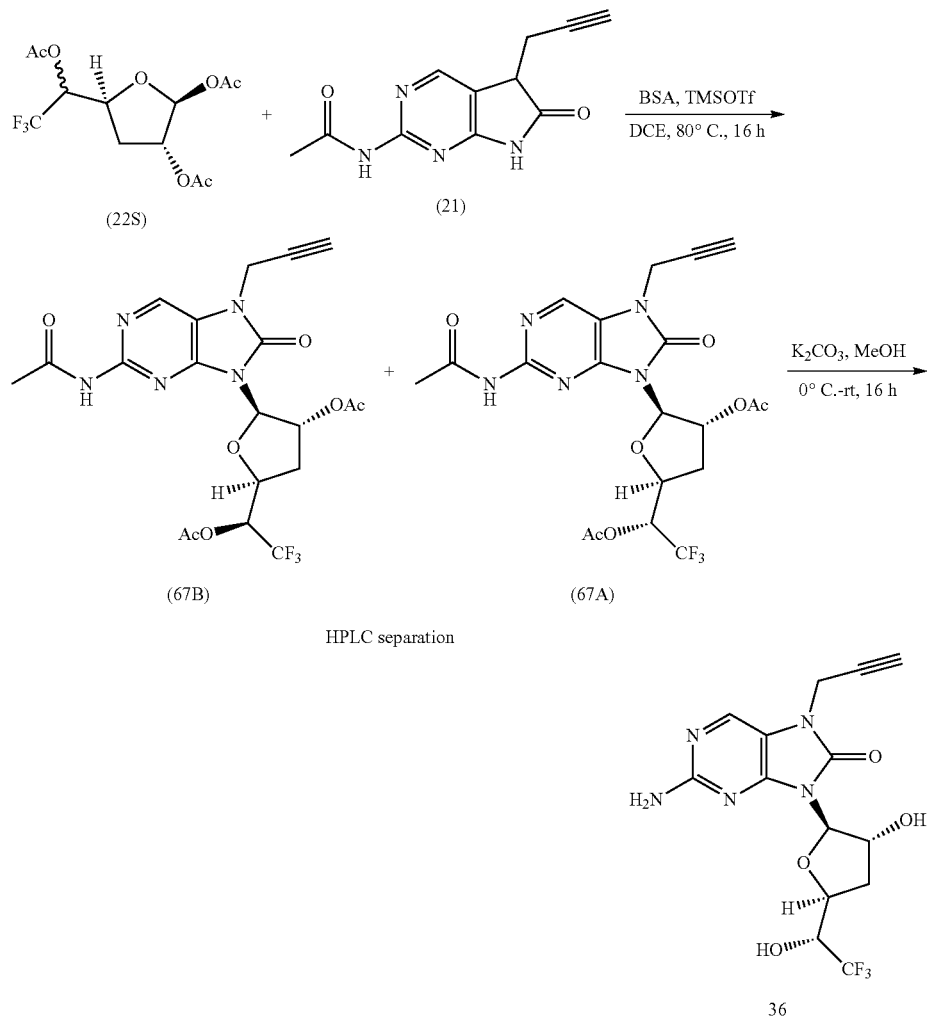

Step 1: (R)-1-((2S,4R,5R)-5-(2-Acetamido-8-oxo-7-(prop-2-yn-1-yl)-7,8-dihydro-9H-purin-9-yl)-4-acetoxytetrahydrofuran-2-yl)-2,2,2-trifluoroethyl acetate (67A) and (S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)-2,2,2-trifluoroethyl acetate (67B)

To N-(8-oxo-7-(prop-2-yn-1-yl)-8,9-dihydro-7H-purin-2-yl)acetamide (21) (500 mg, 2.1 mmol) and (2S,3R,5S)-5-(1-acetoxy-2,2,2-trifluoroethyl)tetrahydrofuran-2,3-diyl diacetate (22S) (855 mg, 2.6 mmol) in 1,2-dichloroethane (20 mL) was added BSA (1.64 mL, 6.52 mmol). The reaction mixture was stirred at 80° C. for 30 min under argon, then allowed to cool to RT and 1,2-dichloroethane was removed under vacuum. The residue was taken up in MeCN (20 mL) followed by addition of TMSOTf (0.6 mL, 3.2 mmol). The reaction mixture was heated at 80° C. for 16 h, cooled to room temperature and concentrated under vacuum. To the residue was added sat. aq·NaHCO₃ (50 mL) and extracted with EtOAc (3×50 mL). The combined EtOAc layer were washed with water (30 mL), brine (30 mL), dried over Na₂SO₄, filtered and concentrated under vacuum. The crude product was purified by GRACE flash chromatography (80% EtOAc in pet ether) to afford 530 mg of a diastereomeric mixture of (R,S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)-2,2,2-trifluoroethyl acetate (~1.7:1) as an off-white solid. Separation the diastereomers by Prep-HPLC (Column: X-SELECT-C18 (50*19), 5 u Mobile phase: 0.1% TFA in H₂O:MeCN Gradient: (T % B):—0/10, 8/50, 10/50, 10.1/98, 11/98, 11.1/10, 13/10; Flow Rate: 17 mL/min) to give 230 mg of (R)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)-2,2,2-trifluoroethyl acetate (67A) and 100 mg of (S)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)-2,2,2-trifluoroethylacetate (67B). (67A): $C_{20}H_{20}F_3N_5O_7$: ¹H NMR (500 MHz, DMSO-d₆): δ 8.42 (s, 1H), 5.84 (d, J=1.0 Hz, 1H), 5.70 (m, 2H), 4.80 (d, J=2.5 Hz, 2H), 4.56 (m, 2H), 3.46 (t, J=2.5 Hz, 1H), 3.29 (m, 1H), 2.18 (m, 1H), 2.12 (s, 3H), 2.08 (s, 6H). ES+, m/z 499.9 [M+H]⁺. (67B): (*Loss of an —Ac group was observed by LC/MS and ¹H NMR after HPLC purification) $C_{18}H_{18}F_3N_5O_6$: ¹H NMR (400 MHz, DMSO-d₆): δ 8.14 (s, 1H), 7.40 (bs, 1H), 5.81 (d, J=2.0 Hz, 1H), 5.75 (m, 2H), 4.80-4.60 (b, 1H), 4.67 (t, J=2.0 Hz, 2H), 4.59 (m, 1H), 3.46 (t, J=2.4 Hz, 1H), 3.02-2.94 (m, 1H), 2.16 (dd, J=13.6 Hz, 5.6 Hz, 1H), 2.09 (s, 3H), 2.08 (s, 3H). ES+, m/z 458.1 [M+H]⁺.

Step 2: 2-Amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-8H-purin-8-one (Compound 36)

To a solution of (R)-1-((2S,4R,5R)-5-(2-acetamido-8-oxo-7-(prop-2-yn-1-yl)-7,8-dihydro-9H-purin-9-yl)-4-acetoxytetrahydrofuran-2-yl)-2,2,2-trifluoroethyl acetate (67A) (230 mg, 0.46 mmol) in MeOH (20 mL) was added $K_2CO_3$ (95 mg, 0.69 mmol) at 0° C. The reaction mixture was stirred at rt for 16 h, and then methanol was removed under reduced pressure at 30° C. The residue was applied directly to reverse phase GRACE flash chromatography (10 mM ammonium bicarbonate in $H_2O$). The pure fractions were lyophilized to yield 80 mg (46%) of 2-amino-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-8H-purin-8-one (Compound 36) as an off-white solid. $C_{14}H_{14}F_3N_5O_4$: $^1$H NMR (500 MHz, DMSO-$d_6$): δ 8.04 (s, 1H), 6.37 (s, 2H), 6.29 (bs, 1H), 5.67 (d, J=2.5 Hz, 1H), 5.58 (brs, 1H), 4.79 (m, 1H), 4.64 (d, J=2.0 Hz, 2H), 4.34 (m, 1H), 4.06 (m, 1H), 3.41 (d, J 2.5 Hz, 1H), 2.62 (m, 1H), 1.96 (m, 1H). ES+, m/z 374.31 [M+H]$^+$.

Example 33: Compound 37 and 38

2-Amino-9-((2R,3R,5S)-3-hydroxy-5-propionyltetrahydrofuran-2-yl)-7-(prop-2-yn-1-yl)-7,9-dihydro-1H-purine-6,8-dione, Compound 37

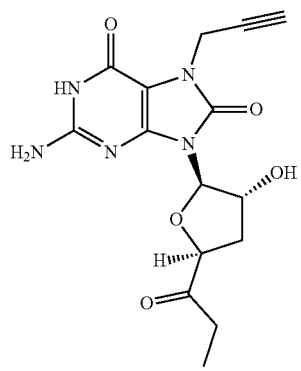 [SMILES: C#CCn1c(=O)n([C@@H]2O[C@H](C(=O)CC)C[C@H]2O)c2nc(N)[nH]c(=O)c21]

2-Amino-9-((2R,3R,5R)-3-hydroxy-5-propionyltetrahydrofuran-2-yl)-7-(prop-2-yn-1-yl)-7,9-dihydro-1H-purine-6,8-dione, Compound 38

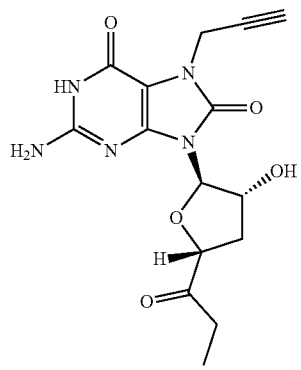 [SMILES: C#CCn1c(=O)n([C@@H]2O[C@@H](C(=O)CC)C[C@H]2O)c2nc(N)[nH]c(=O)c21]

Compounds 37 and 38 were prepared according to the following multi-step procedures.

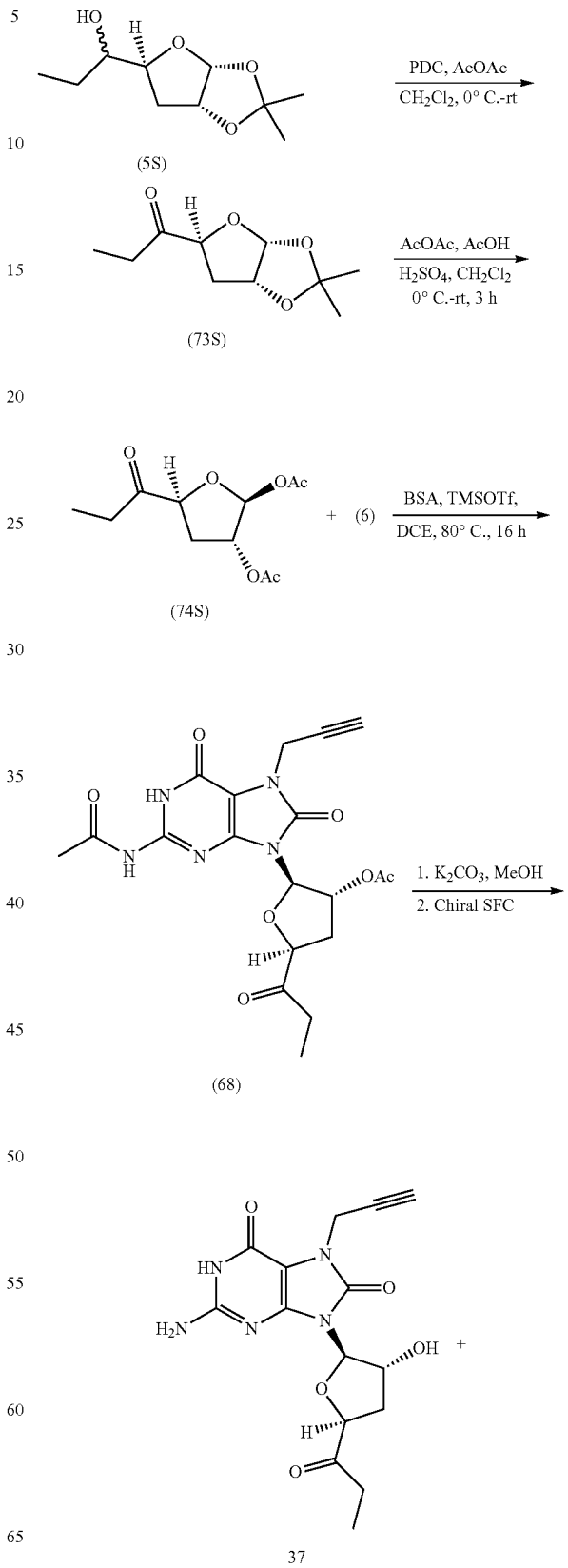

-continued

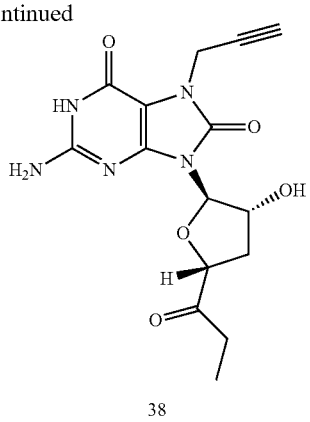

38

Step 1: 1-((3aR,5S,6aR)-2,2-Dimethyltetrahydrofuro[2,3-d][1,3]dioxol-5-yl)propan-1-one (73S)

To a solution of 1-((3aR,5S,6aR)-2,2-dimethyltetrahydrofuro[2,3-d][1,3]dioxol-5-yl)propan-1-ol (5S) (2.3 g, 11.38 mmol) in $CH_2Cl_2$ (46 mL), was added pyridinium dichromate (5.14 g, 13.66 mmol) and acetic anhydride (2.3 mL, 1 vol) at 0° C. The reaction mixture was monitored by TLC and stirred for 16 h at rt. The reaction mixture was concentrated and the residue was purified by column chromatography on silica gel (100-200 mesh, 50% EtOAc in petroleum ether) to afford 1-((3aR,5S,6aR)-2,2-dimethyltetrahydrofuro[2,3-d][1,3]dioxol-5-yl)propan-1-one (73S) (2.1 g, 90%) as a pale yellow liquid. $C_{10}H_{16}O_4$: $^1H$ NMR (400 MHz, $CDCl_3$): δ 5.91 (d, J=3.6 Hz, 1H), 4.75 (t, J=4.2 Hz, 1H), 4.63 (dd, J=11.2, 4.8 Hz, 1H), 2.61 (dq, J=7.2, 2.0 Hz, 2H), 2.37 (dd, J=13.4, 5.0 Hz, 1H), 1.76 (dd, J=15.8, 9.9, 3.5 Hz, 1H), 1.52 (s, 3H), 1.43 (s, 3H), 1.05 (t, J=7.2 Hz, 3H).

Step 2: (2S,3R,5S)-5-Propionyltetrahydrofuran-2,3-diyl diacetate (74S)

To a solution of 1-((3aR,5S,6aR)-2,2-dimethyltetrahydrofuro[2,3-d][1,3]dioxol-5-yl)propan-1-one (73S) (2.1 g, 10.48 mmol), acetic acid (6.34 mL, 104.87 mmol) and acetic anhydride (5.39 mL, 52.43 mmol) in anhydrous $CH_2Cl_2$ (40 mL) was added concentrated $H_2SO_4$ (0.1 mL) at 0° C. After being stirred at 25° C. for 3 h, the pH of the reaction mixture was made basic by the addition of a saturated aq. $NaHCO_3$ solution (200 mL). The organic layer was separated and the aqueous phase was extracted with $CH_2C_2$ (2×200 mL). The combined organic layers were dried over $Na_2SO_4$, filtered and concentrated in vacuum. The crude product was purified by column chromatography on silica gel (100-200 mesh, 20% EtOAc in petroleum ether) to afford predominately (2S,3R,5S)-5-propionyltetrahydrofuran-2,3-diyl diacetate (74S) (1.3 g, 52%) as a colourless liquid. $C_{11}H_{16}O_6$: $^1H$ NMR (500 MHz, DMSO-$d_6$): δ 6.07 (d, J=2.0 Hz, 1H), 5.09 (t, J=3.0 Hz, 1H), 4.78 (t, J=8.3 Hz, 1H), 2.56-2.50 (m, 2H), 2.28 (dd, J=8.5, 3.5 Hz, 2H), 2.05 (s, 3H), 2.01 (s, 3H), 0.93 (t, J=7.3 Hz, 3H).

Step 3: (2R,3R,5S)-2-(2-Acetamido-6,8-dioxo-7-(prop-2-yn-1-yl)-1,6,7,8-tetrahydro-9H-purin-9-yl)-5-propionyltetrahydrofuran-3-yl acetate (68)

N-(6,8-dioxo-7-(prop-2-yn-1-yl)-6,7,8,9-tetrahydro-1H-purin-2-yl)acetamide (6) (500 mg, 2.024 mmol), (2S,3R,5S)-5-propionyltetrahydrofuran-2,3-diyl diacetate (74S) (692 mg, 2.83 mmol) and BSA (1.54 mL, 6.07 mmol) were dissolved in 1,2-dichloroethane (50 mL) and the reaction mixture was stirred at 80° C. for 30 min under argon. The reaction mixture was cooled to rt and 1,2-dichloroethane was removed by vacuum. The residue was dissolved in MeCN (50 mL) followed by addition of TMSOTf (0.561 mL, 3.03 mmol). The reaction mixture was heated at 80° C. for 16 h, cooled to room temperature and concentrated under vacuum. To the residue was added sat. aq. $NaHCO_3$ (100 mL) and extracted with EtOAc (2×200 mL). The combined EtOAc layer was washed with water (50 mL), brine (50 mL), dried over $Na_2SO_4$, filtered and concentrated under vacuum. The crude compound was purified by flash column (80% EtOAc in pet ether) to afford (2R,3R,5S)-2-(2-acetamido-6,8-dioxo-7-(prop-2-yn-1-yl)-1,6,7,8-tetrahydro-9H-purin-9-yl)-5-propionyltetrahydrofuran-3-yl acetate (68) (310 mg, 28%) as an off-white solid. $C_{19}H_{21}N_5O_7$: ES+, m/z 432.2 $[M+H]^+$.

Step 4: 2-Amino-9-((2R,3R,5S)-3-hydroxy-5-propionyltetrahydrofuran-2-yl)-7-(prop-2-yn-1-yl)-7,9-dihydro-1H-purine-6,8-dione (Compound 37) and 2-Amino-9-((2R,3R,5R)-3-hydroxy-5-propionyltetrahydrofuran-2-yl)-7-(prop-2-yn-1-yl)-7,9-dihydro-1H-purine-6,8-dione (Compound 38)

To a stirred solution of (2R,3R,5S)-2-(2-acetamido-6,8-dioxo-7-(prop-2-yn-1-yl)-1,6,7,8-tetrahydro-9H-purin-9-yl)-5-propionyltetrahydrofuran-3-yl acetate (68) (300 mg, 0.69 mmol) in methanol (10 mL) was added $K_2CO_3$ (96 mg, 0.69 mmol) at room temperature. The progress of the reaction was monitored by LC/MS. After 16 hrs. LC/MS indicated complete conversion of starting material to the product along with some epimerization at C-5. The reaction mixture was concentrated under reduced pressure to afford a solid that was applied directly to GRACE reverse phase chromatography (0.1% $HCO_2H$:MeCN) to afford a diastereomeric mixture of 2-amino-9-((2R,3R)-3-hydroxy-5-propionyltetrahydrofuran-2-yl)-7-(prop-2-yn-1-yl)-7,9-dihydro-1H-purine-6,8-dione (60 mg, 25%). This mixture was further purified by Chiral SFC-150-080 HPLC (Chiralcel OJ-H OX-H; 250×30×5µ; 80% $CO_2$, 20% MeOH; Total Flow: 90.0 g/min.; Back pressure: 100.0 bar; 30° C.; UV: 214.0 nm; Stack time: 11.0 mins; Load/injection: 10.0 mgs) to give 2-amino-9-((2R,3R,5S)-3-hydroxy-5-propionyltetrahydrofuran-2-yl)-7-(prop-2-yn-1-yl)-7,9-dihydro-1H-purine-6,8-dione (Compound 37) (15 mg) and 2-amino-9-((2R,3R,5R)-3-hydroxy-5-propionyltetrahydrofuran-2-yl)-7-(prop-2-yn-1-yl)-7,9-dihydro-1H-purine-6,8-dione (Compound 38) (16 mg), both as off-white solids. (Compound 37): $C_{15}H_{17}N_5O_5$: $^1H$ NMR (400 MHz, DMSO-$d_6$): 11.56 (bs, 1H), 6.71 (s, 2H), 5.66 (d, J=2.0 Hz, 1H), 5.56 (d, J=4.4 Hz, 1H), 4.75 (m, 1H), 4.60 (d, J=2.0 Hz, 2H), 4.53 (dd, J=9.0, 7.4 Hz, 1H), 3.19 (t, J=2.4 Hz, 1H), 2.79-2.72 (m, 1H), 2.67-2.60 (m, 1H), 2.43 (dd, J=7.2, 4.4 Hz, 1H), 2.02 (ddd, J=12.8, 7.2, 2.4 Hz, 1H), 0.87 (t, J=7.2 Hz, 3H). ES+, m/z 348.3 $[M+H]^+$. (Compound 38): $C_{15}H_{17}N_5O_5$: $^1H$ NMR (400 MHz, DMSO-$d_6$): δ 11.71 (bs, 1H), 6.65 (bs, 2H), 5.73 (d, J=2.8 Hz, 1H), 5.50 (d, J=4.0 Hz, 1H), 4.83 (s, 1H), 4.76 (t, J=7.6 Hz, 1H), 4.61 (s, 2H), 3.18 (m, 1H), 2.91 (dt, J=12.4, 7.2 Hz, 1H), 2.66 (m, 1H), 2.60 (dd, J=16.8, 7.2 Hz, 1H), 1.89 (m, 1H), 0.93 (t, J=7.2 Hz, 3H). ES+, m/z 348.3 $[M+H]^+$.

Example 34: Methyl(2S,4R,5R)-5-(2-amino-6,8-dioxo-7-(prop-2-yn-1-yl)-1,6,7,8-tetrahydro-9H-purin-9-yl)-4-hydroxytetrahydrofuran-2-carboxylate, Compound 39

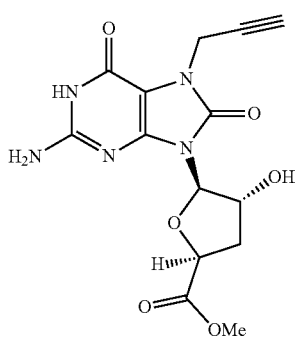 [SMILES: C#CCn1c(=O)n([C@@H]2O[C@H](C(=O)OC)C[C@H]2O)c2nc(N)[nH]c(=O)c21]

Compound 39 was prepared according to the following multi-step procedure.

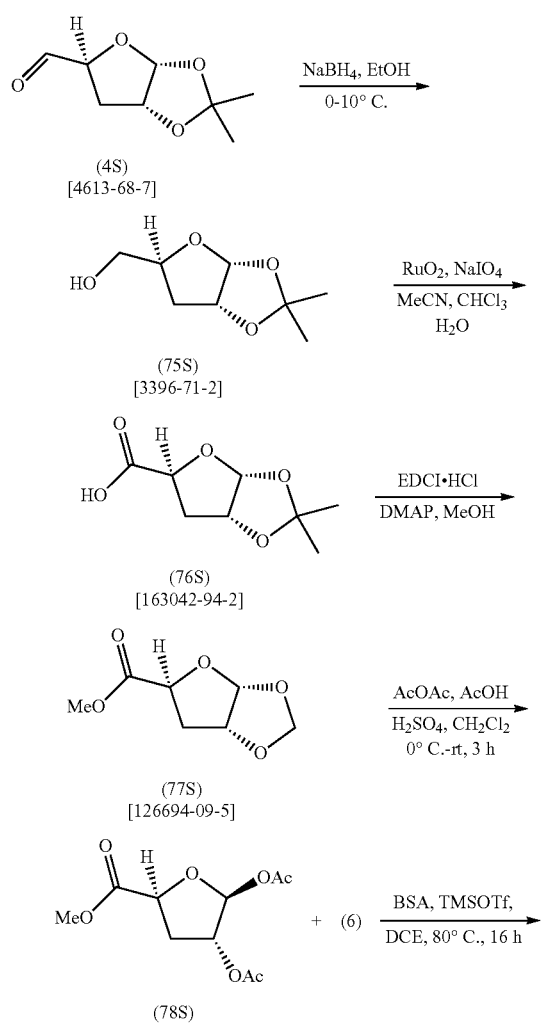

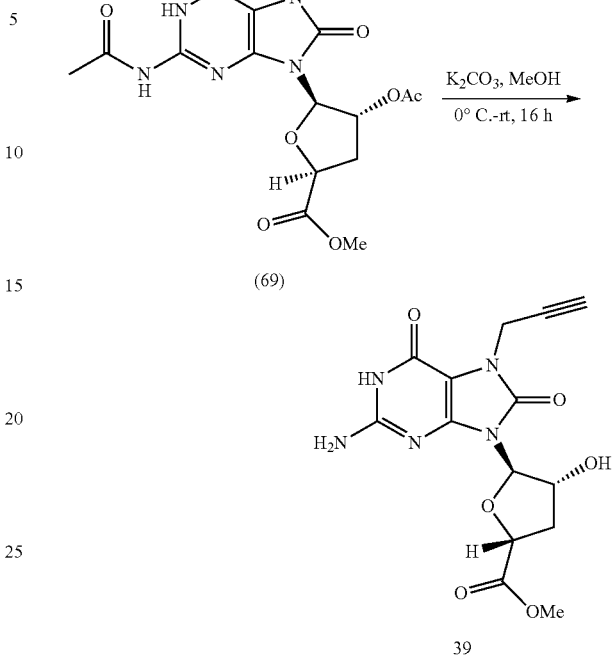

Step 1: ((3aR,5S,6aR)-2,2-Dimethyltetrahydrofuro[2,3-d][1,3]dioxol-5-yl)methanol (75S)

To a solution of (3aR,5S,6aR)-2,2-dimethyltetrahydrofuro[2,3-d][1,3]dioxole-5-carbaldehyde (4S) [4613-68-7] (20 g, 116.2 mmol) in EtOH (250 mL) was added NaBH$_4$ (4.39 g, 28.0 mmol) while maintaining the temperature between 0-5° C. The reaction mixture was warmed to 10° C. and stirred for 2 h. EtOH was removed under vacuum and the residue was diluted with water (300 mL) and extracted with CHCl$_3$ (2×300 mL). The combined organic layers were dried over Na$_2$SO$_4$, filtered, and concentrated under reduced pressure. The residue was purified by column chromatography on silica gel (100-200 mesh, 50% EtOAc in pet-ether) to give ((3aR,5S,6aR)-2,2-dimethyltetrahydrofuro[2,3-d][1,3]dioxol-5-yl)methanol (75S) [3396-71-2] (8.8 g, 43%) as a white solid. C$_8$H$_{14}$O$_4$: $^1$H NMR (400 MHz, CDCl$_3$): δ 5.83 (d, J=3.6 Hz, 1H), 4.76 (t, J=4.2 Hz, 1H), 4.35 (m, 1H), 3.90 (dd. J=12.2, 2.6 Hz, 1H). 3.57 (dd, J=12.0, 3.6 Hz, 1H), 2.01 (dd, J=13.4, 4.6 Hz, 1H), 1.88 (bs, 1H), 1.87-1.81 (m, 1H), 1.52 (s, 3H), 1.33 (s, 3H). ES+, m/z 175.1 [M+H]$^+$.

Step 2: (3aR,5S,6aR)-2,2-Dimethyltetrahydrofuro[2,3-d][1,3]dioxole-5-carboxylic acid (76S)

A mixture of ((3aR,5S,6aR)-2,2-dimethyltetrahydrofuro[2,3-d][1,3]dioxol-5-yl)methanol (75S) [3396-71-2] (3.1 g, 17.8 mmol), ruthenium oxide (228 mg), and sodium periodate (15.22 g, 213.8 mmol) in acetonitrile:chloroform:water (24:24:36 mL) was stirred vigorously for 4-6 h at room temperature. After separation of the two layers, the aqueous layer was extracted with chloroform (3×50 mL). The combined organic layers were washed with brine, dried over anhydrous Na$_2$SO$_4$, filtered and concentrated to dryness in vacuum to give (3aR,5S,6aR)-2,2-dimethyltetrahydrofuro

[2,3-d][1,3]dioxole-5-carboxylic acid (76S) [163042-94-2] (3.0 g, 89%) as a black liquid. The crude product was used in the next step without purification.

Step 3: Methyl (3aR,5S,6aR)-2,2-dimethyltetrahydrofuro[2,3-d][1,3]dioxole-5-carboxylate (77S)

A mixture of (3aR,5S,6aR)-2,2-dimethyltetrahydrofuro[2,3-d][1,3]dioxole-5-carboxylic acid (76S) [163042-94-2] (3.0 g, 18.95 mmol), EDCI·HCl (7.61 g, 39.89 mmol), and DMAP (194 mg, 1.59 mmol) in anhydrous methanol (50 mL) was stirred for 24 h at room temperature. MeOH was removed under vacuum and the residue obtained was dissolved in $CH_2Cl_2$ (100 mL) and washed with water (2×50 mL). The layers were separated and the aqueous phase was extracted with $CH_2Cl_2$ (3×30 mL). The combined organic layer were washed with brine, dried over anhydrous $NaSO_4$, filtered and concentrated to dryness. The residue was purified by column chromatography on silica gel (100-200 mesh, 20% EtOAc in pet-ether) to give methyl (3aR,5S,6aR)-2,2-dimethyltetrahydrofuro[2,3-d][1,3]dioxole-5-carboxylate (77S) [126694-09-5] (2.5 g, 78%) as a colourless liquid. $C_9H_{14}O_5$: $^1$H NMR (500 MHz, $CDCl_3$): δ 5.95 (d, J=3.5 Hz, 1H), 4.78 (t, J=4.0 Hz, 1H), 4.71 (dd, J=11.0, 5.0 Hz, 1H), 3.78 (s, 3H), 2.42 (dd, J=13.5, 5.0 Hz, 1H), 1.96 (ddd, J=14.5, 10.0, 3.5 Hz, 1H), 1.52 (s, 3H), 1.33 (s, 3H).

Step 4: (2S,3R,5S)-5-(Methoxycarbonyl)tetrahydrofuran-2,3-diyl diacetate (78S)

To a solution of methyl (3aR,5S,6aR)-2,2-dimethyltetrahydrofuro[2,3-d][1,3]dioxole-5-carboxylate (77S) [126694-09-5] (2.0 g, 9.9 mmol), acetic acid (5.66 mL, 99 mmol) and acetic anhydride (4.9 mL, 49.5 mmol) in anhydrous $CH_2Cl_2$ (30 mL) was added concentrated $H_2SO_4$ (0.2 mL) at 0° C. After being stirred at RT for 3 hours, the pH of reaction mixture was made basic by the addition of saturated aq. $NaHCO_3$ solution (100 mL). The organic layer was separated and the aqueous phase was extracted with $CH_2Cl_2$ (2×100 mL). The combined organic layers were dried over $Na_2SO_4$, filtered and concentrated in vacuum. The crude product was purified by column chromatography on silica gel (100-200 mesh, 40% EtOAc in petroleum ether) to afford 1.4 g (58%) of (2S,3R,5S)-5-(methoxycarbonyl)tetrahydrofuran-2,3-diyl diacetate (78S) as a colorless oil. $C_{10}H_{14}O_7$: $^1$H NMR (400 MHz, $CDCl_3$): δ 6.21 (s, 1H), 5.21 (d, J=4.8 Hz, 1H), 4.82 (t, J=8.2 Hz, 1H), 3.77 (s, 3H), 2.51-2.39 (m, 2H), 2.15 (s, 3H), 2.07 (s, 3H).

Step 5: Methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (69)

N-(6,8-Dioxo-7-(prop-2-yn-1-yl)-6,7,8,9-tetrahydro-1H-purin-2-yl)acetamide (6) (200.8 mg, 0.813 mmol), ((2S,3R,5S)-5-(methoxycarbonyl)tetrahydrofuran-2,3-diyl diacetate (78S) (200 mg, 0.813 mmol) and BSA (0.6 mL, 2.43 mmol) were dissolved in 1,2-dichloroethane (10 mL) and the reaction mixture was stirred at 80° C. for 30 min under argon. The reaction mixture was allowed then cooled to RT and 1,2-dichloroethane was removed under vacuum. The residue was dissolved in MeCN (20 mL) and TMSOTf (0.26 mL, 1.21 mmol) was added. The reaction mixture was heated at 80° C. for 16 h, cooled to room temperature and concentrated under vacuum. To the residue was added sat. aq. $NaHCO_3$ (50 mL) and then extracted with EtOAc (3×50 mL). The combined EtOAc layers were washed with water (30 mL), brine (30 mL), dried over anhydrous $Na_2SO_4$, filtered and concentrated under vacuum. The crude product was purified by GRACE flash chromatography (80% EtOAc in pet ether) to afford 150 mg (34.6%) of methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (69) as an brown solid. $C_{18}H_{19}N_5O_8$: H NMR (400 MHz, DMSO-$d_6$): δ 12.20 (s, 1H), 11.67 (s, 1H), 5.81 (d, J=1.2 Hz, 1H), 5.76 (t, J=3.4 Hz, 1H), 4.86 (t, J=8.2 Hz, 1H), 4.67 (d, J=2.4 Hz, 2H), 3.64 (m, 1H), 3.31 (s, 3H), 3.17 (m, 1H), 2.41 (m, 1H), 2.19 (s, 3H), 2.08 (s, 3H). ES+, m/z 434.2 [M+H]$^+$.

Step 6: Methyl (2S,4R,5R)-5-(2-amino-6,8-dioxo-7-(prop-2-yn-1-yl)-1,6,7,8-tetrahydro-9H-purin-9-yl)-4-hydroxytetrahydrofuran-2-carboxylate (Compound 39)

To a solution of methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (69) (150 mg, 0.346 mmol) in MeOH (20 mL) was added $K_2CO_3$ (47.8 mg, 0.346 mmol) at 0° C. The reaction mixture was stirred at RT for 16 h and then methanol was removed under reduced pressure at 30° C. The residue obtained was subjected directly to reverse phase prep-HPLC (using X-BRIDGE-$C_{18}$ (250*19), 5 u Mobile phase: 0.1% $HCO_2H$ in $H_2O$:MeCN; Gradient: (T % B):—0/5, 28/5, 8/40, 9/40, 9.10/98, 11/98, 14/5; Flow rate: 18 mL/min.; Diluent: MeCN+$H_2O$+THF). The pure fractions were lyophilized to afford 32 mg (30%) of methyl (2S,4R,5R)-5-(2-amino-6,8-dioxo-7-(prop-2-yn-1-yl)-1,6,7,8-tetrahydro-9H-purin-9-yl)-4-hydroxytetrahydrofuran-2-carboxylate (Compound 39) as a white solid. $C_{14}H_{15}N_5O_6$: $^1$H NMR (500 MHz, DMSO-$d_6$): δ 10.85 (brs, 1H), 6.56 (brs, 2H), 5.62 (d, J=2.0 Hz, 1H), 5.58 (d, J=4.0 Hz, 1H), 4.84 (m, 1H), 4.72 (t, J=8.0 Hz, 1H), 4.57 (d, J=2.0 Hz, 2H), 3.60 (s, 3H), 3.22 (t, J=2.3 Hz, 1H), 2.87 (m, 1H), 2.12 (ddd, J=12.8, 7.3, 2.0 Hz, 1H). ES+, m/z 350.2 [M+H]$^+$.

Example 35: (2S,4R,5R)-5-(2-Amino-6,8-dioxo-7-(prop-2-yn-1-yl)-1,6,7,8-tetrahydro-9H-purin-9-yl)-4-hydroxytetrahydrofuran-2-carboxylic acid, Compound 40

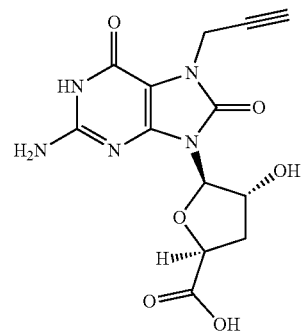 [SMILES: C#CCn1c(=O)n([C@@H]2O[C@H](C(=O)O)C[C@H]2O)c2nc(N)[nH]c(=O)c21]

Compound 40 was prepared according to the following procedure.

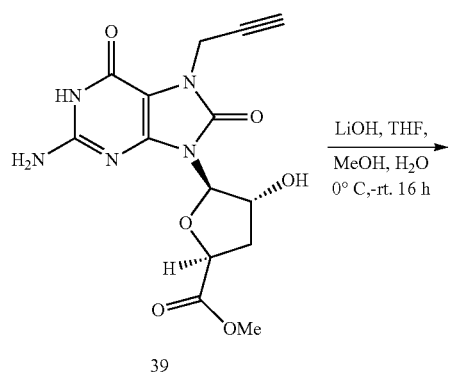

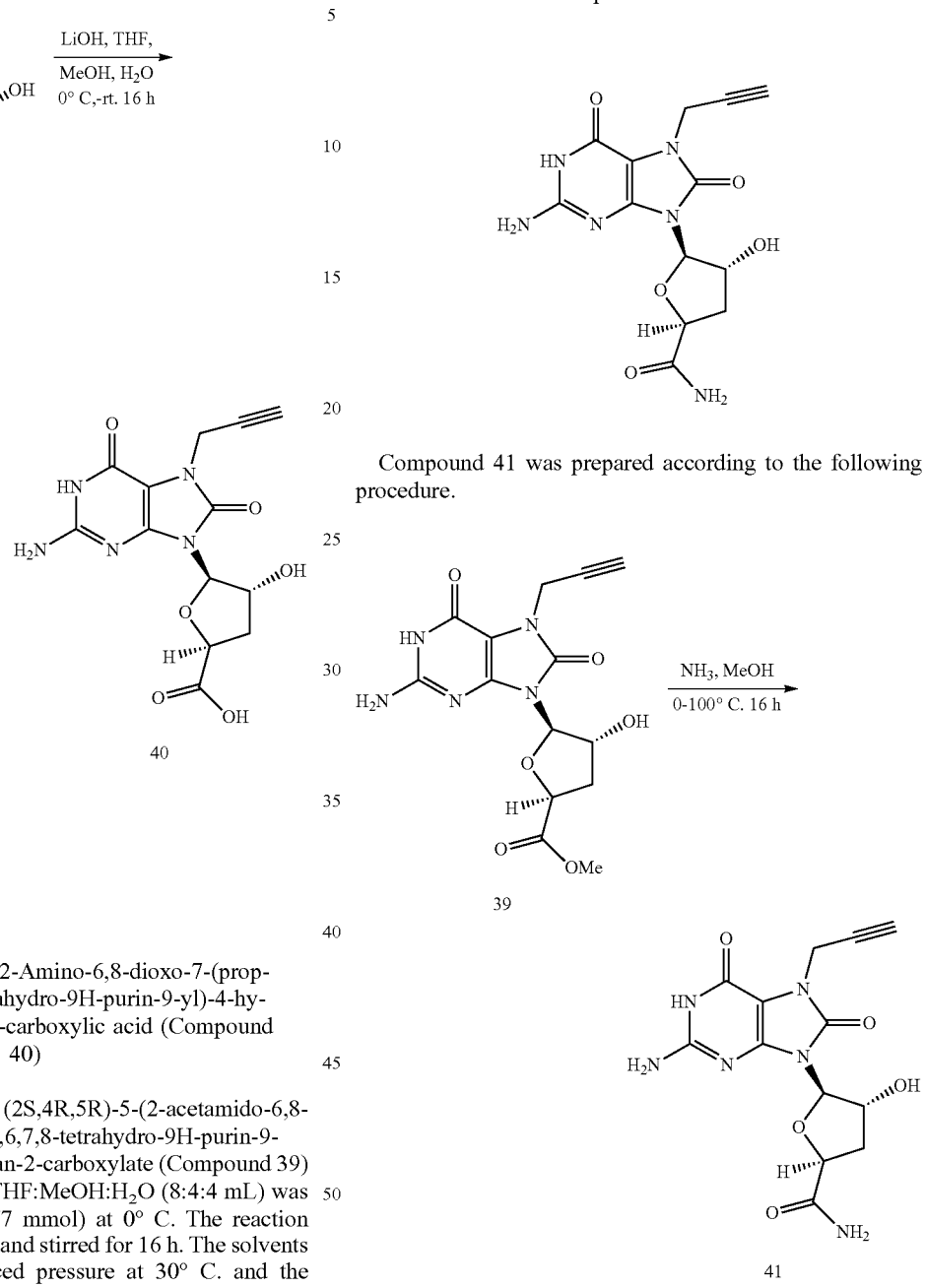

Example 36: (2S,4R,5R)-5-(2-Amino-6,8-dioxo-7-(prop-2-yn-1-yl)-1,6,7,8-tetrahydro-9H-purin-9-yl)-4-hydroxytetrahydrofuran-2-carboxamide, Compound 41

Compound 41 was prepared according to the following procedure.

Step 1: (2S,4R,5R)-5-(2-Amino-6,8-dioxo-7-(prop-2-yn-1-yl)-1,6,7,8-tetrahydro-9H-purin-9-yl)-4-hydroxytetrahydrofuran-2-carboxylic acid (Compound 40)

To a solution of methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (Compound 39) (300 mg, 0.692 mmol) in THF:MeOH:H$_2$O (8:4:4 mL) was added LiOH (116 mg, 2.77 mmol) at 0° C. The reaction mixture was warmed to RT and stirred for 16 h. The solvents was removed under reduced pressure at 30° C. and the residue was subjected directly to reverse phase prep-HPLC (using X-SELECT-C18 (250*19), 5 u Mobile phase: 0.1% HCO$_2$H in H$_2$O:MeCN Gradient: (T % B):—0/2, 2/2, 6/5, 10/30, 14/45, 14.1/98, 16/98, 16.1/2, 20/20; Flow rate: 16 mL/min; Diluent: MeOH+H$_2$O+THF). The pure fractions were subjected to lyophilization to yield 32 mg (30%) of (2S,4R,5R)-5-(2-amino-6,8-dioxo-7-(prop-2-yn-1-yl)-1,6,7,8-tetrahydro-9H-purin-9-yl)-4-hydroxytetrahydrofuran-2-carboxylic acid, (Compound 40) as an white solid. C$_{13}$H$_{13}$N$_5$O$_6$: $^1$H NMR (400 MHz, DMSO-d$_6$): 9.12 (brs, 1H), 6.71 (brs, 2H), 5.50 (d, J=2.0 Hz, 1H), 5.41 (bs, 1H), 4.80 (m, 1H), 4.58 (d, J=2.0 Hz, 2H), 4.40 (dd, J=10.0 Hz, 6.4 Hz, 1H), 3.19 (t, J=2.4 Hz, 1H), 2.67-2.59 (m, 1H), 2.00 (dd, J=12.2, 7.0 Hz, 1H). ES+, m/z 336.2 [M+H]$^+$.

Step 1: (2S,4R,5R)-5-(2-Amino-6,8-dioxo-7-(prop-2-yn-1-yl)-1,6,7,8-tetrahydro-9H-purin-9-yl)-4-hydroxytetrahydrofuran-2-carboxamide (Compound 41)

To a solution of methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (Compound 39) (100 mg, 0.23 mmol) in methanol (5 mL) was added 7 N ammonia in methanol (5 mL) at 0° C. The reaction mixture was stirred in a sealed vessel at 100° C. for 16 h. The reaction mixture was cooled and vented carefully, and the solvent was removed under reduced pressure at 30° C. The residue was subjected directly to reverse phase prep-HPLC (using LUNA OMEGA C18 (250*21.2), 5 u Mobile phase: 0.1% HCO$_2$H in H$_2$O:MeCN Gradient: (T % B):—0/2, 2/2, 8/40, 10/40, 10.1/98, 13/98, 13.1/2, 16/2; Flow rate: 16 mL/min.; Diluent: MeCN+H$_2$O+THF). The pure fractions were lyophilized to give 25 mg (32%) of (2S,4R,5R)-5-(2-amino-6,8-dioxo-7-(prop-2-yn-1-yl)-1,6,7,8-tetrahydro-9H-purin-9-yl)-4-hydroxy tetrahydrofuran-2-carboxamide (Compound 41) as an off-white solid. C$_{13}$H$_{14}$N$_6$O$_5$: $^1$H NMR indicated formation of the formic acid salt. $^1$H NMR (500 MHz, DMSO-d$_6$): δ 12.48 (brs, 1H), 8.48 (brs, 2H), 7.75 (bs, 1H), 7.18 (s, 1H), 7.09 (m, 2H), 5.60 (bs, 1H), 5.55 (d, J=5.0 Hz, 1H), 4.77 (m, 1H), 4.62 (s, 2H), 4.34 (dd, J=8.5, 6.0 Hz, 1H) 3.22 (t, J=2.2 Hz, 1H), 2.40 (m, 1H), 2.20 (m, 1H). ES+, m/z 335.22 [M+H]$^+$.

Example 37: (2S,4R,5R)-5-(2-Amino-6,8-dioxo-7-(prop-2-yn-1-yl)-1,6,7,8-tetrahydro-9H-purin-9-yl)-4-hydroxy-N-methyltetrahydrofuran-2-carboxamide, Compound 42

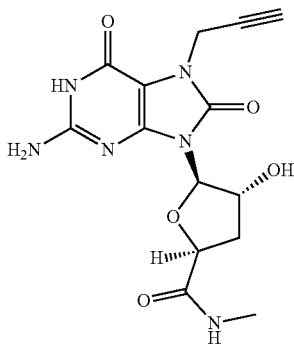 [SMILES: C#CCn1c(=O)n([C@@H]2O[C@H](C(=O)NC)C[C@H]2O)c2nc(N)[nH]c(=O)c21]

Compound 42 was prepared according to the following procedure.

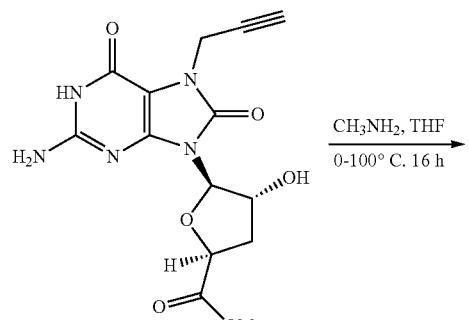

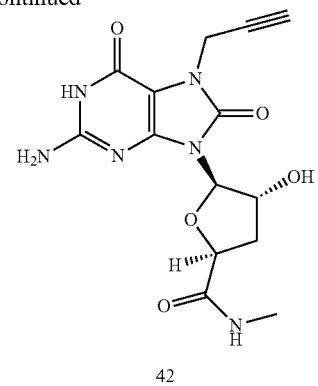

42

Step 1: (2S,4R,5R)-5-(2-Amino-6,8-dioxo-7-(prop-2-yn-1-yl)-1,6,7,8-tetrahydro-9H-purin-9-yl)-4-hydroxy-N-methyltetrahydrofuran-2-carboxamide (Compound 42)

To a solution of methyl (2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-carboxylate (Compound 39) (100 mg, 0.23 mmol) in THF (4 mL) was added methylamine in THF (2M)(3 mL) at 0° C. The reaction mixture was stirred in a sealed vessel at 100° C. for 16 h. The reaction mixture was cooled and vented carefully, and the solvent was removed under reduced pressure at 30° C. The residue was subjected directly to reverse phase GRACE flash chromatography (0.1% NH$_4$HCO$_3$ in H$_2$O:MeCN). The pure fractions were lyophilized to give 22 mg (32%) of (2S,4R,5R)-5-(2-amino-6,8-dioxo-7-(prop-2-yn-1-yl)-1,6,7,8-tetrahydro-9H-purin-9-yl)-4-hydroxy-N-methyltetrahydrofuran-2-carboxamide (Compound 42) as an off-white solid. C$_{14}$H$_{16}$N$_6$O$_5$: $^1$H NMR (500 MHz, DMSO-d$_6$): δ 11.04 (brs, 1H), 7.69 (d, J=4.5 Hz, 1H), 6.59 (s, 2H), 5.57 (dd, J=12.8, 4.3 Hz, 2H), 4.80 (m, 1H), 4.61 (d, J=1.0 Hz, 2H), 4.43 (t, J=7.8 Hz, 1H), 3.24 (t, J=2.3 Hz, 1H), 2.61 (d, J=4.5 Hz, 3H), 2.53 (m, 1H), 2.15 (m, 1H). ES+, m/z 349.0[M+H]$^+$.

Example 38: 2-Amino-9-((2R,3R,5S)-3-hydroxy-5-((S)-1-hydroxypropyl)tetrahydrofuran-2-yl)-7-(2,2,2-trifluoroethyl)-7,9-dihydro-1H-purine-6,8-dione, Compound 43

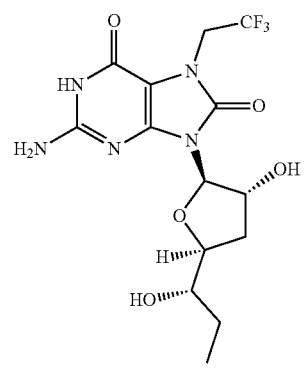 [SMILES: CC[C@H](O)[C@@H]1C[C@@H](O)[C@H](n2c(=O)n(CC(F)(F)F)c3c(=O)[nH]c(N)nc32)O1]

Compound 43 was prepared according to the following multi-step procedure.

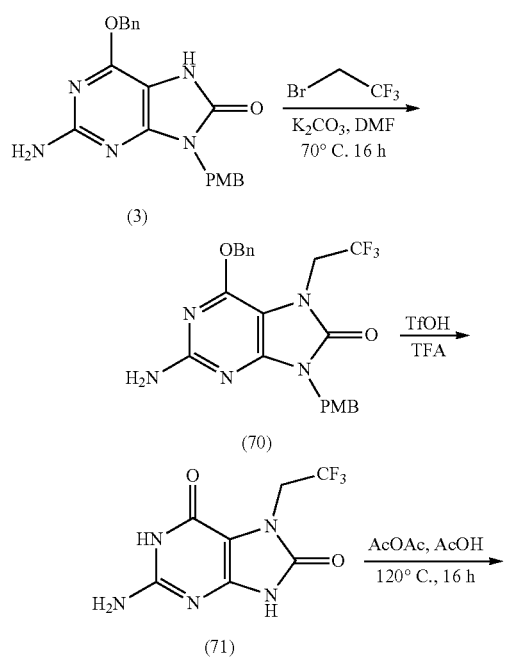

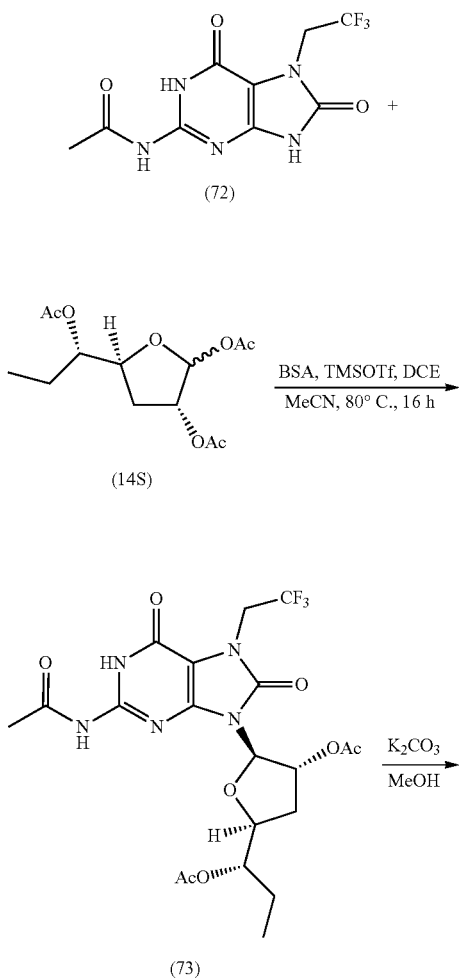

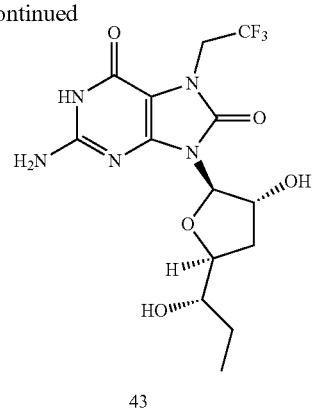

Step 1: 2-Amino-6-(benzyloxy)-9-(4-methoxybenzyl)-7-(2,2,2-trifluoroethyl)-7,9-dihydro-8H-purin-8-one (70)

2-Bromo-1,1,1-trifluoroethane (4.5 g, 27.85 mmol) was added to a suspension of 2-amino-6-(benzyloxy)-9-(4-methoxybenzyl)-7,9-dihydro-8H-purin-8-one (6) (7 g, 18.5 mmol) and $K_2CO_3$ (6.4 g, 46.41 mmol) in DMF (70 mL) at rt and stirred in sealed tube at 70° C. for 16 h. The reaction mixture was cooled to rt and ice water (500 mL) was added. The resulting precipitated solid was filtered, washed with water and diethyl ether (200 mL) and dried to afford 2-amino-6-(benzyloxy)-9-(4-methoxybenzyl)-7-(2,2,2-trifluoroethyl)-7,9-dihydro-8H-purin-8-one (70) (6.4 g, 75%) as an off white solid. $C_{22}H_{20}F_3N_5O_3$: $^1$H NMR (400 MHz, DMSO-$d_6$): δ 7.46 (d, J=7.6 Hz, 2H), 7.41-7.31 (m, 3H), 7.23 (d, J=8.4 Hz, 2H), 6.89 (d, J=8.8 Hz, 2H), 6.54 (s, 2H), 5.42 (s, 2H), 4.85 (s, 2H), 4.55 (m, 2H), 3.71 (s, 3H). ES+, m/z 460.1 [M+H]$^+$.

Step 2: 2-Amino-7-(2,2,2-trifluoroethyl)-7,9-dihydro-1H-purine-6,8-dione (71)

Trifluoromethanesulfonic acid (7.3 mL, 83.6 mmol) was added to a suspension of 2-amino-6-(benzyloxy)-9-(4-methoxybenzyl)-7-(2,2,2-trifluoroethyl)-7,9-dihydro-8H-purin-8-one (70) (6.4 g, 13.94 mmol) in TFA (6.8 mL, 83.6 mmol) at room temperature under an argon atmosphere. The reaction mixture was stirred at room temperature for 16 h under argon atmosphere at which time ice cold water was added and the pH of the mixture was made basic with a sat. NaHCO$_3$ solution. Vigorous stirring was continued and the mixture was then filtered. The solid was taken up in ethyl acetate, stirred for 30 min., filtered and dried to afford 2-amino-7-(2,2,2-trifluoroethyl)-7,9-dihydro-1H-purine-6,8-dione (71) (2.4 g, 70%) as a brown solid. $C_7H_6F_3N_5O_2$: $^1$H NMR (400 MHz, DMSO-$d_6$): δ 11.37 (s, 1H), 10.78 (s, 1H), 6.46 (s, 2H), 4.53 (m, 2H). ES+, m/z 250.0 [M+H]$^+$.

Step 3: N-(6,8-Dioxo-7-(2,2,2-trifluoroethyl)-6,7,8,9-tetrahydro-1H-purin-2-yl)acetamide (72)

Acetic anhydride (2.86 mL, 28.9 mmol) was added to a solution of 2-amino-7-(2,2,2-trifluoroethyl)-7,9-dihydro-1H-purine-6,8-dione (71) (2.4 g, 9.63 mmol) in AcOH (30 mL) at room temperature under an argon atmosphere and the resulting reaction mixture was stirred at 120° C. for 16 h. The stirred reaction mixture was cooled to 0° C. whereupon a solid formed. After being stirred for 30 minutes the product was filtered, washed with diethyl ether and dried under vacuum to afford N-(6,8-dioxo-7-(2,2,2-trifluoroethyl)-6,7,8,9-tetrahydro-1H-purin-2-yl)acetamide (72) (2.1 g, 75%) as a brown solid. $C_9H_8F_3N_5O_3$: $^1$H NMR (400 MHz, DMSO-$d_6$): δ 12.07 (s, 1H), 11.97 (s, 1H), 11.70 (s, 1H), 4.62 (q, J=8.8 Hz, 2H), 2.16 (s, 3H). ES+, m/z 292.0 [M+H]$^+$.

Step 4: (S)-1-((2S,4R,5R)-5-(2-Acetamido-6,8-dioxo-7-(2,2,2-trifluoroethyl)-1,6,7,8-tetrahydro-9H-purin-9-yl)-4-acetoxytetrahydrofuran-2-yl)propyl acetate (73)

A mixture of N-(6,8-dioxo-7-(2,2,2-trifluoroethyl)-6,7,8,9-tetrahydro-1H-purin-2-yl)acetamide (72) (400 mg, 1.37 mmol), (3R,5S)-5-((S)-1-acetoxypropyl)tetrahydrofuran-2,3-diyl diacetate (14S) (475 mg, 1.64 mmol) and BSA (1.04 mL, 4.12 mmol) dissolved in 1,2-dichloroethane (25 mL) was stirred at 80° C. for 30 min under argon. The reaction mixture was allowed to cooled to RT and 1,2-dichloroethane was removed under vacuum. The residue was dissolved in MeCN (25 mL) and TMSOTf (0.38 mL, 2.06 mmol) was added. The stirred reaction mixture was heated at 80° C. for 16 h, cooled to room temperature and concentrated under vacuum. The residue was diluted with sat. aq. NaHCO$_3$ (60 mL) and extracted with EtOAc (3×50 mL). The combined EtOAc layer was washed with water (20 mL), brine (20 mL), dried over anhydrous Na$_2$SO$_4$, filtered and concentrated under vacuum. The crude product was purified by silica-gel column chromatography (80% EtOAc in Pet ether) to afford (S)-1-((2S,4R,5R)-5-(2-acetamido-6,8-dioxo-7-(2,2,2-trifluoroethyl)-1,6,7,8-tetrahydro-9H-purin-9-yl)-4-acetoxytetrahydrofuran-2-yl)propyl acetate (73) (180 mg, 25%) as a light yellow solid. $C_{20}H_{24}F_3N_5O_8$: $^1$H NMR (500 MHz, CDCl3): δ 9.00 (s, 1H), 5.83 (d, J=2.5 Hz, 1H), 5.68 (m, 1H), 5.19 (m, 1H), 4.66 (m, 8.8 2H), 4.35 (m, 1H), 2.55 (m, 1H), 2.28 (s, 3H), 2.12 (m, 2H), 2.10 (s, 3H), 2.06 (s, 3H), 1.56-1.69 (m, 2H), 0.93 (t, J=7.5 Hz, 3H). ES+, m/z 520.1 [M+H]$^+$.

Step 5: 2-Amino-9-((2R,3R,5S)-3-hydroxy-5-((S)-1-hydroxypropyl)tetrahydrofuran-2-yl)-7-(2,2,2-trifluoroethyl)-7,9-dihydro-1H-purine-6,8-dione (Compound 43)

To a solution of (S)-1-((2S,4R,5R)-5-(2-acetamido-6,8-dioxo-7-(2,2,2-trifluoroethyl)-1,6,7,8-tetrahydro-9H-purin-9-yl)-4-acetoxytetrahydrofuran-2-yl)propyl acetate (73) (180 mg, 0.34 mmol) in methanol (10 mL) at rt was added K$_2$CO$_3$ (71.7 mg, 0.52 mmol). The progress of the reaction was followed by LC/MS. After the reaction mixture was stirred at room temperature for 16 h. it was concentrated under reduced pressure, and the crude product was purified by Prep-HPLC: Column; KROMOSIL-C18 (150*25 MM), 7 u Mobile phase: 10 mM ammonium bicarbonate in H$_2$O: MeCN; Gradient: (T % B) 0/5, 2/5, 8/40, 9/40, 9.1/98, 14/98, 14.1/5, 16/5; Flow Rate: 22 mL/min. to afford 2-amino-9-((2R,3R,5S)-3-hydroxy-5-((S)-1-hydroxypropyl)tetrahydrofuran-2-yl)-7-(2,2,2-trifluoroethyl)-7,9-dihydro-1H-purine-6,8-dione (Compound 43) (55 mg, 40.4%) as an off-white solid. $C_{14}H_{18}F_3N_5O_5$: $^1$H NMR (400 MHz, DMSO-$d_6$): δ 11.09 (s, 1H), 6.62 (s, 2H), 5.52 (d, J=2.8 Hz, 1H), 5.40 (d, J=4.8 Hz, 1H), 4.73 (m, 1H), 4.61 (q, J=8.8 Hz, 2H), 4.53 (d, J=6.8 Hz, 1H), 4.00 (dt, J=8.8, 6.0 Hz, 1H), 3.27 (m, 1H), 2.42-2.35 (m, 1H), 1.76 (ddd, J=12.4, 6.4, 2.8 Hz, 1H), 1.43-1.37 (m, 1H), 1.30-1.22 (m, 1H), 0.87 (t J=7.2 Hz, 3H). ES+, m/z 394.1 [M+H]$^+$.

Example 39: 2-Amino-9-((2R,3S,4R,5R)-4-fluoro-3-hydroxy-5-((S)-1-hydroxypropyl)tetrahydrofuran-2-yl)-7-(2,2,2-trifluoroethyl)-7,9-dihydro-1H-purine-6,8-dione, Compound 44

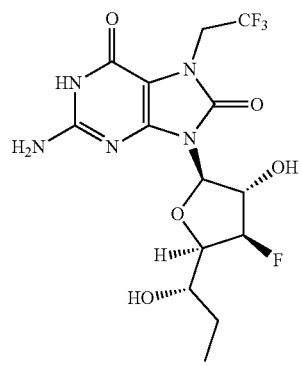 [SMILES: CC[C@H](O)[C@H]1O[C@@H](n2c(=O)n(CC(F)(F)F)c3c(=O)[nH]c(N)nc32)[C@H](O)[C@H]1F]

Compound 44 was prepared according to the following two step procedure.

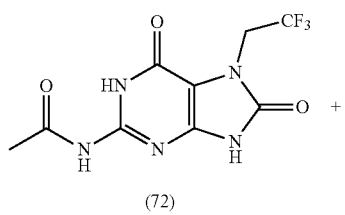
(72)

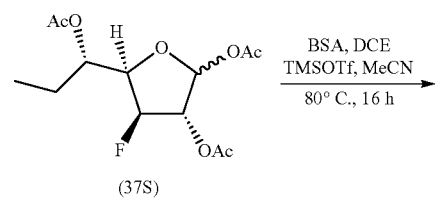
(37S)

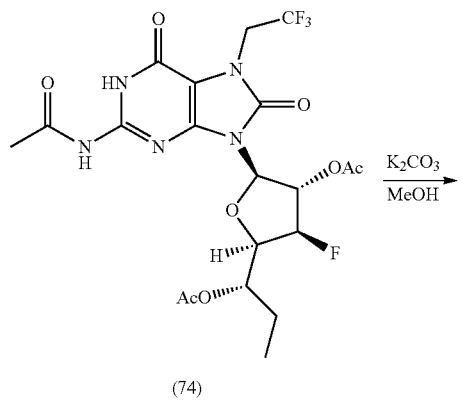
(74)

-continued

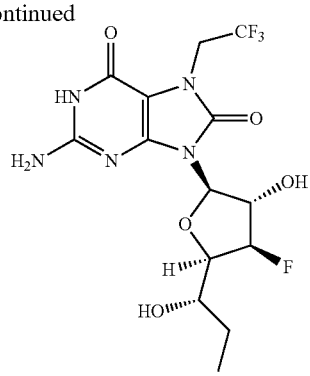

44

Step 1: (S)-1-((2R,3S,4S,5R)-5-(2-Acetamido-6,8-dioxo-7-(2,2,2-trifluoroethyl)-1,6,7,8-tetrahydro-9H-purin-9-yl)-4-acetoxy-3-fluorotetrahydrofuran-2-yl) propyl acetate (74)

To N-(6,8-dioxo-7-(2,2,2-trifluoroethyl)-6,7,8,9-tetrahydro-1H-purin-2-yl)acetamide (72) (400 mg, 1.37 mmol), (3S,4S,5R)-5-((S)-1-acetoxypropyl)-4-fluorotetrahydrofuran-2,3-diyl diacetate (37S) (504.7 mg, 1.64 mmol) in 1,2-dichloroethane (25 mL), was added BSA (1.04 mL, 4.12 mmol). The reaction mixture was stirred at 80° C. for 30 min under argon, allowed to cool to RT and 1,2-dichloroethane was removed under vacuum. The residue was dissolved in MeCN (25 mL) and TMSOTf (0.38 mL, 2.06 mmol) was added. The reaction mixture was heated at 80° C. for 16 h, cooled to room temperature and concentrated under vacuum. To the residue was added sat. aq. NaHCO$_3$ (60 mL) and the mixture was extracted with EtOAc (3×30 mL). The combined EtOAc layer was washed with water (25 mL), brine (25 mL), dried over anhydrous Na$_2$SO$_4$, filtered and concentrated under vacuum. The crude product was purified by column chromatography on silica gel (80% EtOAc in Pet ether) to afford (S)-1-((2R,3S,4S,5R)-5-(2-acetamido-6,8-dioxo-7-(2,2,2-trifluoroethyl)-1,6,7,8-tetrahydro-9H-purin-9-yl)-4-acetoxy-3-fluorotetrahydrofuran-2-yl)propyl acetate (74) (225 mg, 30.4%) as a brown solid. C$_{20}$H$_{23}$F$_4$N$_5$O$_8$: $^1$H NMR (400 MHz, CDCl$_3$): δ 9.50 (s, 1H), 5.84 (m, 2H), 5.72 (m, 1H), 5.22 (m, 1H), 5.00-5.14 (m, 1H), 4.68 (m, 1H), 4.26 (m, 1H), 2.30 (s, 3H), 2.15 (s, 3H), 2.10 (s, 3H), 2.02 (m, 1H), 1.68-1.78 (m, 2H), 0.98 (t, J=7.4 Hz, 3H). ES+, m/z 538.1 [M+H]$^+$.

Step 2: 2-Amino-9-((2R,3S,4R,5R)-4-fluoro-3-hydroxy-5-((S)-1-hydroxypropyl)tetrahydrofuran-2-yl)-7-(2,2,2-trifluoroethyl)-7,9-dihydro-1H-purine-6,8-dione (Compound 44)

To (S)-1-((2R,3S,4S,5R)-5-(2-acetamido-6,8-dioxo-7-(2,2,2-trifluoroethyl)-1,6,7,8-tetrahydro-9H-purin-9-yl)-4-acetoxy-3-fluorotetrahydrofuran-2-yl)propyl acetate (74) (225 mg, 0.41 mmol) in methanol (10 mL) was added K$_2$CO$_3$ (86.7 mg, 1.22 mmol) at rt. The progress of the reaction was followed be LC/MS. After the mixture was stirred at room temperature for about 16 h. it was concentrated under reduced the vacuum to afford a thick paste. The crude product was purified by GRACE reverse phase chromatography (0.1% ammonium bicarbonate:MeCN) to afford 2-amino-9-((2R,3S,4R,5R)-4-fluoro-3-hydroxy-5-((S)-1-hydroxypropyl)tetrahydrofuran-2-yl)-7-(2,2,2-trifluoroethyl)-7,9-dihydro-1H-purine-6,8-dione (Compound 44) (95 mg, 55%) as an off-white solid. C$_{14}$H$_{17}$F$_4$N$_5$O$_5$: $^1$H NMR (400 MHz, DMSO-d$_6$, D$_2$O): δ 5.43 (d, J=7.2 Hz, 1H), 5.27 (ddd, J=34.4, 7.2, 4.4 Hz, 1H), 5.06 (ddd, J=54.2, 6.0, 4.6 Hz, 1H), 4.70 (q, J=9.2 Hz, 2H), 3.96 (ddd, J=15.6, 6.0, 4.8 Hz, 1H), 3.44 (m, 1H), 1.46-1.35 (m, 2H), 0.90 (t, J=7.4 Hz, 3H). ES+, m/z 412.1 [M+H]$^+$.

Example 40: 2-Amino-9-((2R,3R,5S)-3-hydroxy-5-((R)-1-hydroxy-2-(methylthio)ethyl)tetrahydrofuran-2-yl)-7-(prop-2-yn-1-yl)-7,9-dihydro-1H-purine-6,8-dione, Compound 45

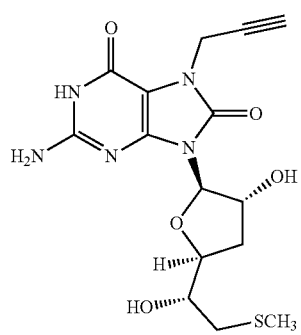 [SMILES: C#CCn1c(=O)n([C@@H]2O[C@H]([C@@H](O)CSC)C[C@H]2O)c2nc(N)[nH]c(=O)c21]

Compound 45 was prepared according to the following multi-step procedure.

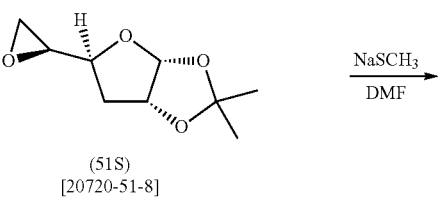

(51S)
[20720-51-8]

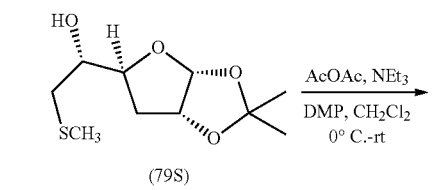

(79S)

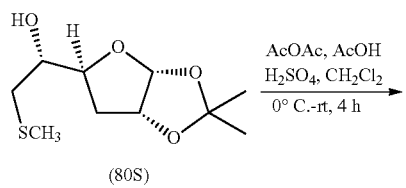

(80S)

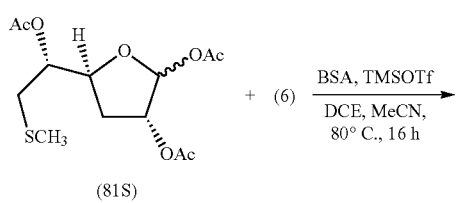

(81S)

-continued

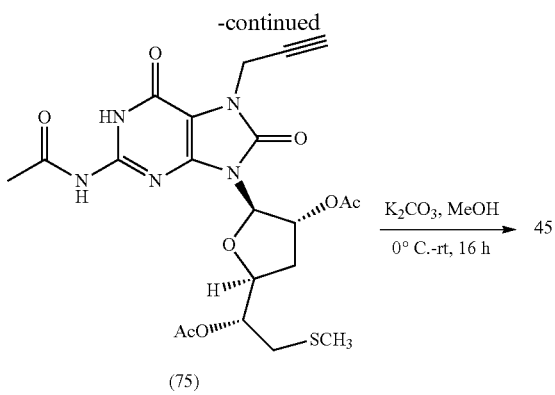

(75)

Step 1: (R)-1-((3aR,5S,6aR)-2,2-Dimethyltetrahydrofuro[2,3-d][1,3]dioxol-5-yl)-2-(methylthio)ethan-1-ol (79S)

To a stirred solution of (3aR,5S,6aR)-2,2-dimethyl-5-((S)-oxiran-2-yl)tetrahydrofuro[2,3-d][1,3]dioxole (51S) (2.0 g, 10.75 mmol) in DMF (20 mL, 10 vol) was added sodium methanethiolate (1.5 g, 21.50 mmol) at 0° C. The reaction was monitored by TLC. After being stirred at 25° C. for 2 h the reaction mixture was poured into ice cold water (200 ml) and the aqueous phase was extracted with EtOAc (2×100 mL). The combined organic layers were dried over anhydrous $Na_2SO_4$, filtered and concentrated in vacuum. The crude product was purified by column chromatography over silica gel (100-200 mesh, 25% EtOAc in petroleum ether) to afford (R)-1-((3aR,5S,6aR)-2,2-dimethyltetrahydrofuro[2,3-d][1,3]dioxol-5-yl)-2-(methylthio)ethan-1-ol (79S) (1.6 g, 64%) as a viscous oil. $C_{10}H_{18}O_4S$: $^1$H NMR (400 MHz, DMSO-$d_6$): δ 5.72 (d, J=3.6 Hz, 1H), 4.91 (d, J=6.4 Hz, 1H), 4.71 (t, J=4.2 Hz, 1H), 4.16 (dt, J=10.4, 4.2 Hz, 1H), 3.51 (m, 1H), 2.58-2.50 (m, 2H), 2.08 (s, 3H), 1.86 (m, 1H), 1.79-1.74 (m, 1H), 1.38 (s, 3H), 1.23 (s, 3H).

Step 2: (R)-1-((3aR,5S,6aR)-2,2-Dimethyltetrahydrofuro[2,3-d][1,3]dioxol-5-yl)-2-(methylthio)ethyl acetate (80S)

To a stirred solution of (R)-1-((3aR,5S,6aR)-2,2-dimethyltetrahydrofuro[2,3-d][1,3]dioxol-5-yl)-2-(methylthio)ethan-1-ol (79S) (1.3 g, 5.55 mmol), TEA (2.4 mL, 16.65 mmol) and DMAP (0.135 g, 1.11 mmol) in anhydrous $CH_2Cl_2$ (26 mL) was added acetic anhydride (1.13 mL, 11.11 mmol). The reaction mixture was stirred at 25° C. for 16 h, poured into water (60 mL) and the organic layer was separated. The aqueous phase was extracted with $CH_2Cl_2$ (2×60 mL). The combined organic layers were dried over anhydrous $Na_2SO_4$, filtered and concentrated under vacuum. The crude product was purified by column chromatography on silica gel (100-200 mesh, 20% EtOAc in petroleum ether) to afford (R)-1-((3aR,5S,6aR)-2,2-dimethyltetrahydrofuro[2,3-d][1,3]dioxol-5-yl)-2-(methylthio)ethyl acetate (80S) (1.2 g, 78%) as a viscous oil. $C_{12}H_{20}O_5S$: $^1$H NMR (400 MHz, $CDCl_3$): δ 5.82 (d, J=3.6 Hz 1H), 5.05 (ddd, J=7.2, 6.2, 3.8 Hz, 1H), 4.74 (t, J=4.2 Hz, 1H), 4.49 (dt, J=10.8, 4.2 Hz, 1H), 2.76 (ddd, J=14.0, 7.6, 6.0 Hz, 2H), 2.15 (s, 3H), 2.12 (s, 3H), 2.06 (dd, J=13.2, 4.4 Hz, 1H), 1.68-1.61 (m, 1H), 1.52 (s, 3H), 1.32 (s, 3H).

Step 3: (3R,5S)-5-((R)-1-Acetoxy-2-(methylthio) ethyl)tetrahydrofuran-2,3-diyl diacetate (81S)

To a solution of (R)-1-((3aR,5S,6aR)-2,2-dimethyltetrahydrofuro[2,3-d][1,3]dioxol-5-yl)-2-(methylthio)ethyl acetate (80S) (1.2 g, 4.34 mmol), acetic acid (1.57 mL, 26.086 mmol) and acetic anhydride (2.68 mL, 26.08 mmol) in anhydrous $CH_2Cl_2$ (24 mL) was added concentrated $H_2SO_4$ (0.12 mL) at 0° C. The reaction mixture was stirred at 25° C. for 4 h, and then the pH was made basic by the addition of saturated aq·$NaHCO_3$ solution (200 mL). The organic layer was separated and the aqueous phase was extracted with $CH_2Cl_2$ (2×200 mL). The combined organic layers were dried over $Na_2SO_4$, filtered and concentrated in vacuum. The crude product was purified by column chromatography on silica gel (100-200 mesh, 20% EtOAc in petroleum ether) to afford (3R,5S)-5-((R)-1-acetoxy-2-(methylthio)ethyl)tetrahydrofuran-2,3-diyl diacetate (81S) (600 mg, 43%) as a viscous oil. $C_{13}H_{20}O_7S$: $^1$H NMR (400 MHz, $CDCl_3$): δ 6.12 (s, 1H), 5.18 (d, J=4.4 Hz, 1H), 5.02 (m, 1H), 4.61 (m, 1H), 2.75-2.68 (m, 2H), 2.15 (s, 3H), 2.12 (s, 3H), 2.10 (s, 3H), 2.09 (s, 3H), 2.05 (m, 2H).

Step 4: (R)-1-((2S,4R,5R)-5-(2-Acetamido-6,8-dioxo-7-(prop-2-yn-1-yl)-1,6,7,8-tetrahydro-9H-purin-9-yl)-4-acetoxytetrahydrofuran-2-yl)-2-(methylthio) ethyl acetate (75)

N-(6,8-dioxo-7-(prop-2-yn-1-yl)-6,7,8,9-tetrahydro-1H-purin-2-yl)acetamide (6) (350 mg, 1.417 mmol), (3R,5S)-5-((R)-1-acetoxy-2-(methylthio)ethyl)tetrahydrofuran-2,3-diyl diacetate (81S) (544 mg, 1.700 mmol) and BSA (1.078 mL, 4.251 mmol) were dissolved in 1,2-dichloroethane (25 mL) and the reaction mixture was stirred at 80° C. for 30 min under argon. The reaction mixture was cooled to RT and 1,2-dichloroethane was evaporated under vacuum. The residue was dissolved in MeCN (25 mL) followed by the addition of TMSOTf (0.393 mL, 2.125 mmol). The reaction mixture was heated at 80° C. for 16 h, cooled to room temperature and concentrated under vacuum. To the residue was added sat. aq. $NaHCO_3$ (50 mL) and extracted with EtOAc (3×60 mL). The combined EtOAc layer was washed with water (50 mL), brine (40 mL), dried over anhydrous $Na_2SO_4$, filtered and concentrated under vacuum. The crude product was purified by flash column chromatography (90% EtOAc in Pet ether) to afford (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-(methylthio) ethyl acetate (75) (180 mg, 25%) as an off-white solid. $C_{21}H_{25}N_5O_8S$: $^1$H NMR (400 MHz, DMSO-$d_6$): δ 12.18 (s, 1H), 11.64 (s, 1H), 5.69 (d, J=1.6 Hz, 1H), 5.67 (d, J=4.0 Hz, 1H), 5.04 (m, 1H), 4.67 (d, J=2.4 Hz, 2H), 4.38 (m, 1H), 3.29 (t, J=2.4 Hz, 2H), 2.75 (m, 2H), 2.64 (dd, J=14.0, 8.4 Hz, 1H), 2.19 (s, 3H), 2.10 (s, 3H), 2.07 (s, 3H), 1.91 (s, 3H). ES+, m/z 508.1 [M+H]$^+$.

Step 5: 2-Amino-9-((2R,3R,5S)-3-hydroxy-5-((R)-1-hydroxy-2-(methylthio)ethyl)tetrahydrofuran-2-yl)-7-(prop-2-yn-1-yl)-7,9-dihydro-1H-purine-6,8-dione, (Compound 45)

To a solution of (R)-1-((2S,4R,5R)-5-(2-acetamido-6,8-dioxo-7-(prop-2-yn-1-yl)-1,6,7,8-tetrahydro-9H-purin-9-yl)-4-acetoxytetrahydrofuran-2-yl)-2-(methylthio)ethyl acetate (75) (160 mg, 0.315 mmol) in methanol (10 mL) at room temperature was added $K_2CO_3$ (87 mg, 0.631 mmol). The reaction was monitored by LC/MS and after stirring for ~16 h the mixture was concentrated under vacuum to afford a thick pastey solid. The crude product was purified by GRACE reverse phase chromatography (0.1% $HCO_2H$: MeCN) to afford 2-amino-9-((2R,3R,5S)-3-hydroxy-5-((R)-1-hydroxy-2-(methylthio)ethyl)tetrahydrofuran-2-yl)-7-

(prop-2-yn-1-yl)-7,9-dihydro-1H-purine-6,8-dione (Compound 45) (55 mg, 45%) as an off-white solid. $C_{15}H_{19}N_5O_5S$: $^1$H NMR (400 MHz, DMSO-$d_6$): δ 10.97 (s, 1H), 6.53 (s, 2H), 5.52 (d, J=3.2 Hz, 1H), 5.43 (d, J=4.4 Hz, 1H), 4.95 (d, J=7.2 Hz, 1H), 4.75 (m, 1H), 4.59 (d, J=2.4 Hz, 2H), 4.19 (m, 1H), 3.57 (m, 1H), 3.23 (t, J=2.4 Hz, 1H), 2.56 (dd, J=13.2, 4.8 Hz, 1H), 2.46-2.40 (m, 2H), 2.06 (s, 3H), 1.83 (m, 1H). ES+, m/z 382.2 [M+H]$^+$.

Example 41: 2-Amino-9-((2R,3S,4R,5R)-4-fluoro-3-hydroxy-5-((S)-1-hydroxypropyl)tetrahydrofuran-2-yl)-7-(2-(methylthio)ethyl)-7,9-dihydro-1H-purine-6,8-dione, Compound 46

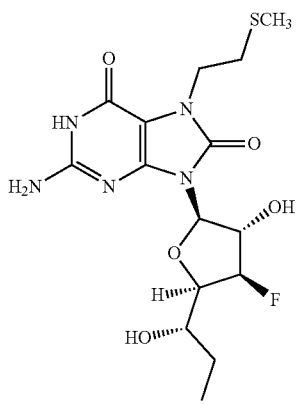 [SMILES: CC[C@H](O)[C@H]1O[C@@H](n2c(=O)n(CCSC)c3c(=O)[nH]c(N)nc32)[C@H](O)[C@H]1F]

Compound 46 was prepared according to the following two step procedure.

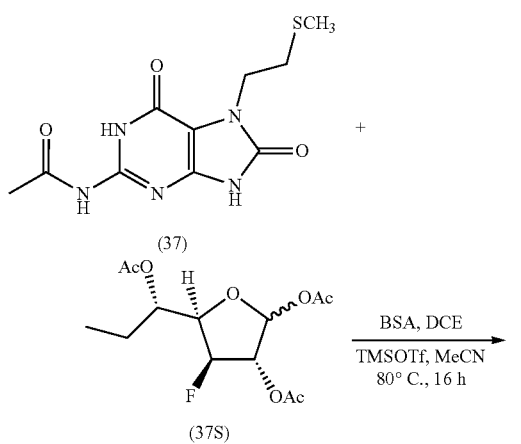

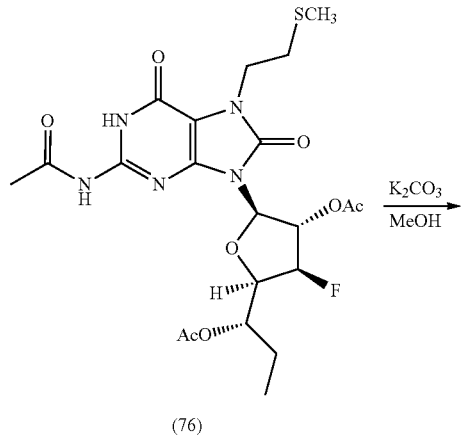

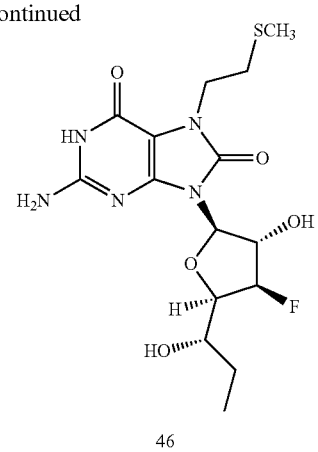

46

Step 1: (S)-1-((2R,3S,4S,5R)-5-(2-Acetamido-7-(2-(methylthio)ethyl)-6,8-dioxo-1,6,7,8-tetrahydro-9H-purin-9-yl)-4-acetoxy-3-fluorotetrahydrofuran-2-yl) propyl acetate (76)

To N-(7-(2-(methylthio)ethyl)-6,8-dioxo-6,7,8,9-tetrahydro-1H-purin-2-yl)acetamide (37) (400 mg, 1.41 mmol) and (3S,4S,5R)-5-((S)-1-acetoxypropyl)-4-fluorotetrahydrofuran-2,3-diyl diacetate (37S) (519 mg, 1.69 mmol) in 1,2-dichloroethane (25 mL) was added BSA (1.07 mL, 4.24 mmol). The reaction mixture was stirred at 80° C. for 30 min under argon, cooled to RT and 1,2-dichloroethane was removed under vacuum. The residue was taken up in MeCN (30 mL) and TMSOTf (0.39 mL, 2.12 mmol) was added. The reaction mixture was heated at 80° C. for 16 h, cooled to room temperature and concentrated under vacuum. To the residue was added sat. aq. NaHCO$_3$ (60 mL) and extracted with EtOAc (3×60 mL). The combined EtOAc layer was washed with water (40 mL), brine (30 mL), dried over anhydrous Na$_2$SO$_4$, filtered and concentrated under vacuum. The crude product was purified by silica gel column chromatography (80% EtOAc in petroleum ether) to afford (S)-1-((2R,3S,4S,5R)-5-(2-acetamido-7-(2-(methylthio)ethyl)-6,8-dioxo-1,6,7,8-tetrahydro-9H-purin-9-yl)-4-acetoxy-3-fluorotetrahydrofuran-2-yl)propyl acetate (76) (200 mg, 27%) as light yellow solid. $C_{21}H_{28}FN_5O_8S$: ES–, m/z 528.1 [M−H]$^-$.

Step 6: 2-Amino-9-((2R,3S,4R,5R)-4-fluoro-3-hydroxy-5-((S)-1-hydroxypropyl)tetrahydrofuran-2-yl)-7-(2-(methylthio)ethyl)-7,9-dihydro-1H-purine-6,8-dione (Compound 46)

To a stirred solution of (S)-1-((2R,3S,4S,5R)-5-(2-acetamido-7-(2-(methylthio)ethyl)-6,8-dioxo-1,6,7,8-tetrahydro-9H-purin-9-yl)-4-acetoxy-3-fluorotetrahydrofuran-2-yl)propyl acetate (76) (200 mg, 0.37 mmol) in methanol (10 mL), was added K$_2$CO$_3$ (78.2 mg, 0.56 mmol). The reaction mixture was stirred at room temperature for 16 h and concentrated under vacuum to afford a thick paste. The crude product was purified by Prep-HPLC Column: LUNA OMEGA C18(250*21.2), 5 u Mobile phase: 10 mM ammonium bicarbonate in H$_2$O:ACN gradient: (T % B): 0/10, 8/55, 10/55, 10.1/98, 13/98, 13.1/10, 16/10. Flow Rate 17 mL/min. Diluent: MeCN+H$_2$O+THF). Lyophilization of the pure fractions afforded 2-amino-9-((2R,3S,4R,5R)-4-fluoro-3-hydroxy-5-((S)-1-hydroxypropyl)tetrahydrofuran-2-yl)-7-

(2-(methylthio)ethyl)-7,9-dihydro-1H-purine-6,8-dione (Compound 46) (45 mg, 29%) as an off-white solid. $C_{15}H_{22}FN_5O_5S$: $^1$H NMR (400 MHz, DMSO-$d_6$): δ 11.05 (s, 1H), 6.57 (s, 2H), 5.91 (d, J=5.2 Hz, 1H), 5.38-5.31 (m, 2H), 5.05-4.90 (m, 1H), 4.85 (d, J=7.2 Hz, 1H), 3.97 (t, J=6.8 Hz, 2H) 3.81 (dt, J=22.8, 5.7 Hz, 1H) 3.53 (m, 1H), 2.79 (t, J=6.8 Hz, 2H), 2.10 (s, 3H), 1.48 (m, 1H), 1.33 (m, 1H), 0.91 (t, J=7.4 Hz, 3H). ES+, m/z 404.4 [M+H]$^+$.

Example 42: 2-Amino-9-((2R,3S,4R,5R)-4-fluoro-3-hydroxy-5-((S)-1-hydroxypropyl)tetrahydrofuran-2-yl)-6-methoxy-7-propyl-7,9-dihydro-8H-purin-8-one, Compound 47

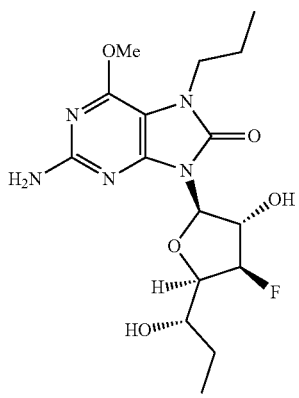 [SMILES: CCCn1c(=O)n([C@@H]2O[C@H]([C@@H](O)CC)[C@H](F)[C@H]2O)c2nc(N)nc(OC)c21]

Compound 47 was prepared according to the following multi-step procedure.

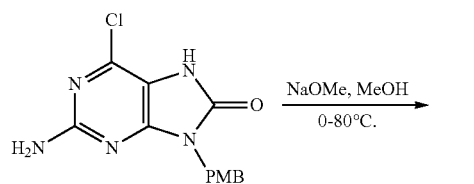

(2)

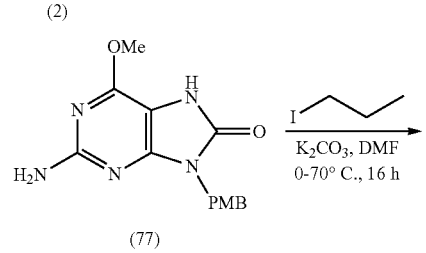

(77)

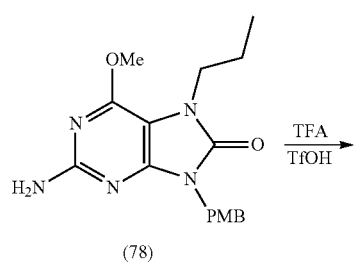

(78)

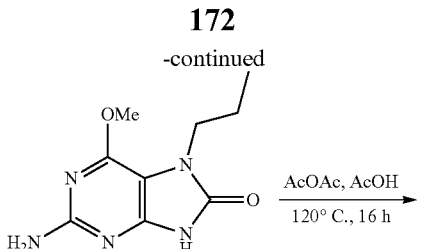

(79)

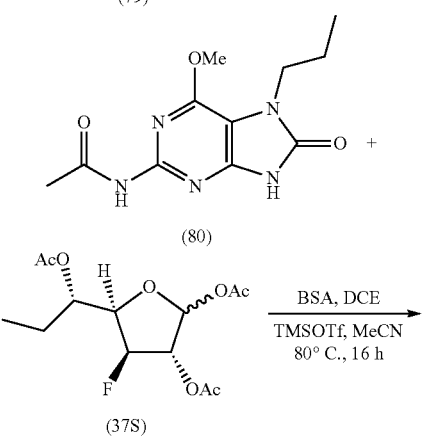

(80)

(37S)

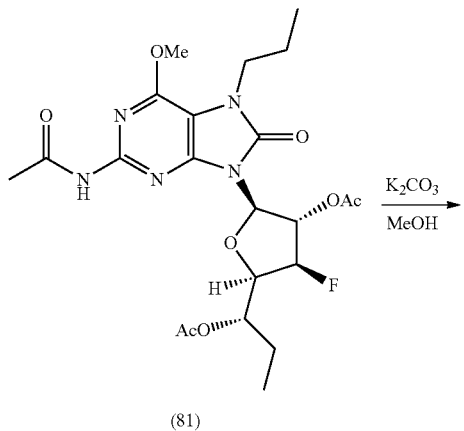

(81)

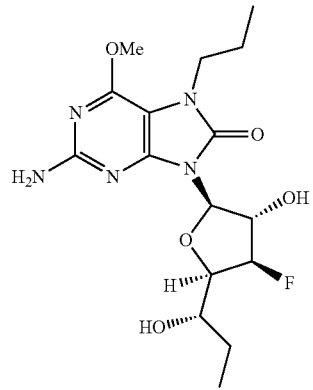

47

Step 1: 2-Amino-6-methoxy-9-(4-methoxybenzyl)-7,9-dihydro-8H-purin-8-one (77)

A 30% sodium methoxide solution in MeOH (5.724 mL, 31.8 mmol) was added to a solution of 2-amino-6-chloro-9-(4-methoxybenzyl)-7,9-dihydro-8H-purin-8-one (2) (3 g, 7.95 mmol) in MeOH (30 mL) at 0° C. The reaction mixture was warmed to 80° C. and stirred for 16 h. The mixture was then concentrated and diluted with water (200 mL) and extracted with EtOAc (4×300 mL). The combined organic layer was washed with water (100 mL), brine (100 mL), dried over $Na_2SO_4$, filtered and concentrated under reduced pressure, to afford 2-amino-6-methoxy-9-(4-methoxybenzyl)-7,9-dihydro-8H-purin-8-one (77) (2.5 g, 50%) as an off-white solid. The crude compound was used in the next step reaction without further purification. $C_{14}H_{15}N_5O_3$: $^1$H NMR (500 MHz, DMSO-$d_6$): δ 10.79 (brs, 1H), 7.20 (d, J=8.5 Hz, 2H), 6.87 (d, J=8.5 Hz, 2H), 6.25 (s, 2H), 4.78 (s, 2H), 3.87 (s, 3H), 3.71 (s, 3H). ES+, m/z 302.1 [M+H]$^+$.

Step 2: 2-Amino-6-methoxy-9-(4-methoxybenzyl)-7-propyl-7,9-dihydro-8H-purin-8-one (78)

1-Iodopropane (1.21 mL, 12.43 mmol) was added to a suspension of 2-amino-6-methoxy-9-(4-methoxybenzyl)-7,9-dihydro-8H-purin-8-one (77) (2.5 g, 8.305 mmol) and $K_2CO_3$ (2.5 g, 18.27 mmol) in DMF (25 mL) at 0° C. and stirred at 70° C. for 16 h. To the reaction mixture was added ice water (120 mL) followed by diethyl ether (50 mL) with stirring for 15 min. The precipitate that formed was collected by filtration, washed with water and dried to afford 2-amino-6-methoxy-9-(4-methoxybenzyl)-7-propyl-7,9-dihydro-8H-purin-8-one (78) (2.2 g, 78%) as an off-white solid and used as is in the next step. $C_{17}H_{21}N_5O_3$: $^1$H NMR (400 MHz, DMSO-$d_6$): δ 7.19 (d, J=8.8 Hz, 2H), 6.87 (d, J=8.8 Hz, 2H), 6.34 (s, 2H), 4.81 (s, 2H), 3.91 (s, 3H), 3.73-3.68 (m, 2H), 3.71 (s, 3H), 1.61 (m, 2H), 0.81 (t, J=7.4 Hz, 3H). ES+, m/z 344.2 [M+H]$^+$.

Step 3: 2-Amino-6-methoxy-7-propyl-7,9-dihydro-8H-purin-8-one (79)

Trifluoromethanesulfonic acid (1.13 mL, 12.82 mmol) was added to a suspension of 2-amino-6-methoxy-9-(4-methoxybenzyl)-7-propyl-7,9-dihydro-8H-purin-8-one (78) (2.2 g, 6.41 mmol) in TFA (0.98 mL, 12.82 mmol) at 0° C. under argon atmosphere and the reaction mixture was slowly warmed to room temperature and stirred for 16 h. To the reaction mixture was added ice cold water (50 mL) and the pH was made basic with sat. aq. $NaHCO_3$ (300 mL) with vigorous stirring. The residual solid was filtered and taken into diethyl ether (100 mL), stirred for 30 min, filtered and dried to afford 2-amino-6-methoxy-7-propyl-7,9-dihydro-8H-purin-8-one (79) (1.0 g, 70%) as an off-white solid. $C_9H_{13}N_5O_2$: $^1$H NMR (400 MHz, DMSO-$d_6$): δ 11.23 (s, 1H), 6.18 (s, 2H), 3.89 (s, 3H), 3.66 (t, J=6.8 Hz, 2H), 1.60 (m, 2H), 0.82 (t, J=7.4 Hz, 3H). ES+, m/z 224.1 [M+H]$^+$.

Step 4: N-(6-Methoxy-8-oxo-7-propyl-8,9-dihydro-7H-purin-2-yl)acetamide (80)

Acetic anhydride (1.38 mL, 13.45 mmol) was added to a solution of 2-amino-6-methoxy-7-propyl-7,9-dihydro-8H-purin-8-one (79) (1.0 g, 4.48 mmol) in AcOH (10 mL) at ambient temperature under argon atmosphere and the resulting reaction mixture was heated at 120° C. for 4 h. The reaction mixture was cooled to 0° C. and stirring was continued for 30 minutes. The solid product that formed upon cooling was filtered and dried under vacuum to afford N-(6-methoxy-8-oxo-7-propyl-8,9-dihydro-7H-purin-2-yl)acetamide (80) (0.7 g, 63%) as an off-white solid. $C_{11}H_{15}N_5O_3$: $^1$H NMR (400 MHz, DMSO-$d_6$): δ 11.82 (brs, 1H), 10.22 (s, 1H), 3.99 (s, 3H), 3.74 (t, J=6.8 Hz, 2H), 2.17 (s, 3H), 1.63 (m, 2H), 0.83 (t, J=7.4 Hz, 3H). ES+, m/z 266.1 [M+H]$^+$.

Step 5: (S)-1-((2R,3S,4S,5R)-5-(2-Acetamido-6-methoxy-8-oxo-7-propyl-7,8-dihydro-9H-purin-9-yl)-4-acetoxy-3-fluorotetrahydrofuran-2-yl)propyl acetate (81)

N-(6-Methoxy-8-oxo-7-propyl-8,9-dihydro-7H-purin-2-yl)acetamide (80) (200 mg, 0.754 mmol), (3S,4S,5R)-5-((S)-1-acetoxypropyl)-4-fluorotetrahydrofuran-2,3-diyl diacetate (37S) (342 mg, 1.13 mmol) and BSA (0.573 mL, 2.26 mmol) were dissolved in 1,2-dichloroethane (15 mL), and the reaction mixture was stirred at 80° C. for 30 min under argon. The reaction mixture was cooled to rt, concentrated under vacuum and then taken up in acetonitrile (15 mL). TMSOTf (0.20 mL, 1.13 mmol) was added at rt. and the reaction mixture was heated at 80° C. for 16 h. The reaction mixture was concentrated and diluted with water (50 mL) and extracted with EtOAc (3×50 mL). The combined organic layer was washed with brine (50 mL), dried over $Na_2SO_4$, filtered and concentrated under reduced pressure. The crude product was purified by flash column chromatography ($SiO_2$, 0 to 80% EtOAc-pet-ether) to afford (S)-1-((2R,3S,4S,5R)-5-(2-acetamido-6-methoxy-8-oxo-7-propyl-7,8-dihydro-9H-purin-9-yl)-4-acetoxy-3-fluorotetrahydrofuran-2-yl)propyl acetate (81) (120 mg, 31%) as an off-white solid. $C_{22}H_{30}FN_5O_8$. $^1$H NMR (400 MHz, DMSO-$d_6$): δ 10.30 (s, 1H), 6.28 (dd, J=24.0, 5.6 Hz, 1H), 5.67 (d, J=5.6 Hz, 1H), 5.36 (dd, J=53.2, 2.8 Hz, 1H), 5.09 (m, 1H), 4.23 (dd, J=27.6, 5.2 Hz, 1H), 4.01 (s, 3H), 3.80 (t, J=6.8 Hz, 2H), 2.22 (s, 3H), 2.07 (s, 3H), 2.04 (s, 3H), 1.69-1.55 (m, 4H), 0.86 (m, 6H). ES+, m/z 512.6 [M+H]$^+$.

Step 6: 2-Amino-9-((2R,3S,4R,5R)-4-fluoro-3-hydroxy-5-((S)-1-hydroxypropyl)tetrahydrofuran-2-yl)-6-methoxy-7-propyl-7,9-dihydro-8H-purin-8-one (Compound 47)

To a solution of (S)-1-((2R,3S,4S,5R)-5-(2-acetamido-6-methoxy-8-oxo-7-propyl-7,8-dihydro-9H-purin-9-yl)-4-acetoxy-3-fluorotetrahydrofuran-2-yl)propyl acetate (81) (120 mg, 0.234 mmol) in methanol (5 mL) was added $K_2CO_3$ (65 mg, 0.46 mmol) at 0° C. The reaction mixture was stirred at room temperature for 16 h. and applied directly to reverse phase flash chromatography (0.1% $HCO_2H$:MeCN). Lyophilization of the pure fractions afforded 2-amino-9-((2R,3S,4R,5R)-4-fluoro-3-hydroxy-5-((S)-1-hydroxypropyl)tetrahydrofuran-2-yl)-6-methoxy-7-propyl-7,9-dihydro-8H-purin-8-one (Compound 47) (43 mg, 47%) as an off-white solid. $C_{16}H_{24}FN_5O_5$: $^1$H NMR (400 MHz, DMSO-$d_6$): δ 6.36 (s, 2H), 5.92 (d, J=5.2 Hz, 1H), 5.46 (d, J=7.2 Hz, 1H), 5.42-5.31 (m, 1H), 5.00 (ddd, J=53.4, 4.8, 2.6 Hz, 1H), 4.86 (d, J=7.2 Hz, 1H), 3.93 (s, 3H), 3.87-3.81 (m, 1H), 3.73 (t, J=7.0 Hz, 2H), 3.53 (m, 1H), 1.63 (m, 2H), 1.49 (m, 1H), 1.34 (m, 1H), 0.91 (t, J=7.4 Hz, 3H), 0.85 (t, J=7.4 Hz, 3H). ES+, m/z 386.2 [M+H]$^+$.

Example 43: 2-Amino-7-butyl-9-((2R,3S,4R,5R)-4-fluoro-3-hydroxy-5-((S)-1-hydroxypropyl)tetrahydrofuran-2-yl)-6-methoxy-7,9-dihydro-8H-purin-8-one, Compound 48

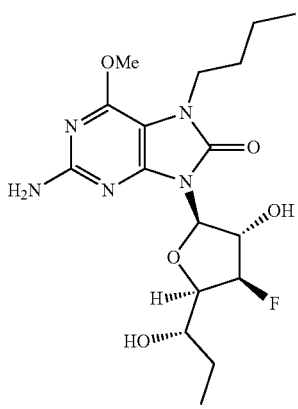 [SMILES: CCCCn1c(=O)n([C@@H]2O[C@H]([C@@H](O)CC)[C@H](F)[C@H]2O)c2nc(N)nc(OC)c21]

Compound 48 was prepared according to the following multi-step procedure.

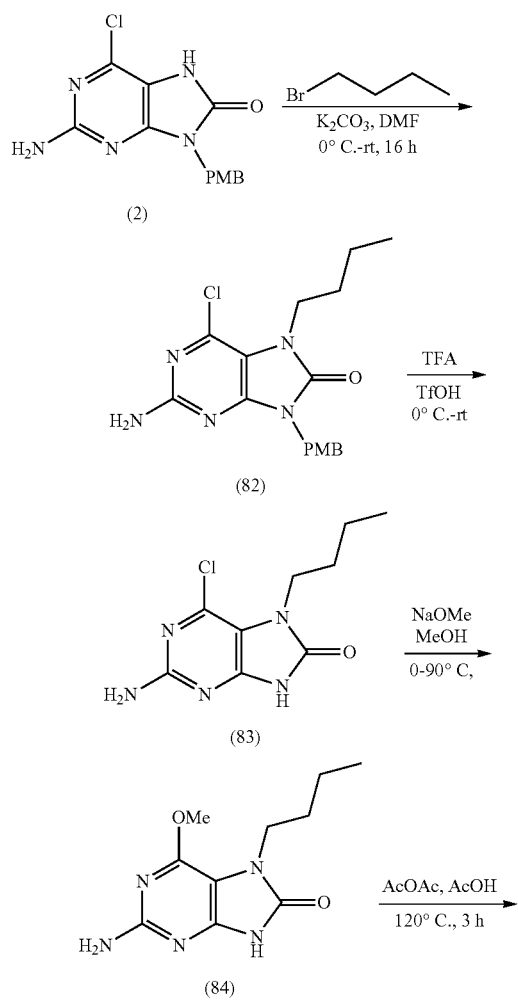

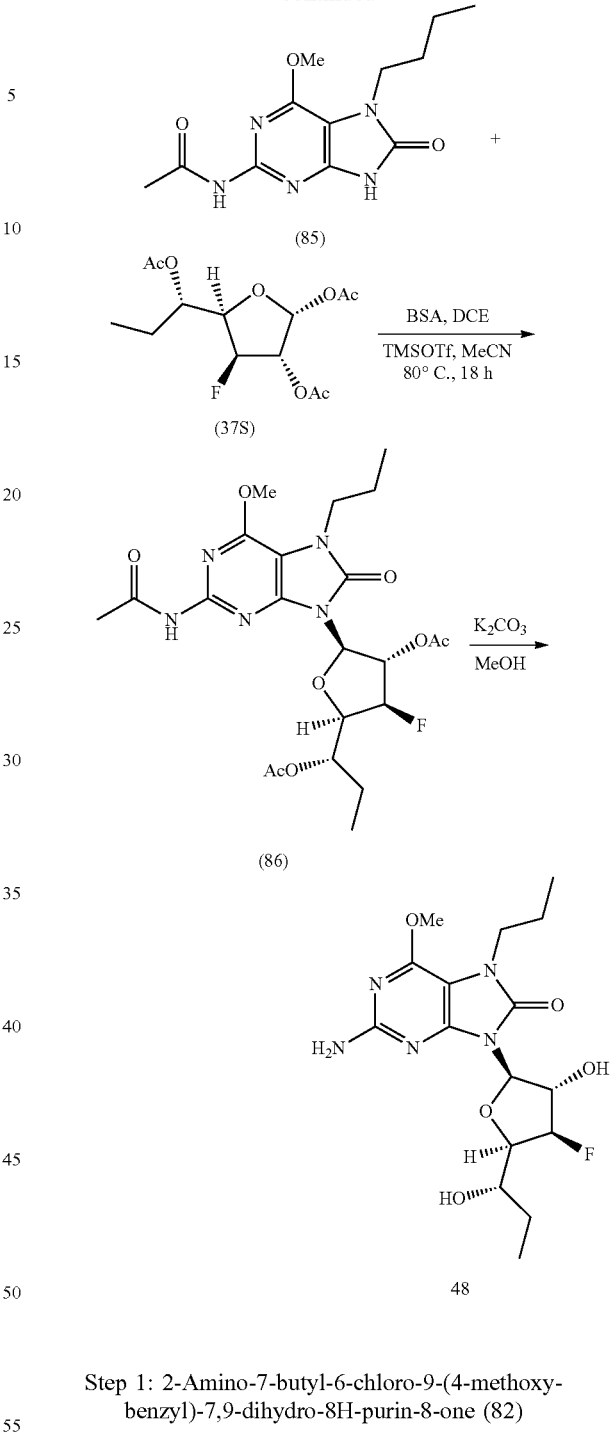

Step 1: 2-Amino-7-butyl-6-chloro-9-(4-methoxybenzyl)-7,9-dihydro-8H-purin-8-one (82)

1-Bromobutane (3.37 g, 24.59 mmol) was added to a suspension 2-amino-6-chloro-9-(4-methoxybenzyl)-7,9-dihydro-8H-purin-8-one (2) (5 g, 16.39 mmol), $K_2CO_3$ (3.39 g, 24.59 mmol) in DMF (50 mL) at 0° C. The reaction mixture was stirred at room temperature for 24 h, poured in to ice cold water and stirred for 30 mins at room temperature. The precipitated solid product was collected by filtration and dried under vacuum to afford 2-amino-7-butyl-6-chloro-9-(4-methoxybenzyl)-7,9-dihydro-8H-purin-8-one (82) (3 g, 50.6%) as a brown solid. $C_{17}H_{20}ClN_5O_2$: $^1$H NMR (400 MHz, DMSO-$d_6$): 7.23 (d, J=8.8 Hz, 2H), 6.88 (d, J=8.4 Hz, 2H), 6.73 (s, 2H), 4.85 (s, 2H), 3.89 (t, J=7.2 Hz, 2H), 3.72 (s, 3H), 1.62 (m, 2H), 1.31 (m, 2H), 0.87 (t, J=7.4 Hz, 3H). ES+, m/z 362.1 [M+H]+.

Step 2: 2-Amino-7-butyl-6-chloro-7,9-dihydro-8H-purin-8-one (83)

Trifluoromethane sulphonic acid (2.077 g, 13.85 mmol) was added to a stirred solution of 2-amino-7-butyl-6-chloro-9-(4-methoxybenzyl)-7,9-dihydro-8H-purin-8-one (82) (2.5 g, 6.92 mmol) in TFA (1.578 g, 13.85 mmol) at 0° C. under an argon atmosphere and the reaction mixture was stirred at RT for 16 h. To the mixture was added ice cold water and the pH was made basic with sat. aq. $NaHCO_3$ while being vigorously stirred. The residual solids were filtered, taken up in diethyl ether (100 mL) and stirred for 30 min. The solids were then filtered and dried to afford 2-amino-7-butyl-6-chloro-7,9-dihydro-8H-purin-8-one (83) (1 g; 60%) as a brown solid. $C_9H_{12}ClN_5O$: $^1H$ NMR (400 MHz, DMSO-$d_6$): δ 11.78 (s, 1H), 6.56 (s, 2H), 3.82 (t, J=7.2 Hz, 2H), 1.59 (quint, J=7.2 Hz, 2H) 1.29 (sext, J=7.4 Hz, 2H) 0.91 (t, J=7.0 Hz, 3H). ES+, m/z 242.1 [M+H]+.

Step 3: 2-Amino-7-butyl-6-chloro-7,9-dihydro-8H-purin-8-one (84)

A 30% solution of sodium methoxide in MeOH (2.87 mL, 16.59 mmol) was added to a solution of 2-amino-7-butyl-6-chloro-7,9-dihydro-8H-purin-8-one (83) (1 g, 4.149 mmol) in MeOH (10 mL) at ambient temperature under argon atmosphere. The reaction mixture was stirred at 90° C. for 16 h, cooled to RT and concentrated under vacuum. To the crude product was added EtOAc (100 mL) and the organic phase was washed with water (50 mL), brine (2×30 mL), separated, dried over anhydrous $Na_2SO_4$, and concentrated under vacuum to afford 2-amino-7-butyl-6-methoxy-7,9-dihydro-8H-purin-8-one (84) (200 mg, 20.3%) as a yellow solid. $C_{10}H_{15}N_5O_2$: $^1H$ NMR (400 MHz, CDCl3): δ 10.58 (s, 1H), 6.78 (bs, 2H), 3.98 (s, 3H), 3.89 (t, J=7.2 Hz, 2H), 1.71-1.65 (m, 2H), 1.37 (m, 2H), 0.94 (t, J=7.6 Hz, 3H). ES+, m/z 238.1 [M+H]+.

Step 4: N-(7-Butyl-6-methoxy-8-oxo-8,9-dihydro-7H-purin-2-yl)acetamide (85)

Acetic anhydride (0.2 mL, 1.61 mmol) was added to a solution of 2-amino-7-butyl-6-methoxy-7,9-dihydro-8H-purin-8-one (84) (200 mg, 0.81 mmol) in acetic acid (5 mL) at ambient temperature under argon atmosphere and the resulting reaction mixture was stirred at 120° C. for 3 h. The reaction mixture was cooled to rt and concentrated under vacuum crude compound was obtained. The crude compound was stirred in diethyl ether (10 mL) for 30 min. whereupon a solid formed. The product was filtered and dried under vacuum to afford N-(7-butyl-6-methoxy-8-oxo-8,9-dihydro-7H-purin-2-yl)acetamide (85) (170 mg, 72.3%) as a yellow solid. $C_{12}H_{17}N_5O_3$: $^1H$ NMR (400 MHz, DMSO-$d_6$): δ 11.83 (s, 1H), 10.21 (s, 1H), 3.98 (s, 3H), 3.79-3.76 (t, J=7.0 Hz, 2H), 2.17 (s, 3H), 1.61 (quint, J=7.2 Hz, 2H), 1.25 (m, 2H), 0.89 (t, J=7.4 Hz, 3H). ES+, m/z 280.1 [M+H]+.

Step 5: (S)-1-((2R,3S,4S,5R)-5-(2-Acetamido-7-butyl-6-methoxy-8-oxo-7,8-dihydro-9H-purin-9-yl)-4-acetoxy-3-fluorotetrahydrofuran-2-yl)propyl acetate (86)

N-(7-Butyl-6-methoxy-8-oxo-8,9-dihydro-7H-purin-2-yl)acetamide (85) (170 mg, 0.60 mmol), (3S,4S,5R)-5-((S)-1-acetoxypropyl)-4-fluorotetrahydrofuran-2,3-diyl diacetate (37S) (276 mg, 0.91 mmol) and BSA (369 mg, 1.82 mmol) were dissolved in 1,2-dichloroethane (10 mL) and the resulting reaction mixture was stirred at 80° C. for 30 min. under argon. The reaction mixture was concentrated under reduced pressure and to the residue was added MeCN (20 mL) followed by TMSOTf (202 mg, 0.91 mmol). The reaction mixture was heated at 80° C. for 18 h, cooled to room temperature and the solvent was removed by rotary evaporation. The remaining solids were dissolved in ethyl acetate (50 mL) and extracted with saturated aqueous $NaHCO_3$ (2×25 mL). The organic phase was dried with $Na_2SO_4$, filtered and concentrated. The crude product was purified by GRACE reverse phase chromatography (0.1% $HCO_2H$ in $H_2O$:MeCN) to afford (S)-1-((2R,3S,4S,5R)-5-(2-acetamido-7-butyl-6-methoxy-8-oxo-7,8-dihydro-9H-purin-9-yl)-4-acetoxy-3-fluorotetrahydrofuran-2-yl)propyl acetate (86) (80 mg, 25%) as an yellow solid. $C_{23}H_{32}FN_5O_8$: ES+, m/z 526.2 [M+H]+.

Step 6: 2-Amino-7-butyl-9-((2R,3S,4R,5R)-4-fluoro-3-hydroxy-5-((S)-1-hydroxypropyl)tetrahydrofuran-2-yl)-6-methoxy-7,9-dihydro-8H-purin-8-one (Compound 48)

To a solution of (S)-1-((2R,3S,4S,5R)-5-(2-acetamido-7-butyl-6-methoxy-8-oxo-7,8-dihydro-9H-purin-9-yl)-4-acetoxy-3-fluorotetrahydrofuran-2-yl)propyl acetate (86) (80 mg, 0.15 mmol) in methanol (5.0 mL) was added $K_2CO_3$ (42 mg, 0.30 mmol) at 0° C. The reaction mixture was stirred at room temperature for 16 h. The reaction mixture was applied directly to GRACE reverse phase chromatography (0.1% $HCO_2H$ in $H_2O$:MeCN) and the purified fractions were lyophilized to afford 2-amino-7-butyl-9-((2R,3S,4R,5R)-4-fluoro-3-hydroxy-5-((S)-1-hydroxypropyl)tetrahydrofuran-2-yl)-6-methoxy-7,9-dihydro-8H-purin-8-one (Compound 48) (15 mg, 24.7%), as an off-white solid. $C_{17}H_{26}FN_5O_5$: $^1H$ NMR (500 MHz, DMSO-$d_6$): δ 6.35 (s, 2H), 5.90 (d, J=6.0 Hz, 1H), 5.44 (d, J=7.0 Hz, 1H), 5.40-5.32 (m, 1H), 5.00 (ddd, J=53.5, 4.8, 2.8 Hz, 1H), 4.86 (d, J=7.0 Hz, 1H), 3.93 (s, 3H), 3.84 (ddd, J=22.5, 6.5, 5.0 Hz, 1H), 3.76 (t, J=7.0 Hz, 2H), 3.53 (m, 1H), 1.59 (m, 2H), 1.48 (m, 1H), 1.33 (m, 1H), 1.27 (m, 2H), 0.92-0.88 (m, 6H). ES+, m/z 400.4 [M+H]+.

Example 44: 2-Amino-9-((2R,3R,5S)-3-hydroxy-5-((S)-1-hydroxypropyl)tetrahydrofuran-2-yl)-7-propyl-7,9-dihydro-1H-purine-6,8-dione, Compound 49

Compound 49 can be prepared according to the procedure in Example 2 with (43) and (14S).

Example 45: 2-Amino-7-butyl-9-((2R,3R,5S)-3-hydroxy-5-((S)-1-hydroxypropyl)tetrahydrofuran-2-yl)-7,9-dihydro-1H-purine-6,8-dione, Compound 50

Compound 50 can be prepared according to the procedure in Example 2 with (55) and (14S).

Example 46: 2-Amino-9-((2R,3R,5S)-3-hydroxy-5-((R)-2,2,2-trifluoro-1-hydroxyethyl)tetrahydrofuran-2-yl)-7-(2,2,2-trifluoroethyl)-7,9-dihydro-1H-purine-6,8-dione, Compound 51

Compound 51 can be prepared according to the procedure in Example 9 with (72) and (22S).

Example 47: 2-Amino-7-(cyclopropylmethyl)-9-((2R,3R,5S)-5-((R)-2-fluoro-1-hydroxyethyl)-3-hydroxytetrahydrofuran-2-yl)-7,9-dihydro-1H-purine-6,8-dione, Compound 52

Compound 52 can be prepared according to the procedure in Example 21 with (12) and (67S).

Example 48: 2-Amino-9-((2R,3R,5S)-5-((R)-2-fluoro-1-hydroxyethyl)-3-hydroxytetrahydrofuran-2-yl)-7-propyl-7,9-dihydro-1H-purine-6,8-dione, Compound 53

Compound 53 can be prepared according to the procedure in Example 21 with (43) and (67S).

Example 49: 2-Amino-7-butyl-9-((2R,3R,5S)-5-((R)-2-fluoro-1-hydroxyethyl)-3-hydroxytetrahydrofuran-2-yl)-7,9-dihydro-1H-purine-6,8-dione, Compound 54

Compound 54 can be prepared according to the procedure in Example 21 with (55) and (67S).

Example 50: 2-Amino-9-((2R,3R,5S)-5-((R)-2-fluoro-1-hydroxyethyl)-3-hydroxytetrahydrofuran-2-yl)-7-(2,2,2-trifluoroethyl)-7,9-dihydro-1H-purine-6,8-dione, Compound 55

Compound 55 can be prepared according to the procedure in Example 21 with (72) and (67S).

Example 51: 2-Amino-9-((2R,3R,5S)-3-hydroxy-5-(1-hydroxycyclopropyl)tetrahydrofuran-2-yl)-7-(prop-2-yn-1-yl)-7,9-dihydro-1H-purine-6,8-dione, Compound 56

Compound 56 can be prepared according to the procedure in Example 16 with (6) and (3R,5S)-5-(1-(2,2,2-trifluoroacetoxy)cyclopropyl)tetrahydrofuran-2,3-diyl diacetate.

Example 52: 2-Amino-9-((2R,3R,5S)-3-hydroxy-5-(2,2,2-trifluoroacetyl)tetrahydrofuran-2-yl)-7-(prop-2-yn-1-yl)-7,9-dihydro-1H-purine-6,8-dione, Compound 57

Compound 57 can be prepared from Compound 10 and/or 11.

Example 53: 2-Amino-7-(cyclopropylmethyl)-9-((2R,3R,5S)-3-hydroxy-5-(2,2,2-trifluoroacetyl)tetrahydrofuran-2-yl)-7,9-dihydro-1H-purine-6,8-dione, Compound 58

Compound 58 can be prepared from Compound 29.

Example 54: 2-Amino-9-((2R,3R,5S)-3-hydroxy-5-(2,2,2-trifluoroacetyl)tetrahydrofuran-2-yl)-7-propyl-7,9-dihydro-1H-purine-6,8-dione, Compound 59

Compound 59 can be prepared from Compound 25.

Example 55: 2-Amino-7-butyl-9-((2R,3R,5S)-3-hydroxy-5-(2,2,2-trifluoroacetyl)tetrahydrofuran-2-yl)-7,9-dihydro-1H-purine-6,8-dione, Compound 60

Compound 60 can be prepared from Compound 31.

Example 56: 2-Amino-9-((2R,3R,5S)-3-hydroxy-5-(2,2,2-trifluoroacetyl)tetrahydrofuran-2-yl)-7-(3,3,3-trifluoropropyl)-7,9-dihydro-1H-purine-6,8-dione, Compound 61

Compound 61 can be prepared from Compound 28.

Example 57: 2-Amino-9-((2R,3R,5S)-3-hydroxy-5-((S)-1-hydroxypropyl)tetrahydrofuran-2-yl)-7-(2-(methylsulfinyl)ethyl)-7,9-dihydro-1H-purine-6,8-dione, Compound 62

Compound 62 can be prepared by the oxidation of Compound 22.

Example 58: 2-Amino-9-((2R,3R,5S)-3-hydroxy-5-((S)-1-hydroxypropyl)tetrahydrofuran-2-yl)-7-(2-(methylsulfonyl)ethyl)-7,9-dihydro-1H-purine-6,8-dione, Compound 63

Compound 63 can be prepared by the oxidation of Compound 22 or Compound 62.

Example 59: 2-Amino-9-((2R,3S,4R,5R)-4-fluoro-3-hydroxy-5-((S)-1-hydroxypropyl)tetrahydrofuran-2-yl)-7-(2-(methylsulfinyl)ethyl)-7,9-dihydro-1H-purine-6,8-dione, Compound 64

Compound 64 can be prepared by the oxidation of Compound 46.

Example 60: 2-Amino-9-((2R,3S,4R,5R)-4-fluoro-3-hydroxy-5-((S)-1-hydroxypropyl)tetrahydrofuran-2-yl)-7-(2-(methylsulfonyl)ethyl)-7,9-dihydro-1H-purine-6,8-dione, Compound 65

Compound 65 can be prepared by the oxidation of Compound 46 or Compound 64.

Example 61: 2-Amino-9-((2R,3S,4R,5R)-4-fluoro-3-hydroxy-5-((R)-2,2,2-trifluoro-1-hydroxyethyl)tetrahydrofuran-2-yl)-7-(prop-2-yn-1-yl)-7,9-dihydro-1H-purine-6,8-dione, Compound 66

Compound 66 can be prepared according to the procedure in Example 9 with (6) and (3S,4S,5R)-5-(1-(benzoyloxy)-2,2,2-trifluoroethyl)-4-fluorotetrahydrofuran-2,3-diyl diacetate.

Example 62: 2-Amino-7-(cyclopropylmethyl)-9-((2R,3S,4R,5R)-4-fluoro-3-hydroxy-5-((R)-2,2,2-trifluoro-1-hydroxyethyl)tetrahydrofuran-2-yl)-7,9-dihydro-1H-purine-6,8-dione, Compound 67

Compound 67 can be prepared according to the procedure in Example 26 with (12) and (3S,4S,5R)-5-(1-(benzoyloxy)-2,2,2-trifluoroethyl)-4-fluorotetrahydrofuran-2,3-diyl diacetate.

Example 63: 2-Amino-9-((2R,3S,4R,5R)-4-fluoro-3-hydroxy-5-((R)-2,2,2-trifluoro-1-hydroxyethyl)tetrahydrofuran-2-yl)-7-propyl-7,9-dihydro-1H-purine-6,8-dione, Compound 68

Compound 68 can be prepared according to the procedure in Example 22 with (43) and (3S,4S,5R)-5-(1-(benzoyloxy)-2,2,2-trifluoroethyl)-4-fluorotetrahydrofuran-2,3-diyl diacetate.

Example 64: 2-Amino-7-butyl-9-((2R,3S,4R,5R)-4-fluoro-3-hydroxy-5-((R)-2,2,2-trifluoro-1-hydroxyethyl)tetrahydrofuran-2-yl)-7,9-dihydro-1H-purine-6,8-dione, Compound 69

Compound 69 can be prepared according to the procedure in Example 28 with (55) and (3S,4S,5R)-5-(1-(benzoyloxy)-2,2,2-trifluoroethyl)-4-fluorotetrahydrofuran-2,3-diyl diacetate.

Example 65: 2-Amino-9-((2R,3S,4R,5R)-4-fluoro-3-hydroxy-5-((R)-2,2,2-trifluoro-1-hydroxyethyl)tetrahydrofuran-2-yl)-7-(2,2,2-trifluoroethyl)-7,9-dihydro-1H-purine-6,8-dione, Compound 70

Compound 70 can be prepared according to the procedure in Example 25 with (72) and (3S,4S,5R)-5-(1-(benzoyloxy)-2,2,2-trifluoroethyl)-4-fluorotetrahydrofuran-2,3-diyl diacetate.

Example 66: 2-Amino-9-((2R,3S,4R,5R)-4-fluoro-3-hydroxy-5-((R)-2,2,2-trifluoro-1-hydroxyethyl)tetrahydrofuran-2-yl)-7-(3,3,3-trifluoropropyl)-7,9-dihydro-1H-purine-6,8-dione, Compound 71

Compound 71 can be prepared according to the procedure in Example 25 with (49) and (3S,4S,5R)-5-(1-(benzoyloxy)-2,2,2-trifluoroethyl)-4-fluorotetrahydrofuran-2,3-diyl diacetate.

Example 67: 2-Amino-9-((2R,3S,4R,5R)-4-fluoro-3-hydroxy-5-((S)-1-hydroxypropyl)tetrahydrofuran-2-yl)-7-((R)-2-hydroxypropyl)-7,9-dihydro-1H-purine-6,8-dione, Compound 72

Compound 72 can be prepared according to the procedure in Example 30 with (64) and (37S).

Example 68: 2-Amino-9-((2R,3S,4R,5R)-4-fluoro-3-hydroxy-5-((S)-1-hydroxypropyl)tetrahydrofuran-2-yl)-7-((S)-2-hydroxypropyl)-7,9-dihydro-1H-purine-6,8-dione, Compound 73

Compound 73 can be prepared according to the procedure in Example 30 with (64) and (37S).

Example 69: 2-Amino-9-((2R,3S,4R,5R)-4-fluoro-3-hydroxy-5-((R)-2,2,2-trifluoro-1-hydroxyethyl)tetrahydrofuran-2-yl)-7-((R)-2-hydroxypropyl)-7,9-dihydro-1H-purine-6,8-dione, Compound 74

Compound 74 can be prepared according to the procedure in Example 9 with (64) and (3S,4S,5R)-5-(1-(benzoyloxy)-2,2,2-trifluoroethyl)-4-fluorotetrahydrofuran-2,3-diyl diacetate.

Example 70: 2-Amino-9-((2R,3S,4R,5R)-4-fluoro-3-hydroxy-5-((R)-2,2,2-trifluoro-1-hydroxyethyl)tetrahydrofuran-2-yl)-7-((S)-2-hydroxypropyl)-7,9-dihydro-1H-purine-6,8-dione, Compound 75

Compound 75 can be prepared according to the procedure in Example 9 with (64) and (3S,4S,5R)-5-(1-(benzoyloxy)-2,2,2-trifluoroethyl)-4-fluorotetrahydrofuran-2,3-diyl diacetate.

Example 71: (S)-1-((2S,4R,5R)-4-Acetoxy-5-(2-amino-8-oxo-7-(prop-2-yn-1-yl)-7,8-dihydro-9H-purin-9-yl)tetrahydrofuran-2-yl)propyl acetate, Compound 76

Compound 76 can be prepared by the selective mild O-acetylation of the secondary hydroxyl groups of Compound 6 with acetic anhydride.

Example 72: (S)-1-((2S,4R,5R)-4-Acetoxy-5-(2-amino-7-(cyclopropylmethyl)-8-oxo-7,8-dihydro-9H-purin-9-yl)tetrahydrofuran-2-yl)propyl acetate, Compound 77

Compound 77 can be prepared by the selective mild O-acetylation of the secondary hydroxyl groups of Compound 5 with acetic anhydride.

Example 73: 2-Amino-9-((2R,3R,5S)-3-hydroxy-5-((S)-1-hydroxypropyl)tetrahydrofuran-2-yl)-7-propyl-7,9-dihydro-8H-purin-8-one, Compound 78

Compound 78 can be prepared using the procedure described in Example 5 substituting propargyl bromide with 1-iodopropane.

Example 74: (S)-1-((2S,4R,5R)-4-Acetoxy-5-(2-amino-8-oxo-7-propyl-7,8-dihydro-9H-purin-9-yl)tetrahydrofuran-2-yl)propyl acetate, Compound 79

Compound 79 can be prepared by the selective mild O-acetylation of the secondary hydroxyl groups of Compound 78 with acetic anhydride.

Example 75: 2-Amino-7-butyl-9-((2R,3R,5S)-3-hydroxy-5-((S)-1-hydroxypropyl)tetrahydrofuran-2-yl)-7,9-dihydro-8H-purin-8-one, Compound 80

Compound 80 can be prepared using the procedure described in Example 5 substituting propargyl bromide with 1-bromobutane.

Example 76: (S)-1-((2S,4R,5R)-4-Acetoxy-5-(2-amino-7-butyl-8-oxo-7,8-dihydro-9H-purin-9-yl)tetrahydrofuran-2-yl)propyl acetate, Compound 81

Compound 81 can be prepared by the selective mild O-acetylation of the secondary hydroxyl groups of Compound 80 with acetic anhydride.

Example 77: 2-Amino-9-((2R,3R,5S)-3-hydroxy-5-((S)-1-hydroxypropyl)tetrahydrofuran-2-yl)-7-(2,2,2-trifluoroethyl)-7,9-dihydro-8H-purin-8-one, Compound 82

Compound 82 can be prepared using the procedure described in Example 5 substituting propargyl bromide with 2-bromo-1,1,1-trifluoroethane.

Example 78: (S)-1-((2S,4R,5R)-4-acetoxy-5-(2-amino-8-oxo-7-(2,2,2-trifluoroethyl)-7,8-dihydro-9H-purin-9-yl)tetrahydrofuran-2-yl)propyl acetate, Compound 83

Compound 83 can be prepared by the selective mild O-acetylation of the secondary hydroxyl groups of Compound 82 with acetic anhydride.

Example 79: (2R,3R,5S)-5-((R)-1-acetoxy-2,2,2-trifluoroethyl)-2-(2-amino-8-oxo-7-(prop-2-yn-1-yl)-7,8-dihydro-9H-purin-9-yl)tetrahydrofuran-3-yl acetate, Compound 84

Compound 84 can be prepared by the selective mild O-acetylation of the secondary hydroxyl groups of Compound 36 with acetic anhydride.

Example 80: 2-Amino-7-(cyclopropylmethyl)-9-((2R,3R,5S)-3-hydroxy-5-((R)-2,2,2-trifluoro-1-hydroxyethyl)tetrahydrofuran-2-yl)-7,9-dihydro-8H-purin-8-one, Compound 85

Compound 85 can be prepared using the procedure described in Example 32 and substituting (21) with (14).

Example 81: (2R,3R,5S)-5-((R)-1-Acetoxy-2,2,2-trifluoroethyl)-2-(2-amino-7-(cyclopropylmethyl)-8-oxo-7,8-dihydro-9H-purin-9-yl)tetrahydrofuran-3-yl acetate, Compound Compound 86 can be prepared by the selective mild O-acetylation of the secondary hydroxyl groups of Compound 85 with acetic anhydride.

Example 82: 2-Amino-9-((2R,3R,5S)-3-hydroxy-5-((R)-2,2,2-trifluoro-1-hydroxyethyl)tetrahydrofuran-2-yl)-7-propyl-7,9-dihydro-8H-purin-8-one, Compound 87

Compound 87 can be prepared using the procedures described in Examples 5 and 32 with (22S) and where propargyl bromide is replaced with 1-iodopropane.

Example 83: (2R,3R,5S)-5-((R)-1-Acetoxy-2,2,2-trifluoroethyl)-2-(2-amino-8-oxo-7-propyl-7,8-dihydro-9H-purin-9-yl)tetrahydrofuran-3-yl acetate, Compound 88

Compound 88 can be prepared by the selective mild O-acetylation of the secondary hydroxyl groups of Compound 87 with acetic anhydride.

Example 84: 2-Amino-7-butyl-9-((2R,3R,5S)-3-hydroxy-5-((R)-2,2,2-trifluoro-1-hydroxyethyl)tetrahydrofuran-2-yl)-7,9-dihydro-8H-purin-8-one, Compound 89

Compound 89 can be prepared using the procedures described in Examples 5 and 32 with (22S) and where propargyl bromide is replaced with 1-bromobutane.

Example 85: (2R,3R,5S)-5-((R)-1-Acetoxy-2,2,2-trifluoroethyl)-2-(2-amino-7-butyl-8-oxo-7,8-dihydro-9H-purin-9-yl)tetrahydrofuran-3-yl acetate, Compound 90

Compound 90 can be prepared by the selective mild O-acetylation of the secondary hydroxyl groups of Compound 89 with acetic anhydride.

Example 86: 2-Amino-9-((2R,3R,5S)-3-hydroxy-5-((R)-2,2,2-trifluoro-1-hydroxyethyl)tetrahydrofuran-2-yl)-7-(2,2,2-trifluoroethyl)-7,9-dihydro-8H-purin-8-one, Compound 91

Compound 91 can be prepared using the procedures described in Examples 5 and 32 with (22S) and where propargyl bromide is replaced with 2-bromo-1,1,1-trifluoroethane.

Example 87: (2R,3R,5S)-5-((R)-1-Acetoxy-2,2,2-trifluoroethyl)-2-(2-amino-8-oxo-7-(2,2,2-trifluoroethyl)-7,8-dihydro-9H-purin-9-yl)tetrahydrofuran-3-yl acetate, Compound 92

Compound 92 can be prepared by the selective mild O-acetylation of the secondary hydroxyl groups of Compound 91 with acetic anhydride.

Example 88: 2-Amino-9-((2R,3R,5S)-5-((R)-2-fluoro-1-hydroxyethyl)-3-hydroxytetrahydrofuran-2-yl)-7-(prop-2-yn-1-yl)-7,9-dihydro-8H-purin-8-one, Compound 93

Compound 93 can be prepared using the procedures described in Example 5 with (21) and (67S).

Example 89: (2R,3R,5S)-5-((R)-1-acetoxy-2-fluoroethyl)-2-(2-amino-8-oxo-7-(prop-2-yn-1-yl)-7,8-dihydro-9H-purin-9-yl)tetrahydrofuran-3-yl acetate, Compound 94

Compound 94 can be prepared by the selective mild O-acetylation of the secondary hydroxyl groups of Compound 93 with acetic anhydride.

Example 90: 2-Amino-7-(cyclopropylmethyl)-9-((2R,3R,5S)-5-((R)-2-fluoro-1-hydroxyethyl)-3-hydroxytetrahydrofuran-2-yl)-7,9-dihydro-8H-purin-8-one, Compound 95

Compound 95 can be prepared using the procedures described in Example 4 with (14) and (67S).

Example 91: (2R,3R,5S)-5-((R)-1-acetoxy-2-fluoroethyl)-2-(2-amino-7-(cyclopropylmethyl)-8-oxo-7,8-dihydro-9H-purin-9-yl)tetrahydrofuran-3-yl acetate, Compound 96

Compound 96 can be prepared by the selective mild O-acetylation of the secondary hydroxyl groups of Compound 95 with acetic anhydride.

Example 92: 2-Amino-9-((2R,3R,5S)-5-((R)-2-fluoro-1-hydroxyethyl)-3-hydroxytetrahydrofuran-2-yl)-7-propyl-7,9-dihydro-8H-purin-8-one, Compound 97

Compound 97 can be prepared using the procedures described in Examples 5 with (67S) where propargyl bromide is replaced with 1-iodopropane.

Example 93: (2R,3R,5S)-5-((R)-1-Acetoxy-2-fluoroethyl)-2-(2-amino-8-oxo-7-propyl-7,8-dihydro-9H-purin-9-yl)tetrahydrofuran-3-yl acetate, Compound 98

Compound 98 can be prepared by the selective mild O-acetylation of the secondary hydroxyl groups of Compound 97 with acetic anhydride.

Example 94: 2-Amino-7-butyl-9-((2R,3R,5S)-5-((R)-2-fluoro-1-hydroxyethyl)-3-hydroxytetrahydrofuran-2-yl)-7,9-dihydro-8H-purin-8-one, Compound 99

Compound 99 can be prepared using the procedures described in Examples 5 with (67S) where propargyl bromide is replaced with 1-bromobutane.

Example 95: (2R,3R,5S)-5-((R)-1-acetoxy-2-fluoroethyl)-2-(2-amino-7-butyl-8-oxo-7,8-dihydro-9H-purin-9-yl)tetrahydrofuran-3-yl acetate, Compound 100

Compound 100 can be prepared by the selective mild O-acetylation of the secondary hydroxyl groups of Compound 99 with acetic anhydride.

Example 96: 2-Amino-9-((2R,3R,5S)-5-((R)-2-fluoro-1-hydroxyethyl)-3-hydroxytetrahydrofuran-2-yl)-7-(2,2,2-trifluoroethyl)-7,9-dihydro-8H-purin-8-one, Compound 101

Compound 101 can be prepared using the procedures described in Examples 5 with (67S) where propargyl bromide is replaced with 2-bromo-1,1,1-trifluoroethane.

Example 97: (2R,3R,5S)-5-((R)-1-Acetoxy-2-fluoroethyl)-2-(2-amino-8-oxo-7-(2,2,2-trifluoroethyl)-7,8-dihydro-9H-purin-9-yl)tetrahydrofuran-3-yl acetate, Compound 102

Compound 102 can be prepared by the selective mild O-acetylation of the secondary hydroxyl groups of Compound 101 with acetic anhydride.

Example 98: 2-Amino-9-((2R,3R,5S)-3-hydroxy-5-(1-hydroxycyclopropyl)tetrahydrofuran-2-yl)-7-(prop-2-yn-1-yl)-7,9-dihydro-8H-purin-8-one, Compound 103

Compound 103 can be prepared according to the procedure in Example 5 with (21) and (3R,5S)-5-(1-(2,2,2-trifluoroacetoxy)cyclopropyl)tetrahydrofuran-2,3-diyl diacetate.

Example 99: 1-((2S,4R,5R)-4-Acetoxy-5-(2-amino-8-oxo-7-(prop-2-yn-1-yl)-7,8-dihydro-9H-purin-9-yl)tetrahydrofuran-2-yl)cyclopropyl acetate, Compound 104

Compound 104 can be prepared by the selective mild O-acetylation of the secondary hydroxyl groups of Compound 103 with acetic anhydride.

Example 100: 2-Amino-9-((2R,3R,5S)-3-hydroxy-5-(2-hydroxypropan-2-yl)tetrahydrofuran-2-yl)-7-(prop-2-yn-1-yl)-7,9-dihydro-8H-purin-8-one, Compound 105

Compound 105 can be prepared according to the procedure in Example 5 with (21) and (58S).

Example 101: 2-((2S,4R,5R)-4-Acetoxy-5-(2-amino-8-oxo-7-(prop-2-yn-1-yl)-7,8-dihydro-9H-purin-9-yl)tetrahydrofuran-2-yl)propan-2-yl acetate, Compound 106

Compound 106 can be prepared by the selective mild O-acetylation of the secondary hydroxyl groups of Compound 105 with acetic anhydride.

Example 102: 2-Amino-9-((2R,3R,5S)-3-hydroxy-5-(2,2,2-trifluoroacetyl)tetrahydrofuran-2-yl)-7-(prop-2-yn-1-yl)-7,9-dihydro-8H-purin-8-one, Compound 107

Compound 107 can be prepared from Compound 36.

Example 103: 2-((2S,4R,5R)-4-Acetoxy-5-(2-amino-8-oxo-7-(prop-2-yn-1-yl)-7,8-dihydro-9H-purin-9-yl)tetrahydrofuran-2-yl)propan-2-yl acetate, Compound 108

Compound 108 can be prepared by the O-acetylation of Compound 107 with acetic anhydride.

Example 104: 2-Amino-7-(cyclopropylmethyl)-9-((2R,3R,5S)-3-hydroxy-5-(2,2,2-trifluoroacetyl)tetrahydrofuran-2-yl)-7,9-dihydro-8H-purin-8-one, Compound 109

Compound 109 can be prepared from Compound 85.

Example 105: (2R,3R,5S)-2-(2-Amino-7-(cyclopropylmethyl)-8-oxo-7,8-dihydro-9H-purin-9-yl)-5-(2,2,2-trifluoroacetyl)tetrahydrofuran-3-yl acetate, Compound 110

Compound 110 can be prepared by the O-acetylation of Compound 109 with acetic anhydride.

Example 106: 2-Amino-9-((2R,3R,5S)-3-hydroxy-5-(2,2,2-trifluoroacetyl)tetrahydrofuran-2-yl)-7-propyl-7,9-dihydro-8H-purin-8-one, Compound 111

Compound 111 can be prepared from Compound 87.

Example 107: (2R,3R,5S)-2-(2-Amino-8-oxo-7-propyl-7,8-dihydro-9H-purin-9-yl)-5-(2,2,2-trifluoroacetyl)tetrahydrofuran-3-yl acetate, Compound 112

Compound 112 can be prepared by the O-acetylation of Compound 111 with acetic anhydride.

Example 108: 2-Amino-7-butyl-9-((2R,3R,5S)-3-hydroxy-5-(2,2,2-trifluoroacetyl)tetrahydrofuran-2-yl)-7,9-dihydro-8H-purin-8-one, Compound 113

Compound 113 can be prepared from Compound 89.

Example 109: (2R,3R,5S)-2-(2-Amino-7-butyl-8-oxo-7,8-dihydro-9H-purin-9-yl)-5-(2,2,2-trifluoroacetyl)tetrahydrofuran-3-yl acetate, Compound 114

Compound 114 can be prepared by the O-acetylation of Compound 113 with acetic anhydride.

Example 110: 2-Amino-9-((2R,3R,5S)-3-hydroxy-5-(2,2,2-trifluoroacetyl)tetrahydrofuran-2-yl)-7-(2,2,2-trifluoroethyl)-7,9-dihydro-1H-purine-6,8-dione, Compound 115

Compound 115 can be prepared from Compound 51.

Example 111: 2-Amino-9-((2R,3R,5S)-3-hydroxy-5-(2,2,2-trifluoroacetyl)tetrahydrofuran-2-yl)-7-(2,2,2-trifluoroethyl)-7,9-dihydro-8H-purin-8-one, Compound 116

Compound 116 can be prepared from Compound 91

Example 112: (2R,3R,5S)-2-(2-Amino-8-oxo-7-(2,2,2-trifluoroethyl)-7,8-dihydro-9H-purin-9-yl)-5-(2,2,2-trifluoroacetyl)tetrahydrofuran-3-yl acetate, Compound 117

Compound 117 can be prepared by the O-acetylation of Compound 116 with acetic anhydride.

Example 113: 2-Amino-9-((2R,3R,5S)-3-hydroxy-5-((R)-2,2,2-trifluoro-1-hydroxyethyl)tetrahydrofuran-2-yl)-7-(3,3,3-trifluoropropyl)-7,9-dihydro-8H-purin-8-one, Compound 118

Compound 118 can be prepared using the procedures described in Examples 5 and 32 with (22S) and where propargyl bromide is replaced with (46).

Example 114: 2-Amino-9-((2R,3R,5S)-3-hydroxy-5-(2,2,2-trifluoroacetyl)tetrahydrofuran-2-yl)-7-(3,3,3-trifluoropropyl)-7,9-dihydro-8H-purin-8-one, Compound 119

Compound 119 can be prepared from Compound 118.

Example 115: (2R,3R,5S)-2-(2-Amino-8-oxo-7-(3,3,3-trifluoropropyl)-7,8-dihydro-9H-purin-9-yl)-5-(2,2,2-trifluoroacetyl)tetrahydrofuran-3-yl acetate, Compound 120

Compound 120 can be prepared by the O-acetylation of Compound 119 with acetic anhydride.

Example 116: 2-Amino-9-((2R,3R,5S)-3-hydroxy-5-((S)-1-hydroxypropyl)tetrahydrofuran-2-yl)-7-(2-(methylthio)ethyl)-7,9-dihydro-8H-purin-8-one, Compound 121

Compound 121 can be prepared using the procedures described in Example 5 with (14S) where propargyl bromide is replaced with (2-chloroethyl)(methyl)sulfane.

Example 117: (S)-1-((2S,4R,5R)-4-acetoxy-5-(2-amino-7-(2-(methylthio)ethyl)-8-oxo-7,8-dihydro-9H-purin-9-yl)tetrahydrofuran-2-yl)propyl acetate, Compound 122

Compound 122 can be prepared by the selective mild O-acetylation of the secondary hydroxyl groups of Compound 121 with acetic anhydride.

Example 118: 2-Amino-9-((2R,3R,5S)-3-hydroxy-5-((S)-1-hydroxypropyl)tetrahydrofuran-2-yl)-7-(2-(methylsulfinyl)ethyl)-7,9-dihydro-8H-purin-8-one, Compound 123

Compound 123 can be prepared by the oxidation of 121 with $H_2O_2$ or m-chloroperbenzoic acid.

Example 119: (1S)-1-((2S,4R,5R)-4-Acetoxy-5-(2-amino-7-(2-(methylsulfinyl)ethyl)-8-oxo-7,8-dihydro-9H-purin-9-yl)tetrahydrofuran-2-yl)propyl acetate, Compound 124

Compound 124 can be prepared by the oxidation of 122 with $H_2O_2$ or m-chloroperbenzoic acid.

Example 120: 2-Amino-9-((2R,3R,5S)-3-hydroxy-5-((S)-1-hydroxypropyl)tetrahydrofuran-2-yl)-7-(2-(methylsulfonyl)ethyl)-7,9-dihydro-8H-purin-8-one, Compound 125

Compound 125 can be prepared by the oxidation of 121 or 123 with $H_2O_2$ or m-chloroperbenzoic acid.

Example 121: (S)-1-((2S,4R,5R)-4-Acetoxy-5-(2-amino-7-(2-(methylsulfonyl)ethyl)-8-oxo-7,8-dihydro-9H-purin-9-yl)tetrahydrofuran-2-yl)propyl acetate, Compound 126

Compound 126 can be prepared by the oxidation of 122 or 124 with $H_2O_2$ or m-chloroperbenzoic acid.

Example 122: 2-Amino-9-((2R,3R,5S)-3-hydroxy-5-((S)-1-hydroxypropyl)tetrahydrofuran-2-yl)-7-((R)-2-hydroxypropyl)-7,9-dihydro-8H-purin-8-one, Compound 127

Compound 127 can be prepared using the procedures described in Example 5 with (14S) and where propargyl bromide is replaced with (R)-1-bromopropan-2-yl acetate [99457-42-8].

Example 123: (R)-1-(9-((2R,3R,5S)-3-Acetoxy-5-((S)-1-acetoxypropyl)tetrahydrofuran-2-yl)-2-amino-8-oxo-8,9-dihydro-7H-purin-7-yl)propan-2-yl acetate, Compound 128

Compound 128 can be prepared by the selective mild O-acetylation of the secondary hydroxyl groups of Compound 127 with acetic anhydride.

Example 124: 2-Amino-9-((2R,3R,5S)-3-hydroxy-5-((S)-1-hydroxypropyl)tetrahydrofuran-2-yl)-7-((S)-2-hydroxypropyl)-7,9-dihydro-8H-purin-8-one, Compound 129

Compound 129 can be prepared using the procedures described in Example 5 with (14S) and where propargyl bromide is replaced with (S)-1-bromopropan-2-yl acetate [39968-99-5].

Example 125: (S)-1-(9-((2R,3R,5S)-3-Acetoxy-5-((R)-1-acetoxypropyl)tetrahydrofuran-2-yl)-2-amino-8-oxo-8,9-dihydro-7H-purin-7-yl)propan-2-yl acetate, Compound 130

Compound 130 can be prepared by the selective mild O-acetylation of the secondary hydroxyl groups of Compound 129 with acetic anhydride.

Example 126: 2-Amino-9-((2R,3R,5S)-3-hydroxy-5-((R)-1-hydroxy-2-(methylthio)ethyl)tetrahydrofuran-2-yl)-7-(prop-2-yn-1-yl)-7,9-dihydro-8H-purin-8-one, Compound 131

Compound 131 can be prepared using the procedures described in Example 5 with (21) and (81S).

Example 127: (2R,3R,5S)-5-((R)-1-Acetoxy-2-(methylthio)ethyl)-2-(2-amino-8-oxo-7-(prop-2-yn-1-yl)-7,8-dihydro-9H-purin-9-yl)tetrahydrofuran-3-yl acetate, Compound 132

Compound 132 can be prepared by the selective mild O-acetylation of the secondary hydroxyl groups of Compound 131 with acetic anhydride.

Example 128: 2-Amino-9-((2R,3R,5S)-3-hydroxy-5-((S)-1-hydroxybut-3-yn-1-yl)tetrahydrofuran-2-yl)-7-(prop-2-yn-1-yl)-7,9-dihydro-8H-purin-8-one, Compound 133

Compound 133 can be prepared using the procedures described in Example 5 with (21) and (72S).

Example 129: (S)-1-((2S,4R,5R)-4-Acetoxy-5-(2-amino-8-oxo-7-(prop-2-yn-1-yl)-7,8-dihydro-9H-purin-9-yl)tetrahydrofuran-2-yl)but-3-yn-1-yl acetate, Compound 134

Compound 134 can be prepared by the selective mild O-acetylation of the secondary hydroxyl groups of Compound 133 with acetic anhydride.

Example 130: (S)-1-((2R,3S,4S,5R)-4-Acetoxy-5-(2-amino-8-oxo-7-(prop-2-yn-1-yl)-7,8-dihydro-9H-purin-9-yl)-3-fluorotetrahydrofuran-2-yl)propyl acetate, Compound 135

Compound 135 can be prepared by the selective mild O-acetylation of the secondary hydroxyl groups of Compound 20 with acetic anhydride.

Example 131: 2-Amino-7-(cyclopropylmethyl)-9-((2R,3S,4R,5R)-4-fluoro-3-hydroxy-5-((S)-1-hydroxypropyl)tetrahydrofuran-2-yl)-7,9-dihydro-8H-purin-8-one, Compound 136

Compound 136 can be prepared using the procedures described in Example 4 with (14) and (37S).

Example 132: (S)-1-((2R,3S,4S,5R)-4-Acetoxy-5-(2-amino-7-(cyclopropylmethyl)-8-oxo-7,8-dihydro-9H-purin-9-yl)-3-fluorotetrahydrofuran-2-yl)propyl acetate, Compound 137

Compound 137 can be prepared by the selective mild O-acetylation of the secondary hydroxyl groups of Compound 136 with acetic anhydride.

Example 133: 2-Amino-9-((2R,3S,4R,5R)-4-fluoro-3-hydroxy-5-((S)-1-hydroxypropyl)tetrahydrofuran-2-yl)-7-propyl-7,9-dihydro-8H-purin-8-one, Compound 138

Compound 138 can be prepared using the procedures described in Example 5 with (37S) and where propargyl bromide is substituted with 1-iodopropane.

Example 134: (S)-1-((2R,3S,4S,5R)-4-Acetoxy-5-(2-amino-8-oxo-7-propyl-7,8-dihydro-9H-purin-9-yl)-3-fluorotetrahydrofuran-2-yl)propyl acetate, Compound 139

Compound 139 can be prepared by the selective mild O-acetylation of the secondary hydroxyl groups of Compound 138 with acetic anhydride.

Example 135: 2-Amino-7-butyl-9-((2R,3S,4R,5R)-4-fluoro-3-hydroxy-5-((S)-1-hydroxypropyl)tetrahydrofuran-2-yl)-7,9-dihydro-8H-purin-8-one, Compound 140

Compound 140 can be prepared using the procedures described in Example 5 with (37S) and where propargyl bromide is substituted with 1-bromobutane.

Example 136: (S)-1-((2R,3S,4S,5R)-4-Acetoxy-5-(2-amino-7-butyl-8-oxo-7,8-dihydro-9H-purin-9-yl)-3-fluorotetrahydrofuran-2-yl)propyl acetate, Compound 141

Compound 141 can be prepared by the selective mild O-acetylation of the secondary hydroxyl groups of Compound 140 with acetic anhydride.

Example 137: 2-Amino-9-((2R,3S,4R,5R)-4-fluoro-3-hydroxy-5-((S)-1-hydroxypropyl)tetrahydrofuran-2-yl)-7-(2,2,2-trifluoroethyl)-7,9-dihydro-8H-purin-8-one, Compound 142

Compound 142 can be prepared using the procedures described in Example 5 with (37S) and where propargyl bromide is substituted with 2-bromo-1,1,1-trifluoroethane.

Example 138: (S)-1-((2R,3S,4S,5R)-4-Acetoxy-5-(2-amino-8-oxo-7-(2,2,2-trifluoroethyl)-7,8-dihydro-9H-purin-9-yl)-3-fluorotetrahydrofuran-2-yl)propyl acetate, Compound 143

Compound 143 can be prepared by the selective mild O-acetylation of the secondary hydroxyl groups of Compound 142 with acetic anhydride.

Example 139: 2-Amino-9-((2R,3S,4R,5R)-4-fluoro-3-hydroxy-5-((S)-1-hydroxypropyl)tetrahydrofuran-2-yl)-7-(3,3,3-trifluoropropyl)-7,9-dihydro-8H-purin-8-one, Compound 144

Compound 144 can be prepared using the procedures described in Example 5 with (37S) and where propargyl bromide is substituted with (46).

Example 140: (S)-1-((2R,3S,4S,5R)-4-acetoxy-5-(2-amino-8-oxo-7-(3,3,3-trifluoropropyl)-7,8-dihydro-9H-purin-9-yl)-3-fluorotetrahydrofuran-2-yl)propyl acetate, Compound 145

Compound 145 can be prepared by the selective mild O-acetylation of the secondary hydroxyl groups of Compound 144 with acetic anhydride.

Example 141: 2-Amino-9-((2R,3S,4R,5R)-4-fluoro-3-hydroxy-5-((S)-1-hydroxypropyl)tetrahydrofuran-2-yl)-7-(2-(methylthio)ethyl)-7,9-dihydro-8H-purin-8-one, Compound 146

Compound 146 can be prepared using the procedures described in Example 5 with (37S) and where propargyl bromide is substituted with (2-chloroethyl)(methyl)sulfane.

Example 142: (S)-1-((2R,3S,4S,5R)-4-acetoxy-5-(2-amino-7-(2-(methylthio)ethyl)-8-oxo-7,8-dihydro-9H-purin-9-yl)-3-fluorotetrahydrofuran-2-yl)propyl acetate, Compound 147

Compound 147 can be prepared by the selective mild O-acetylation of the secondary hydroxyl groups of Compound 146 with acetic anhydride.

Example 143: 2-Amino-9-((2R,3S,4R,5R)-4-fluoro-3-hydroxy-5-((R)-2,2,2-trifluoro-1-hydroxyethyl)tetrahydrofuran-2-yl)-7-(prop-2-yn-1-yl)-7,9-dihydro-8H-purin-8-one, Compound 148

Compound 148 can be prepared using the procedures described in Example 5 with (21) and (3S,4S,5R)-5-(1-(benzoyloxy)-2,2,2-trifluoroethyl)-4-fluorotetrahydrofuran-2,3-diyl diacetate.

Example 144: (2R,3S,4S,5R)-5-((R)-1-Acetoxy-2,2,2-trifluoroethyl)-2-(2-amino-8-oxo-7-(prop-2-yn-1-yl)-7,8-dihydro-9H-purin-9-yl)-4-fluorotetrahydrofuran-3-yl acetate, Compound 149

Compound 149 can be prepared by the selective mild O-acetylation of the secondary hydroxyl groups of Compound 148 with acetic anhydride.

Example 145: 2-Amino-7-(cyclopropylmethyl)-9-((2R,3S,4R,5R)-4-fluoro-3-hydroxy-5-((R)-2,2,2-trifluoro-1-hydroxyethyl)tetrahydrofuran-2-yl)-7,9-dihydro-8H-purin-8-one, Compound 150

Compound 150 can be prepared using the procedures described in Example 4 with (14) and (3S,4S,5R)-5-(1-(benzoyloxy)-2,2,2-trifluoroethyl)-4-fluorotetrahydrofuran-2,3-diyl diacetate.

Example 146: (2R,3S,4S,5R)-5-((R)-1-Acetoxy-2,2,2-trifluoroethyl)-2-(2-amino-7-(cyclopropylmethyl)-8-oxo-7,8-dihydro-9H-purin-9-yl)-4-fluorotetrahydrofuran-3-yl acetate, Compound 151

Compound 151 can be prepared by the selective mild O-acetylation of the secondary hydroxyl groups of Compound 150 with acetic anhydride.

Example 147: 2-Amino-9-((2R,3S,4R,5R)-4-fluoro-3-hydroxy-5-((R)-2,2,2-trifluoro-1-hydroxyethyl)tetrahydrofuran-2-yl)-7-propyl-7,9-dihydro-8H-purin-8-one, Compound 152

Compound 152 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is substituted with 1-iodopropane.

Example 148: (2R,3S,4S,5R)-5-((R)-1-Acetoxy-2,2,2-trifluoroethyl)-2-(2-amino-8-oxo-7-propyl-7,8-dihydro-9H-purin-9-yl)-4-fluorotetrahydrofuran-3-yl acetate, Compound 153

Compound 153 can be prepared by the selective mild O-acetylation of the secondary hydroxyl groups of Compound 152 with acetic anhydride.

Example 149: 2-Amino-7-butyl-9-((2R,3S,4R,5R)-4-fluoro-3-hydroxy-5-((R)-2,2,2-trifluoro-1-hydroxyethyl)tetrahydrofuran-2-yl)-7,9-dihydro-8H-purin-8-one, Compound 154

Compound 154 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is substituted with 1-bromobutane.

Example 150: (2R,3S,4S,5R)-5-((R)-1-Acetoxy-2,2,2-trifluoroethyl)-2-(2-amino-7-butyl-8-oxo-7,8-dihydro-9H-purin-9-yl)-4-fluorotetrahydrofuran-3-yl acetate, Compound 155

Compound 155 can be prepared by the selective mild O-acetylation of the secondary hydroxyl groups of Compound 154 with acetic anhydride.

Example 151: 2-Amino-9-((2R,3S,4R,5R)-4-fluoro-3-hydroxy-5-((R)-2,2,2-trifluoro-1-hydroxyethyl)tetrahydrofuran-2-yl)-7-(2,2,2-trifluoroethyl)-7,9-dihydro-8H-purin-8-one, Compound 156

Compound 156 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is substituted with 2-bromo-1,1,1-trifluoroethane.

Example 152: (2R,3S,4S,5R)-5-((R)-1-acetoxy-2,2,2-trifluoroethyl)-2-(2-amino-8-oxo-7-(2,2,2-trifluoroethyl)-7,8-dihydro-9H-purin-9-yl)-4-fluorotetrahydrofuran-3-yl acetate, Compound 157

Compound 157 can be prepared by the selective mild O-acetylation of the secondary hydroxyl groups of Compound 156 with acetic anhydride.

Example 153: 2-Amino-9-((2R,3S,4R,5R)-4-fluoro-3-hydroxy-5-((R)-2,2,2-trifluoro-1-hydroxyethyl)tetrahydrofuran-2-yl)-7-(3,3,3-trifluoropropyl)-7,9-dihydro-8H-purin-8-one, Compound 158

Compound 158 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is substituted with (46).

Example 154: (2R,3S,4S,5R)-5-((R)-1-Acetoxy-2,2,2-trifluoroethyl)-2-(2-amino-8-oxo-7-(3,3,3-trifluoropropyl)-7,8-dihydro-9H-purin-9-yl)-4-fluorotetrahydrofuran-3-yl acetate, Compound 159

Compound 159 can be prepared by the selective mild O-acetylation of the secondary hydroxyl groups of Compound 158 with acetic anhydride.

Example 155: (S)-1-((2R,3S,4S,5R)-4-Acetoxy-5-(2-amino-6-methoxy-8-oxo-7-propyl-7,8-dihydro-9H-purin-9-yl)-3-fluorotetrahydrofuran-2-yl)propyl acetate, Compound 160

Compound 160 can be prepared by the selective mild O-acetylation of the secondary hydroxyl groups of Compound 47 with acetic anhydride.

Example 156: (S)-1-((2R,3S,4S,5R)-4-Acetoxy-5-(2-amino-7-butyl-6-methoxy-8-oxo-7,8-dihydro-9H-purin-9-yl)-3-fluorotetrahydrofuran-2-yl)propyl acetate, Compound 161

Compound 161 can be prepared by the selective mild O-acetylation of the secondary hydroxyl groups of Compound 48 with acetic anhydride.

Example 157: 2-Amino-9-((2R,3S,4R,5R)-4-fluoro-3-hydroxy-5-((S)-1-hydroxypropyl)tetrahydrofuran-2-yl)-6-methoxy-7-(prop-2-yn-1-yl)-7,9-dihydro-8H-purin-8-one, Compound 162

Compound 162 can be prepared using the procedures described in Example 43 with (37S) and (2) where 1-bromobutane is replaced with propargyl bromide.

Example 158: (S)-1-((2R,3S,4S,5R)-4-Acetoxy-5-(2-amino-6-methoxy-8-oxo-7-(prop-2-yn-1-yl)-7,8-dihydro-9H-purin-9-yl)-3-fluorotetrahydrofuran-2-yl)propyl acetate, Compound 163

Compound 163 can be prepared by the selective mild O-acetylation of the secondary hydroxyl groups of Compound 162 with acetic anhydride.

Example 159: 2-Amino-7-(cyclopropylmethyl)-9-((2R,3S,4R,5R)-4-fluoro-3-hydroxy-5-((S)-1-hydroxypropyl)tetrahydrofuran-2-yl)-6-methoxy-7,9-dihydro-8H-purin-8-one, Compound 164

Compound 164 can be prepared using the procedures described in Example 42 with (9) and (37S).

Example 160: (S)-1-((2R,3S,4S,5R)-4-Acetoxy-5-(2-amino-7-(cyclopropylmethyl)-6-methoxy-8-oxo-7,8-dihydro-9H-purin-9-yl)-3-fluorotetrahydrofuran-2-yl)propyl acetate, Compound 165

Compound 165 can be prepared by the selective mild O-acetylation of the secondary hydroxyl groups of Compound 164 with acetic anhydride.

Example 161: 2-Amino-9-((2R,3S,4R,5R)-4-fluoro-3-hydroxy-5-((S)-1-hydroxypropyl)tetrahydrofuran-2-yl)-6-methoxy-7-(2,2,2-trifluoroethyl)-7,9-dihydro-8H-purin-8-one, Compound 166

Compound 166 can be prepared using the procedures described in Example 43 with (37S) and (2) where 1-bromobutane is replaced with 2-bromo-1,1,1-trifluoroethane.

Example 162: (S)-1-((2R,3S,4S,5R)-4-Acetoxy-5-(2-amino-6-methoxy-8-oxo-7-(2,2,2-trifluoroethyl)-7,8-dihydro-9H-purin-9-yl)-3-fluorotetrahydrofuran-2-yl)propyl acetate, Compound 167

Compound 167 can be prepared by the selective mild O-acetylation of the secondary hydroxyl groups of Compound 166 with acetic anhydride.

Example 163: 2-Amino-9-((2R,3S,4R,5R)-4-fluoro-3-hydroxy-5-((S)-1-hydroxypropyl)tetrahydrofuran-2-yl)-6-methoxy-7-(3,3,3-trifluoropropyl)-7,9-dihydro-8H-purin-8-one, Compound 168

Compound 168 can be prepared using the procedures described in Example 43 with (37S) and (2) where 1-bromobutane is replaced with (46).

Example 164: (S)-1-((2R,3S,4S,5R)-4-Acetoxy-5-(2-amino-6-methoxy-8-oxo-7-(3,3,3-trifluoropropyl)-7,8-dihydro-9H-purin-9-yl)-3-fluorotetrahydrofuran-2-yl)propyl acetate, Compound 169

Compound 169 can be prepared by the selective mild O-acetylation of the secondary hydroxyl groups of Compound 168 with acetic anhydride.

Example 165: 2-Amino-9-((2R,3R,5S)-3-hydroxy-5-((S)-1-hydroxypropyl)tetrahydrofuran-2-yl)-6-methoxy-7-(prop-2-yn-1-yl)-7,9-dihydro-8H-purin-8-one, Compound 170

Compound 170 can be prepared using the procedures described in Example 43 with (14S) and (2) where 1-bromobutane is replaced with propargyl bromide.

Example 166: (S)-1-((2S,4R,5R)-4-Acetoxy-5-(2-amino-6-methoxy-8-oxo-7-(prop-2-yn-1-yl)-7,8-dihydro-9H-purin-9-yl)tetrahydrofuran-2-yl)propyl acetate, Compound 171

Compound 171 can be prepared by the selective mild O-acetylation of the secondary hydroxyl groups of Compound 170 with acetic anhydride.

Example 167: 2-Amino-7-(cyclopropylmethyl)-9-((2R,3R,5S)-3-hydroxy-5-((S)-1-hydroxypropyl)tetrahydrofuran-2-yl)-6-methoxy-7,9-dihydro-8H-purin-8-one, Compound 172

Compound 172 can be prepared using the procedures described in Example 42 with (9) and (14S).

Example 168: (S)-1-((2S,4R,5R)-4-Acetoxy-5-(2-amino-7-(cyclopropylmethyl)-6-methoxy-8-oxo-7,8-dihydro-9H-purin-9-yl)tetrahydrofuran-2-yl)propyl acetate, Compound 173

Compound 173 can be prepared by the selective mild O-acetylation of the secondary hydroxyl groups of Compound 172 with acetic anhydride.

Example 169: 2-Amino-9-((2R,3R,5S)-3-hydroxy-5-((S)-1-hydroxypropyl)tetrahydrofuran-2-yl)-6-methoxy-7-propyl-7,9-dihydro-8H-purin-8-one, Compound 174

Compound 174 can be prepared using the procedures described in Example 42 with (14S) and (80).

Example 170: (S)-1-((2S,4R,5R)-4-Acetoxy-5-(2-amino-6-methoxy-8-oxo-7-propyl-7,8-dihydro-9H-purin-9-yl)tetrahydrofuran-2-yl)propyl acetate, Compound 175

Compound 175 can be prepared by the selective mild O-acetylation of the secondary hydroxyl groups of Compound 174 with acetic anhydride.

Example 171: 2-Amino-7-butyl-9-((2R,3R,5S)-3-hydroxy-5-((S)-1-hydroxypropyl)tetrahydrofuran-2-yl)-6-methoxy-7,9-dihydro-8H-purin-8-one, Compound 176

Compound 176 can be prepared using the procedures described in Example 43 with (14S) and (84).

Example 172: (S)-1-((2S,4R,5R)-4-Acetoxy-5-(2-amino-7-butyl-6-methoxy-8-oxo-7,8-dihydro-9H-purin-9-yl)tetrahydrofuran-2-yl)propyl acetate, Compound 177

Compound 177 can be prepared by the selective mild O-acetylation of the secondary hydroxyl groups of Compound 176 with acetic anhydride.

Example 173: 2-Amino-9-((2R,3R,5S)-3-hydroxy-5-((S)-1-hydroxypropyl)tetrahydrofuran-2-yl)-6-methoxy-7-(2,2,2-trifluoroethyl)-7,9-dihydro-8H-purin-8-one, Compound 178

Compound 178 can be prepared using the procedures described in Example 43 with (14S) and (2) where 1-bromobutane is replaced with 2-bromo-1,1,1-trifluoroethane.

Example 174: (S)-1-((2S,4R,5R)-4-Acetoxy-5-(2-amino-6-methoxy-8-oxo-7-(2,2,2-trifluoroethyl)-7,8-dihydro-9H-purin-9-yl)tetrahydrofuran-2-yl)propyl acetate, Compound 179

Compound 179 can be prepared by the selective mild O-acetylation of the secondary hydroxyl groups of Compound 178 with acetic anhydride.

Example 175: 2-Amino-9-((2R,3R,5S)-3-hydroxy-5-((S)-1-hydroxypropyl)tetrahydrofuran-2-yl)-6-methoxy-7-(3,3,3-trifluoropropyl)-7,9-dihydro-8H-purin-8-one, Compound 180

Compound 180 can be prepared using the procedures described in Example 43 with (14S) and (2) where 1-bromobutane is replaced with (46).

Example 176: (S)-1-((2S,4R,5R)-4-Acetoxy-5-(2-amino-6-methoxy-8-oxo-7-(3,3,3-trifluoropropyl)-7,8-dihydro-9H-purin-9-yl)tetrahydrofuran-2-yl)propyl acetate, Compound 181

Compound 181 can be prepared by the selective mild O-acetylation of the secondary hydroxyl groups of Compound 180 with acetic anhydride.

Example 177: 2-Amino-9-((2R,3R,5S)-3-hydroxy-5-((R)-2,2,2-trifluoro-1-hydroxyethyl)tetrahydrofuran-2-yl)-6-methoxy-7-(prop-2-yn-1-yl)-7,9-dihydro-8H-purin-8-one, Compound 182

Compound 182 can be prepared using the procedures described in Example 43 with (22S) and (2) where 1-bromobutane is replaced with propargyl bromide.

Example 178: (2R,3R,5S)-5-((R)-1-Acetoxy-2,2,2-trifluoroethyl)-2-(2-amino-6-methoxy-8-oxo-7-(prop-2-yn-1-yl)-7,8-dihydro-9H-purin-9-yl)tetrahydrofuran-3-yl acetate, Compound 183

Compound 183 can be prepared by the selective mild O-acetylation of the secondary hydroxyl groups of Compound 182 with acetic anhydride.

Example 179: 2-Amino-7-(cyclopropylmethyl)-9-((2R,3R,5S)-3-hydroxy-5-((R)-2,2,2-trifluoro-1-hydroxyethyl)tetrahydrofuran-2-yl)-6-methoxy-7,9-dihydro-8H-purin-8-one, Compound 184

Compound 184 can be prepared using the procedures described in Example 42 with (9) and (22S).

Example 180: (2R,3R,5S)-5-((R)-1-Acetoxy-2,2,2-trifluoroethyl)-2-(2-amino-7-(cyclopropylmethyl)-6-methoxy-8-oxo-7,8-dihydro-9H-purin-9-yl)tetrahydrofuran-3-yl acetate, Compound 185

Compound 185 can be prepared by the selective mild O-acetylation of the secondary hydroxyl groups of Compound 184 with acetic anhydride.

Example 181: 2-Amino-9-((2R,3R,5S)-3-hydroxy-5-((R)-2,2,2-trifluoro-1-hydroxyethyl)tetrahydrofuran-2-yl)-6-methoxy-7-propyl-7,9-dihydro-8H-purin-8-one, Compound 186

Compound 186 can be prepared using the procedures described in Example 42 with (22S) and (80).

Example 182: (2R,3R,5S)-5-((R)-1-Acetoxy-2,2,2-trifluoroethyl)-2-(2-amino-6-methoxy-8-oxo-7-propyl-7,8-dihydro-9H-purin-9-yl)tetrahydrofuran-3-yl acetate, Compound 187

Compound 187 can be prepared by the selective mild O-acetylation of the secondary hydroxyl groups of Compound 186 with acetic anhydride.

Example 183: 2-Amino-7-butyl-9-((2R,3R,5S)-3-hydroxy-5-((R)-2,2,2-trifluoro-1-hydroxyethyl)tetrahydrofuran-2-yl)-6-methoxy-7,9-dihydro-8H-purin-8-one, Compound 188

Compound 188 can be prepared using the procedures described in Example 43 with (22S) and (84).

Example 184: (2R,3R,5S)-5-((R)-1-Acetoxy-2,2,2-trifluoroethyl)-2-(2-amino-7-butyl-6-methoxy-8-oxo-7,8-dihydro-9H-purin-9-yl)tetrahydrofuran-3-yl acetate, Compound 189

Compound 189 can be prepared by the selective mild O-acetylation of the secondary hydroxyl groups of Compound 188 with acetic anhydride.

Example 185: 2-Amino-9-((2R,3R,5S)-3-hydroxy-5-((R)-2,2,2-trifluoro-1-hydroxyethyl)tetrahydrofuran-2-yl)-6-methoxy-7-(2,2,2-trifluoroethyl)-7,9-dihydro-8H-purin-8-one, Compound 190

Compound 190 can be prepared using the procedures described in Example 43 with (22S) and (2) where 1-bromobutane is replaced with 2-bromo-1,1,1-trifluoroethane.

Example 186: (2R,3R,5S)-5-((R)-1-Acetoxy-2,2,2-trifluoroethyl)-2-(2-amino-6-methoxy-8-oxo-7-(2,2,2-trifluoroethyl)-7,8-dihydro-9H-purin-9-yl)tetrahydrofuran-3-yl acetate, Compound 191

Compound 191 can be prepared by the selective mild O-acetylation of the secondary hydroxyl groups of Compound 190 with acetic anhydride.

Example 187: 2-Amino-9-((2R,3R,5S)-3-hydroxy-5-((R)-2,2,2-trifluoro-1-hydroxyethyl)tetrahydrofuran-2-yl)-6-methoxy-7-(3,3,3-trifluoropropyl)-7,9-dihydro-8H-purin-8-one, Compound 192

Compound 192 can be prepared using the procedures described in Example 43 with (22S) and (2) where 1-bromobutane is replaced with (46).

Example 188: (2R,3R,5S)-5-((R)-1-Acetoxy-2,2,2-trifluoroethyl)-2-(2-amino-6-methoxy-8-oxo-7-(3,3,3-trifluoropropyl)-7,8-dihydro-9H-purin-9-yl)tetrahydrofuran-3-yl acetate, Compound 193

Compound 193 can be prepared by the selective mild O-acetylation of the secondary hydroxyl groups of Compound 192 with acetic anhydride.

Example 189: 2-Amino-9-((2R,3S,4R,5R)-4-fluoro-3-hydroxy-5-((R)-2,2,2-trifluoro-1-hydroxyethyl)tetrahydrofuran-2-yl)-6-methoxy-7-(prop-2-yn-1-yl)-7,9-dihydro-8H-purin-8-one, Compound 194

Compound 194 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with propargyl bromide.

Example 190: (2R,3S,4S,5R)-5-((R)-1-Acetoxy-2,2,2-trifluoroethyl)-2-(2-amino-6-methoxy-8-oxo-7-(prop-2-yn-1-yl)-7,8-dihydro-9H-purin-9-yl)-4-fluorotetrahydrofuran-3-yl acetate, Compound 195

Compound 195 can be prepared by the selective mild O-acetylation of the secondary hydroxyl groups of Compound 194 with acetic anhydride.

Example 191: 2-Amino-7-(cyclopropylmethyl)-9-((2R,3S,4R,5R)-4-fluoro-3-hydroxy-5-((R)-2,2,2-trifluoro-1-hydroxyethyl)tetrahydrofuran-2-yl)-6-methoxy-7,9-dihydro-8H-purin-8-one, Compound 196

Compound 196 can be prepared using the procedures described in Example 42 with (9) and (3S,4S,5R)-5-(1-(benzoyloxy)-2,2,2-trifluoroethyl)-4-fluorotetrahydrofuran-2,3-diyl diacetate.

Example 192: (2R,3S,4S,5R)-5-((R)-1-Acetoxy-2,2,2-trifluoroethyl)-2-(2-amino-7-(cyclopropylmethyl)-6-methoxy-8-oxo-7,8-dihydro-9H-purin-9-yl)-4-fluorotetrahydrofuran-3-yl acetate, Compound 197

Compound 197 can be prepared by the selective mild O-acetylation of the secondary hydroxyl groups of Compound 196 with acetic anhydride.

Example 193: 2-Amino-9-((2R,3S,4R,5R)-4-fluoro-3-hydroxy-5-((R)-2,2,2-trifluoro-1-hydroxyethyl)tetrahydrofuran-2-yl)-6-methoxy-7-propyl-7,9-dihydro-8H-purin-8-one, Compound 198

Compound 198 can be prepared using the procedures described in Example 42 with (3S,4S,5R)-5-(1-(benzoyloxy)-2,2,2-trifluoroethyl)-4-fluorotetrahydrofuran-2,3-diyl diacetate and (80).

Example 194: (2R,3S,4S,5R)-5-((R)-1-Acetoxy-2,2,2-trifluoroethyl)-2-(2-amino-6-methoxy-8-oxo-7-propyl-7,8-dihydro-9H-purin-9-yl)-4-fluorotetrahydrofuran-3-yl acetate, Compound 199

Compound 199 can be prepared by the selective mild O-acetylation of the secondary hydroxyl groups of Compound 198 with acetic anhydride.

Example 195: 2-Amino-7-butyl-9-((2R,3S,4R,5R)-4-fluoro-3-hydroxy-5-((R)-2,2,2-trifluoro-1-hydroxyethyl)tetrahydrofuran-2-yl)-6-methoxy-7,9-dihydro-8H-purin-8-one, Compound 200

Compound 200 can be prepared using the procedures described in Example 43 with (3S,4S,5R)-5-(1-(benzoyloxy)-2,2,2-trifluoroethyl)-4-fluorotetrahydrofuran-2,3-diyl diacetate and (84).

Example 196: (2R,3S,4S,5R)-5-((R)-1-Acetoxy-2,2,2-trifluoroethyl)-2-(2-amino-7-butyl-6-methoxy-8-oxo-7,8-dihydro-9H-purin-9-yl)-4-fluorotetrahydrofuran-3-yl acetate, Compound 201

Compound 201 can be prepared by the selective mild O-acetylation of the secondary hydroxyl groups of Compound 200 with acetic anhydride.

Example 197: 2-Amino-9-((2R,3S,4R,5R)-4-fluoro-3-hydroxy-5-((R)-2,2,2-trifluoro-1-hydroxyethyl)tetrahydrofuran-2-yl)-6-methoxy-7-(2,2,2-trifluoroethyl)-7,9-dihydro-8H-purin-8-one, Compound 202

Compound 202 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with 2-bromo-1,1,1-trifluoroethane.

Example 198: (2R,3S,4S,5R)-5-((R)-1-Acetoxy-2,2,2-trifluoroethyl)-2-(2-amino-6-methoxy-8-oxo-7-(2,2,2-trifluoroethyl)-7,8-dihydro-9H-purin-9-yl)-4-fluorotetrahydrofuran-3-yl acetate, Compound 203

Compound 203 can be prepared by the selective mild O-acetylation of the secondary hydroxyl groups of Compound 202 with acetic anhydride.

Example 199: 2-Amino-9-((2R,3S,4R,5R)-4-fluoro-3-hydroxy-5-((R)-2,2,2-trifluoro-1-hydroxyethyl)tetrahydrofuran-2-yl)-6-methoxy-7-(3,3,3-trifluoropropyl)-7,9-dihydro-8H-purin-8-one, Compound 204

Compound 204 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with (46).

Example 200: (2R,3S,4S,5R)-5-((R)-1-Acetoxy-2,2,2-trifluoroethyl)-2-(2-amino-6-methoxy-8-oxo-7-(3,3,3-trifluoropropyl)-7,8-dihydro-9H-purin-9-yl)-4-fluorotetrahydrofuran-3-yl acetate, Compound 205

Compound 205 can be prepared by the selective mild O-acetylation of the secondary hydroxyl groups of Compound 204 with acetic anhydride.

Example 201: 2-Amino-6-chloro-9-((2R,3R,5S)-3-hydroxy-5-((S)-1-hydroxypropyl)tetrahydrofuran-2-yl)-7-(prop-2-yn-1-yl)-7,9-dihydro-8H-purin-8-one, Compound 206

Compound 206 can be prepared using the procedures described in Example 43 with (14S) and (2) where 1-bromobutane is replaced with propargyl bromide and Step 3 using sodium methoxide is omitted.

Example 202: (S)-1-((2S,4R,5R)-4-acetoxy-5-(2-amino-6-chloro-8-oxo-7-(prop-2-yn-1-yl)-7,8-dihydro-9H-purin-9-yl)tetrahydrofuran-2-yl)propyl acetate, Compound 207

Compound 207 can be prepared by the selective mild O-acetylation of the secondary hydroxyl groups of Compound 206 with acetic anhydride.

Example 203: 2-Amino-6-chloro-7-(cyclopropylmethyl)-9-((2R,3R,5S)-3-hydroxy-5-((S)-1-hydroxypropyl)tetrahydrofuran-2-yl)-7,9-dihydro-8H-purin-8-one, Compound 208

Compound 208 can be prepared using the procedures described in Example 43 with (14S) and (9) where Step 3 using sodium methoxide is omitted.

Example 204: (S)-1-((2S,4R,5R)-4-acetoxy-5-(2-amino-6-chloro-7-(cyclopropylmethyl)-8-oxo-7,8-dihydro-9H-purin-9-yl)tetrahydrofuran-2-yl)propyl acetate, Compound 209

Compound 209 can be prepared by the selective mild O-acetylation of the secondary hydroxyl groups of Compound 208 with acetic anhydride.

Example 205: 2-Amino-6-chloro-9-((2R,3R,5S)-3-hydroxy-5-((S)-1-hydroxypropyl)tetrahydrofuran-2-yl)-7-propyl-7,9-dihydro-8H-purin-8-one, Compound 210

Compound 210 can be prepared using the procedures described in Example 43 with (14S) and (2) where 1-bromobutane is replaced with 1-iodopropane and Step 3 using sodium methoxide is omitted.

Example 206: (S)-1-((2S,4R,5R)-4-Acetoxy-5-(2-amino-6-chloro-8-oxo-7-propyl-7,8-dihydro-9H-purin-9-yl)tetrahydrofuran-2-yl)propyl acetate, Compound 211

Compound 211 can be prepared by the selective mild O-acetylation of the secondary hydroxyl groups of Compound 210 with acetic anhydride.

Example 207: 2-Amino-7-butyl-6-chloro-9-((2R,3R,5S)-3-hydroxy-5-((S)-1-hydroxypropyl)tetrahydrofuran-2-yl)-7,9-dihydro-8H-purin-8-one, Compound 212

Compound 212 can be prepared using the procedures described in Example 43 with (14S) and (83) where Step 3 using sodium methoxide is omitted.

Example 208: (S)-1-((2S,4R,5R)-4-Acetoxy-5-(2-amino-7-butyl-6-chloro-8-oxo-7,8-dihydro-9H-purin-9-yl)tetrahydrofuran-2-yl)propyl acetate, Compound 213

Compound 213 can be prepared by the selective mild O-acetylation of the secondary hydroxyl groups of Compound 212 with acetic anhydride.

Example 209: 2-Amino-6-chloro-9-((2R,3R,5S)-3-hydroxy-5-((S)-1-hydroxypropyl)tetrahydrofuran-2-yl)-7-(2,2,2-trifluoroethyl)-7,9-dihydro-8H-purin-8-one, Compound 214

Compound 214 can be prepared using the procedures described in Example 43 with (14S) and (2) where 1-bromobutane is replaced with 2-bromo-1,1,1-trifluoroethane and Step 3 using sodium methoxide is omitted.

Example 210: (S)-1-((2S,4R,5R)-4-Acetoxy-5-(2-amino-6-chloro-8-oxo-7-(2,2,2-trifluoroethyl)-7,8-dihydro-9H-purin-9-yl)tetrahydrofuran-2-yl)propyl acetate, Compound 215

Compound 215 can be prepared by the selective mild O-acetylation of the secondary hydroxyl groups of Compound 214 with acetic anhydride.

Example 211: 2-Amino-6-chloro-9-((2R,3R,5S)-3-hydroxy-5-((S)-1-hydroxypropyl)tetrahydrofuran-2-yl)-7-(3,3,3-trifluoropropyl)-7,9-dihydro-8H-purin-8-one, Compound 216

Compound 216 can be prepared using the procedures described in Example 43 with (14S) and (2) where 1-bromobutane is replaced with (46) and Step 3 using sodium methoxide is omitted.

Example 212: (S)-1-((2S,4R,5R)-4-Acetoxy-5-(2-amino-6-chloro-8-oxo-7-(3,3,3-trifluoropropyl)-7,8-dihydro-9H-purin-9-yl)tetrahydrofuran-2-yl)propyl acetate, Compound 217

Compound 217 can be prepared by the selective mild O-acetylation of the secondary hydroxyl groups of Compound 216 with acetic anhydride.

Example 213: 2-Amino-6-chloro-9-((2R,3S,4R,5R)-4-fluoro-3-hydroxy-5-((S)-1-hydroxypropyl)tetrahydrofuran-2-yl)-7-(prop-2-yn-1-yl)-7,9-dihydro-8H-purin-8-one, Compound 218

Compound 218 can be prepared using the procedures described in Example 43 with (37S) and (2) where 1-bromobutane is replaced with propargyl bromide and Step 3 using sodium methoxide is omitted.

Example 214: (S)-1-((2R,3S,4S,5R)-4-Acetoxy-5-(2-amino-6-chloro-8-oxo-7-(prop-2-yn-1-yl)-7,8-dihydro-9H-purin-9-yl)-3-fluorotetrahydrofuran-2-yl)propyl acetate, Compound 219

Compound 219 can be prepared by the selective mild O-acetylation of the secondary hydroxyl groups of Compound 218 with acetic anhydride.

Example 215: 2-Amino-6-chloro-7-(cyclopropylmethyl)-9-((2R,3S,4R,5R)-4-fluoro-3-hydroxy-5-((S)-1-hydroxypropyl)tetrahydrofuran-2-yl)-7,9-dihydro-8H-purin-8-one, Compound 220

Compound 220 can be prepared using the procedures described in Example 43 with (37S) and (9) where Step 3 using sodium methoxide is omitted.

Example 216: (S)-1-((2R,3S,4S,5R)-4-Acetoxy-5-(2-amino-6-chloro-7-(cyclopropylmethyl)-8-oxo-7,8-dihydro-9H-purin-9-yl)-3-fluorotetrahydrofuran-2-yl)propyl acetate, Compound 221

Compound 221 can be prepared by the selective mild O-acetylation of the secondary hydroxyl groups of Compound 220 with acetic anhydride.

Example 217: 2-Amino-6-chloro-9-((2R,3S,4R,5R)-4-fluoro-3-hydroxy-5-((S)-1-hydroxypropyl)tetrahydrofuran-2-yl)-7-propyl-7,9-dihydro-8H-purin-8-one, Compound 222

Compound 222 can be prepared using the procedures described in Example 43 with (37S) and (2) where 1-bromobutane is replaced with 1-iodopropane and Step 3 using sodium methoxide is omitted.

Example 218: (S)-1-((2R,3S,4S,5R)-4-Acetoxy-5-(2-amino-6-chloro-8-oxo-7-propyl-7,8-dihydro-9H-purin-9-yl)-3-fluorotetrahydrofuran-2-yl)propyl acetate, Compound 223

Compound 223 can be prepared by the selective mild O-acetylation of the secondary hydroxyl groups of Compound 222 with acetic anhydride.

Example 219: 2-Amino-7-butyl-6-chloro-9-((2R,3S,4R,5R)-4-fluoro-3-hydroxy-5-((S)-1-hydroxypropyl)tetrahydrofuran-2-yl)-7,9-dihydro-8H-purin-8-one, Compound 224

Compound 224 can be prepared using the procedures described in Example 43 with (37S) and (83) where Step 3 using sodium methoxide is omitted.

Example 220: (S)-1-((2R,3S,4S,5R)-4-Acetoxy-5-(2-amino-7-butyl-6-chloro-8-oxo-7,8-dihydro-9H-purin-9-yl)-3-fluorotetrahydrofuran-2-yl)propyl acetate, Compound 225

Compound 225 can be prepared by the selective mild O-acetylation of the secondary hydroxyl groups of Compound 224 with acetic anhydride.

Example 221: 2-Amino-6-chloro-9-((2R,3S,4R,5R)-4-fluoro-3-hydroxy-5-((S)-1-hydroxypropyl)tetrahydrofuran-2-yl)-7-(2,2,2-trifluoroethyl)-7,9-dihydro-8H-purin-8-one, Compound 226

Compound 226 can be prepared using the procedures described in Example 43 with (37S) and (2) where 1-bromobutane is replaced with 2-bromo-1,1,1-trifluoroethane and Step 3 using sodium methoxide is omitted.

Example 222: (S)-1-((2R,3S,4S,5R)-4-Acetoxy-5-(2-amino-6-chloro-8-oxo-7-(2,2,2-trifluoroethyl)-7,8-dihydro-9H-purin-9-yl)-3-fluorotetrahydrofuran-2-yl)propyl acetate, Compound 227

Compound 227 can be prepared by the selective mild O-acetylation of the secondary hydroxyl groups of Compound 226 with acetic anhydride.

Example 223: 2-Amino-6-chloro-9-((2R,3S,4R,5R)-4-fluoro-3-hydroxy-5-((S)-1-hydroxypropyl)tetrahydrofuran-2-yl)-7-(3,3,3-trifluoropropyl)-7,9-dihydro-8H-purin-8-one, Compound 228

Compound 228 can be prepared using the procedures described in Example 43 with (37S) and (2) where 1-bromobutane is replaced with (46) and Step 3 using sodium methoxide is omitted.

Example 224: (S)-1-((2R,3S,4S,5R)-4-Acetoxy-5-(2-amino-6-chloro-8-oxo-7-(3,3,3-trifluoropropyl)-7,8-dihydro-9H-purin-9-yl)-3-fluorotetrahydrofuran-2-yl)propyl acetate, Compound 229

Compound 229 can be prepared by the selective mild O-acetylation of the secondary hydroxyl groups of Compound 228 with acetic anhydride.

Example 225: 2-Amino-6-chloro-9-((2R,3R,5S)-3-hydroxy-5-((R)-2,2,2-trifluoro-1-hydroxyethyl)tetrahydrofuran-2-yl)-7-(prop-2-yn-1-yl)-7,9-dihydro-8H-purin-8-one, Compound 230

Compound 230 can be prepared using the procedures described in Example 43 with (22S) and (2) where 1-bromobutane is replaced with propargyl bromide and Step 3 using sodium methoxide is omitted.

Example 226: (2R,3R,5S)-5-((R)-1-Acetoxy-2,2,2-trifluoroethyl)-2-(2-amino-6-chloro-8-oxo-7-(prop-2-yn-1-yl)-7,8-dihydro-9H-purin-9-yl)tetrahydrofuran-3-yl acetate, Compound 231

Compound 231 can be prepared by the selective mild O-acetylation of the secondary hydroxyl groups of Compound 230 with acetic anhydride.

Example 227: 2-Amino-6-chloro-7-(cyclopropylmethyl)-9-((2R,3R,5S)-3-hydroxy-5-((R)-2,2,2-trifluoro-1-hydroxyethyl)tetrahydrofuran-2-yl)-7,9-dihydro-8H-purin-8-one, Compound 232

Compound 232 can be prepared using the procedures described in Example 43 with (22S) and (9) where Step 3 using sodium methoxide is omitted.

Example 228: (2R,3R,5S)-5-((R)-1-Acetoxy-2,2,2-trifluoroethyl)-2-(2-amino-6-chloro-7-(cyclopropylmethyl)-8-oxo-7,8-dihydro-9H-purin-9-yl)tetrahydrofuran-3-yl acetate, Compound 233

Compound 233 can be prepared by the selective mild O-acetylation of the secondary hydroxyl groups of Compound 232 with acetic anhydride.

Example 229: 2-Amino-6-chloro-9-((2R,3R,5S)-3-hydroxy-5-((R)-2,2,2-trifluoro-1-hydroxyethyl)tetrahydrofuran-2-yl)-7-propyl-7,9-dihydro-8H-purin-8-one, Compound 234

Compound 234 can be prepared using the procedures described in Example 43 with (22S) and (2) where 1-bromobutane is replaced with 1-iodopropane and Step 3 using sodium methoxide is omitted.

Example 230: (2R,3R,5S)-5-((R)-1-Acetoxy-2,2,2-trifluoroethyl)-2-(2-amino-6-chloro-8-oxo-7-propyl-7,8-dihydro-9H-purin-9-yl)tetrahydrofuran-3-yl acetate, Compound 235

Compound 235 can be prepared by the selective mild O-acetylation of the secondary hydroxyl groups of Compound 234 with acetic anhydride.

Example 231: 2-Amino-7-butyl-6-chloro-9-((2R,3R,5S)-3-hydroxy-5-((R)-2,2,2-trifluoro-1-hydroxyethyl)tetrahydrofuran-2-yl)-7,9-dihydro-8H-purin-8-one, Compound 236

Compound 236 can be prepared using the procedures described in Example 43 with (22S) and (83) where Step 3 using sodium methoxide is omitted.

Example 232: (2R,3R,5S)-5-((R)-1-Acetoxy-2,2,2-trifluoroethyl)-2-(2-amino-7-butyl-6-chloro-8-oxo-7,8-dihydro-9H-purin-9-yl)tetrahydrofuran-3-yl acetate, Compound 237

Compound 237 can be prepared by the selective mild O-acetylation of the secondary hydroxyl groups of Compound 236 with acetic anhydride.

Example 233: 2-Amino-6-chloro-9-((2R,3R,5S)-3-hydroxy-5-((R)-2,2,2-trifluoro-1-hydroxyethyl)tetrahydrofuran-2-yl)-7-(2,2,2-trifluoroethyl)-7,9-dihydro-8H-purin-8-one, Compound 238

Compound 238 can be prepared using the procedures described in Example 43 with (22S) and (2) where 1-bromobutane is replaced with 2-bromo-1,1,1-trifluoroethane and Step 3 using sodium methoxide is omitted.

Example 234: (2R,3R,5S)-5-((R)-1-Acetoxy-2,2,2-trifluoroethyl)-2-(2-amino-6-chloro-8-oxo-7-(2,2,2-trifluoroethyl)-7,8-dihydro-9H-purin-9-yl)tetrahydrofuran-3-yl acetate, Compound 239

Compound 239 can be prepared by the selective mild O-acetylation of the secondary hydroxyl groups of Compound 238 with acetic anhydride.

Example 235: 2-Amino-6-chloro-9-((2R,3R,5S)-3-hydroxy-5-((R)-2,2,2-trifluoro-1-hydroxyethyl)tetrahydrofuran-2-yl)-7-(3,3,3-trifluoropropyl)-7,9-dihydro-8H-purin-8-one, Compound 240

Compound 240 can be prepared using the procedures described in Example 43 with (22S) and (2) where 1-bromobutane is replaced with (46) and Step 3 using sodium methoxide is omitted.

Example 236: (2R,3R,5S)-5-((R)-1-Acetoxy-2,2,2-trifluoroethyl)-2-(2-amino-6-chloro-8-oxo-7-(3,3,3-trifluoropropyl)-7,8-dihydro-9H-purin-9-yl)tetrahydrofuran-3-yl acetate, Compound 241

Compound 241 can be prepared by the selective mild O-acetylation of the secondary hydroxyl groups of Compound 240 with acetic anhydride.

Example 237: 2-Amino-6-chloro-9-((2R,3S,4R,5R)-4-fluoro-3-hydroxy-5-((R)-2,2,2-trifluoro-1-hydroxyethyl)tetrahydrofuran-2-yl)-7-(prop-2-yn-1-yl)-7,9-dihydro-8H-purin-8-one, Compound 242

Compound 242 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with propargyl bromide and Step 3 using sodium methoxide is omitted.

Example 238: (2R,3S,4S,5R)-5-((R)-1-Acetoxy-2,2,2-trifluoroethyl)-2-(2-amino-6-chloro-8-oxo-7-(prop-2-yn-1-yl)-7,8-dihydro-9H-purin-9-yl)-4-fluorotetrahydrofuran-3-yl acetate, Compound 243

Compound 243 can be prepared by the selective mild O-acetylation of the secondary hydroxyl groups of Compound 242 with acetic anhydride.

Example 239: 2-Amino-6-chloro-7-(cyclopropylmethyl)-9-((2R,3S,4R,5R)-4-fluoro-3-hydroxy-5-((R)-2,2,2-trifluoro-1-hydroxyethyl)tetrahydrofuran-2-yl)-7,9-dihydro-8H-purin-8-one, Compound 244

Compound 244 can be prepared using the procedures described in Example 43 with (3S,4S,5R)-5-(1-(benzoyloxy)-2,2,2-trifluoroethyl)-4-fluorotetrahydrofuran-2,3-diyl diacetate and (9) where Step 3 using sodium methoxide is omitted.

Example 240: (2R,3S,4S,5R)-5-((R)-1-Acetoxy-2,2,2-trifluoroethyl)-2-(2-amino-6-chloro-7-(cyclopropylmethyl)-8-oxo-7,8-dihydro-9H-purin-9-yl)-4-fluorotetrahydrofuran-3-yl acetate, Compound 245

Compound 245 can be prepared by the selective mild O-acetylation of the secondary hydroxyl groups of Compound 244 with acetic anhydride.

Example 241: 2-Amino-6-chloro-9-((2R,3S,4R,5R)-4-fluoro-3-hydroxy-5-((R)-2,2,2-trifluoro-1-hydroxyethyl)tetrahydrofuran-2-yl)-7-propyl-7,9-dihydro-8H-purin-8-one, Compound 246

Compound 246 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with 1-iodopropane and Step 3 using sodium methoxide is omitted.

Example 242: (2R,3S,4S,5R)-5-((R)-1-Acetoxy-2,2,2-trifluoroethyl)-2-(2-amino-6-chloro-8-oxo-7-propyl-7,8-dihydro-9H-purin-9-yl)-4-fluorotetrahydrofuran-3-yl acetate, Compound 247

Compound 247 can be prepared by the selective mild O-acetylation of the secondary hydroxyl groups of Compound 246 with acetic anhydride.

Example 243: 2-Amino-7-butyl-6-chloro-9-((2R,3S, 4R,5R)-4-fluoro-3-hydroxy-5-((R)-2,2,2-trifluoro-1-hydroxyethyl)tetrahydrofuran-2-yl)-7,9-dihydro-8H-purin-8-one, Compound 248

Compound 248 can be prepared using the procedures described in Example 43 with (3S,4S,5R)-5-(1-(benzoyloxy)-2,2,2-trifluoroethyl)-4-fluorotetrahydrofuran-2,3-diyl diacetate and (83) where Step 3 using sodium methoxide is omitted.

Example 244: (2R,3S,4S,5R)-5-((R)-1-Acetoxy-2,2, 2-trifluoroethyl)-2-(2-amino-7-butyl-6-chloro-8-oxo-7,8-dihydro-9H-purin-9-yl)-4-fluorotetrahydrofuran-3-yl acetate, Compound 249

Compound 249 can be prepared by the selective mild O-acetylation of the secondary hydroxyl groups of Compound 248 with acetic anhydride.

Example 245: 2-Amino-6-chloro-9-((2R,3S,4R,5R)-4-fluoro-3-hydroxy-5-((R)-2,2,2-trifluoro-1-hydroxyethyl)tetrahydrofuran-2-yl)-7-(2,2,2-trifluoroethyl)-7,9-dihydro-8H-purin-8-one, Compound 250

Compound 250 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with 2-bromo-1,1,1-trifluoroethane and Step 3 using sodium methoxide is omitted.

Example 246: (2R,3S,4S,5R)-5-((R)-1-Acetoxy-2,2, 2-trifluoroethyl)-2-(2-amino-6-chloro-8-oxo-7-(2,2, 2-trifluoroethyl)-7,8-dihydro-9H-purin-9-yl)-4-fluorotetrahydrofuran-3-yl acetate, Compound 251

Compound 251 can be prepared by the selective mild O-acetylation of the secondary hydroxyl groups of Compound 250 with acetic anhydride.

Example 247: 2-Amino-6-chloro-9-((2R,3S,4R,5R)-4-fluoro-3-hydroxy-5-((R)-2,2,2-trifluoro-1-hydroxyethyl)tetrahydrofuran-2-yl)-7-(3,3,3-trifluoropropyl)-7,9-dihydro-8H-purin-8-one, Compound 252

Compound 252 can be prepared using the procedures described in Example 43 with (3S,4S,5R)-5-(1-(benzoyloxy)-2,2,2-trifluoroethyl)-4-fluorotetrahydrofuran-2,3-diyl diacetate and (2) where 1-bromobutane is replaced with (46) and Step 3 using sodium methoxide is omitted.

Example 248: (2R,3S,4S,5R)-5-((R)-1-Acetoxy-2,2, 2-trifluoroethyl)-2-(2-amino-6-chloro-8-oxo-7-(3,3, 3-trifluoropropyl)-7,8-dihydro-9H-purin-9-yl)-4-fluorotetrahydrofuran-3-yl acetate, Compound 253

Compound 253 can be prepared by the selective mild O-acetylation of the secondary hydroxyl groups of Compound 252 with acetic anhydride.

Example 249: 2-Amino-9-((2R,3S,4R,5R)-4-fluoro-3-hydroxy-5-((S)-1-hydroxypropyl)tetrahydrofuran-2-yl)-7-((R)-2-hydroxypropyl)-7,9-dihydro-8H-purin-8-one, Compound 254

Compound 254 can be prepared using the procedures described in Example 5 with (37S) and where propargyl bromide is replaced with (R)-1-bromopropan-2-yl acetate [99457-42-8].

Example 250: (R)-1-(9-((2R,3S,4S,5R)-3-Acetoxy-5-((S)-1-acetoxypropyl)-4-fluorotetrahydrofuran-2-yl)-2-amino-8-oxo-8,9-dihydro-7H-purin-7-yl)propan-2-yl acetate, Compound 255

Compound 255 can be prepared by the selective mild O-acetylation of the secondary hydroxyl groups of Compound 254 with acetic anhydride.

Example 251: 2-Amino-9-((2R,3S,4R,5R)-4-fluoro-3-hydroxy-5-((S)-1-hydroxypropyl)tetrahydrofuran-2-yl)-7-((S)-2-hydroxypropyl)-7,9-dihydro-8H-purin-8-one, Compound 256

Compound 256 can be prepared using the procedures described in Example 5 with (37S) and where propargyl bromide is replaced with (S)-1-bromopropan-2-yl acetate [39968-99-5].

Example 252: (S)-1-(9-((2R,3S,4S,5R)-3-acetoxy-5-((S)-1-acetoxypropyl)-4-fluorotetrahydrofuran-2-yl)-2-amino-8-oxo-8,9-dihydro-7H-purin-7-yl)propan-2-yl acetate, Compound 257

Compound 257 can be prepared by the selective mild O-acetylation of the secondary hydroxyl groups of Compound 256 with acetic anhydride.

Example 253: 2-Amino-9-((2R,3R,5S)-3-hydroxy-5-((R)-2,2,2-trifluoro-1-hydroxyethyl)tetrahydrofuran-2-yl)-7-((R)-2-hydroxypropyl)-7,9-dihydro-8H-purin-8-one, Compound 258

Compound 258 can be prepared using the procedures described in Example 5 with (22S) and where propargyl bromide is replaced with (R)-1-bromopropan-2-yl acetate [99457-42-8].

Example 254: (2R,3R,5S)-5-((R)-1-Acetoxy-2,2,2-trifluoroethyl)-2-(7-((R)-2-acetoxypropyl)-2-amino-8-oxo-7,8-dihydro-9H-purin-9-yl)tetrahydrofuran-3-yl acetate, Compound 259

Compound 259 can be prepared by the selective mild O-acetylation of the secondary hydroxyl groups of Compound 258 with acetic anhydride.

Example 255: 2-Amino-9-((2R,3R,5S)-3-hydroxy-5-((R)-2,2,2-trifluoro-1-hydroxyethyl)tetrahydrofuran-2-yl)-7-((S)-2-hydroxypropyl)-7,9-dihydro-8H-purin-8-one, Compound 260

Compound 260 can be prepared using the procedures described in Example 5 with (22S) and where propargyl bromide is replaced with (S)-1-bromopropan-2-yl acetate [39968-99-5].

Example 256: (2R,3R,5S)-5-((R)-1-Acetoxy-2,2,2-trifluoroethyl)-2-(7-((S)-2-acetoxypropyl)-2-amino-8-oxo-7,8-dihydro-9H-purin-9-yl)tetrahydrofuran-3-yl acetate, Compound 261

Compound 261 can be prepared by the selective mild O-acetylation of the secondary hydroxyl groups of Compound 260 with acetic anhydride.

Example 257: 2-Amino-9-((2R,3S,4R,5R)-4-fluoro-3-hydroxy-5-((R)-2,2,2-trifluoro-1-hydroxyethyl)tetrahydrofuran-2-yl)-7-((R)-2-hydroxypropyl)-7,9-dihydro-8H-purin-8-one, Compound 262

Compound 262 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is replaced with (R)-1-bromopropan-2-yl acetate [99457-42-8].

Example 258: (2R,3S,4S,5R)-5-((R)-1-acetoxy-2,2,2-trifluoroethyl)-2-(7-((R)-2-acetoxypropyl)-2-amino-8-oxo-7,8-dihydro-9H-purin-9-yl)-4-fluorotetrahydrofuran-3-yl acetate, Compound 263

Compound 263 can be prepared by the selective mild O-acetylation of the secondary hydroxyl groups of Compound 262 with acetic anhydride.

Example 259: 2-Amino-9-((2R,3S,4R,5R)-4-fluoro-3-hydroxy-5-((R)-2,2,2-trifluoro-1-hydroxyethyl)tetrahydrofuran-2-yl)-7-((S)-2-hydroxypropyl)-7,9-dihydro-8H-purin-8-one, Compound 264

Compound 264 can be prepared using the procedures described in Example 5 with (3S,4S,5R)-5-(1-(benzoyloxy)-2,2,2-trifluoroethyl)-4-fluorotetrahydrofuran-2,3-diyl diacetate and where propargyl bromide is replaced with (S)-1-bromopropan-2-yl acetate [39968-99-5].

Example 260: (2R,3S,4S,5R)-5-((R)-1-Acetoxy-2,2,2-trifluoroethyl)-2-(7-((S)-2-acetoxypropyl)-2-amino-8-oxo-7,8-dihydro-9H-purin-9-yl)-4-fluorotetrahydrofuran-3-yl acetate, Compound 265

Compound 265 can be prepared by the selective mild O-acetylation of the secondary hydroxyl groups of Compound 264 with acetic anhydride.

Example 1. Activity of Compounds as TLR7 and TLR8 Agonists as Measured in Reporter Cell Assays The engagement of TLRs by cognate ligands triggers downstream signaling cascades, leading to the activation of NF-κB and other transcription factors which initiate various immunomodulatory effects. The human embryonic kidney cell line, HEK293, is essentially non-responsive to TLR agonists, but ectopic expression of TLRs in these cells allows cognate agonists to activate endogenous NF-κB. Accordingly, the HEK293-TLR-NF-κB inducible reporter system is used to assay TLR agonists.

HEK293 cell lines stably expressing human TLR7 or TLR8 together with an NF-κB-driven-secreted alkaline phosphatase (SEAP) reporter were invented at InvivoGen (San Diego, Calif., USA) and used to assess compounds of the present invention for TLR7 and TLR8 agonist activities.

Cells were seeded at $2-5 \times 10^4$ cells/well in 96 well plates (200 μl/well) and treated with various concentrations of compound (10 μl) for 15-24 hours. SEAP activity was determined by measuring OD at 650 nm; the media used to culture the cell lines contains the reagents required for SEAP detection. The $EC_{50}$ values in Table 1 are calculated from fitting the dose response of measured SEAP activity for each compound to the following equation: $Y=y_{max}*c^{nh}/(EC_{50}^{nh}+c^{nh})+blank$ where Y is the experimentally measured $OD_{650}$ at concentration c of test article, blank is the observed $OD_{650}$ in the absence of TLR7 agonist, $y_{max}$ is the difference between the measured $OD_{650}$ in the presence of 28.5 μM resiquimod and the blank and values of $EC_{50}$ and nh are determined by nonlinear least squares analysis. Resiquimod is a known TLR7 and TLR8 agonist.

The results of selected compounds tested in TLR7 reporter cells are shown in Table 1. Compound A is 5-amino-3-((2R,3R,5S)-3-hydroxy-5-((S)-1-hydroxypropyl)tetrahydrofuran-2-yl)thiazolo[4,5-d]pyrimidine-2,7(3H,6H)-dione)

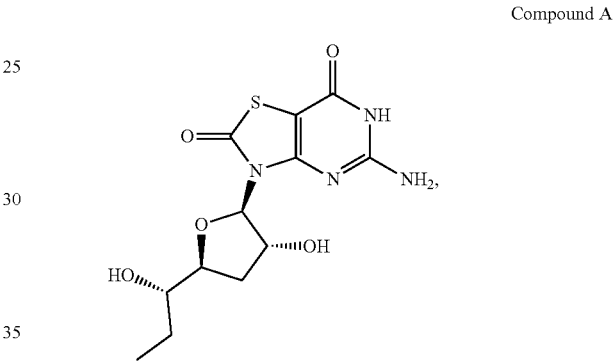

Compound A a known TLR7/TLR8 agonist (International Publication No. WO 2016/146598 A1).

TABLE 1

| | TLR7 Reporter Assay | |
|---|---|---|
| Compound | Response at 500 μM Compound as a Percent of Resiquimod Response | TLR7 Reporter $EC_{50}$ (μM) |
| A | 74 | 51 |
| 1 | 67 | 103 |
| 2 | <5 | |
| 3 | <5 | |
| 4 | 81 | 132 |
| 8 | <5 | |
| 9 | 58 | 182 |
| 10 | 72 | 311 |
| 11 | <5 | |
| 12 | 6 | >500 μM |
| 13 | 92 | 119 |
| 14 | <5 | |
| 15 | <5 | |
| 16 | <5 | |
| 17 | 58 | 358 |
| 18 | <5 | |
| 19 | <5 | |
| 22 | 69 | 224 |
| 23 | <5 | |
| 24 | 52 | 327 |
| 25 | 74 | 324 |
| 26 | 59 | 269 |
| 27 | 61 | 339 |
| 28 | 47 | 519 |
| 29 | 79 | 201 |

TABLE 1-continued

TLR7 Reporter Assay

| Compound | Response at 500 µM Compound as a Percent of Resiquimod Response | TLR7 Reporter EC$_{50}$ (µM) |
|---|---|---|
| 30 | 87 | 94 |
| 31 | 78 | 210 |
| 32 | 68 | 339 |
| 33 | 73 | 287 |
| 34 | 81 | 137 |
| 35 | 91 | 114 |
| 37 | 40 | 462 |
| 38 | <5 | |
| 39 | <5 | |
| 40 | <5 | |
| 41 | <5 | |
| 42 | <5 | |
| 43 | 97 | 55 |
| 44 | 101 | 86 |
| 45 | 66 | 185 |
| 46 | 30 | >500 µM |

With the exception of Compound A, none of the compounds listed in Table 1 displayed significant (>5% of ymax for TLR8 as measured at 28.5 µM resiquimod) activity in a similar TLR8 reporter cell assay at concentrations up to 500 µM.

Example 2. Induction of Interferon-α and IL6 in hPBMCs (Human Peripheral Blood Mononuclear Cells)

Treatment of hPBMCs with a TLR7 agonist typically induces some production of interferon-α as well as lesser amounts of a variety of other cytokines and chemokines. A typical experiment uses hPBMCs isolated from a healthy donor and placed in replicate cell culture wells; typically 1.0-7.5×10$^6$ cells are placed in each well. A test compound is added and the cells are cultured for 24 hours at 37° C. in a humidified atmosphere containing 5% $CO_2$ post-addition; untreated controls are included. Secreted interferon-α production is measured using an a multisubtype interferon-α ELISA kit like those from PBL Assay Sciences or specifically as IFNα$_{2a}$ as part of a panel of cytokines and chemokines using luminex methodologies.

The minimal effective concentration (MEC) is the minimum concentration in a dose response curve where a significant increase in interferon-α production (generally at least 80 pg/ml) is observed above baseline. MEC values for each compound are determined for at least three donors. The weighted MEC for each compound is the geometric mean of all individual MECs across all donors. Concentrations tested typically consist of a two-fold dilution series starting at 100 µM. In the calculation of weighted MEC, any individual MEC value greater the highest concentration tested is arbitrarily set to two times the highest concentration tested unless all MECs for a compound exceed this value. The maximal amount of IFNα2a for each donor is determined from dose dependence for each compound.

In order to normalize for variation in each hPBMC preparation, these values are first transformed by expressing as a percentage of peak response measured with a standard (2-Amino-7-(cyclopropylmethyl)-9-B-D-xylofuranosyl-7,9-dihydro-1H-purine-6,8-dione) and then averaging the results across all donors, this average referred to as IFNrmax. In rare instances, PBMCs from a donor did not produce significant IFNα2a as defined as >80 pg/ml in response to incubation with either 50 or 100 µM standard compound while exhibiting substantial production in response to the test articles and were omitted from calculations of IFNrmax in Table 2 without materially impacting the findings therein.

When hPBMCs were treated with compounds selected from Table 1, including Compound A, several induced interferon-α production as shown in Table 2. Compound B is 2-Amino-9-((2R,3S,4S,5R)-4-fluoro-3-hydroxy-5-(hydroxymethyl)tetrahydrofuran-2-yl)-7-(prop-2-yn-1-yl)-7,9-dihydro-1H-purine-6,8-dione (U.S. patent application Ser. No. 16/422,050) shown below

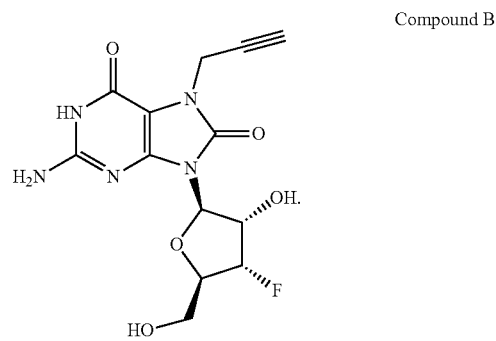 [SMILES: C#CCn1c(=O)n([C@@H]2O[C@H](CO)[C@@H](F)[C@H]2O)c2nc(N)[nH]c(=O)c21]

Compound B

TABLE 2

Weighted MEC values from interferon-α production and scaled peak IFNα2a from hPBMCs in-vitro upon incubation with TLR7 agonists.

| Compound | Weighted MEC (µM) | IFNrmax, Relative Maximal IFNα2a Production (%) |
|---|---|---|
| A | ≤3.1 | 103 |
| B | 17.9 | 260 |
| 1 | ≤2.9 | 316 |
| 2 | 39.7 | 233 |
| 3 | >50 | ≤10 |
| 4 | 12.5 | 226 |
| 8 | 5.4 | 215 |
| 9 | 6.2 | 191 |
| 10 | ≤2.8 | 283 |
| 11 | 12.5 | 128 |
| 12 | 15.7 | 133 |
| 13 | ≤3.3 | 353 |
| 14 | >50 | ≤10 |
| 15 | >50 | ≤10 |
| 16 | >50 | ≤10 |
| 17 | ≤3.1 | 185 |
| 18 | >50 | ≤10 |
| 19 | >50 | ≤10 |
| 22 | 6.3 | 307 |
| 23 | >50 | ≤10 |
| 24 | 12.5 | 205 |
| 25 | 19.8 | 80 |
| 26 | ≤1.6 | 304 |
| 27 | ≤1.6 | 209 |
| 28 | 9.9 | 105 |
| 29 | 6.3 | 83 |
| 30 | 1.6 | 347 |
| 31 | 6.3 | 71 |
| 32 | 7.9 | 223 |
| 33 | 9.9 | 143 |
| 34 | 1.6 | 272 |
| 35 | 3.1 | 207 |
| 37 | 79.4 | 81 |
| 38 | >50 | ≤10 |
| 39 | >50 | ≤10 |
| 40 | >50 | ≤10 |
| 41 | >50 | ≤10 |

TABLE 2-continued

Weighted MEC values from interferon-α production and scaled peak IFNα2a from hPBMCs in-vitro upon incubation with TLR7 agonists.

| Compound | Weighted MEC (μM) | IFNrmax, Relative Maximal IFNα2a Production (%) |
|---|---|---|
| 42 | >50 | ≤10 |
| 43 | 2.5 | 158 |
| 44 | 2.0 | 250 |
| 45 | 5.0 | 321 |
| 46 | 3.1 | 317 |

A compound is of particular interest if it possesses high potency and high IFNα2a production. This combination of features is not typical of known TLR7 agonists.

Example 3. MEC and $IFN_{max}$ from Interferon-α Production from hPBMCs in Three Donors Further insight can be gained by examining the responses in three individual donors as shown in Table 3. $IFN_{max}$ is the maximum amount of IFN observed at any concentration across the evaluated concentration range. MEC and $IFN_{max}$ values for three select compound are shown for three donors (Table 3). The range of tested concentrations were 0.625-5 μM for Imiquimod, 3.125-100 μM for both Compound A and Compound 1, 12.5-100 μM for Compound 2.

TABLE 3

MEC and $IFN_{max}$ values from interferon-α production from hPBMCs in vitro upon incubation with selected TLR7 agonists in the three individual donors*.

| | Donor 1 | | Donor 2 | | Donor 3 | |
|---|---|---|---|---|---|---|
| Compound ID | MEC (μM) | $IFN_{max}$ (pg/ml) | MEC (μM) | $IFN_{max}$ (pg/ml) | MEC (μM) | $IFN_{max}$ (pg/ml) |
| Imiquimod | 5 | 793 | 5 | 193 | 1.25 | 1350 |
| Compound A | ≤3.125 | 1061 | ≤3.125 | 481 | ≤3.125 | 2243 |
| Compound 1 | ≤3.125 | 3775 | 6.25 | 2129 | ≤3.125 | 5623 |
| Compound 2 | 50 | 4523 | >100 | 9 | 100 | 3110 |

*The amount of IFNα2a product observed in the absence of TLR7 agonists was <10 pg/ml for all three donors.

Compound 1 possesses a combination of potency (low MEC value) and interferon production (high $IFN_{max}$ value). Notably, $IFN_{max}$ is substantially greater for Compound 1 than for the two known TLR7 agonists imiquimod and Compound A (4.8-, 11.0- and 4.2-fold for donors 1, 2 and 3, respectively for imiquimod; 3.6-, 4.4- and 2.5-fold for donors 1, 2 and 3, respectively for Compound A). The comparative MECs for Compound 1 versus 2 are ≤3.125 versus 50 for Donor 1, 6.25 vs>100 for Donor 2 and ≤3.125 vs 100 for Donor 3; in every case Compound 1 is ≥16-fold more potent than Compound 2.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A compound having the structure of Formula I:

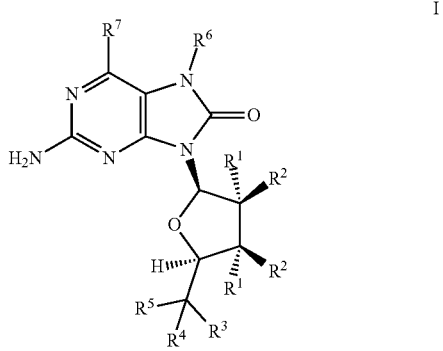

wherein $R^1$ is independently —H, —OH, —O—C(O)—$R^8$ or —F,
$R^2$ is independently —H, —OH, —O—C(O)—$R^8$ or —F,
$R^3$ is —OH, or —O—C(O)—$R^8$,
$R^4$ is —H, —OH, —O—C(O)—$R^8$ or —($C_1$-$C_8$)alkyl,
wherein $R^3$ and $R^4$ can be in the form of a carbonyl oxygen (=O),
$R^5$ is —H, —OH, —O—C(O)—$R^8$, —($C_1$-$C_8$)alkyl, —O—($C_1$-$C_8$)alkyl, —$NH_2$ or —$NHR^8$
wherein $R^4$ and $R^5$ can form a 3-6 membered cycloalkyl ring,
$R^6$ is —H, —($C_1$-$C_8$)alkyl, —C(H)=$CH_2$, —C(H)=CH($C_1$-$C_8$)alkyl), —C(H)=C($C_1$-$C_8$)alkyl)($C_1$-$C_8$)alkyl), —C(H)=C=$CH_2$, —C(H)=C=C($C_1$-$C_8$)alkyl)H, —$CH_2$C≡CH, —OH or —O($C_1$-$C_8$)alkyl,
$R^7$ is —H, —OH, —$OCH_3$, —SH or —Cl,
$R^8$ is independently —($C_1$-$C_8$)alkyl, aryl, —($CH_2$)$_n$(aryl), heteroaryl or —($CH_2$)$_n$(heteroaryl),
n is an integer 1, 2, 3, 4 or 5,
wherein at least one $R^4$ or $R^5$ is not —H,
wherein each alkyl, cycloalkyl, aryl and heteroaryl are independently optionally substituted by one or more of CN, $NO_2$, halogen, ($C_1$-$C_3$)alkyl, ($C_1$-$C_3$)haloalkyl, ($C_1$-$C_3$)cycloalkyl, aryl, heteroaryl, OH, alkenyl, alkynyl, O—($C_1$-$C_3$)alkyl, O—C(O)—$R^9$, O-(alkylene)aryl, O-(alkylene)heteroaryl, C(O)$R^9$, S($C_1$-$C_8$)alkyl, S(O)($C_1$-$C_8$)alkyl, $SO_2$($C_1$-$C_8$)alkyl, C(O)O$R^9$, C(O)$NR^9R^9$, C(O)$NR^9SO_2$($C_1$-$C_8$)alkyl, $NR^9R^9$, $NR^9$(CO)O$R^9$, NH(CO)$R^9$, NH($SO_2$)($C_1$-$C_8$)alkyl or NH($SO_2$)$NR^9R^9$, and $R^9$ is independently —H, —OH, —($C_1$-

C$_8$)alkyl, cycloalkyl, heterocyclyl, or the two R$^9$'s of C(O)NR$^9$R$^9$ or NR$^9$R$^9$ combine together with the nitrogen atom to form a heterocycle;

or a stereoisomer, a tautomer or a pharmaceutically acceptable salt thereof.

2. The compound of claim 1, wherein R$^1$ and R$^2$ are —H, —OH, or F, or a stereoisomer, a tautomer or a pharmaceutically acceptable salt thereof.

3. The compound of claim 1, wherein R$^3$ is —OH or —O—C(O)—CH$_3$, or a stereoisomer, a tautomer or a pharmaceutically acceptable salt thereof.

4. The compound of claim 1, wherein R$^4$ is —H or —(C$_1$-C$_8$)alkyl, or a stereoisomer, a tautomer or a pharmaceutically acceptable salt thereof.

5. The compound of claim 1, wherein R$^4$ is —H or —CH$_2$CH$_3$, or a stereoisomer, a tautomer or a pharmaceutically acceptable salt thereof.

6. The compound of claim 1, wherein R$^5$ is —H or —(C$_1$-C$_8$)alkyl, or a stereoisomer, a tautomer or a pharmaceutically acceptable salt thereof.

7. The compound of claim 1, wherein R$^6$ is —C(H)=CH$_2$ or —CH$_2$C≡CH, or a stereoisomer, a tautomer or a pharmaceutically acceptable salt thereof.

8. The compound of claim 1, wherein R$^7$ is —H or —OH, or a stereoisomer, a tautomer or a pharmaceutically acceptable salt thereof.

9. The compound of claim 1, wherein R$^8$ is —(C$_1$-C$_8$)alkyl, or a stereoisomer, a tautomer or a pharmaceutically acceptable salt thereof.

10. The compound of claim 1, wherein R$^8$ is —CH$_3$, or a stereoisomer, a tautomer or a pharmaceutically acceptable salt thereof.

11. The compound of claim 1, wherein the compound is selected from the group consisting of:

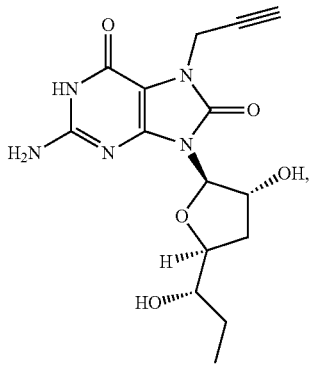

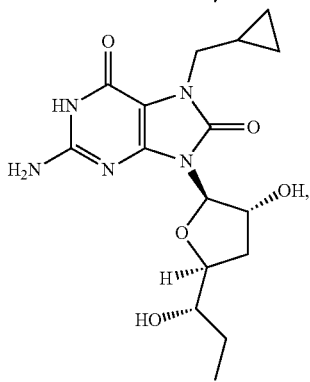

-continued

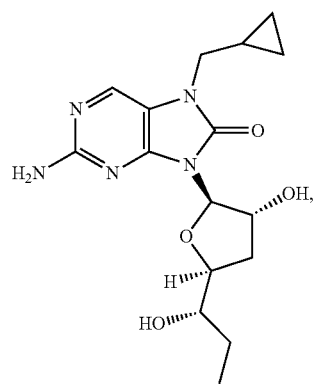

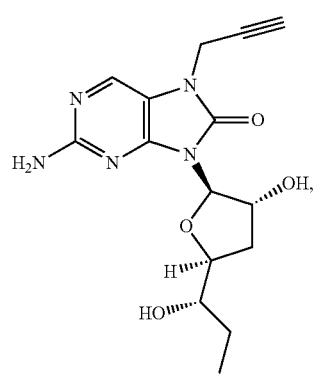

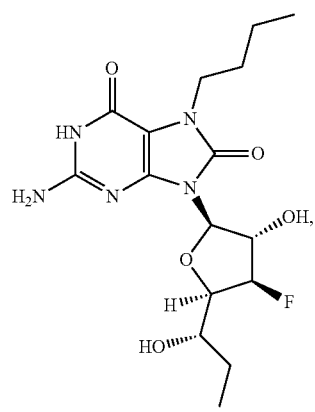

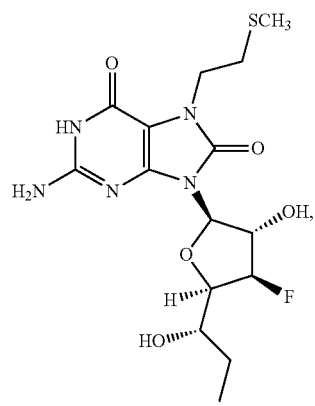

215
-continued
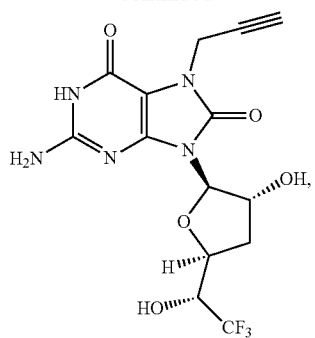
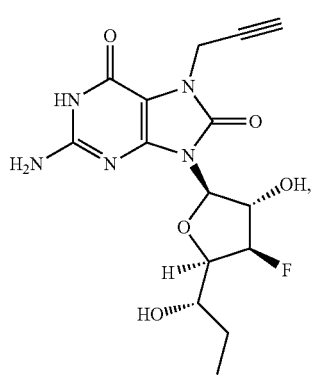
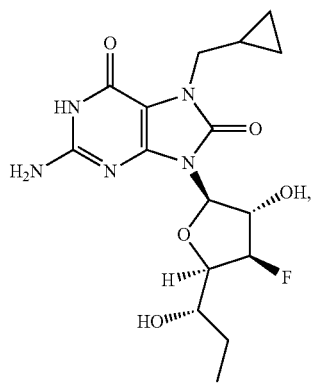
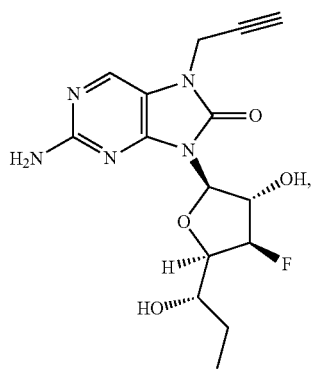
216
-continued
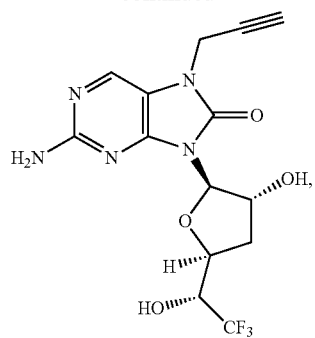
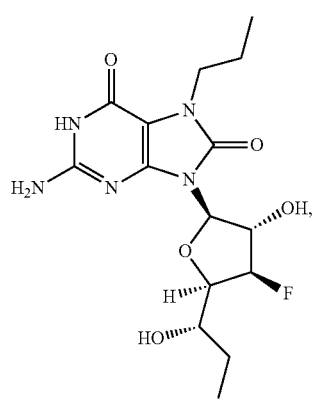
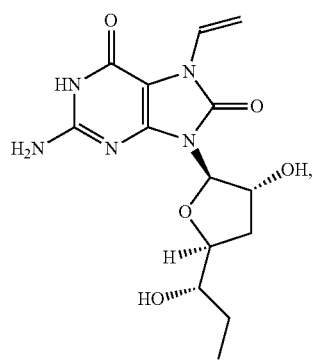
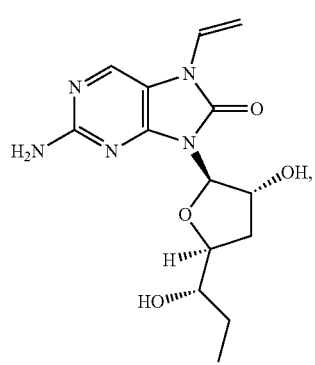

-continued

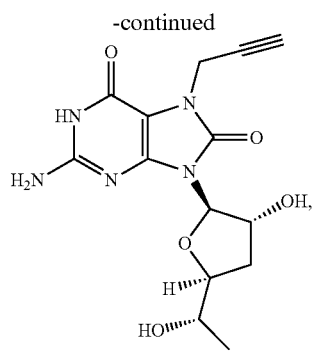
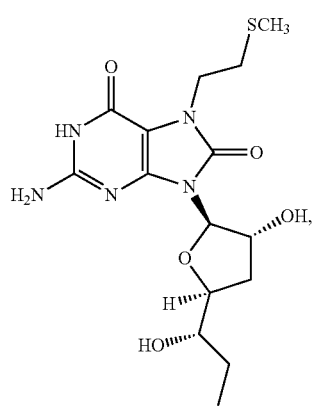
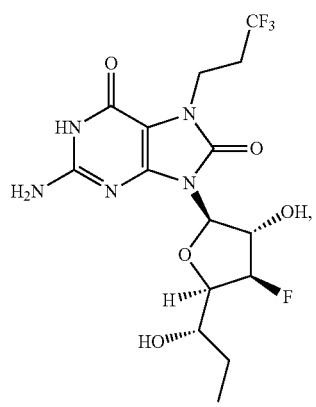
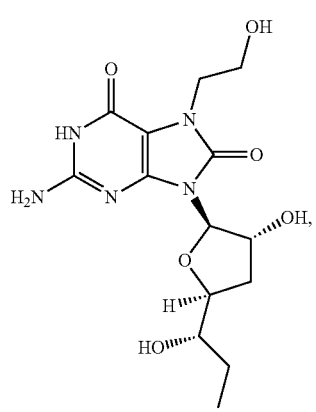

-continued

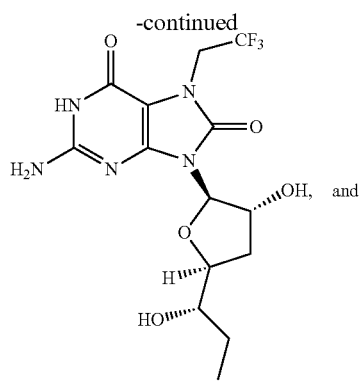
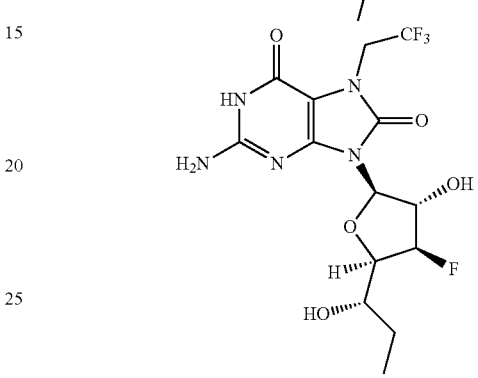

or a stereoisomer, a tautomer or a pharmaceutically acceptable salt thereof.

12. A pharmaceutical composition comprising one or more compounds of claim 1, or a stereoisomer, a tautomer or a pharmaceutically acceptable salt thereof, and a pharmaceutically acceptable excipient.

13. A method for treating or preventing an infectious disease or cancer, the method comprising administering to the individual an effective amount of one or more compounds of claim 1, or a stereoisomer, a tautomer or a pharmaceutically acceptable salt thereof.

14. The method of claim 13, wherein the infectious disease is a viral infection.

15. The method of claim 14, wherein the viral infection is infection with a virus selected from the group consisting of HIV, hepatitis virus A, hepatitis virus B, hepatitis virus C, hepatitis virus D, VZV, HSV-I, HAV-6, HSV-II, CMV, Epstein Barr virus, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, SARS-CoV, MERS, and SARS-CoV-2.

16. The method of claim 13, wherein the method is for treating or preventing cancer.

17. The method of claim 16, wherein the cancer is selected from the group consisting of osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer, liver cancer, breast cancer, and gastric cancer.

18. The method of claim 13 further comprising the administration of one or more additional agents, wherein the one or more agents are each independently an immune checkpoint inhibitor, an OX40 agonist, a 4-1BB agonist, an ICOS agonist, a GITR agonist, an IL-2-receptor agonist, or an antibody mediated by ADCC.

19. The method of claim 18, wherein the one or more agents are each independently an inhibitor of PD-1, PD-L1, CTLA4, TIM3, LAG3, SIRPα or CD47.

20. The method of claim 13, further comprising the administration of one or more additional agents, wherein the one or more additional agents are each independently a small-molecule therapeutic agent, a protein or peptide therapeutic, an antibody, sera from persons that have recovered from a viral infection, or a therapeutic or preventative vaccine.

\* \* \* \* \*